US012129281B2

(12) United States Patent
Lang et al.

(10) Patent No.: US 12,129,281 B2
(45) Date of Patent: Oct. 29, 2024

(54) METHOD FOR PRODUCING AN ANTITUMORAL ARENAVIRUS AS WELL AS ARENAVIRUS MUTANTS

(71) Applicant: ABALOS THERAPEUTICS GMBH, Dusseldorf (DE)

(72) Inventors: Karl Lang, Essen (DE); Cornelia Hardt, Bochum (DE); Michael Bergerhausen, Duisburg (DE); Hilal Bhat, Essen (DE)

(73) Assignee: ABALOS THERAPEUTICS GMBH, Dusseldorf (DE)

( * ) Notice: Subject to any disclaimer, the term of this patent is extended or adjusted under 35 U.S.C. 154(b) by 804 days.

(21) Appl. No.: 17/275,967

(22) PCT Filed: Sep. 12, 2019

(86) PCT No.: PCT/EP2019/074307

§ 371 (c)(1),
(2) Date: Mar. 12, 2021

(87) PCT Pub. No.: WO2020/053324

PCT Pub. Date: Mar. 19, 2020

(65) Prior Publication Data

US 2022/0033445 A1 Feb. 3, 2022

(30) Foreign Application Priority Data

Sep. 12, 2018 (DE) ..................... 10 2018 215 551.8

(51) Int. Cl.

| | |
|---|---|
| ***C07K 14/08*** | (2006.01) |
| ***A61K 35/76*** | (2015.01) |
| ***A61K 35/768*** | (2015.01) |
| ***A61K 45/06*** | (2006.01) |
| ***A61P 35/00*** | (2006.01) |
| ***C07K 14/005*** | (2006.01) |
| ***C12N 7/00*** | (2006.01) |

(52) U.S. Cl.

CPC .......... *C07K 14/005* (2013.01); *A61K 35/768* (2013.01); *A61K 45/06* (2013.01); *A61P 35/00* (2018.01); *C12N 7/00* (2013.01); *C12N 2760/10021* (2013.01); *C12N 2760/10022* (2013.01); *C12N 2760/10032* (2013.01); *C12N 2760/10052* (2013.01); *C12N 2760/10071* (2013.01)

(58) Field of Classification Search

None

See application file for complete search history.

(56) References Cited

U.S. PATENT DOCUMENTS

2008/0124308 A1* 5/2008 Laer ........................ A61P 43/00 424/93.2

FOREIGN PATENT DOCUMENTS

| | | | |
|---|---|---|---|
| DE | 102004034461 | A1 | 2/2006 |
| JP | 2012-503489 | A2 | 2/2012 |
| JP | 2014-502848 | A2 | 2/2014 |
| RU | 2585216 | C2 | 5/2016 |
| WO | 2006008074 | A1 | 1/2006 |
| WO | 2009083210 | A1 | 7/2009 |
| WO | 2012093340 | A2 | 7/2012 |
| WO | 2014089668 | A1 | 6/2014 |
| WO | 2016170176 | A1 | 10/2016 |
| WO | WO/2016/166285 | A1 | 10/2016 |
| WO | 2018/083220 | A2 | 5/2018 |

OTHER PUBLICATIONS

Romanowski et al. Complete sequence of the S RNA of lymphocytic choriomeningitis virus (WE strain) compared to that of Pichinde arenavirus. Virus Research, 3 (1985) 101-114.*
GenBank: M22138.1 Lymphocytic choriomeningitis virus S RNA, complete cds. Dated Aug. 2, 1993.*
Von Laer and Beyer, Retroviral hybrid vectors pseudotyped with LCMV. GenBank: AAN27477.1 Sep. 26, 2002 found Jul. 17, 2023.
Office Action issued in Russian Patent Application No. 2021104395 dated Jul. 19, 2023—incl Engl lang transl Search Report.
Extended European Search Report issued in EP 21205198 dated May 31, 2022 (11 pages).
Office Action issued in Japanese Patent Application No. 2021-514594 dated Jul. 9, 2023—incl Engl lang transl (12 pages total).
International Search Report issued in PCT/EP2019/074307 on Feb. 3, 2020 (7 pages).
Written Opinion issued in PCT/EP2019/074307 on Feb. 3, 2020 (10 pages).
Ciurea et al., Nature Medicine, 2001, pp. 795-800.
Kalkavan et al., Nature Communications, 2017, p. 14447.
Moskophidis et al., Journal of Virology, 1994, 63(3):1951-1955.
Flatz et al., Development of replication-defective lymphocytic choriomeningitis virus vectors for the induction of potent CD8+ T cell immunity. Nat Med. Mar. 2010; 16(3):339-345.
Seiler et al., In Vivo Selection of Neutralization-Resistant Virus Variants But No Evidence of B Cell Tolerance in Lymphocytic Choriomeningitis Virus Carrier Mice Expressing a Transgenic Virus-Neutralizing Antibody. J Immunol. Apr. 15, 1999;162(8):4536-4541.

* cited by examiner

*Primary Examiner* — Nianxiang Zou
(74) *Attorney, Agent, or Firm* — Michael A. Whittaker

(57) ABSTRACT

The invention relates to a mutant of an arenavirus having improved antitumoral properties. The invention also relates to a method of generating such an arenavirus mutant, related pharmaceutical compositions, medical uses, methods of treatment, and isolated proteins and nucleic acids.

22 Claims, 85 Drawing Sheets

Specification includes a Sequence Listing.

Figure 25

A. Lymphocytic choriomeningitis virus (LCMV) strain WE

Source: 1-3376 Segment = S
Protein: Pre-glycoprotein polyprotein GP complex
Gene: GPC
Gene: 79-1575

>LCMV-WE-DUE_GP
ATGGGTCAGATTGTGACAATGTTTGAGGCTTTGCCTCACATCATTGATGAGGTCATCAAC
ATTGTCATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTTAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATAAGCCAGTGTAGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AATACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 9)

CDS: 79-1575
Codon Start = 1; Codons 1-498
*Chain:* *1-498* *Pre-glycoprotein polyprotein GP complex*
*Chain:* *1-58* *Stable signal peptide*
*Chain:* *59-265* *Glycoprotein G1*
*Chain:* *266-498* *Glycoprotein G2*

Translation=

>LCMV-WE-DUE_GP
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
ISQCRTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO:10)

Figure 25 (continued)

Source: 1-3376 Segment = S
Protein: Nucleoprotein
Gene: NP
Gene: 1640-3316 complement >LCMV-WE-DUE_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTTGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAGAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAATAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 11)

CDS: 1640-3316 complement
Codon Start = 1; Codons 1-558

Translation=

>LCMV-WE-DUE_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 12)

Figure 25 (continued)

Source: 1-7235 Segment = L
Protein: RING finger protein Z
Gene: ZP
Gene: 90-362

>LCMV-WE-DUE_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 13)

CDS: 90-362
Codon Start = 1; Codons 1-91
Translation=

>LCMV-WE-DUE_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE

Figure 25 (cont'd)

Source: 1-7235 Segment = L
Protein: RNA-directed RNA polymerase L
Gene: LP
Gene: 574-7203 complement

>LCMV-WE-DUE_LP
ATGGATGAAACTATTGCAGATTTGAGAGAGTTGTGTCTAAATTACATAGAACAGGACGAG
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTGAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGTTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTGAA
AAGGTGTTATTGAGTGCAAAATTCAAGTTTATGTTGAATGTGTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCCAGGAAAACAGAAGTAGACAAATTG
GAAGATGATCCGGTAGATGTGTGTTTCGAGGGGGAGGAGGAGACAAGTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGCTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTATTTTGAATCCTTTTCTAGTTTCTTTTCAGGATCTTGTTTAAACAATGACAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTTCTCCAA
AATCTCAAACTGGGTGATGATCAGTACGTGCGTTCTGGAAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAAAGAAAGAGGCCATCCTTCAATTGGGA
GAGATTCTTGGTCTTGAGGATGATCTTAATGAGTTGGCAAGCATCAATTGGTTGAATCTG
AATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTCTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTTCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATATCTCTGTGAAATTGGAGACA
AAGGACATGAGGGTCTTTCTGGCAGAGCTCGAGGGCTGTGGAAAAATTGGTGATGTCCTC
GGCAGCCTCCTCCTGCACCGATTCAGAACTGGTGAGCACTTGATGGAGTCAGAAATAAGT
ACAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCAGGTCAAAGAACACTGTA
ATGTATGAGACAACTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 15)

CDS: 574-7203 complement
Codon Start = 1; Codons 1-2210
Translation=

>LCMV-WE-DUE_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGKLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMSDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHFFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNISVKLET
KDMRVFLAELEGCGKIGDVLGSLLLHRFRTGEHLMESEISTVLQELCMDRSVMLTPLSFV
PDWFTFRDCRLCFSRSKNTVMYETTGGRFRLKGKSCDDWLAERVAEEID
(SEQ ID NO: 16)

Figure 25 (cont'd)

B. Lymphocytic choriomeningitis virus (LCMV) P42 mutant

Source: 1-3376 Segment = S
Protein: Pre-glycoprotein polyprotein GP complex
Gene: GPC
Gene: 79-1575

>LCMV-P42_GP
ATGGGTCAGATTGTGACAATGTTTGAGGCTTTGCCTCACATCATTGATGAGGTCATCAAC
ATTGTCATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTTAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATGAGCCAGTGTAGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AATACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 17)

CDS: 79-1575
Codon Start = 1; Codons 1-498
*Chain:* *1-498* *Pre-glycoprotein polyprotein GP complex*
*Chain:* *1-58* *Stable signal peptide*
*Chain:* *59-265* *Glycoprotein G1*
*Chain:* *266-498* *Glycoprotein G2*

Translation=

>LCMV-P42_GP
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
MSQCRTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO: 18)

Figure 25 (cont'd)

Source: 1-3376 Segment = S
Protein: Nucleoprotein
Gene: NP
Gene: 1640-3316 complement

>LCMV-P42_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTTGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAGAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAATAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 19)

CDS: 1640-3316 complement
Codon Start = 1; Codons 1-558
Translation=

>LCMV-P42_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 20)

Figure 25 (cont'd)

Source: 1-7235 Segment = L
Protein: RING finger protein Z
Gene: ZP
Gene: 90-362

>LCMV-P42_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 21)

CDS: 90-362
Codon Start = 1; Codons 1-91
Translation=

>LCMV-P42_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE
(SEQ ID NO: 22)

Figure 25 (cont'd)

```
Source:      1-7235   Segment = L
Protein:     RNA-directed RNA polymerase L
Gene:        LP
Gene:        574-7203 complement
```

>LCMV-P42_LP
ATGGATGAAACTATTGCAGATTTGAGAGAGTTGTGTCTAAATTACATAGAACAGGACGAG
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTGAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGTTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTGAA
AAGGTGTTATTGAGTGCAAAATTCAAGTTTATGTTGAATGTGTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCCAGGAAAACAGAAGTAGACAAATTG
GAAGATGATCCGGTAGATGTGTGTTTCGAGGGGGAGGAGGAGACAAGTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGCTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTATTTTGAATCCTTTTCTAGTTTCTTTTCAGGATCTTGTTTAAACAATGACAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTYCTCCAA
AATCTCAAACTGGGTGATGATCAGTACGTGCGTTCTGGAAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAAAGAAAGAGGCCATCCTTCAATTGGGA
GAGATTCTTGGTCTTGAGGATGATCTTAATGAGTTGGCAAGCATCAATTGGTTGAATCTG
AATGAAATGTTCCCATTGAGGATGGTTCTGAGACAAAAAGTGGTTTACCCATCAGTRATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTTTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTTCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATATCTCTGTGAAATTGGAGACA
AAGGACATGAGRGTCTTTCTGGCAGAGCTCGAGGGCTGTGGAAAAATTGGTGATGTCCTC
GGCAGCCTCCTCCTGCACCGATTCAGAACTGGTGAGCACTTGATGGAGTCAGAAATAAGT
ACAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCAGGTCAAAGAACACTGTR
ATGTATGAGACAACTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 23)

CDS: 574-7203 complement
Codon Start = 1; Codons 1-2210
Translation=

>LCMV-P42_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGKLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMFDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHFFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNISVKLET
KDMRVFLAELEGCGKIGDVLGSLLLHRFRTGEHLMESEISTVLQELCMDRSVMLTPLSFV
PDWFTFRDCRLCFSRSKNTVMYETTGGRFRLKGKSCDDWLAERVAEEID
(SEQ ID NO: 24)

Figure 25 (cont'd)

C. Lymphocytic choriomeningitis virus (LCMV) P52 mutant

Source: 1-3376 Segment = S
Protein: Pre-glycoprotein polyprotein GP complex
Gene: GPC
Gene: 79-1575

>LCMV-P52_GP
ATGGGTCAGATTGTGACAATGTTTGAGGCTTTGCCTCACATCATTGATGAGGTCATCAAC
ATTGTCATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTTAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATGAGCCAGTGTTGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AATACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 25)

CDS: 79-1575
Codon Start = 1; Codons 1-498
*Chain:* *1-498* *Pre-glycoprotein polyprotein GP complex*
*Chain:* *1-58* *Stable signal peptide*
*Chain:* *59-265* *Glycoprotein G1*
*Chain:* *266-498* *Glycoprotein G2*

Translation=

>LCMV-P52_GP
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
MSQCWTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO: 26)

Figure 25 (cont'd)

Source: 1-3376 Segment = S
Protein: Nucleoprotein
Gene: NP
Gene: 1640-3316 complement

>LCMV-P52_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTTGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAGAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAAYAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 27)

CDS: 1640-3316 complement
Codon Start = 1; Codons 1-558
Translation=

>LCMV-P52_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 28)

Figure 25 (cont'd)

Organism: Lymphocytic choriomeningitis virus (LCMV strain WE)
Subtype: P52
Source: 1-7235 Segment = L
Protein: RING finger protein Z
Gene: ZP
Gene: 90-362

>LCMV-P52_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 29)

CDS: 90-362
Codon Start = 1; Codons 1-91
Translation=

>LCMV-P52_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE
(SEQ ID NO: 30)

Figure 25 (cont'd)

Source: 1-7235 Segment = L
Protein: RNA-directed RNA polymerase L
Gene: LP
Gene: 574-7203 complement

>LCMV-P52_LP
ATGGATGAAACTATTGCAGATTTGAGAGAGTTGTGTCTAAATTACATAGAACAGGACGAG
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTGAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGTTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTGAA
AAGGTGTTATTGAGTGCAAAATTCAAGTTTATGTTGAATGTRTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCCAGGAAAACAGAAGTAGACAAATTG
GAAGATGATCCGGTAGATGTGTGTTTCGAGGGGGAGGAGGAGACAAGTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGCTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTATTTTGAATCCTTTTCTAGTTTCTTTTCAGGATCTTGTTTAAACAATGACAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTTCTCCAA
AATCTCAAACTGGGTGATGATCAGTACGTGCGTTCTGGAAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAAAGAAAGAGGCCATCCTTCAATTGGGA
GAGATTCTTGGTCTTGAGGATGATCTTAATGAGTTGGCAAGCATCAATTGGTTGAATCTG
AATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTCTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTCCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATRTCTCTGTGAAATTGGAGACA
AAGGACATGAGGGTCTTTCTGGCAGAGCTCGAGGGCTGTGGAAAAATTGGTGATGTCCTC
GGCAGCCTCCTCCTGCACCGATTCAGAACTGGTGAGCACTTGATGGAGTCAGAAATAAGT
RCAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCAGGTCAAAGAACACTGTA
ATGTATGAGACAACTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 31)

CDS: 574-7203 complement
Codon Start = 1; Codons 1-2210
Translation=

>LCMV-P52_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGKLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMSDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHSFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNXSVKLET X=I/V
KDMRVFLAELEGCGKIGDVLGSLLLHRFRTGEHLMESEISXVLQELCMDRSVMLTPLSFV X=T/A
PDWFTFRDCRLCFSRSKNTVMYETTGGRFRLKGKSCDDWLAERVAEEID
(SEQ ID NO: 32)

Figure 25 (cont'd)

D. Lymphocytic choriomeningitis virus (LCMV) P91 mutant

Source: 1-3376 Segment = S
Protein: Pre-glycoprotein polyprotein GP complex
Gene: GPC
Gene: 79-1575

>LCMV-P91_GP
ATGGGTCAGATTGTGACAATGTTTGAGGCTTTGCCTCACATCATTGATGAGGTCATCAAC
ATTGTCATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTTAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATGAGCCAGTGTTGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AATACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 33)

CDS: 79-1575
Codon Start = 1; Codons 1-498
*Chain:* *1-498* *Pre-glycoprotein polyprotein GP complex*
*Chain:* *1-58* *Stable signal peptide*
*Chain:* *59-265* *Glycoprotein G1*
*Chain:* *266-498* *Glycoprotein G2*

Translation=

>LCMV-P91_GP
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
MSQCWTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO: 34)

Figure 25 (cont'd)

Source: 1-3376 Segment = S
Protein: Nucleoprotein
Gene: NP
Gene: 1640-3316 complement

>LCMV-P91_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTTGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAGAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAATAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 35)

CDS: 1640-3316 complement
Codon Start = 1; Codons 1-558
Translation=

>LCMV-P91_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 36)

Figure 25 (cont'd)

Source: 1-7235 Segment = L
Protein: RING finger protein Z
Gene: ZP
Gene: 90-362

>LCMV-P91_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 37)

CDS: 90-362
Codon Start = 1; Codons 1-91
Translation=

>LCMV-P91_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE
(SEQ ID NO: 38)

Source: 1-7235 Segment = L

Figure 25 (cont'd)

Protein: RNA-directed RNA polymerase L
Gene: LP
Gene: 574-7203 complement

>LCMV-P91_LP

ATGGATGAAACTATTGCAGATTTGAGAGAGTTGTGTCTAAATTACATAGAACAGGACGAG
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTGAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGCTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTGAA
AAGGTGTTATTGAGTGCAAAATTCAAGTTTATGTTGAATGTGTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCCAGGAAAACAGAAGTAGACAAATTG
GAAGATGATCCGGTAGATGTGTGTTTCGAGGGGGAGGAGGAGACAAGTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGCTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTATTTTGAATCCTTTTCTAGTTTCTTTTCAGGATCTTGTTTAAACAATGATAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTTCTCCAA
AATCTCAAACTGGGTGATGATCAGTACGTGCGTTCTGGAAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAAAGGAAGAGGCCATCCTTCAATTGGGA
GAGATTCTTGGTCTTGAGGATGATCTTAATGAGTTGGCAAGCATCAATTGGTTGAATCTG
AATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTCTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTCCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATATCTCTGTGAAATTGGAGACA
AAGGACATGAGGGTCTTTCTGGCAGAGCTCGAGGGCTGTGGAAAAATTGGTGATGTCCTC
GGCAGCCTCCTCCTGCACCGATTCAGAACTGGTGAGCACTTGATGGAGTCAGAAATAAGT
ACAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCARGTCAAAGAACACTGTA
ATGTATGAGACAACTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 39)

CDS: 574-7203 complement
Codon Start = 1; Codons 1-2210
Translation=

>LCMV-P91_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGKLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREKEEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMSDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHSFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNISVKLET
KDMRVFLAELEGCGKIGDVLGSLLLHRFRTGEHLMESEISTVLQELCMDRSVMLTPLSFV
PDWFTFRDCRLCFSXSKNTVMYETTGGRFRLKGKSCDDWLAERVAEEID X=R/K
(SEQ ID NO: 40)

Figure 25 (cont'd)

E. Lymphocytic choriomeningitis virus (LCMV) P52-1 mutant

Source: 1-3376 Segment = S
Protein: Pre-glycoprotein polyprotein GP complex
Gene: GPC
Gene: 79-1575

>LCMV-P52-1
ATGGGTCAGATTGTGACAATGTTTGAGGCTTTGCCTCACATCATTGATGAGGTCATCAAC
ATTGTCATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTCAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATGAGCCAGTGTTGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AATACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 41)

CDS: 79-1575
Codon Start = 1; Codons 1-498
*Chain:* *1-498* *Pre-glycoprotein polyprotein GP complex*
*Chain:* *1-58* *Stable signal peptide*
*Chain:* *59-265* *Glycoprotein G1*
*Chain:* *266-498* *Glycoprotein G2*

Translation=

>LCMV-P52-1
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
MSQCWTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO: 42)

Figure 25 (cont'd)

Source: 1-3376 Segment = S
Protein: Nucleoprotein
Gene: NP
Gene: 1640-3316 complement

>LCMV-P52-1_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTTGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAGAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAATAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 43)

CDS: 1640-3316 complement
Codon Start = 1; Codons 1-558
Translation=

>LCMV-P52-1_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 44)

Figure 25 (cont'd)

Source: 1-7235 Segment = L
Protein: RING finger protein Z
Gene: ZP
Gene: 90-362

>LCMV-P52-1_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 45)

CDS: 90-362
Codon Start = 1; Codons 1-91
Translation=

>LCMV-P52-1_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE
(SEQ ID NO: 46)

Figure 25 (cont'd)

Source: 1-7235 Segment = L
Protein: RNA-directed RNA polymerase L
Gene: LP
Gene: 574-7203 complement >LCMV-P52-1_LP
ATGGATGAAACTATTGCAGATTTGAGAGAGTTGTGTCTAAATTACATAGAACAGGACGAG
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAGACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTGAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGTTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTCAA
AAGGTGTTATTGAGTGCAAAATTCAAGTTTATGTTGAATGTGTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCTAGGAAAACAGAAGTAGACAAATTG
GAAGATGATCCGGTAGATGTGTGTTTCGAGGGGGAGGAGGAGACAACTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGTTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTATTTTGAATCCTTTTCTAGTTTCTTTTCAGGATCTTGTTTAAACAATGACAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTTCTCCAA
AATCTCAAACTGGGTGATGATCAGTACGTGCGTTCTGGGAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAATGAAAGAGGCCATCCTTCAATTGGGA
GAGATTCTTGGTCTTGAGGATGATCTCAATGAGTTGGCAAGCATCAATTGGTTGAATCTG
AATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTCTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTTCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATATCTCTGTGAAATTGGAGACA
AAGGACATGAGGGTCTTTCTGGCAGAGCTCGAGGGCTGTGGAGAAATTGGTGATGTCCTC
GGCAGCCTCCTCCTGCACCGATTCAGAACTGGTGAGCACTTGATGGAGTCAGAAATAAGT
RCAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCAGGTCAAAGAACACTGTA
ATGTATGAGACAGCTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 47)

CDS: 574-7203 complement
Codon Start = 1; Codons 1-2210
Translation=

>LCMV-P52-1_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGRLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREMKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMSDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHFFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNISVKLET
KDMRVFLAELEGCGEIGDVLGSLLLHRFRTGEHLMESEISTVLQELCMDRSVMLTPLSFV
PDWFTFRDCRLCFSRSKNTVMYETAGGRFRLKGKSCDDWLAERVAEEID
(SEQ ID NO: 48)

Figure 25 (cont'd)

F. Lymphocytic choriomeningitis virus (LCMV) p52-1.3

```
Source:     1-3376  Segment = S
Protein:    Pre-glycoprotein polyprotein GP complex
Gene:       GPC
Gene:       79-1575
```

```
>LCMV-p52-1.3_GP
ATGGGTCAGATTGTGACAATGTTTGAGGCTTTGCCTCACATCATTGATGAGGTCATCAAC
ATTGTCATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTTAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATAAGCCAGTGTTGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AACACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 49)
```

```
CDS:        79-1575
            Codon Start = 1; Codons 1-498
Chain:      1-498       Pre-glycoprotein polyprotein GP complex
Chain:      1-58        Stable signal peptide
Chain:      59-265      Glycoprotein G1
Chain:      266-498     Glycoprotein G2
```

Translation=

```
>LCMV-p52-1.3_GP
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
ISQCWTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO: 50)
```

Figure 25 (cont'd)

Source: 1-3376 Segment = S
Protein: Nucleoprotein
Gene: NP
Gene: 1640-3316 complement

>LCMV-p52-1.3_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTCGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAGAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAATAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 51)

CDS: 1640-3316 complement
Codon Start = 1; Codons 1-558
Translation=

>LCMV-p52-1.3_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 52)

Figure 25 (cont'd)

Source: 1-7235 Segment = L
Protein: RING finger protein Z
Gene: ZP
Gene: 90-362

>LCMV-p52-1.3_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 53)

CDS: 90-362
Codon Start = 1; Codons 1-91
Translation=

>LCMV-p52-1.3_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE
(SEQ ID NO: 54)

Figure 25 (cont'd)

Source: 1-7235 Segment = L
Protein: RNA-directed RNA polymerase L
Gene: LP
Gene: 574-7203 complement >LCMV-p52-1.3_LP
ATGGATGAAACTATTGCAGATTTGAGAGAGTTGTGTCTAAATTACATAGAACAGGACGAG
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTAAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGTTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTGAA
AAGGTGTTATTGAGTGCAAAATTCAAGTTTATGTTGAATGTGTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCCAGGAAAACAGAAGTAGACAAATTA
GAAGATGATCCGGTAGATGTGTGTTTCGAGGGGGAGGAGGAGACAAGTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGCTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTACTTTGAATCCTTTTCTAGTTTCTTTTCAGGATCTTGTTTAAACAATGACAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTTCTCCAA
AATCTCAAACTGGGTGATGATCAGTACGTGCGTTCTGGAAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAAAGAAAGAGGCCATCCTTCAATTGGGA
GAGATTCTTGGTCTTGAGGATGATCTTAATGAGTTGGCAAGCATCAATTGGTTGAATCTG
AATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTCTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTCCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATATCTCTGTGAAATTGGAGACA
AAGGACATGAGGGTCTTTCTGGCAGAGCTCGAGGGCTGTGGAAAAATTGGTGATGTCCTC
GGCAGCCTCCTCCTGCACCGATTCAGAACTGGTGAGCACTTGATGGAGTCAGAAATAAGT
ACAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCAGGTCAAAGAACACTGTA
ATGTATGAGACAACTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 55)

CDS: 574-7203 complement
Codon Start = 1; Codons 1-2210
Translation=

>LCMV-p52-1.3_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGKLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMSDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHSFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNISVKLET
KDMRVFLAELEGCGKIGDVLGSLLLHRFRTGEHLMESEISTVLQELCMDRSVMLTPLSFV
PDWFTFRDCRLCFSRSKNTVMYETTGGRFRLKGKSCDDWLAERVAEEID
(SEQ ID NO: 56)

Figure 25 (cont'd)

G. Lymphocytic choriomeningitis virus (LCMV) P52-2.1

Source: 1-3376 Segment = S
Protein: Pre-glycoprotein polyprotein GP complex
Gene: GPC
Gene: 79-1575

>LCMV-p52-2.1_GP
ATGGGTCAGATTGTGACAATGTTTGAGGCTTTGCCTCACATCATTGATGAGGTCATCAAC
ATTGTTATTATTGTGCTCATTATAATCACGAGCATCAAAGCTGTGTACAATTTCGCCACC
TGTGGGATATTAGCACTGGTCAGCTTCCTTTTTTTGGCTGGTAGGTCCTGTGGCATGTAC
GGCCTTAATGGTCCCGACATCTATAAAGGGGTTTACCAGTTCAAATCAGTGGAGTTTGAT
ATGTCTCACTTAAATCTGACGATGCCCAATGCGTGCTCAGCCAACAACTCTCATCACTAC
ATCAGTATGGGAAGCTCTGGACTGGAGCTAACTTTCACTAACGACTCCATCCTTAATCAC
AATTTTTGCAACTTAACCTCCGCTTTCAACAAAAAGACTTTTGACCATACACTCATGAGT
ATAGTCTCGAGTCTGCACCTCAGTATTAGAGGGAATTCCAACCACAAAGCAGTGTCTTGT
GATTTTAACAATGGCATCACCATTCAATACAACTTGTCATTTTCGGACCCACAGAGCGCT
ATGAGCCAGTGTAGGACTTTCAGAGGTAGAGTCTTGGACATGTTTAGAACTGCCTTTGGA
GGAAAATACATGAGAAGTGGCTGGGGCTGGGCAGGTTCAGATGGCAAGACCACTTGGTGC
AGCCAAACAAGCTATCAGTACCTAATCATACAAAACAGGACTTGGGAAAACCACTGTAGA
TATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAAT
CCAGGTGGTTATTGCCTGACCAAATGGATGATCCTTGCTGCAGAGCTCAAATGTTTTGGG
AATACAGCTGTTGCAAAATGTAATGTCAATCATGATGAAGAGTTCTGTGACATGCTACGA
CTAATTGATTACAACAAGGCCGCCCTGAGTAAGTTCAAGCAAGATGTAGAGTCTGCCTTG
CATGTATTCAAAACAACAGTAAATTCTCTGATTTCCGATCAGCTGTTGATGAGGAATCAT
CTAAGAGATCTAATGGGGGTACCATACTGTAATTACTCAAAGTTCTGGTATCTGGAACAT
GCTAAGACTGGTGAGACTAGTGTACCCAAGTGCTGGCTTGTCACTAATGGCTCCTACTTG
AATGAGACCCACTTTAGTGATCAAATCGAACAAGAAGCAGATAACATGATCACAGAGATG
TTGAGGAAGGACTACATAAAAAGACAAGGGAGTACTCCTTTAGCCTTAATGGATCTTTTG
ATGTTTTCAACATCAGCATATCTAATCAGCATCTTTCTGCATCTTGTGAAGATACCAACA
CATAGACACATAAAGGGCGGTTCATGTCCAAAGCCACACCGCTTGACCAACAAGGGGATC
TGTAGTTGTGGTGCATTCAAGGTGCCTGGTGTAAAAACTATCTGGAAAAGACGCTGA
(SEQ ID NO: 57)

CDS: 79-1575
Codon Start = 1; Codons 1-498
*Chain:* *1-498* *Pre-glycoprotein polyprotein GP complex*
*Chain:* *1-58* *Stable signal peptide*
*Chain:* *59-265* *Glycoprotein G1*
*Chain:* *266-498* *Glycoprotein G2*

Translation=
>LCMV-p52-2.1_GP
MGQIVTMFEALPHIIDEVINIVIIVLIIITSIKAVYNFATCGILALVSFLFLAGRSCGMY
GLNGPDIYKGVYQFKSVEFDMSHLNLTMPNACSANNSHHYISMGSSGLELTFTNDSILNH
NFCNLTSAFNKKTFDHTLMSIVSSLHLSIRGNSNHKAVSCDFNNGITIQYNLSFSDPQSA
MSQCRTFRGRVLDMFRTAFGGKYMRSGWGWAGSDGKTTWCSQTSYQYLIIQNRTWENHCR
YAGPFGMSRILFAQEKTKFLTRRLAGTFTWTLSDSSGVENPGGYCLTKWMILAAELKCFG
NTAVAKCNVNHDEEFCDMLRLIDYNKAALSKFKQDVESALHVFKTTVNSLISDQLLMRNH
LRDLMGVPYCNYSKFWYLEHAKTGETSVPKCWLVTNGSYLNETHFSDQIEQEADNMITEM
LRKDYIKRQGSTPLALMDLLMFSTSAYLISIFLHLVKIPTHRHIKGGSCPKPHRLTNKGI
CSCGAFKVPGVKTIWKRR
(SEQ ID NO: 58)

Figure 25 (cont'd)

```
Source:     1-3376  Segment = S
Protein:    Nucleoprotein
Gene:       NP
Gene:       1640-3316  complement
```

>LCMV-p52-2.1_NP
ATGTCTTTGTCCAAAGAAGTCAAAAGCTTTCAGTGGACACAGGCGTTGAGGAGGGAGTTG
CAGAGTTTTACATCAGATGTAAAGGCTGCCGTCATCAAGGACGCAACCAGTCTTCTAAAT
GGGTTGGACTTTTCTGAAGTCAGCAACGTTCAGAGGATCATGAGAAAGGAAAGGAGGGAT
GATAAAGACTTGCAGAGACTCAGGAGTCTTAACCAGACTGTGCATTCTCTTGTTGATCTG
AAGTCTACATCAAAGAAAAATGTTCTGAAAGTGGGAAGACTTAGTGCAGAGGAATTGATG
ACCCTTGCAGCTGATCTTGAGAAGCTGAAGGCCAAAATTATGAGAACTGAGAGGCCTCAA
GCTTCTGGAGTCTACATGGGAAATTTGACAGCACAACAACTTGATCAAAGATCCCAAATA
CTGCAAATGGTTGGGATGAGAAGACCTCAGCAGGGTGCAAGTGGTGTAGTAAGGGTTTGG
GATGTGAAGGACTCATCACTTCTGAACAATCAGTTCGGCACAATGCCAAGCCTGACAATG
GCTTGCATGGCAAAACAGTCACAGACCCCACTCAATGATGTTGTGCAGGCACTCACAGAC
CTTGGCTTACTTTACACAGTCAAATACCCGAATCTCAGTGATCTTGAAAGGCTAAAGGAT
AAACACCCAGTTCTGGGGGTCATTACTGAACAGCAATCTAGTATCAATATCTCTGGTTAT
AATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGG
GCCAAAAAGAAACTCAACATGTTTGTCTCAGATCAAGTTGGAGATAGAAATCCCTATGAA
AACATCCTTTATAAAGTCTGTCTTTCAGGTGAAGGATGGCCATACATAGCCTGTAGAACG
TCAGTTGTGGGGAGAGCATGGGAGAACACAACAATTGATCTCACAAATGAAAAACTTGTT
GCCAACTCATCTAGGCCAGTGCCTGGAGCAGCAGGCCCACCTCAGGTGGGCTTGAGTTAC
AGTCAGACAATGCTGTTGAAAGACTTGATGGGAGGGATTGATCCCAATGCTCCCACATGG
ATTGACATTGAGGGCAGGTTCAATGATCCAGTGGAGATAGCAATATTCCAACCACAAAAT
GGGCAATTCATACATTTTTACAGGGAACCTACGGACCAGAAGCAATTCAAGCAGGACTCA
AAGTATTCACACGGCATGGATCTTGCTGATCTCTTCAATGCACAGCCTGGGCTGACCTCA
TCAGTTATAGGTGCTCTCCCACAAGGGATGGTTTTGAGCTGTCAAGGTTCTGATGACATC
AGAAAGCTTCTGGACTCACAAAATAGAAGGGACATAAAACTCATTGATGTTGAGATGACC
AAGGAGGCCTCAAGAGAATATGAAGATAAAGTGTGGGACAAATATGGCTGGCTATGCAAA
ATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTT
CACAACATCCTGCCACATGATTTAATCTTCAGAGGACCCAATGTTGTGACACTCTAA
(SEQ ID NO: 59)

CDS: 1640-3316 complement
Codon Start = 1; Codons 1-558
Translation=

>LCMV-p52-2.1_NP
MSLSKEVKSFQWTQALRRELQSFTSDVKAAVIKDATSLLNGLDFSEVSNVQRIMRKERRD
DKDLQRLRSLNQTVHSLVDLKSTSKKNVLKVGRLSAEELMTLAADLEKLKAKIMRTERPQ
ASGVYMGNLTAQQLDQRSQILQMVGMRRPQQGASGVVRVWDVKDSSLLNNQFGTMPSLTM
ACMAKQSQTPLNDVVQALTDLGLLYTVKYPNLSDLERLKDKHPVLGVITEQQSSINISGY
NFSLGAAVKAGAALLDGGNMLESILIKPSNSEDLLKAVLGAKKKLNMFVSDQVGDRNPYE
NILYKVCLSGEGWPYIACRTSVVGRAWENTTIDLTNEKLVANSSRPVPGAAGPPQVGLSY
SQTMLLKDLMGGIDPNAPTWIDIEGRFNDPVEIAIFQPQNGQFIHFYREPTDQKQFKQDS
KYSHGMDLADLFNAQPGLTSSVIGALPQGMVLSCQGSDDIRKLLDSQNRRDIKLIDVEMT
KEASREYEDKVWDKYGWLCKMHTGVVRDKKKKEITPHCALMDCIIFESASKARLPDLKTV
HNILPHDLIFRGPNVVTL
(SEQ ID NO: 60)

Figure 25 (cont'd)

Source: 1-7235 Segment = L
Protein: RING finger protein Z
Gene: ZP
Gene: 90-362

>LCMV-p52-2.1_ZP
ATGGGCCAAGGCAAGTCCAAAGAAGAAAGGGACACCAGCAATACAGGCAGAGCAGAGCTT
TTGCCAGACACCACCTATCTTGGTCCTCTAAATTGTAAATCATGTTGGCAGAAATTTGAC
AGCTTGGTTAGATGCCATGACCACTATCTTTGCAGACACTGTCTGAATCTCCTGCTGTCA
GTTTCCGACAGATGTCCTCTCTGTAAGTATCCACTGCCAACCAAACTGAAGGTGTCAACA
GTCCCAAGCTCCCCACCTCCCTATGAGGAGTGA
(SEQ ID NO: 61)

CDS: 90-362
Codon Start = 1; Codons 1-91
Translation=

>LCMV-p52-2.1_ZP
MGQGKSKEERDTSNTGRAELLPDTTYLGPLNCKSCWQKFDSLVRCHDHYLCRHCLNLLLS
VSDRCPLCKYPLPTKLKVSTVPSSPPPYEE
(SEQ ID NO: 62)

Figure 25 (cont'd)

Source: 1-7235 Segment = L
Protein: RNA-directed RNA polymerase L
Gene: LP
Gene: 574-7203 complement >LCMV-p52-2.1_LP
ATGGATGAAACTATTGCAGATTTGAGAGAGTTGTGTCTAAATTACATAGAACAGGACGAA
AGGCTGTCAAGGCAAAAACTCAACTTCCTGGGACAAAGAGAACCCAGAATGGTGCTAATT
GAGGGACTCAAATTGTTATCACGCTGTATAGAGATAGACAGTGCAGACAAAAGTGGTTGC
ATACACAACCACGATGACAAATCTGTTGAAACAATCCTAATAGACTCTGGGATTGTGTGT
CCAGGACTGCCACTCATCATCCCTGATGGTTATAAGTTGATTGACAATTCCCTTATTCTT
CTTGAATGTTTTGTTAGAAGCACACCAGCTAGTTTTGAAAAGAAGTTCATTGAGGACACC
AACAAACTAGCATGCATCAAAGAAGATCTTGCTGTTGCAGGCATCACACTGGTTCCAATA
GTGGATGGTCGTTGTGATTATGATAACAGTTTCATGCCAGAATGGGTGAATTTTAAGTTC
AGAGACCTCCTATTTAAACTCCTGGAGTATTCTAGTCAAGATGAGAAAGTTTTTGAGGAG
TCTGAATACTTCAGGCTCTGTGAGTCTCTTAAGACCACTGTTGACAAACGTTCCGGCATG
GACTCAATGAAAATTTTGAAAGACGCAAGATCATTTCATAACGATGAGATTATGAAAATG
TGCCACGATGGTGTCAACCCCAACATGAGTTGCGATGATGTGGTCTTTGGCATAAATTCC
TTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAAT
GATGACATATTAATGTTGAGCAAAGAGGCAGTTGAATCCTGCCCCTTAATGAGGTTCATT
ACAGCAGAGACCCATGGGCATGAGAGAGGAAGCGATGCTAACACTGAGTATGAAAGGCTA
CTCTCTATGTTGAACAAGGTGAAAAGTTTAAAATTATTAAACACTAGAAGGAGACAGCTG
CTGAACTTAGATGTCTTATGTCTTTCTTCACTTATTAAGCAGTCAATTTCCAAAGGGTTG
GAAAATGATAAACATTGGGTTGGTTGTTGCTACAGTAGTGTGAATGATAGGCTTGTGAGC
CTTCAAAGTACCAAAGAAGAATTCATGAGACTTTTGAAGAACAGAAGAAAATCAAGAGTG
CACAAAAAGGCATCTCTTGATGAGCTTTTTAGGGTATCCATAAATGAGTTCATAGCAAAA
ATCCAGAAATGCCTATCAACAGTGGGACTTAGTTTTGAGCATTACGGACTATCAGAATGC
CTCGTGCAAGAATGCCATATACCATTTGCTGAATTTGAGAACTTTATGAGAGCCGGGACT
CATCCTGTAATGCATTACACAAAATTTGAAGATTACACTTTCCAGCCTAACATAGAGCAA
TTGAGGGGTTTACAGAGTTTGAGAAAACTGTCATCTGTTTGTTTGGCTCTAACAAACAGC
ATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCAT
CTACTATATCAGAAAACTGGAGAATCATCGAGGTGTTATTCCATACAAGGTCCGGATGGT
CACTTGATTTCCTTTTACGCAGATCCAAAAAGGTTCTTTTTACCAATTTTTTCAGATGAG
GTGTTGCACAACATGATAGACACAATGATTTCATGGATTAGGTCATGCCCTGACTTAAAA
GATTCTCTTATTGACATTGAGACTGCACTAAGGACATTGATCCTACTGATGCTCACCAAC
CCAACAAAGAGAAATCAAAAGCAGGTTCAAAATATTAGGTATTTAGTGATGGCCATCGTC
TCAGACTTTTCATCGACCTCATTAATGGATAAGTTGAAGGAGGATCTAATCACACCTGCC
GAGAAAGTGGTGTACAGGCTGCTTCGGTTTTTGATTAGGACAATTTTTGGTACTGGTGAA
AAGGTGTTATTGAGTGCAAAATTTAAGTTTATGTTGAATGTGTCATACCTGTGTCATTTG
ATCACAAAGGAGACCCCTGATAGATTGACAGATCAGATAAAATGTTTTGAAAAGTTCTTT
GAGCCCAAGAGTGAGTTTGGTTTCTTTGTCAACCCTAAGGAAACAATCACACCCGAAGAG
GAATGTGTTTTTTATGAACAAATGAAGAAGTTCACCGGTAAAGATATTGATTGTCAGCAT
TCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGA
TGTGCGACAGCATTAGATCTCGCAAGCAACAAAAGTGTGGTTGTCAATAAACATCTGAAT
GGAGAACGGCTTTTGGAGTATGATTTTAACAAATTGCTTGTTAGTGCTGTGAGCCAAATT
ACAGAGGGCTTCATGAGGAAACAAAAGTATAAGCTGAGACACTCAGATTACGAATATAAG
GTCTCAAAGCTTGTCTCTAGATTAGTCATCGGTTCCAGGAAAACAGAAGTAGACAAATTG
GAAGATGATCCGGTAGATGTGTGTTTCGAGGGGGAGGAGGAGACAAGTTTTTTCAGGAGT
TTAGAAGATAAGGTCAGCTCCACAATAACACGGTATAATAGAGGCACTAGGCTTAATGAA
GGGCAAGGGGAGGGAGAATTCAAGAACACAAAAGGACTACACCACCTTCAGATTATTTTG
TCAGGTAAAAGAGCTTATCTGAGGAAAGTCATTTTATCAGAAATTTCATTTCATCTAGTA
GAGGACTTTGATCCATCCTGTCTCACCAATGACGACATGAGGTTTATTTGTGAGGCTGTT
GAAGGTTCAACAGAACTGTCACCATTGTATTTTACATCAGCTGTCAAAGAACAATGTGGT
CTGGATGAGATGGCAAGAAACCTCTGTAGAAAGTTCTTCTCAGAGGGTGATTGGTTCTCA
TGTATGAAGATGATCTTGTTACAGATGAATGCAAATGCGTATTCAGGGAAGTACAGACAC

Figure 25 (cont'd)

ATGCAGAGGCAGAGCTTAAATTTTAAATTTGACTGGGACAAATTGGAAGAAGATGTAAGA
ATTAGTGAAAGGGAAAGCAATTCTGAATCTCTAAGTAAGGCCCTTTCATTGACAAAATGC
ATGAGTGCTGCTCTAAAGAATCTGTGTTTTTACTCAGAAGAATCACCAACATCATACACT
TCAGTTGGCCCTGACTCTGGGAGACTAAAATTTGCATTGTCATACAAAGAGCAGGTTGGG
GGAAATAGAGAGCTTTACATTGGGGATTTGAGGACAAAAATGTTCACAAGATTGGTAGAA
GATTATTTTGAATCCTTTTCTAGTTTCTTTTCAGGATCTTGTTTAAACAATGACAAAGAG
TTTGAAAATGCAATCTTGTCAATGACTATCAATGTGAGAGAAGGGTTGTTAAACTACAGC
ATGGATCACAGCAAATGGGGACCAATGATGTGCCCATTCCTATTCTTAATGCTTCTCCAA
AATCTCAAACTGGGTGATGATCAGTACGTGCGTTCTGGAAAAGATCATGTTAGCACCTTG
TTGACTTGGCATATGCATAAACTTGTTGAAGTCCCTTTCCCTGTTGTGAATGCAATGATG
AAATCATATGTTAAATCAAAACTCAAGCTTCTCAAAGGGTCAGGAACGACTGTTACGGAG
AGAATCTTTAGAGAGTATTTTGAAATGGGGGTGGTGCCATCTCACATATCTAGTCTCATT
GACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGT
GATGATCAGATCACTTTATTTGACAAGAGATTGAGTGACTTAGTTGATAGTGACCCAGAA
GAAGTCCTTGTCTTGCTGGAATTCCACTCTCACTTAAGTGGTTTGTTGAACAAGTTCATC
AGTCCAAAAAGTGTGGTTGGGCGGTTTGCAGCGGAATTCAAATCCAGATTTTATGTGTGG
GGGGAGGAGGTCCCTCTCCTCACGAAATTTGTGTCTGCGGCACTACACAATGTTAAGTGT
AAAGAACCGCATCAACTTTGTGAGACAATAGATACGATTGCTGATCAAGCTATAGCAAAT
GGAGTTCCAGTTTTTTTAGTAAACTGTATCCAGAGGAGGACACTGGATCTCTTGAAATAT
GCTAATTTCCCTTTAGATCCATTCTTGTTAAACACTCACACTGATGTAAAGGATTGGTTA
GATGGTTCTAGAGGTTATAGAATCCAAAGACTCATTGAAGAATTGTGTCCCAGTGAAACA
AAGATCATGAGAAAACTTGTAAGAAGACTACATCACAAACTCAAGAACGGTGAATGTAAC
GAGGAATTTTTTCTAGACCTCTTCAACAGGGAAAAGAAAGAGGCCATCCTTCAATTGGGA
GAGATTCTTGGTCTTGAGGATGATCTTAATGAGTTGGCAAGCATCAATTGGTTGAATCTG
AATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGT
AAGTTCACAAGAGGTGCACAGAAGCTGTTGTCAGAGGCAATCAACAAATCAGCTTTTCAG
AGTTGTGTCTCATCCGGCTTTATAGGTCTCTGTAAGACTTTAGGAAGTAGGTGTGTGAGA
AATAAAAACAGGGAAAATATGTATATCAGAAAGGTGCTTGAAGATCTGACCATGGATGAA
CATGTCACAAGGGTTCACAAACAAGATGGTGTGATGTTGTACATTTGCGACAAGCAGAGA
CACCCAGAGGCTCACCGTGACCACATCAACCTTTTGAGGCCCCTTCTCTGGGACTACATT
TGCATCTCATTGAGCAACTCTTTTGAGCTGGGTGTTTGGGTTTTAGCAGAACCTGTGAAA
GGAAAGAACGAGAGTAATTCGGCTGTTAGGCACTTAAATCCATGTGATTATGTAGCAAGA
AAACCTGAGAGTTCGAGACTACTAGAGGATAAAGTGAGTTTGAATCATGTAATTCAATCT
GTGAGGCGACTGTACCCCAAAATCTTTGAGGATCAGTTGCTCCCATTCATGTCTGATGTG
AGCTCAAAAAATATGAGATGGAGTCCCAGGATTAAATTCCTTGACCTTTGTGTGCTGATT
GACATCAACTCAGAGTCTTTGTCACTCATTTCTCATGTTGTCAAATGGAAGAGGGACGAA
CATTACACTGTGCTGTTTTCTGATCTCGTCAACTCTCACCAACGGTCAGACTCAAGTTTA
GTTGATGAATTTGTTGTCAGCACAAGGGATGTCTGCAAGAACTTTTTGAAGCAAGTGTAT
TTCGAATCATTTGTACGAGAGTTTGTTGCAACAGCTAGGACCTTAGGTAACTTTTCATGG
TTCCCCCATAAGGACATGATGCCATCTGAAGATGGCGCTGAAGCACTGGGACCCTTCCAA
TCATTTATTTTGAAAGTGGTGAACAAGAAAATAGAGAGGCCCATGTTTAGGAATGACTTG
CAGTTTGGTTTTGGTTGGTTCTCTTATCGTGTGGGGGATGTTGTGTGTAATGCCGCTATG
TTAATTAAGCAGGGTTTGACAGATCCAAAAGCATTTAAATCTTTAAGAGATTTGTGGGAT
TACATGCTCAGCAGCACAGAGGGGATATTGGAGTTCTCAATCACAGTGGATTTCACACAC
AACCAGAACAACACTGACTGCTTGAGGAAATTTTCATTGATCTTTGTGGTTAAATGCCAA
TTACAGAGTCCAGGTGTAGCTGATTACTTATCGTGCTCTCATTTCTTCAAAGGTGAGGTT
GACAGGAGATTATTAGATGAGTGTCTCAATCTGTTGAGGACAGACCCCATCTTTAAAGCG
AATGATGGAGTCTTTGACATTAGGTCTGAAGAGTTTGAAGATTACATGGAAGACCCTTTG
ACACTTGGTGATTCACTAGAACTTGAACTAATAGGTTCTAGAAGGATTCTGAATGAGATC
AAATCTACTGACTTTGAGAGGATAGGGCCTGAGTGGGAACCTGTGCCTCTGACCATAAGG
AAGGGTGCCCTCTTTGAGGGGAGGAACTTTGTTCAGAATATCTCTGTGAAATTGGAGACA
AAGGACATGAGGGTCTTTCTGGCAGAGCTCGAGGGCTGTGGAGAAATTGGTGATGTCCTC
GGCAGCCTCCTCCTGCACCGATTCAGAACTGGTGAGCACTTGATGGAGTCAGAAATAAGT
ACAGTTCTTCAGGAGCTCTGCATGGACAGATCCGTCATGCTGACACCATTATCTTTTGTG
CCAGATTGGTTCACCTTCAGAGATTGTAGGCTCTGCTTCAGCAGGTCAAAGAACACTGTA
ATGTATGAGACAACTGGGGGCAGGTTCAGACTCAAGGGGAAATCCTGTGACGATTGGCTG

Figure 25 (cont'd)

GCGGAGCGGGTGGCCGAGGAGATCGACTAG
(SEQ ID NO: 63)

CDS: 574-7203 complement
Codon Start = 1; Codons 1-2210
Translation=

>LCMV-p52-2.1_LP
MDETIADLRELCLNYIEQDERLSRQKLNFLGQREPRMVLIEGLKLLSRCIEIDSADKSGC
IHNHDDKSVETILIDSGIVCPGLPLIIPDGYKLIDNSLILLECFVRSTPASFEKKFIEDT
NKLACIKEDLAVAGITLVPIVDGRCDYDNSFMPEWVNFKFRDLLFKLLEYSSQDEKVFEE
SEYFRLCESLKTTVDKRSGMDSMKILKDARSFHNDEIMKMCHDGVNPNMSCDDVVFGINS
FFGRFRRDLLNGKLKRNFQKVSPGGLIKEFSELYETLTDNDDILMLSKEAVESCPLMRFI
TAETHGHERGSDANTEYERLLSMLNKVKSLKLLNTRRRQLLNLDVLCLSSLIKQSISKGL
ENDKHWVGCCYSSVNDRLVSLQSTKEEFMRLLKNRRKSRVHKKASLDELFRVSINEFIAK
IQKCLSTVGLSFEHYGLSECLVQECHIPFAEFENFMRAGTHPVMHYTKFEDYTFQPNIEQ
LRGLQSLRKLSSVCLALTNSMKTSSVARLRQNQLGSVRYQVVECKEVFCQIIKLDSEEYH
LLYQKTGESSRCYSIQGPDGHLISFYADPKRFFLPIFSDEVLHNMIDTMISWIRSCPDLK
DSLIDIETALRTLILLMLTNPTKRNQKQVQNIRYLVMAIVSDFSSTSLMDKLKEDLITPA
EKVVYRLLRFLIRTIFGTGEKVLLSAKFKFMLNVSYLCHLITKETPDRLTDQIKCFEKFF
EPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQI
TEGFMRKQKYKLRHSDYEYKVSKLVSRLVIGSRKTEVDKLEDDPVDVCFEGEEETSFFRS
LEDKVSSTITRYNRGTRLNEGQGEGEFKNTKGLHHLQIILSGKRAYLRKVILSEISFHLV
EDFDPSCLTNDDMRFICEAVEGSTELSPLYFTSAVKEQCGLDEMARNLCRKFFSEGDWFS
CMKMILLQMNANAYSGKYRHMQRQSLNFKFDWDKLEEDVRISERESNSESLSKALSLTKC
MSAALKNLCFYSEESPTSYTSVGPDSGRLKFALSYKEQVGGNRELYIGDLRTKMFTRLVE
DYFESFSSFFSGSCLNNDKEFENAILSMTINVREGLLNYSMDHSKWGPMMCPFLFLMLLQ
NLKLGDDQYVRSGKDHVSTLLTWHMHKLVEVPFPVVNAMMKSYVKSKLKLLKGSGTTVTE
RIFREYFEMGVVPSHISSLIDMGQGILHNASDFYGLISERFINYCIGVIFGERPEAYTSS
DDQITLFDKRLSDLVDSDPEEVLVLLEFHSHLSGLLNKFISPKSVVGRFAAEFKSRFYVW
GEEVPLLTKFVSAALHNVKCKEPHQLCETIDTIADQAIANGVPVFLVNCIQRRTLDLLKY
ANFPLDPFLLNTHTDVKDWLDGSRGYRIQRLIEELCPSETKIMRKLVRRLHHKLKNGECN
EEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVR
NKNRENMYIRKVLEDLTMDEHVTRVHKQDGVMLYICDKQRHPEAHRDHINLLRPLLWDYI
CISLSNSFELGVWVLAEPVKGKNESNSAVRHLNPCDYVARKPESSRLLEDKVSLNHVIQS
VRRLYPKIFEDQLLPFMSDVSSKNMRWSPRIKFLDLCVLIDINSESLSLISHVVKWKRDE
HYTVLFSDLVNSHQRSDSSLVDEFVVSTRDVCKNFLKQVYFESFVREFVATARTLGNFSW
FPHKDMMPSEDGAEALGPFQSFILKVVNKKIERPMFRNDLQFGFGWFSYRVGDVVCNAAM
LIKQGLTDPKAFKSLRDLWDYMLSSTEGILEFSITVDFTHNQNNTDCLRKFSLIFVVKCQ
LQSPGVADYLSCSHFFKGEVDRRLLDECLNLLRTDPIFKANDGVFDIRSEEFEDYMEDPL
TLGDSLELELIGSRRILNEIKSTDFERIGPEWEPVPLTIRKGALFEGRNFVQNISVKLET
KDMRVFLAELEGCGEIGDVLGSLLLHRFRTGEHLMESEISTVLQELCMDRSVMLTPLSFV
PDWFTFRDCRLCFSRSKNTVMYETTGGRFRLKGKSCDDWLAERVAEEID
(SEQ ID NO: 64)

Source: 1-3376 Segment = S
Protein: Pre-glycoprotein polyprotein GP complex
Gene: GPC
Gene: 79-1575
Sequence Alignment: Nucleotide

```
LCMV-WE_GP          ATGGGTCAGATTGTGACAATGTTTGAGGCTTTGCCTCACATCATTGATGAGGTCATCAAC    60
LCMV-P42_GP         ATGGGTCAGATTGTGACAATGTTTGAGGCTTTGCCTCACATCATTGATGAGGTCATCAAC    60
LCMV-P52_GP         ATGGGTCAGATTGTGACAATGTTTGAGGCTTTGCCTCACATCATTGATGAGGTCATCAAC    60
LCMV-P91_GP         ATGGGTCAGATTGTGACAATGTTTGAGGCTTTGCCTCACATCATTGATGAGGTCATCAAC    60
LCMV-P52-1          ATGGGTCAGATTGTGACAATGTTTGAGGCTTTGCCTCACATCATTGATGAGGTCATCAAC    60
LCMV-P52-1.3_GP     ATGGGTCAGATTGTGACAATGTTTGAGGCTTTGCCTCACATCATTGATGAGGTCATCAAC    60
LCMV-P52-2.1_GP     ATGGGTCAGATTGTGACAATGTTTGAGGCTTTGCCTCACATCATTGATGAGGTCATCAAC    60
                    ************************************************************

LCMV-WE_GP          ATTGTCATTATTGTGCTCATTATAATCACGAGCATCAAAGCTGTGTACAATTTCGCCACC    120
LCMV-P42_GP         ATTGTCATTATTGTGCTCATTATAATCACGAGCATCAAAGCTGTGTACAATTTCGCCACC    120
LCMV-P52_GP         ATTGTCATTATTGTGCTCATTATAATCACGAGCATCAAAGCTGTGTACAATTTCGCCACC    120
LCMV-P91_GP         ATTGTCATTATTGTGCTCATTATAATCACGAGCATCAAAGCTGTGTACAATTTCGCCACC    120
LCMV-P52-1          ATTGTCATTATTGTGCTCATTATAATCACGAGCATCAAAGCTGTGTACAATTTCGCCACC    120
LCMV-P52-1.3_GP     ATTGTCATTATTGTGCTCATTATAATCACGAGCATCAAAGCTGTGTACAATTTCGCCACC    120
LCMV-P52-2.1_GP     ATTGTTATTATTGTGCTCATTATAATCACGAGCATCAAAGCTGTGTACAATTTCGCCACC    120
                    ***** ******************************************************

LCMV-WE_GP          TGTGGGATATTAGCACTGGTCAGCTTCCTTTTTTTGGCTGGTAGGTCCTGTGGCATGTAC    180
LCMV-P42_GP         TGTGGGATATTAGCACTGGTCAGCTTCCTTTTTTTGGCTGGTAGGTCCTGTGGCATGTAC    180
LCMV-P52_GP         TGTGGGATATTAGCACTGGTCAGCTTCCTTTTTTTGGCTGGTAGGTCCTGTGGCATGTAC    180
LCMV-P91_GP         TGTGGGATATTAGCACTGGTCAGCTTCCTTTTTTTGGCTGGTAGGTCCTGTGGCATGTAC    180
LCMV-P52-1          TGTGGGATATTAGCACTGGTCAGCTTCCTTTTTTTGGCTGGTAGGTCCTGTGGCATGTAC    180
LCMV-P52-1.3_GP     TGTGGGATATTAGCACTGGTCAGCTTCCTTTTTTTGGCTGGTAGGTCCTGTGGCATGTAC    180
LCMV-P52-2.1_GP     TGTGGGATATTAGCACTGGTCAGCTTCCTTTTTTTGGCTGGTAGGTCCTGTGGCATGTAC    180
                    ************************************************************

LCMV-WE_GP          GGCCTTAATGGTCCCGACATCTATAAAGGGGTTTACCAGTTCAAATCAGTGGAGTTTGAT    240
LCMV-P42_GP         GGCCTTAATGGTCCCGACATCTATAAAGGGGTTTACCAGTTCAAATCAGTGGAGTTTGAT    240
LCMV-P52_GP         GGCCTTAATGGTCCCGACATCTATAAAGGGGTTTACCAGTTCAAATCAGTGGAGTTTGAT    240
LCMV-P91_GP         GGCCTTAATGGTCCCGACATCTATAAAGGGGTTTACCAGTTCAAATCAGTGGAGTTTGAT    240
LCMV-P52-1          GGCCTCAATGGTCCCGACATCTATAAAGGGGTTTACCAGTTCAAATCAGTGGAGTTTGAT    240
LCMV-P52-1.3_GP     GGCCTTAATGGTCCCGACATCTATAAAGGGGTTTACCAGTTCAAATCAGTGGAGTTTGAT    240
LCMV-P52-2.1_GP     GGCCTTAATGGTCCCGACATCTATAAAGGGGTTTACCAGTTCAAATCAGTGGAGTTTGAT    240
                    ***** ******************************************************

LCMV-WE_GP          ATGTCTCACTTAAATCTGACGATGCCCAATGCGTGCTCAGCCAACAACTCTCATCACTAC    300
LCMV-P42_GP         ATGTCTCACTTAAATCTGACGATGCCCAATGCGTGCTCAGCCAACAACTCTCATCACTAC    300
LCMV-P52_GP         ATGTCTCACTTAAATCTGACGATGCCCAATGCGTGCTCAGCCAACAACTCTCATCACTAC    300
LCMV-P91_GP         ATGTCTCACTTAAATCTGACGATGCCCAATGCGTGCTCAGCCAACAACTCTCATCACTAC    300
LCMV-P52-1          ATGTCTCACTTAAATCTGACGATGCCCAATGCGTGCTCAGCCAACAACTCTCATCACTAC    300
LCMV-P52-1.3_GP     ATGTCTCACTTAAATCTGACGATGCCCAATGCGTGCTCAGCCAACAACTCTCATCACTAC    300
LCMV-P52-2.1_GP     ATGTCTCACTTAAATCTGACGATGCCCAATGCGTGCTCAGCCAACAACTCTCATCACTAC    300
                    ************************************************************

LCMV-WE_GP          ATCAGTATGGGAAGCTCTGGACTGGAGCTAACTTTCACTAACGACTCCATCCTTAATCAC    360
LCMV-P42_GP         ATCAGTATGGGAAGCTCTGGACTGGAGCTAACTTTCACTAACGACTCCATCCTTAATCAC    360
LCMV-P52_GP         ATCAGTATGGGAAGCTCTGGACTGGAGCTAACTTTCACTAACGACTCCATCCTTAATCAC    360
LCMV-P91_GP         ATCAGTATGGGAAGCTCTGGACTGGAGCTAACTTTCACTAACGACTCCATCCTTAATCAC    360
LCMV-P52-1          ATCAGTATGGGAAGCTCTGGACTGGAGCTAACTTTCACTAACGACTCCATCCTTAATCAC    360
LCMV-P52-1.3_GP     ATCAGTATGGGAAGCTCTGGACTGGAGCTAACTTTCACTAACGACTCCATCCTTAATCAC    360
LCMV-P52-2.1_GP     ATCAGTATGGGAAGCTCTGGACTGGAGCTAACTTTCACTAACGACTCCATCCTTAATCAC    360
                    ************************************************************

LCMV-WE_GP          AATTTTTGCAACTTAACCTCCGCTTTCAACAAAAAGACTTTTGACCATACACTCATGAGT    420
LCMV-P42_GP         AATTTTTGCAACTTAACCTCCGCTTTCAACAAAAAGACTTTTGACCATACACTCATGAGT    420
LCMV-P52_GP         AATTTTTGCAACTTAACCTCCGCTTTCAACAAAAAGACTTTTGACCATACACTCATGAGT    420
LCMV-P91_GP         AATTTTTGCAACTTAACCTCCGCTTTCAACAAAAAGACTTTTGACCATACACTCATGAGT    420
LCMV-P52-1          AATTTTTGCAACTTAACCTCCGCTTTCAACAAAAAGACTTTTGACCATACACTCATGAGT    420
LCMV-P52-1.3_GP     AATTTTTGCAACTTAACCTCCGCTTTCAACAAAAAGACTTTTGACCATACACTCATGAGT    420
LCMV-P52-2.1_GP     AATTTTTGCAACTTAACCTCCGCTTTCAACAAAAAGACTTTTGACCATACACTCATGAGT    420
                    ************************************************************
```

Figure 26 (cont'd)

```
LCMV-WE_GP          ATAGTCTCGAGTCTGCACCTCAGTATTAGAGGGAATTCCAACCACAAAGCAGTGTCTTGT    480
LCMV-P42_GP         ATAGTCTCGAGTCTGCACCTCAGTATTAGAGGGAATTCCAACCACAAAGCAGTGTCTTGT    480
LCMV-P52_GP         ATAGTCTCGAGTCTGCACCTCAGTATTAGAGGGAATTCCAACCACAAAGCAGTGTCTTGT    480
LCMV-P91_GP         ATAGTCTCGAGTCTGCACCTCAGTATTAGAGGGAATTCCAACCACAAAGCAGTGTCTTGT    480
LCMV-P52-1          ATAGTCTCGAGTCTGCACCTCAGTATTAGAGGGAATTCCAACCACAAAGCAGTGTCTTGT    480
LCMV-P52-1.3_GP     ATAGTCTCGAGTCTGCACCTCAGTATTAGAGGGAATTCCAACCACAAAGCAGTGTCTTGT    480
LCMV-P52-2.1_GP     ATAGTCTCGAGTCTGCACCTCAGTATTAGAGGGAATTCCAACCACAAAGCAGTGTCTTGT    480
                    ************************************************************

LCMV-WE_GP          GATTTTAACAATGGCATCACCATTCAATACAACTTGTCATTTTCGGACCCACAGAGCGCT    540
LCMV-P42_GP         GATTTTAACAATGGCATCACCATTCAATACAACTTGTCATTTTCGGACCCACAGAGCGCT    540
LCMV-P52_GP         GATTTTAACAATGGCATCACCATTCAATACAACTTGTCATTTTCGGACCCACAGAGCGCT    540
LCMV-P91_GP         GATTTTAACAATGGCATCACCATTCAATACAACTTGTCATTTTCGGACCCACAGAGCGCT    540
LCMV-P52-1          GATTTTAACAATGGCATCACCATTCAATACAACTTGTCATTTTCGGACCCACAGAGCGCT    540
LCMV-P52-1.3_GP     GATTTTAACAATGGCATCACCATTCAATACAACTTGTCATTTTCGGACCCACAGAGCGCT    540
LCMV-P52-2.1_GP     GATTTTAACAATGGCATCACCATTCAATACAACTTGTCATTTTCGGACCCACAGAGCGCT    540
                    ************************************************************

LCMV-WE_GP          ATAAGCCAGTGTAGGACTTTCAGAGGTAGAGTCTTGGACATGTTTAGAACTGCCTTTGGA    600
LCMV-P42_GP         ATGAGCCAGTGTAGGACTTTCAGAGGTAGAGTCTTGGACATGTTTAGAACTGCCTTTGGA    600
LCMV-P52_GP         ATGAGCCAGTGTTGGACTTTCAGAGGTAGAGTCTTGGACATGTTTAGAACTGCCTTTGGA    600
LCMV-P91_GP         ATGAGCCAGTGTTGGACTTTCAGAGGTAGAGTCTTGGACATGTTTAGAACTGCCTTTGGA    600
LCMV-P52-1          ATGAGCCAGTGTTGGACTTTCAGAGGTAGAGTCTTGGACATGTTTAGAACTGCCTTTGGA    600
LCMV-P52-1.3_GP     ATAAGCCAGTGTTGGACTTTCAGAGGTAGAGTCTTGGACATGTTTAGAACTGCCTTTGGA    600
LCMV-P52-2.1_GP     ATGAGCCAGTGTAGGACTTTCAGAGGTAGAGTCTTGGACATGTTTAGAACTGCCTTTGGA    600
                    ** ********* ***********************************************

LCMV-WE_GP          GGAAAATACATGAGAAGTGGCTGGGGCTGGGCAGGTTCAGATGGCAAGACCACTTGGTGC    660
LCMV-P42_GP         GGAAAATACATGAGAAGTGGCTGGGGCTGGGCAGGTTCAGATGGCAAGACCACTTGGTGC    660
LCMV-P52_GP         GGAAAATACATGAGAAGTGGCTGGGGCTGGGCAGGTTCAGATGGCAAGACCACTTGGTGC    660
LCMV-P91_GP         GGAAAATACATGAGAAGTGGCTGGGGCTGGGCAGGTTCAGATGGCAAGACCACTTGGTGC    660
LCMV-P52-1          GGAAAATACATGAGAAGTGGCTGGGGCTGGGCAGGTTCAGATGGCAAGACCACTTGGTGC    660
LCMV-P52-1.3_GP     GGAAAATACATGAGAAGTGGCTGGGGCTGGGCAGGTTCAGATGGCAAGACCACTTGGTGC    660
LCMV-P52-2.1_GP     GGAAAATACATGAGAAGTGGCTGGGGCTGGGCAGGTTCAGATGGCAAGACCACTTGGTGC    660
                    ************************************************************

LCMV-WE_GP          AGCCAAACAAGCTATCAGTACCTAATCATACAAAACAGGACTTGGGAAAACCACTGTAGA    720
LCMV-P42_GP         AGCCAAACAAGCTATCAGTACCTAATCATACAAAACAGGACTTGGGAAAACCACTGTAGA    720
LCMV-P52_GP         AGCCAAACAAGCTATCAGTACCTAATCATACAAAACAGGACTTGGGAAAACCACTGTAGA    720
LCMV-P91_GP         AGCCAAACAAGCTATCAGTACCTAATCATACAAAACAGGACTTGGGAAAACCACTGTAGA    720
LCMV-P52-1          AGCCAAACAAGCTATCAGTACCTAATCATACAAAACAGGACTTGGGAAAACCACTGTAGA    720
LCMV-P52-1.3_GP     AGCCAAACAAGCTATCAGTACCTAATCATACAAAACAGGACTTGGGAAAACCACTGTAGA    720
LCMV-P52-2.1_GP     AGCCAAACAAGCTATCAGTACCTAATCATACAAAACAGGACTTGGGAAAACCACTGTAGA    720
                    ************************************************************

LCMV-WE_GP          TATGCAGGCCCTTTTGGGATGTCTAGAATCCTCTTTGCTCAGGAAAAGACAAAGTTTCTC    780
LCMV-P42_GP         TATGCAGGCCCTTTTGGGATGTCTAGAATCCTCTTTGCTCAGGAAAAGACAAAGTTTCTC    780
LCMV-P52_GP         TATGCAGGCCCTTTTGGGATGTCTAGAATCCTCTTTGCTCAGGAAAAGACAAAGTTTCTC    780
LCMV-P91_GP         TATGCAGGCCCTTTTGGGATGTCTAGAATCCTCTTTGCTCAGGAAAAGACAAAGTTTCTC    780
LCMV-P52-1          TATGCAGGCCCTTTTGGGATGTCTAGAATCCTCTTTGCTCAGGAAAAGACAAAGTTTCTC    780
LCMV-P52-1.3_GP     TATGCAGGCCCTTTTGGGATGTCTAGAATCCTCTTTGCTCAGGAAAAGACAAAGTTTCTC    780
LCMV-P52-2.1_GP     TATGCAGGCCCTTTTGGGATGTCTAGAATCCTCTTTGCTCAGGAAAAGACAAAGTTTCTC    780
                    ************************************************************

LCMV-WE_GP          ACTAGGAGACTTGCAGGCACATTCACCTGGACCCTGTCAGACTCCTCAGGAGTAGAAAAT    840
LCMV-P42_GP         ACTAGGAGACTTGCAGGCACATTCACCTGGACCCTGTCAGACTCCTCAGGAGTAGAAAAT    840
LCMV-P52_GP         ACTAGGAGACTTGCAGGCACATTCACCTGGACCCTGTCAGACTCCTCAGGAGTAGAAAAT    840
LCMV-P91_GP         ACTAGGAGACTTGCAGGCACATTCACCTGGACCCTGTCAGACTCCTCAGGAGTAGAAAAT    840
LCMV-P52-1          ACTAGGAGACTTGCAGGCACATTCACCTGGACCCTGTCAGACTCCTCAGGAGTAGAAAAT    840
LCMV-P52-1.3_GP     ACTAGGAGACTTGCAGGCACATTCACCTGGACCCTGTCAGACTCCTCAGGAGTAGAAAAT    840
LCMV-P52-2.1_GP     ACTAGGAGACTTGCAGGCACATTCACCTGGACCCTGTCAGACTCCTCAGGAGTAGAAAAT    840
                    ************************************************************

LCMV-WE_GP          CCAGGTGGTTATTGCCTGACCAAATGGATGATCCTTGCTGCAGAGCTCAAATGTTTTGGG    900
LCMV-P42_GP         CCAGGTGGTTATTGCCTGACCAAATGGATGATCCTTGCTGCAGAGCTCAAATGTTTTGGG    900
LCMV-P52_GP         CCAGGTGGTTATTGCCTGACCAAATGGATGATCCTTGCTGCAGAGCTCAAATGTTTTGGG    900
LCMV-P91_GP         CCAGGTGGTTATTGCCTGACCAAATGGATGATCCTTGCTGCAGAGCTCAAATGTTTTGGG    900
LCMV-P52-1          CCAGGTGGTTATTGCCTGACCAAATGGATGATCCTTGCTGCAGAGCTCAAATGTTTTGGG    900
LCMV-P52-1.3_GP     CCAGGTGGTTATTGCCTGACCAAATGGATGATCCTTGCTGCAGAGCTCAAATGTTTTGGG    900
LCMV-P52-2.1_GP     CCAGGTGGTTATTGCCTGACCAAATGGATGATCCTTGCTGCAGAGCTCAAATGTTTTGGG    900
                    ************************************************************
```

Figure 26 (cont'd)

```
LCMV-WE_GP          AATACAGCTGTTGCAAAATGTAATGTCAATCATGATGAAGAGTTCTGTGACATGCTACGA   960
LCMV-P42_GP         AATACAGCTGTTGCAAAATGTAATGTCAATCATGATGAAGAGTTCTGTGACATGCTACGA   960
LCMV-P52_GP         AATACAGCTGTTGCAAAATGTAATGTCAATCATGATGAAGAGTTCTGTGACATGCTACGA   960
LCMV-P91_GP         AATACAGCTGTTGCAAAATGTAATGTCAATCATGATGAAGAGTTCTGTGACATGCTACGA   960
LCMV-P52-1          AATACAGCTGTTGCAAAATGTAATGTCAATCATGATGAAGAGTTCTGTGACATGCTACGA   960
LCMV-P52-1.3_GP     AACACAGCTGTTGCAAAATGTAATGTCAATCATGATGAAGAGTTCTGTGACATGCTACGA   960
LCMV-P52-2.1_GP     AATACAGCTGTTGCAAAATGTAATGTCAATCATGATGAAGAGTTCTGTGACATGCTACGA   960
                    ** *********************************************************

LCMV-WE_GP          CTAATTGATTACAACAAGGCCGCCCTGAGTAAGTTCAAGCAAGATGTAGAGTCTGCCTTG   1020
LCMV-P42_GP         CTAATTGATTACAACAAGGCCGCCCTGAGTAAGTTCAAGCAAGATGTAGAGTCTGCCTTG   1020
LCMV-P52_GP         CTAATTGATTACAACAAGGCCGCCCTGAGTAAGTTCAAGCAAGATGTAGAGTCTGCCTTG   1020
LCMV-P91_GP         CTAATTGATTACAACAAGGCCGCCCTGAGTAAGTTCAAGCAAGATGTAGAGTCTGCCTTG   1020
LCMV-P52-1          CTAATTGATTACAACAAGGCCGCCCTGAGTAAGTTCAAGCAAGATGTAGAGTCTGCCTTG   1020
LCMV-P52-1.3_GP     CTAATTGATTACAACAAGGCCGCCCTGAGTAAGTTCAAGCAAGATGTAGAGTCTGCCTTG   1020
LCMV-P52-2.1_GP     CTAATTGATTACAACAAGGCCGCCCTGAGTAAGTTCAAGCAAGATGTAGAGTCTGCCTTG   1020
                    ************************************************************

LCMV-WE_GP          CATGTATTCAAAACAACAGTAAATTCTCTGATTTCCGATCAGCTGTTGATGAGGAATCAT   1080
LCMV-P42_GP         CATGTATTCAAAACAACAGTAAATTCTCTGATTTCCGATCAGCTGTTGATGAGGAATCAT   1080
LCMV-P52_GP         CATGTATTCAAAACAACAGTAAATTCTCTGATTTCCGATCAGCTGTTGATGAGGAATCAT   1080
LCMV-P91_GP         CATGTATTCAAAACAACAGTAAATTCTCTGATTTCCGATCAGCTGTTGATGAGGAATCAT   1080
LCMV-P52-1          CATGTATTCAAAACAACAGTAAATTCTCTGATTTCCGATCAGCTGTTGATGAGGAATCAT   1080
LCMV-P52-1.3_GP     CATGTATTCAAAACAACAGTAAATTCTCTGATTTCCGATCAGCTGTTGATGAGGAATCAT   1080
LCMV-P52-2.1_GP     CATGTATTCAAAACAACAGTAAATTCTCTGATTTCCGATCAGCTGTTGATGAGGAATCAT   1080
                    ************************************************************

LCMV-WE_GP          CTAAGAGATCTAATGGGGGTACCATACTGTAATTACTCAAAGTTCTGGTATCTGGAACAT   1140
LCMV-P42_GP         CTAAGAGATCTAATGGGGGTACCATACTGTAATTACTCAAAGTTCTGGTATCTGGAACAT   1140
LCMV-P52_GP         CTAAGAGATCTAATGGGGGTACCATACTGTAATTACTCAAAGTTCTGGTATCTGGAACAT   1140
LCMV-P91_GP         CTAAGAGATCTAATGGGGGTACCATACTGTAATTACTCAAAGTTCTGGTATCTGGAACAT   1140
LCMV-P52-1          CTAAGAGATCTAATGGGGGTACCATACTGTAATTACTCAAAGTTCTGGTATCTGGAACAT   1140
LCMV-P52-1.3_GP     CTAAGAGATCTAATGGGGGTACCATACTGTAATTACTCAAAGTTCTGGTATCTGGAACAT   1140
LCMV-P52-2.1_GP     CTAAGAGATCTAATGGGGGTACCATACTGTAATTACTCAAAGTTCTGGTATCTGGAACAT   1140
                    ************************************************************

LCMV-WE_GP          GCTAAGACTGGTGAGACTAGTGTACCCAAGTGCTGGCTTGTCACTAATGGCTCCTACTTG   1200
LCMV-P42_GP         GCTAAGACTGGTGAGACTAGTGTACCCAAGTGCTGGCTTGTCACTAATGGCTCCTACTTG   1200
LCMV-P52_GP         GCTAAGACTGGTGAGACTAGTGTACCCAAGTGCTGGCTTGTCACTAATGGCTCCTACTTG   1200
LCMV-P91_GP         GCTAAGACTGGTGAGACTAGTGTACCCAAGTGCTGGCTTGTCACTAATGGCTCCTACTTG   1200
LCMV-P52-1          GCTAAGACTGGTGAGACTAGTGTACCCAAGTGCTGGCTTGTCACTAATGGCTCCTACTTG   1200
LCMV-P52-1.3_GP     GCTAAGACTGGTGAGACTAGTGTACCCAAGTGCTGGCTTGTCACTAATGGCTCCTACTTG   1200
LCMV-P52-2.1_GP     GCTAAGACTGGTGAGACTAGTGTACCCAAGTGCTGGCTTGTCACTAATGGCTCCTACTTG   1200
                    ************************************************************

LCMV-WE_GP          AATGAGACCCACTTTAGTGATCAAATCGAACAAGAAGCAGATAACATGATCACAGAGATG   1260
LCMV-P42_GP         AATGAGACCCACTTTAGTGATCAAATCGAACAAGAAGCAGATAACATGATCACAGAGATG   1260
LCMV-P52_GP         AATGAGACCCACTTTAGTGATCAAATCGAACAAGAAGCAGATAACATGATCACAGAGATG   1260
LCMV-P91_GP         AATGAGACCCACTTTAGTGATCAAATCGAACAAGAAGCAGATAACATGATCACAGAGATG   1260
LCMV-P52-1          AATGAGACCCACTTTAGTGATCAAATCGAACAAGAAGCAGATAACATGATCACAGAGATG   1260
LCMV-P52-1.3_GP     AATGAGACCCACTTTAGTGATCAAATCGAACAAGAAGCAGATAACATGATCACAGAGATG   1260
LCMV-P52-2.1_GP     AATGAGACCCACTTTAGTGATCAAATCGAACAAGAAGCAGATAACATGATCACAGAGATG   1260
                    ************************************************************

LCMV-WE_GP          TTGAGGAAGGACTACATAAAAAGACAAGGGAGTACTCCTTTAGCCTTAATGGATCTTTTG   1320
LCMV-P42_GP         TTGAGGAAGGACTACATAAAAAGACAAGGGAGTACTCCTTTAGCCTTAATGGATCTTTTG   1320
LCMV-P52_GP         TTGAGGAAGGACTACATAAAAAGACAAGGGAGTACTCCTTTAGCCTTAATGGATCTTTTG   1320
LCMV-P91_GP         TTGAGGAAGGACTACATAAAAAGACAAGGGAGTACTCCTTTAGCCTTAATGGATCTTTTG   1320
LCMV-P52-1          TTGAGGAAGGACTACATAAAAAGACAAGGGAGTACTCCTTTAGCCTTAATGGATCTTTTG   1320
LCMV-P52-1.3_GP     TTGAGGAAGGACTACATAAAAAGACAAGGGAGTACTCCTTTAGCCTTAATGGATCTTTTG   1320
LCMV-P52-2.1_GP     TTGAGGAAGGACTACATAAAAAGACAAGGGAGTACTCCTTTAGCCTTAATGGATCTTTTG   1320
                    ************************************************************

LCMV-WE_GP          ATGTTTTCAACATCAGCATATCTAATCAGCATCTTTCTGCATCTTGTGAAGATACCAACA   1380
LCMV-P42_GP         ATGTTTTCAACATCAGCATATCTAATCAGCATCTTTCTGCATCTTGTGAAGATACCAACA   1380
LCMV-P52_GP         ATGTTTTCAACATCAGCATATCTAATCAGCATCTTTCTGCATCTTGTGAAGATACCAACA   1380
LCMV-P91_GP         ATGTTTTCAACATCAGCATATCTAATCAGCATCTTTCTGCATCTTGTGAAGATACCAACA   1380
LCMV-P52-1          ATGTTTTCAACATCAGCATATCTAATCAGCATCTTTCTGCATCTTGTGAAGATACCAACA   1380
LCMV-P52-1.3_GP     ATGTTTTCAACATCAGCATATCTAATCAGCATCTTTCTGCATCTTGTGAAGATACCAACA   1380
LCMV-P52-2.1_GP     ATGTTTTCAACATCAGCATATCTAATCAGCATCTTTCTGCATCTTGTGAAGATACCAACA   1380
                    ************************************************************
```

Figure 26 (cont'd)

```
LCMV-WE_GP          CATAGACACATAAAGGGCGGTTCATGTCCAAAGCCACACCGCTTGACCAACAAGGGGATC     1440
LCMV-P42_GP         CATAGACACATAAAGGGCGGTTCATGTCCAAAGCCACACCGCTTGACCAACAAGGGGATC     1440
LCMV-P52_GP         CATAGACACATAAAGGGCGGTTCATGTCCAAAGCCACACCGCTTGACCAACAAGGGGATC     1440
LCMV-P91_GP         CATAGACACATAAAGGGCGGTTCATGTCCAAAGCCACACCGCTTGACCAACAAGGGGATC     1440
LCMV-P52-1          CATAGACACATAAAGGGCGGTTCATGTCCAAAGCCACACCGCTTGACCAACAAGGGGATC     1440
LCMV-P52-1.3_GP     CATAGACACATAAAGGGCGGTTCATGTCCAAAGCCACACCGCTTGACCAACAAGGGGATC     1440
LCMV-P52-2.1_GP     CATAGACACATAAAGGGCGGTTCATGTCCAAAGCCACACCGCTTGACCAACAAGGGGATC     1440
                    ************************************************************

LCMV-WE_GP          TGTAGTTGTGGTGCATTCAAGGTGCCTGGTGTAAAAACTATCTGGAAAAGACGCTGA        1497
LCMV-P42_GP         TGTAGTTGTGGTGCATTCAAGGTGCCTGGTGTAAAAACTATCTGGAAAAGACGCTGA        1497
LCMV-P52_GP         TGTAGTTGTGGTGCATTCAAGGTGCCTGGTGTAAAAACTATCTGGAAAAGACGCTGA        1497
LCMV-P91_GP         TGTAGTTGTGGTGCATTCAAGGTGCCTGGTGTAAAAACTATCTGGAAAAGACGCTGA        1497
LCMV-P52-1          TGTAGTTGTGGTGCATTCAAGGTGCCTGGTGTAAAAACTATCTGGAAAAGACGCTGA        1497
LCMV-P52-1.3_GP     TGTAGTTGTGGTGCATTCAAGGTGCCTGGTGTAAAAACTATCTGGAAAAGACGCTGA        1497
LCMV-P52-2.1_GP     TGTAGTTGTGGTGCATTCAAGGTGCCTGGTGTAAAAACTATCTGGAAAAGACGCTGA        1497
                    *********************************************************

LCMV-WE_GP:      SEQ ID NO: 9
LCMV-P42_GP:     SEQ ID NO: 17
LCMV-P52_GP:     SEQ ID NO: 25
LCMV-P91_GP:     SEQ ID NO: 33
LCMV-P52-1:      SEQ ID NO: 41
LCMV-P52-1.3_GP: SEQ ID NO: 49
LCMV-P52-2.1_GP: SEQ ID NO: 57
```

Source: 1-3376 Segment = S
Protein: Pre-glycoprotein polyprotein GP complex
Gene: GPC
Gene: 79-1575
Sequence Alignment: Aminoacid

```
LCMV-WE_GP          MGQIVTMFEALPHIIDEVINIVIIVLIIITSIKAVYNFATCGILALVSFLFLAGRSCGMY    60
LCMV-P42_GP         MGQIVTMFEALPHIIDEVINIVIIVLIIITSIKAVYNFATCGILALVSFLFLAGRSCGMY    60
LCMV-P52_GP         MGQIVTMFEALPHIIDEVINIVIIVLIIITSIKAVYNFATCGILALVSFLFLAGRSCGMY    60
LCMV-P91_GP         MGQIVTMFEALPHIIDEVINIVIIVLIIITSIKAVYNFATCGILALVSFLFLAGRSCGMY    60
LCMV-P52-1          MGQIVTMFEALPHIIDEVINIVIIVLIIITSIKAVYNFATCGILALVSFLFLAGRSCGMY    60
LCMV-P52-1.3_GP     MGQIVTMFEALPHIIDEVINIVIIVLIIITSIKAVYNFATCGILALVSFLFLAGRSCGMY    60
LCMV-P52-2.1_GP     MGQIVTMFEALPHIIDEVINIVIIVLIIITSIKAVYNFATCGILALVSFLFLAGRSCGMY    60
                    ************************************************************

LCMV-WE_GP          GLNGPDIYKGVYQFKSVEFDMSHLNLTMPNACSANNSHHYISMGSSGLELTFTNDSILNH    120
LCMV-P42_GP         GLNGPDIYKGVYQFKSVEFDMSHLNLTMPNACSANNSHHYISMGSSGLELTFTNDSILNH    120
LCMV-P52_GP         GLNGPDIYKGVYQFKSVEFDMSHLNLTMPNACSANNSHHYISMGSSGLELTFTNDSILNH    120
LCMV-P91_GP         GLNGPDIYKGVYQFKSVEFDMSHLNLTMPNACSANNSHHYISMGSSGLELTFTNDSILNH    120
LCMV-P52-1          GLNGPDIYKGVYQFKSVEFDMSHLNLTMPNACSANNSHHYISMGSSGLELTFTNDSILNH    120
LCMV-P52-1.3_GP     GLNGPDIYKGVYQFKSVEFDMSHLNLTMPNACSANNSHHYISMGSSGLELTFTNDSILNH    120
LCMV-P52-2.1_GP     GLNGPDIYKGVYQFKSVEFDMSHLNLTMPNACSANNSHHYISMGSSGLELTFTNDSILNH    120
                    ************************************************************

LCMV-WE_GP          NFCNLTSAFNKKTFDHTLMSIVSSLHLSIRGNSNHKAVSCDFNNGITIQYNLSFSDPQSA    180
LCMV-P42_GP         NFCNLTSAFNKKTFDHTLMSIVSSLHLSIRGNSNHKAVSCDFNNGITIQYNLSFSDPQSA    180
LCMV-P52_GP         NFCNLTSAFNKKTFDHTLMSIVSSLHLSIRGNSNHKAVSCDFNNGITIQYNLSFSDPQSA    180
LCMV-P91_GP         NFCNLTSAFNKKTFDHTLMSIVSSLHLSIRGNSNHKAVSCDFNNGITIQYNLSFSDPQSA    180
LCMV-P52-1          NFCNLTSAFNKKTFDHTLMSIVSSLHLSIRGNSNHKAVSCDFNNGITIQYNLSFSDPQSA    180
LCMV-P52-1.3_GP     NFCNLTSAFNKKTFDHTLMSIVSSLHLSIRGNSNHKAVSCDFNNGITIQYNLSFSDPQSA    180
LCMV-P52-2.1_GP     NFCNLTSAFNKKTFDHTLMSIVSSLHLSIRGNSNHKAVSCDFNNGITIQYNLSFSDPQSA    180
                    ************************************************************

LCMV-WE_GP          ISQCRTFRGRVLDMFRTAFGGKYMRSGWGWAGSDGKTTWCSQTSYQYLIIQNRTWENHCR    240
LCMV-P42_GP         MSQCRTFRGRVLDMFRTAFGGKYMRSGWGWAGSDGKTTWCSQTSYQYLIIQNRTWENHCR    240
LCMV-P52_GP         MSQCWTFRGRVLDMFRTAFGGKYMRSGWGWAGSDGKTTWCSQTSYQYLIIQNRTWENHCR    240
LCMV-P91_GP         MSQCWTFRGRVLDMFRTAFGGKYMRSGWGWAGSDGKTTWCSQTSYQYLIIQNRTWENHCR    240
LCMV-P52-1          MSQCWTFRGRVLDMFRTAFGGKYMRSGWGWAGSDGKTTWCSQTSYQYLIIQNRTWENHCR    240
LCMV-P52-1.3_GP     ISQCWTFRGRVLDMFRTAFGGKYMRSGWGWAGSDGKTTWCSQTSYQYLIIQNRTWENHCR    240
LCMV-P52-2.1_GP     MSQCRTFRGRVLDMFRTAFGGKYMRSGWGWAGSDGKTTWCSQTSYQYLIIQNRTWENHCR    240
                     *** *******************************************************

LCMV-WE_GP          YAGPFGMSRILFAQEKTKFLTRRLAGTFTWTLSDSSGVENPGGYCLTKWMILAAELKCFG    300
LCMV-P42_GP         YAGPFGMSRILFAQEKTKFLTRRLAGTFTWTLSDSSGVENPGGYCLTKWMILAAELKCFG    300
LCMV-P52_GP         YAGPFGMSRILFAQEKTKFLTRRLAGTFTWTLSDSSGVENPGGYCLTKWMILAAELKCFG    300
LCMV-P91_GP         YAGPFGMSRILFAQEKTKFLTRRLAGTFTWTLSDSSGVENPGGYCLTKWMILAAELKCFG    300
LCMV-P52-1          YAGPFGMSRILFAQEKTKFLTRRLAGTFTWTLSDSSGVENPGGYCLTKWMILAAELKCFG    300
LCMV-P52-1.3_GP     YAGPFGMSRILFAQEKTKFLTRRLAGTFTWTLSDSSGVENPGGYCLTKWMILAAELKCFG    300
LCMV-P52-2.1_GP     YAGPFGMSRILFAQEKTKFLTRRLAGTFTWTLSDSSGVENPGGYCLTKWMILAAELKCFG    300
                    ************************************************************

LCMV-WE_GP          NTAVAKCNVNHDEEFCDMLRLIDYNKAALSKFKQDVESALHVFKTTVNSLISDQLLMRNH    360
LCMV-P42_GP         NTAVAKCNVNHDEEFCDMLRLIDYNKAALSKFKQDVESALHVFKTTVNSLISDQLLMRNH    360
LCMV-P52_GP         NTAVAKCNVNHDEEFCDMLRLIDYNKAALSKFKQDVESALHVFKTTVNSLISDQLLMRNH    360
LCMV-P91_GP         NTAVAKCNVNHDEEFCDMLRLIDYNKAALSKFKQDVESALHVFKTTVNSLISDQLLMRNH    360
LCMV-P52-1          NTAVAKCNVNHDEEFCDMLRLIDYNKAALSKFKQDVESALHVFKTTVNSLISDQLLMRNH    360
LCMV-P52-1.3_GP     NTAVAKCNVNHDEEFCDMLRLIDYNKAALSKFKQDVESALHVFKTTVNSLISDQLLMRNH    360
LCMV-P52-2.1_GP     NTAVAKCNVNHDEEFCDMLRLIDYNKAALSKFKQDVESALHVFKTTVNSLISDQLLMRNH    360
                    ************************************************************

LCMV-WE_GP          LRDLMGVPYCNYSKFWYLEHAKTGETSVPKCWLVTNGSYLNETHFSDQIEQEADNMITEM    420
LCMV-P42_GP         LRDLMGVPYCNYSKFWYLEHAKTGETSVPKCWLVTNGSYLNETHFSDQIEQEADNMITEM    420
LCMV-P52_GP         LRDLMGVPYCNYSKFWYLEHAKTGETSVPKCWLVTNGSYLNETHFSDQIEQEADNMITEM    420
LCMV-P91_GP         LRDLMGVPYCNYSKFWYLEHAKTGETSVPKCWLVTNGSYLNETHFSDQIEQEADNMITEM    420
LCMV-P52-1          LRDLMGVPYCNYSKFWYLEHAKTGETSVPKCWLVTNGSYLNETHFSDQIEQEADNMITEM    420
LCMV-P52-1.3_GP     LRDLMGVPYCNYSKFWYLEHAKTGETSVPKCWLVTNGSYLNETHFSDQIEQEADNMITEM    420
LCMV-P52-2.1_GP     LRDLMGVPYCNYSKFWYLEHAKTGETSVPKCWLVTNGSYLNETHFSDQIEQEADNMITEM    420
                    ************************************************************
```

Figure 26 (cont'd)

```
LCMV-WE_GP           LRKDYIKRQGSTPLALMDLLMFSTSAYLISIFLHLVKIPTHRHIKGGSCPKPHRLTNKGI     480
LCMV-P42_GP          LRKDYIKRQGSTPLALMDLLMFSTSAYLISIFLHLVKIPTHRHIKGGSCPKPHRLTNKGI     480
LCMV-P52_GP          LRKDYIKRQGSTPLALMDLLMFSTSAYLISIFLHLVKIPTHRHIKGGSCPKPHRLTNKGI     480
LCMV-P91_GP          LRKDYIKRQGSTPLALMDLLMFSTSAYLISIFLHLVKIPTHRHIKGGSCPKPHRLTNKGI     480
LCMV-P52-1           LRKDYIKRQGSTPLALMDLLMFSTSAYLISIFLHLVKIPTHRHIKGGSCPKPHRLTNKGI     480
LCMV-P52-1.3_GP      LRKDYIKRQGSTPLALMDLLMFSTSAYLISIFLHLVKIPTHRHIKGGSCPKPHRLTNKGI     480
LCMV-P52-2.1_GP      LRKDYIKRQGSTPLALMDLLMFSTSAYLISIFLHLVKIPTHRHIKGGSCPKPHRLTNKGI     480
                     ************************************************************

LCMV-WE_GP           CSCGAFKVPGVKTIWKRR        498
LCMV-P42_GP          CSCGAFKVPGVKTIWKRR        498
LCMV-P52_GP          CSCGAFKVPGVKTIWKRR        498
LCMV-P91_GP          CSCGAFKVPGVKTIWKRR        498
LCMV-P52-1           CSCGAFKVPGVKTIWKRR        498
LCMV-P52-1.3_GP      CSCGAFKVPGVKTIWKRR        498
LCMV-P52-2.1_GP      CSCGAFKVPGVKTIWKRR        498
                     ******************


LCMV-WE_GP:      SEQ ID NO: 10
LCMV-P42_GP:     SEQ ID NO: 18
LCMV-P52_GP:     SEQ ID NO: 26
LCMV-P91_GP:     SEQ ID NO: 34
LCMV-P52-1:      SEQ ID NO: 42
LCMV-P52-1.3_GP: SEQ ID NO: 50
LCMV-P52-2.1_GP: SEQ ID NO: 58
```

Source: 1-3376 Segment = S
Protein: Nucleoprotein
Gene: NP
Gene: 1640-3316 complement
Sequence Alignment: Nucleotide

```
LCMV-WE_NP          ATGTCTTTGTCCAAAGAAGTCAAAAGCTTTCAGTGGACACAGGCGTTGAGGAGGGAGTTG    60
LCMV-P42_NP         ATGTCTTTGTCCAAAGAAGTCAAAAGCTTTCAGTGGACACAGGCGTTGAGGAGGGAGTTG    60
LCMV-P52_NP         ATGTCTTTGTCCAAAGAAGTCAAAAGCTTTCAGTGGACACAGGCGTTGAGGAGGGAGTTG    60
LCMV-P91_NP         ATGTCTTTGTCCAAAGAAGTCAAAAGCTTTCAGTGGACACAGGCGTTGAGGAGGGAGTTG    60
LCMV-P52-1_NP       ATGTCTTTGTCCAAAGAAGTCAAAAGCTTTCAGTGGACACAGGCGTTGAGGAGGGAGTTG    60
LCMV-P52-1.3_NP     ATGTCTTTGTCCAAAGAAGTCAAAAGCTTTCAGTGGACACAGGCGTTGAGGAGGGAGTTG    60
LCMV-P52-2.1_NP     ATGTCTTTGTCCAAAGAAGTCAAAAGCTTTCAGTGGACACAGGCGTTGAGGAGGGAGTTG    60
                    ************************************************************

LCMV-WE_NP          CAGAGTTTTACATCAGATGTAAAGGCTGCCGTCATCAAGGACGCAACCAGTCTTCTAAAT    120
LCMV-P42_NP         CAGAGTTTTACATCAGATGTAAAGGCTGCCGTCATCAAGGACGCAACCAGTCTTCTAAAT    120
LCMV-P52_NP         CAGAGTTTTACATCAGATGTAAAGGCTGCCGTCATCAAGGACGCAACCAGTCTTCTAAAT    120
LCMV-P91_NP         CAGAGTTTTACATCAGATGTAAAGGCTGCCGTCATCAAGGACGCAACCAGTCTTCTAAAT    120
LCMV-P52-1_NP       CAGAGTTTTACATCAGATGTAAAGGCTGCCGTCATCAAGGACGCAACCAGTCTTCTAAAT    120
LCMV-P52-1.3_NP     CAGAGTTTTACATCAGATGTAAAGGCTGCCGTCATCAAGGACGCAACCAGTCTTCTAAAT    120
LCMV-P52-2.1_NP     CAGAGTTTTACATCAGATGTAAAGGCTGCCGTCATCAAGGACGCAACCAGTCTTCTAAAT    120
                    ************************************************************

LCMV-WE_NP          GGGTTGGACTTTTCTGAAGTCAGCAACGTTCAGAGGATCATGAGAAAGGAAAGGAGGGAT    180
LCMV-P42_NP         GGGTTGGACTTTTCTGAAGTCAGCAACGTTCAGAGGATCATGAGAAAGGAAAGGAGGGAT    180
LCMV-P52_NP         GGGTTGGACTTTTCTGAAGTCAGCAACGTTCAGAGGATCATGAGAAAGGAAAGGAGGGAT    180
LCMV-P91_NP         GGGTTGGACTTTTCTGAAGTCAGCAACGTTCAGAGGATCATGAGAAAGGAAAGGAGGGAT    180
LCMV-P52-1_NP       GGGTTGGACTTTTCTGAAGTCAGCAACGTTCAGAGGATCATGAGAAAGGAAAGGAGGGAT    180
LCMV-P52-1.3_NP     GGGTTGGACTTTTCTGAAGTCAGCAACGTTCAGAGGATCATGAGAAAGGAAAGGAGGGAT    180
LCMV-P52-2.1_NP     GGGTTGGACTTTTCTGAAGTCAGCAACGTTCAGAGGATCATGAGAAAGGAAAGGAGGGAT    180
                    ************************************************************

LCMV-WE_NP          GATAAAGACTTGCAGAGACTCAGGAGTCTTAACCAGACTGTGCATTCTCTTGTTGATCTG    240
LCMV-P42_NP         GATAAAGACTTGCAGAGACTCAGGAGTCTTAACCAGACTGTGCATTCTCTTGTTGATCTG    240
LCMV-P52_NP         GATAAAGACTTGCAGAGACTCAGGAGTCTTAACCAGACTGTGCATTCTCTTGTTGATCTG    240
LCMV-P91_NP         GATAAAGACTTGCAGAGACTCAGGAGTCTTAACCAGACTGTGCATTCTCTTGTTGATCTG    240
LCMV-P52-1_NP       GATAAAGACTTGCAGAGACTCAGGAGTCTTAACCAGACTGTGCATTCTCTTGTTGATCTG    240
LCMV-P52-1.3_NP     GATAAAGACTTGCAGAGACTCAGGAGTCTTAACCAGACTGTGCATTCTCTTGTTGATCTG    240
LCMV-P52-2.1_NP     GATAAAGACTTGCAGAGACTCAGGAGTCTTAACCAGACTGTGCATTCTCTTGTTGATCTG    240
                    ************************************************************

LCMV-WE_NP          AAGTCTACATCAAAGAAAAATGTTCTGAAAGTGGGAAGACTTAGTGCAGAGGAATTGATG    300
LCMV-P42_NP         AAGTCTACATCAAAGAAAAATGTTCTGAAAGTGGGAAGACTTAGTGCAGAGGAATTGATG    300
LCMV-P52_NP         AAGTCTACATCAAAGAAAAATGTTCTGAAAGTGGGAAGACTTAGTGCAGAGGAATTGATG    300
LCMV-P91_NP         AAGTCTACATCAAAGAAAAATGTTCTGAAAGTGGGAAGACTTAGTGCAGAGGAATTGATG    300
LCMV-P52-1_NP       AAGTCTACATCAAAGAAAAATGTTCTGAAAGTGGGAAGACTTAGTGCAGAGGAATTGATG    300
LCMV-P52-1.3_NP     AAGTCTACATCAAAGAAAAATGTTCTGAAAGTGGGAAGACTTAGTGCAGAGGAATTGATG    300
LCMV-P52-2.1_NP     AAGTCTACATCAAAGAAAAATGTTCTGAAAGTGGGAAGACTTAGTGCAGAGGAATTGATG    300
                    ************************************************************

LCMV-WE_NP          ACCCTTGCAGCTGATCTTGAGAAGCTGAAGGCCAAAATTATGAGAACTGAGAGGCCTCAA    360
LCMV-P42_NP         ACCCTTGCAGCTGATCTTGAGAAGCTGAAGGCCAAAATTATGAGAACTGAGAGGCCTCAA    360
LCMV-P52_NP         ACCCTTGCAGCTGATCTTGAGAAGCTGAAGGCCAAAATTATGAGAACTGAGAGGCCTCAA    360
LCMV-P91_NP         ACCCTTGCAGCTGATCTTGAGAAGCTGAAGGCCAAAATTATGAGAACTGAGAGGCCTCAA    360
LCMV-P52-1_NP       ACCCTTGCAGCTGATCTTGAGAAGCTGAAGGCCAAAATTATGAGAACTGAGAGGCCTCAA    360
LCMV-P52-1.3_NP     ACCCTTGCAGCTGATCTCGAGAAGCTGAAGGCCAAAATTATGAGAACTGAGAGGCCTCAA    360
LCMV-P52-2.1_NP     ACCCTTGCAGCTGATCTTGAGAAGCTGAAGGCCAAAATTATGAGAACTGAGAGGCCTCAA    360
                    ***************** ******************************************

LCMV-WE_NP          GCTTCTGGAGTCTACATGGGAAATTTGACAGCACAACAACTTGATCAAAGATCCCAAATA    420
LCMV-P42_NP         GCTTCTGGAGTCTACATGGGAAATTTGACAGCACAACAACTTGATCAAAGATCCCAAATA    420
LCMV-P52_NP         GCTTCTGGAGTCTACATGGGAAATTTGACAGCACAACAACTTGATCAAAGATCCCAAATA    420
LCMV-P91_NP         GCTTCTGGAGTCTACATGGGAAATTTGACAGCACAACAACTTGATCAAAGATCCCAAATA    420
LCMV-P52-1_NP       GCTTCTGGAGTCTACATGGGAAATTTGACAGCACAACAACTTGATCAAAGATCCCAAATA    420
LCMV-P52-1.3_NP     GCTTCTGGAGTCTACATGGGAAATTTGACAGCACAACAACTTGATCAAAGATCCCAAATA    420
LCMV-P52-2.1_NP     GCTTCTGGAGTCTACATGGGAAATTTGACAGCACAACAACTTGATCAAAGATCCCAAATA    420
                    ************************************************************
```

Figure 26 (cont'd)

```
LCMV-WE_NP          CTGCAAATGGTTGGGATGAGAAGACCTCAGCAGGGTGCAAGTGGTGTAGTAAGGGTTTGG    480
LCMV-P42_NP         CTGCAAATGGTTGGGATGAGAAGACCTCAGCAGGGTGCAAGTGGTGTAGTAAGGGTTTGG    480
LCMV-P52_NP         CTGCAAATGGTTGGGATGAGAAGACCTCAGCAGGGTGCAAGTGGTGTAGTAAGGGTTTGG    480
LCMV-P91_NP         CTGCAAATGGTTGGGATGAGAAGACCTCAGCAGGGTGCAAGTGGTGTAGTAAGGGTTTGG    480
LCMV-P52-1_NP       CTGCAAATGGTTGGGATGAGAAGACCTCAGCAGGGTGCAAGTGGTGTAGTAAGGGTTTGG    480
LCMV-P52-1.3_NP     CTGCAAATGGTTGGGATGAGAAGACCTCAGCAGGGTGCAAGTGGTGTAGTAAGGGTTTGG    480
LCMV-P52-2.1_NP     CTGCAAATGGTTGGGATGAGAAGACCTCAGCAGGGTGCAAGTGGTGTAGTAAGGGTTTGG    480
                    ************************************************************

LCMV-WE_NP          GATGTGAAGGACTCATCACTTCTGAACAATCAGTTCGGCACAATGCCAAGCCTGACAATG    540
LCMV-P42_NP         GATGTGAAGGACTCATCACTTCTGAACAATCAGTTCGGCACAATGCCAAGCCTGACAATG    540
LCMV-P52_NP         GATGTGAAGGACTCATCACTTCTGAACAATCAGTTCGGCACAATGCCAAGCCTGACAATG    540
LCMV-P91_NP         GATGTGAAGGACTCATCACTTCTGAACAATCAGTTCGGCACAATGCCAAGCCTGACAATG    540
LCMV-P52-1_NP       GATGTGAAGGACTCATCACTTCTGAACAATCAGTTCGGCACAATGCCAAGCCTGACAATG    540
LCMV-P52-1.3_NP     GATGTGAAGGACTCATCACTTCTGAACAATCAGTTCGGCACAATGCCAAGCCTGACAATG    540
LCMV-P52-2.1_NP     GATGTGAAGGACTCATCACTTCTGAACAATCAGTTCGGCACAATGCCAAGCCTGACAATG    540
                    ************************************************************

LCMV-WE_NP          GCTTGCATGGCAAAACAGTCACAGACCCCACTCAATGATGTTGTGCAGGCACTCACAGAC    600
LCMV-P42_NP         GCTTGCATGGCAAAACAGTCACAGACCCCACTCAATGATGTTGTGCAGGCACTCACAGAC    600
LCMV-P52_NP         GCTTGCATGGCAAAACAGTCACAGACCCCACTCAATGATGTTGTGCAGGCACTCACAGAC    600
LCMV-P91_NP         GCTTGCATGGCAAAACAGTCACAGACCCCACTCAATGATGTTGTGCAGGCACTCACAGAC    600
LCMV-P52-1_NP       GCTTGCATGGCAAAACAGTCACAGACCCCACTCAATGATGTTGTGCAGGCACTCACAGAC    600
LCMV-P52-1.3_NP     GCTTGCATGGCAAAACAGTCACAGACCCCACTCAATGATGTTGTGCAGGCACTCACAGAC    600
LCMV-P52-2.1_NP     GCTTGCATGGCAAAACAGTCACAGACCCCACTCAATGATGTTGTGCAGGCACTCACAGAC    600
                    ************************************************************

LCMV-WE_NP          CTTGGCTTACTTTACACAGTCAAATACCCGAATCTCAGTGATCTTGAAAGGCTAAAGGAT    660
LCMV-P42_NP         CTTGGCTTACTTTACACAGTCAAATACCCGAATCTCAGTGATCTTGAAAGGCTAAAGGAT    660
LCMV-P52_NP         CTTGGCTTACTTTACACAGTCAAATACCCGAATCTCAGTGATCTTGAAAGGCTAAAGGAT    660
LCMV-P91_NP         CTTGGCTTACTTTACACAGTCAAATACCCGAATCTCAGTGATCTTGAAAGGCTAAAGGAT    660
LCMV-P52-1_NP       CTTGGCTTACTTTACACAGTCAAATACCCGAATCTCAGTGATCTTGAAAGGCTAAAGGAT    660
LCMV-P52-1.3_NP     CTTGGCTTACTTTACACAGTCAAATACCCGAATCTCAGTGATCTTGAAAGGCTAAAGGAT    660
LCMV-P52-2.1_NP     CTTGGCTTACTTTACACAGTCAAATACCCGAATCTCAGTGATCTTGAAAGGCTAAAGGAT    660
                    ************************************************************

LCMV-WE_NP          AAACACCCAGTTCTGGGGGTCATTACTGAACAGCAATCTAGTATCAATATCTCTGGTTAT    720
LCMV-P42_NP         AAACACCCAGTTCTGGGGGTCATTACTGAACAGCAATCTAGTATCAATATCTCTGGTTAT    720
LCMV-P52_NP         AAACACCCAGTTCTGGGGGTCATTACTGAACAGCAATCTAGTATCAATATCTCTGGTTAT    720
LCMV-P91_NP         AAACACCCAGTTCTGGGGGTCATTACTGAACAGCAATCTAGTATCAATATCTCTGGTTAT    720
LCMV-P52-1_NP       AAACACCCAGTTCTGGGGGTCATTACTGAACAGCAATCTAGTATCAATATCTCTGGTTAT    720
LCMV-P52-1.3_NP     AAACACCCAGTTCTGGGGGTCATTACTGAACAGCAATCTAGTATCAATATCTCTGGTTAT    720
LCMV-P52-2.1_NP     AAACACCCAGTTCTGGGGGTCATTACTGAACAGCAATCTAGTATCAATATCTCTGGTTAT    720
                    ************************************************************

LCMV-WE_NP          AATTTCAGTCTTGGTGCAGCTGTGAAAGCGGGGGCAGCTCTGCTAGATGGAGGGAACATG    780
LCMV-P42_NP         AATTTCAGTCTTGGTGCAGCTGTGAAAGCGGGGGCAGCTCTGCTAGATGGAGGGAACATG    780
LCMV-P52_NP         AATTTCAGTCTTGGTGCAGCTGTGAAAGCGGGGGCAGCTCTGCTAGATGGAGGGAACATG    780
LCMV-P91_NP         AATTTCAGTCTTGGTGCAGCTGTGAAAGCGGGGGCAGCTCTGCTAGATGGAGGGAACATG    780
LCMV-P52-1_NP       AATTTCAGTCTTGGTGCAGCTGTGAAAGCGGGGGCAGCTCTGCTAGATGGAGGGAACATG    780
LCMV-P52-1.3_NP     AATTTCAGTCTTGGTGCAGCTGTGAAAGCGGGGGCAGCTCTGCTAGATGGAGGGAACATG    780
LCMV-P52-2.1_NP     AATTTCAGTCTTGGTGCAGCTGTGAAAGCGGGGGCAGCTCTGCTAGATGGAGGGAACATG    780
                    ************************************************************

LCMV-WE_NP          CTGGAATCTATCTTGATCAAACCGAGCAACAGTGAGGATCTCCTAAAAGCAGTCCTCGGG    840
LCMV-P42_NP         CTGGAATCTATCTTGATCAAACCGAGCAACAGTGAGGATCTCCTAAAAGCAGTCCTCGGG    840
LCMV-P52_NP         CTGGAATCTATCTTGATCAAACCGAGCAACAGTGAGGATCTCCTAAAAGCAGTCCTCGGG    840
LCMV-P91_NP         CTGGAATCTATCTTGATCAAACCGAGCAACAGTGAGGATCTCCTAAAAGCAGTCCTCGGG    840
LCMV-P52-1_NP       CTGGAATCTATCTTGATCAAACCGAGCAACAGTGAGGATCTCCTAAAAGCAGTCCTCGGG    840
LCMV-P52-1.3_NP     CTGGAATCTATCTTGATCAAACCGAGCAACAGTGAGGATCTCCTAAAAGCAGTCCTCGGG    840
LCMV-P52-2.1_NP     CTGGAATCTATCTTGATCAAACCGAGCAACAGTGAGGATCTCCTAAAAGCAGTCCTCGGG    840
                    ************************************************************

LCMV-WE_NP          GCCAAGAAGAAACTCAACATGTTTGTCTCAGATCAAGTTGGAGATAGAAATCCCTATGAA    900
LCMV-P42_NP         GCCAAGAAGAAACTCAACATGTTTGTCTCAGATCAAGTTGGAGATAGAAATCCCTATGAA    900
LCMV-P52_NP         GCCAAGAAGAAACTCAACATGTTTGTCTCAGATCAAGTTGGAGATAGAAATCCCTATGAA    900
LCMV-P91_NP         GCCAAGAAGAAACTCAACATGTTTGTCTCAGATCAAGTTGGAGATAGAAATCCCTATGAA    900
LCMV-P52-1_NP       GCCAAGAAGAAACTCAACATGTTTGTCTCAGATCAAGTTGGAGATAGAAATCCCTATGAA    900
LCMV-P52-1.3_NP     GCCAAGAAGAAACTCAACATGTTTGTCTCAGATCAAGTTGGAGATAGAAATCCCTATGAA    900
LCMV-P52-2.1_NP     GCCAAAAAGAAACTCAACATGTTTGTCTCAGATCAAGTTGGAGATAGAAATCCCTATGAA    900
                    ***** ******************************************************
```

Figure 26 (cont'd)

```
LCMV-WE_NP          AACATCCTTTATAAAGTCTGTCTTTCAGGTGAAGGATGGCCATACATAGCCTGTAGAACG   960
LCMV-P42_NP         AACATCCTTTATAAAGTCTGTCTTTCAGGTGAAGGATGGCCATACATAGCCTGTAGAACG   960
LCMV-P52_NP         AACATCCTTTATAAAGTCTGTCTTTCAGGTGAAGGATGGCCATACATAGCCTGTAGAACG   960
LCMV-P91_NP         AACATCCTTTATAAAGTCTGTCTTTCAGGTGAAGGATGGCCATACATAGCCTGTAGAACG   960
LCMV-P52-1_NP       AACATCCTTTATAAAGTCTGTCTTTCAGGTGAAGGATGGCCATACATAGCCTGTAGAACG   960
LCMV-P52-1.3_NP     AACATCCTTTATAAAGTCTGTCTTTCAGGTGAAGGATGGCCATACATAGCCTGTAGAACG   960
LCMV-P52-2.1_NP     AACATCCTTTATAAAGTCTGTCTTTCAGGTGAAGGATGGCCATACATAGCCTGTAGAACG   960
                    ************************************************************

LCMV-WE_NP          TCAGTTGTGGGGAGAGCATGGGAGAACACAACAATTGATCTCACAAATGAAAAACTTGTT   1020
LCMV-P42_NP         TCAGTTGTGGGGAGAGCATGGGAGAACACAACAATTGATCTCACAAATGAAAAACTTGTT   1020
LCMV-P52_NP         TCAGTTGTGGGGAGAGCATGGGAGAACACAACAATTGATCTCACAAATGAAAAACTTGTT   1020
LCMV-P91_NP         TCAGTTGTGGGGAGAGCATGGGAGAACACAACAATTGATCTCACAAATGAAAAACTTGTT   1020
LCMV-P52-1_NP       TCAGTTGTGGGGAGAGCATGGGAGAACACAACAATTGATCTCACAAATGAAAAACTTGTT   1020
LCMV-P52-1.3_NP     TCAGTTGTGGGGAGAGCATGGGAGAACACAACAATTGATCTCACAAATGAAAAACTTGTT   1020
LCMV-P52-2.1_NP     TCAGTTGTGGGGAGAGCATGGGAGAACACAACAATTGATCTCACAAATGAAAAACTTGTT   1020
                    ************************************************************

LCMV-WE_NP          GCCAACTCATCTAGGCCAGTGCCTGGAGCAGCAGGCCCACCTCAGGTGGGCTTGAGTTAC   1080
LCMV-P42_NP         GCCAACTCATCTAGGCCAGTGCCTGGAGCAGCAGGCCCACCTCAGGTGGGCTTGAGTTAC   1080
LCMV-P52_NP         GCCAACTCATCTAGGCCAGTGCCTGGAGCAGCAGGCCCACCTCAGGTGGGCTTGAGTTAC   1080
LCMV-P91_NP         GCCAACTCATCTAGGCCAGTGCCTGGAGCAGCAGGCCCACCTCAGGTGGGCTTGAGTTAC   1080
LCMV-P52-1_NP       GCCAACTCATCTAGGCCAGTGCCTGGAGCAGCAGGCCCACCTCAGGTGGGCTTGAGTTAC   1080
LCMV-P52-1.3_NP     GCCAACTCATCTAGGCCAGTGCCTGGAGCAGCAGGCCCACCTCAGGTGGGCTTGAGTTAC   1080
LCMV-P52-2.1_NP     GCCAACTCATCTAGGCCAGTGCCTGGAGCAGCAGGCCCACCTCAGGTGGGCTTGAGTTAC   1080
                    ************************************************************

LCMV-WE_NP          AGTCAGACAATGCTGTTGAAAGACTTGATGGGAGGGATTGATCCCAATGCTCCCACATGG   1140
LCMV-P42_NP         AGTCAGACAATGCTGTTGAAAGACTTGATGGGAGGGATTGATCCCAATGCTCCCACATGG   1140
LCMV-P52_NP         AGTCAGACAATGCTGTTGAAAGACTTGATGGGAGGGATTGATCCCAATGCTCCCACATGG   1140
LCMV-P91_NP         AGTCAGACAATGCTGTTGAAAGACTTGATGGGAGGGATTGATCCCAATGCTCCCACATGG   1140
LCMV-P52-1_NP       AGTCAGACAATGCTGTTGAAAGACTTGATGGGAGGGATTGATCCCAATGCTCCCACATGG   1140
LCMV-P52-1.3_NP     AGTCAGACAATGCTGTTGAAAGACTTGATGGGAGGGATTGATCCCAATGCTCCCACATGG   1140
LCMV-P52-2.1_NP     AGTCAGACAATGCTGTTGAAAGACTTGATGGGAGGGATTGATCCCAATGCTCCCACATGG   1140
                    ************************************************************

LCMV-WE_NP          ATTGACATTGAGGGCAGGTTCAATGATCCAGTGGAGATAGCAATATTCCAACCACAAAAT   1200
LCMV-P42_NP         ATTGACATTGAGGGCAGGTTCAATGATCCAGTGGAGATAGCAATATTCCAACCACAAAAT   1200
LCMV-P52_NP         ATTGACATTGAGGGCAGGTTCAATGATCCAGTGGAGATAGCAATATTCCAACCACAAAAT   1200
LCMV-P91_NP         ATTGACATTGAGGGCAGGTTCAATGATCCAGTGGAGATAGCAATATTCCAACCACAAAAT   1200
LCMV-P52-1_NP       ATTGACATTGAGGGCAGGTTCAATGATCCAGTGGAGATAGCAATATTCCAACCACAAAAT   1200
LCMV-P52-1.3_NP     ATTGACATTGAGGGCAGGTTCAATGATCCAGTGGAGATAGCAATATTCCAACCACAAAAT   1200
LCMV-P52-2.1_NP     ATTGACATTGAGGGCAGGTTCAATGATCCAGTGGAGATAGCAATATTCCAACCACAAAAT   1200
                    ************************************************************

LCMV-WE_NP          GGGCAATTCATACATTTTTACAGGGAACCTACGGACCAGAAGCAATTCAAGCAGGACTCA   1260
LCMV-P42_NP         GGGCAATTCATACATTTTTACAGGGAACCTACGGACCAGAAGCAATTCAAGCAGGACTCA   1260
LCMV-P52_NP         GGGCAATTCATACATTTTTACAGGGAACCTACGGACCAGAAGCAATTCAAGCAGGACTCA   1260
LCMV-P91_NP         GGGCAATTCATACATTTTTACAGGGAACCTACGGACCAGAAGCAATTCAAGCAGGACTCA   1260
LCMV-P52-1_NP       GGGCAATTCATACATTTTTACAGGGAACCTACGGACCAGAAGCAATTCAAGCAGGACTCA   1260
LCMV-P52-1.3_NP     GGGCAATTCATACATTTTTACAGGGAACCTACGGACCAGAAGCAATTCAAGCAGGACTCA   1260
LCMV-P52-2.1_NP     GGGCAATTCATACATTTTTACAGGGAACCTACGGACCAGAAGCAATTCAAGCAGGACTCA   1260
                    ************************************************************

LCMV-WE_NP          AAGTATTCACACGGCATGGATCTTGCTGATCTCTTCAATGCACAGCCTGGGCTGACCTCA   1320
LCMV-P42_NP         AAGTATTCACACGGCATGGATCTTGCTGATCTCTTCAATGCACAGCCTGGGCTGACCTCA   1320
LCMV-P52_NP         AAGTATTCACACGGCATGGATCTTGCTGATCTCTTCAATGCACAGCCTGGGCTGACCTCA   1320
LCMV-P91_NP         AAGTATTCACACGGCATGGATCTTGCTGATCTCTTCAATGCACAGCCTGGGCTGACCTCA   1320
LCMV-P52-1_NP       AAGTATTCACACGGCATGGATCTTGCTGATCTCTTCAATGCACAGCCTGGGCTGACCTCA   1320
LCMV-P52-1.3_NP     AAGTATTCACACGGCATGGATCTTGCTGATCTCTTCAATGCACAGCCTGGGCTGACCTCA   1320
LCMV-P52-2.1_NP     AAGTATTCACACGGCATGGATCTTGCTGATCTCTTCAATGCACAGCCTGGGCTGACCTCA   1320
                    ************************************************************

LCMV-WE_NP          TCAGTTATAGGTGCTCTCCCACAAGGGATGGTTTTGAGCTGTCAAGGTTCTGATGACATC   1380
LCMV-P42_NP         TCAGTTATAGGTGCTCTCCCACAAGGGATGGTTTTGAGCTGTCAAGGTTCTGATGACATC   1380
LCMV-P52_NP         TCAGTTATAGGTGCTCTCCCACAAGGGATGGTTTTGAGCTGTCAAGGTTCTGATGACATC   1380
LCMV-P91_NP         TCAGTTATAGGTGCTCTCCCACAAGGGATGGTTTTGAGCTGTCAAGGTTCTGATGACATC   1380
LCMV-P52-1_NP       TCAGTTATAGGTGCTCTCCCACAAGGGATGGTTTTGAGCTGTCAAGGTTCTGATGACATC   1380
LCMV-P52-1.3_NP     TCAGTTATAGGTGCTCTCCCACAAGGGATGGTTTTGAGCTGTCAAGGTTCTGATGACATC   1380
LCMV-P52-2.1_NP     TCAGTTATAGGTGCTCTCCCACAAGGGATGGTTTTGAGCTGTCAAGGTTCTGATGACATC   1380
                    ************************************************************
```

Figure 26 (cont'd)

```
LCMV-WE_NP          AGAAAGCTTCTGGACTCACAAAATAGAAGGGACATAAAACTCATTGATGTTGAGATGACC     1440
LCMV-P42_NP         AGAAAGCTTCTGGACTCACAAAATAGAAGGGACATAAAACTCATTGATGTTGAGATGACC     1440
LCMV-P52_NP         AGAAAGCTTCTGGACTCACAAAAYAGAAGGGACATAAAACTCATTGATGTTGAGATGACC     1440
LCMV-P91_NP         AGAAAGCTTCTGGACTCACAAAATAGAAGGGACATAAAACTCATTGATGTTGAGATGACC     1440
LCMV-P52-1_NP       AGAAAGCTTCTGGACTCACAAAATAGAAGGGACATAAAACTCATTGATGTTGAGATGACC     1440
LCMV-P52-1.3_NP     AGAAAGCTTCTGGACTCACAAAATAGAAGGGACATAAAACTCATTGATGTTGAGATGACC     1440
LCMV-P52-2.1_NP     AGAAAGCTTCTGGACTCACAAAATAGAAGGGACATAAAACTCATTGATGTTGAGATGACC     1440
                    *********************** ************************************

LCMV-WE_NP          AAGGAGGCCTCAAGAGAATATGAAGATAAAGTGTGGGACAAATATGGCTGGCTATGCAAA     1500
LCMV-P42_NP         AAGGAGGCCTCAAGAGAATATGAAGATAAAGTGTGGGACAAATATGGCTGGCTATGCAAA     1500
LCMV-P52_NP         AAGGAGGCCTCAAGAGAATATGAAGATAAAGTGTGGGACAAATATGGCTGGCTATGCAAA     1500
LCMV-P91_NP         AAGGAGGCCTCAAGAGAATATGAAGATAAAGTGTGGGACAAATATGGCTGGCTATGCAAA     1500
LCMV-P52-1_NP       AAGGAGGCCTCAAGAGAATATGAAGATAAAGTGTGGGACAAATATGGCTGGCTATGCAAA     1500
LCMV-P52-1.3_NP     AAGGAGGCCTCAAGAGAATATGAAGATAAAGTGTGGGACAAATATGGCTGGCTATGCAAA     1500
LCMV-P52-2.1_NP     AAGGAGGCCTCAAGAGAATATGAAGATAAAGTGTGGGACAAATATGGCTGGCTATGCAAA     1500
                    ************************************************************

LCMV-WE_NP          ATGCACACTGGGGTAGTGAGAGACAAAAAGAAGAAAGAGATCACCCCACACTGTGCACTC     1560
LCMV-P42_NP         ATGCACACTGGGGTAGTGAGAGACAAAAAGAAGAAAGAGATCACCCCACACTGTGCACTC     1560
LCMV-P52_NP         ATGCACACTGGGGTAGTGAGAGACAAAAAGAAGAAAGAGATCACCCCACACTGTGCACTC     1560
LCMV-P91_NP         ATGCACACTGGGGTAGTGAGAGACAAAAAGAAGAAAGAGATCACCCCACACTGTGCACTC     1560
LCMV-P52-1_NP       ATGCACACTGGGGTAGTGAGAGACAAAAAGAAGAAAGAGATCACCCCACACTGTGCACTC     1560
LCMV-P52-1.3_NP     ATGCACACTGGGGTAGTGAGAGACAAAAAGAAGAAAGAGATCACCCCACACTGTGCACTC     1560
LCMV-P52-2.1_NP     ATGCACACTGGGGTAGTGAGAGACAAAAAGAAGAAAGAGATCACCCCACACTGTGCACTC     1560
                    ************************************************************

LCMV-WE_NP          ATGGACTGCATCATTTTTGAGAGTGCTTCCAAGGCAAGACTCCCTGATCTAAAAACCGTT     1620
LCMV-P42_NP         ATGGACTGCATCATTTTTGAGAGTGCTTCCAAGGCAAGACTCCCTGATCTAAAAACCGTT     1620
LCMV-P52_NP         ATGGACTGCATCATTTTTGAGAGTGCTTCCAAGGCAAGACTCCCTGATCTAAAAACCGTT     1620
LCMV-P91_NP         ATGGACTGCATCATTTTTGAGAGTGCTTCCAAGGCAAGACTCCCTGATCTAAAAACCGTT     1620
LCMV-P52-1_NP       ATGGACTGCATCATTTTTGAGAGTGCTTCCAAGGCAAGACTCCCTGATCTAAAAACCGTT     1620
LCMV-P52-1.3_NP     ATGGACTGCATCATTTTTGAGAGTGCTTCCAAGGCAAGACTCCCTGATCTAAAAACCGTT     1620
LCMV-P52-2.1_NP     ATGGACTGCATCATTTTTGAGAGTGCTTCCAAGGCAAGACTCCCTGATCTAAAAACCGTT     1620
                    ************************************************************

LCMV-WE_NP          CACAACATCCTGCCACATGATTTAATCTTCAGAGGACCCAATGTTGTGACACTCTAA        1677
LCMV-P42_NP         CACAACATCCTGCCACATGATTTAATCTTCAGAGGACCCAATGTTGTGACACTCTAA        1677
LCMV-P52_NP         CACAACATCCTGCCACATGATTTAATCTTCAGAGGACCCAATGTTGTGACACTCTAA        1677
LCMV-P91_NP         CACAACATCCTGCCACATGATTTAATCTTCAGAGGACCCAATGTTGTGACACTCTAA        1677
LCMV-P52-1_NP       CACAACATCCTGCCACATGATTTAATCTTCAGAGGACCCAATGTTGTGACACTCTAA        1677
LCMV-P52-1.3_NP     CACAACATCCTGCCACATGATTTAATCTTCAGAGGACCCAATGTTGTGACACTCTAA        1677
LCMV-P52-2.1_NP     CACAACATCCTGCCACATGATTTAATCTTCAGAGGACCCAATGTTGTGACACTCTAA        1677
                    *********************************************************

LCMV-WE_NP:      SEQ ID NO: 11
LCMV-P42_NP:     SEQ ID NO: 19
LCMV-P52_NP:     SEQ ID NO: 27
LCMV-P91_NP:     SEQ ID NO: 35
LCMV-P52-1_NP:   SEQ ID NO: 43
LCMV-P52-1.3_NP: SEQ ID NO: 51
LCMV-P52-2.1_NP: SEQ ID NO: 59
```

Source: 1-3376 Segment = S
Protein: Nucleoprotein
Gene: NP
Gene: 1640-3316 complement
Sequence Alignment: Aminoacid

```
LCMV-WE_NP          MSLSKEVKSFQWTQALRRELQSFTSDVKAAVIKDATSLLNGLDFSEVSNVQRIMRKERRD   60
LCMV-P42_NP         MSLSKEVKSFQWTQALRRELQSFTSDVKAAVIKDATSLLNGLDFSEVSNVQRIMRKERRD   60
LCMV-P52_NP         MSLSKEVKSFQWTQALRRELQSFTSDVKAAVIKDATSLLNGLDFSEVSNVQRIMRKERRD   60
LCMV-P91_NP         MSLSKEVKSFQWTQALRRELQSFTSDVKAAVIKDATSLLNGLDFSEVSNVQRIMRKERRD   60
LCMV-P52-1_NP       MSLSKEVKSFQWTQALRRELQSFTSDVKAAVIKDATSLLNGLDFSEVSNVQRIMRKERRD   60
LCMV-P52-1.3_NP     MSLSKEVKSFQWTQALRRELQSFTSDVKAAVIKDATSLLNGLDFSEVSNVQRIMRKERRD   60
LCMV-P52-2.1_NP     MSLSKEVKSFQWTQALRRELQSFTSDVKAAVIKDATSLLNGLDFSEVSNVQRIMRKERRD   60
                    ************************************************************

LCMV-WE_NP          DKDLQRLRSLNQTVHSLVDLKSTSKKNVLKVGRLSAEELMTLAADLEKLKAKIMRTERPQ   120
LCMV-P42_NP         DKDLQRLRSLNQTVHSLVDLKSTSKKNVLKVGRLSAEELMTLAADLEKLKAKIMRTERPQ   120
LCMV-P52_NP         DKDLQRLRSLNQTVHSLVDLKSTSKKNVLKVGRLSAEELMTLAADLEKLKAKIMRTERPQ   120
LCMV-P91_NP         DKDLQRLRSLNQTVHSLVDLKSTSKKNVLKVGRLSAEELMTLAADLEKLKAKIMRTERPQ   120
LCMV-P52-1_NP       DKDLQRLRSLNQTVHSLVDLKSTSKKNVLKVGRLSAEELMTLAADLEKLKAKIMRTERPQ   120
LCMV-P52-1.3_NP     DKDLQRLRSLNQTVHSLVDLKSTSKKNVLKVGRLSAEELMTLAADLEKLKAKIMRTERPQ   120
LCMV-P52-2.1_NP     DKDLQRLRSLNQTVHSLVDLKSTSKKNVLKVGRLSAEELMTLAADLEKLKAKIMRTERPQ   120
                    ************************************************************

LCMV-WE_NP          ASGVYMGNLTAQQLDQRSQILQMVGMRRPQQGASGVVRVWDVKDSSLLNNQFGTMPSLTM   180
LCMV-P42_NP         ASGVYMGNLTAQQLDQRSQILQMVGMRRPQQGASGVVRVWDVKDSSLLNNQFGTMPSLTM   180
LCMV-P52_NP         ASGVYMGNLTAQQLDQRSQILQMVGMRRPQQGASGVVRVWDVKDSSLLNNQFGTMPSLTM   180
LCMV-P91_NP         ASGVYMGNLTAQQLDQRSQILQMVGMRRPQQGASGVVRVWDVKDSSLLNNQFGTMPSLTM   180
LCMV-P52-1_NP       ASGVYMGNLTAQQLDQRSQILQMVGMRRPQQGASGVVRVWDVKDSSLLNNQFGTMPSLTM   180
LCMV-P52-1.3_NP     ASGVYMGNLTAQQLDQRSQILQMVGMRRPQQGASGVVRVWDVKDSSLLNNQFGTMPSLTM   180
LCMV-P52-2.1_NP     ASGVYMGNLTAQQLDQRSQILQMVGMRRPQQGASGVVRVWDVKDSSLLNNQFGTMPSLTM   180
                    ************************************************************

LCMV-WE_NP          ACMAKQSQTPLNDVVQALTDLGLLYTVKYPNLSDLERLKDKHPVLGVITEQQSSINISGY   240
LCMV-P42_NP         ACMAKQSQTPLNDVVQALTDLGLLYTVKYPNLSDLERLKDKHPVLGVITEQQSSINISGY   240
LCMV-P52_NP         ACMAKQSQTPLNDVVQALTDLGLLYTVKYPNLSDLERLKDKHPVLGVITEQQSSINISGY   240
LCMV-P91_NP         ACMAKQSQTPLNDVVQALTDLGLLYTVKYPNLSDLERLKDKHPVLGVITEQQSSINISGY   240
LCMV-P52-1_NP       ACMAKQSQTPLNDVVQALTDLGLLYTVKYPNLSDLERLKDKHPVLGVITEQQSSINISGY   240
LCMV-P52-1.3_NP     ACMAKQSQTPLNDVVQALTDLGLLYTVKYPNLSDLERLKDKHPVLGVITEQQSSINISGY   240
LCMV-P52-2.1_NP     ACMAKQSQTPLNDVVQALTDLGLLYTVKYPNLSDLERLKDKHPVLGVITEQQSSINISGY   240
                    ************************************************************

LCMV-WE_NP          NFSLGAAVKAGAALLDGGNMLESILIKPSNSEDLLKAVLGAKKKLNMFVSDQVGDRNPYE   300
LCMV-P42_NP         NFSLGAAVKAGAALLDGGNMLESILIKPSNSEDLLKAVLGAKKKLNMFVSDQVGDRNPYE   300
LCMV-P52_NP         NFSLGAAVKAGAALLDGGNMLESILIKPSNSEDLLKAVLGAKKKLNMFVSDQVGDRNPYE   300
LCMV-P91_NP         NFSLGAAVKAGAALLDGGNMLESILIKPSNSEDLLKAVLGAKKKLNMFVSDQVGDRNPYE   300
LCMV-P52-1_NP       NFSLGAAVKAGAALLDGGNMLESILIKPSNSEDLLKAVLGAKKKLNMFVSDQVGDRNPYE   300
LCMV-P52-1.3_NP     NFSLGAAVKAGAALLDGGNMLESILIKPSNSEDLLKAVLGAKKKLNMFVSDQVGDRNPYE   300
LCMV-P52-2.1_NP     NFSLGAAVKAGAALLDGGNMLESILIKPSNSEDLLKAVLGAKKKLNMFVSDQVGDRNPYE   300
                    ************************************************************

LCMV-WE_NP          NILYKVCLSGEGWPYIACRTSVVGRAWENTTIDLTNEKLVANSSRPVPGAAGPPQVGLSY   360
LCMV-P42_NP         NILYKVCLSGEGWPYIACRTSVVGRAWENTTIDLTNEKLVANSSRPVPGAAGPPQVGLSY   360
LCMV-P52_NP         NILYKVCLSGEGWPYIACRTSVVGRAWENTTIDLTNEKLVANSSRPVPGAAGPPQVGLSY   360
LCMV-P91_NP         NILYKVCLSGEGWPYIACRTSVVGRAWENTTIDLTNEKLVANSSRPVPGAAGPPQVGLSY   360
LCMV-P52-1_NP       NILYKVCLSGEGWPYIACRTSVVGRAWENTTIDLTNEKLVANSSRPVPGAAGPPQVGLSY   360
LCMV-P52-1.3_NP     NILYKVCLSGEGWPYIACRTSVVGRAWENTTIDLTNEKLVANSSRPVPGAAGPPQVGLSY   360
LCMV-P52-2.1_NP     NILYKVCLSGEGWPYIACRTSVVGRAWENTTIDLTNEKLVANSSRPVPGAAGPPQVGLSY   360
                    ************************************************************

LCMV-WE_NP          SQTMLLKDLMGGIDPNAPTWIDIEGRFNDPVEIAIFQPQNGQFIHFYREPTDQKQFKQDS   420
LCMV-P42_NP         SQTMLLKDLMGGIDPNAPTWIDIEGRFNDPVEIAIFQPQNGQFIHFYREPTDQKQFKQDS   420
LCMV-P52_NP         SQTMLLKDLMGGIDPNAPTWIDIEGRFNDPVEIAIFQPQNGQFIHFYREPTDQKQFKQDS   420
LCMV-P91_NP         SQTMLLKDLMGGIDPNAPTWIDIEGRFNDPVEIAIFQPQNGQFIHFYREPTDQKQFKQDS   420
LCMV-P52-1_NP       SQTMLLKDLMGGIDPNAPTWIDIEGRFNDPVEIAIFQPQNGQFIHFYREPTDQKQFKQDS   420
LCMV-P52-1.3_NP     SQTMLLKDLMGGIDPNAPTWIDIEGRFNDPVEIAIFQPQNGQFIHFYREPTDQKQFKQDS   420
LCMV-P52-2.1_NP     SQTMLLKDLMGGIDPNAPTWIDIEGRFNDPVEIAIFQPQNGQFIHFYREPTDQKQFKQDS   420
                    ************************************************************
```

Figure 26 (cont'd)

```
LCMV-WE_NP          KYSHGMDLADLFNAQPGLTSSVIGALPQGMVLSCQGSDDIRKLLDSQNRRDIKLIDVEMT     480
LCMV-P42_NP         KYSHGMDLADLFNAQPGLTSSVIGALPQGMVLSCQGSDDIRKLLDSQNRRDIKLIDVEMT     480
LCMV-P52_NP         KYSHGMDLADLFNAQPGLTSSVIGALPQGMVLSCQGSDDIRKLLDSQNRRDIKLIDVEMT     480
LCMV-P91_NP         KYSHGMDLADLFNAQPGLTSSVIGALPQGMVLSCQGSDDIRKLLDSQNRRDIKLIDVEMT     480
LCMV-P52-1_NP       KYSHGMDLADLFNAQPGLTSSVIGALPQGMVLSCQGSDDIRKLLDSQNRRDIKLIDVEMT     480
LCMV-P52-1.3_NP     KYSHGMDLADLFNAQPGLTSSVIGALPQGMVLSCQGSDDIRKLLDSQNRRDIKLIDVEMT     480
LCMV-P52-2.1_NP     KYSHGMDLADLFNAQPGLTSSVIGALPQGMVLSCQGSDDIRKLLDSQNRRDIKLIDVEMT     480
                    ************************************************************

LCMV-WE_NP          KEASREYEDKVWDKYGWLCKMHTGVVRDKKKKEITPHCALMDCIIFESASKARLPDLKTV     540
LCMV-P42_NP         KEASREYEDKVWDKYGWLCKMHTGVVRDKKKKEITPHCALMDCIIFESASKARLPDLKTV     540
LCMV-P52_NP         KEASREYEDKVWDKYGWLCKMHTGVVRDKKKKEITPHCALMDCIIFESASKARLPDLKTV     540
LCMV-P91_NP         KEASREYEDKVWDKYGWLCKMHTGVVRDKKKKEITPHCALMDCIIFESASKARLPDLKTV     540
LCMV-P52-1_NP       KEASREYEDKVWDKYGWLCKMHTGVVRDKKKKEITPHCALMDCIIFESASKARLPDLKTV     540
LCMV-P52-1.3_NP     KEASREYEDKVWDKYGWLCKMHTGVVRDKKKKEITPHCALMDCIIFESASKARLPDLKTV     540
LCMV-P52-2.1_NP     KEASREYEDKVWDKYGWLCKMHTGVVRDKKKKEITPHCALMDCIIFESASKARLPDLKTV     540
                    ************************************************************

LCMV-WE_NP          HNILPHDLIFRGPNVVTL          558
LCMV-P42_NP         HNILPHDLIFRGPNVVTL          558
LCMV-P52_NP         HNILPHDLIFRGPNVVTL          558
LCMV-P91_NP         HNILPHDLIFRGPNVVTL          558
LCMV-P52-1_NP       HNILPHDLIFRGPNVVTL          558
LCMV-P52-1.3_NP     HNILPHDLIFRGPNVVTL          558
LCMV-P52-2.1_NP     HNILPHDLIFRGPNVVTL          558
                    ******************
```

```
LCMV-WE_NP:      SEQ ID NO: 12
LCMV-P42_NP:     SEQ ID NO: 20
LCMV-P52_NP:     SEQ ID NO: 28
LCMV-P91_NP:     SEQ ID NO: 36
LCMV-P52-1_NP:   SEQ ID NO: 44
LCMV-P52-1.3_NP: SEQ ID NO: 52
LCMV-P52-2.1_NP: SEQ ID NO: 60
```

Source: 1-7235 Segment = L
Protein: RING finger protein Z
Gene: ZP
Gene: 90-362
Sequence Alignment: Nucleotide

```
LCMV-WE_ZP           ATGGGCCAAGGCAAGTCCAAAGAAGAAAGGGACACCAGCAATACAGGCAGAGCAGAGCTT    60
LCMV-P42_ZP          ATGGGCCAAGGCAAGTCCAAAGAAGAAAGGGACACCAGCAATACAGGCAGAGCAGAGCTT    60
LCMV-P52_ZP          ATGGGCCAAGGCAAGTCCAAAGAAGAAAGGGACACCAGCAATACAGGCAGAGCAGAGCTT    60
LCMV-P91_ZP          ATGGGCCAAGGCAAGTCCAAAGAAGAAAGGGACACCAGCAATACAGGCAGAGCAGAGCTT    60
LCMV-P52-1_ZP        ATGGGCCAAGGCAAGTCCAAAGAAGAAAGGGACACCAGCAATACAGGCAGAGCAGAGCTT    60
LCMV-P52-1.3_ZP      ATGGGCCAAGGCAAGTCCAAAGAAGAAAGGGACACCAGCAATACAGGCAGAGCAGAGCTT    60
LCMV-P52-2.1_ZP      ATGGGCCAAGGCAAGTCCAAAGAAGAAAGGGACACCAGCAATACAGGCAGAGCAGAGCTT    60
                     ************************************************************

LCMV-WE_ZP           TTGCCAGACACCACCTATCTTGGTCCTCTAAATTGTAAATCATGTTGGCAGAAATTTGAC    120
LCMV-P42_ZP          TTGCCAGACACCACCTATCTTGGTCCTCTAAATTGTAAATCATGTTGGCAGAAATTTGAC    120
LCMV-P52_ZP          TTGCCAGACACCACCTATCTTGGTCCTCTAAATTGTAAATCATGTTGGCAGAAATTTGAC    120
LCMV-P91_ZP          TTGCCAGACACCACCTATCTTGGTCCTCTAAATTGTAAATCATGTTGGCAGAAATTTGAC    120
LCMV-P52-1_ZP        TTGCCAGACACCACCTATCTTGGTCCTCTAAATTGTAAATCATGTTGGCAGAAATTTGAC    120
LCMV-P52-1.3_ZP      TTGCCAGACACCACCTATCTTGGTCCTCTAAATTGTAAATCATGTTGGCAGAAATTTGAC    120
LCMV-P52-2.1_ZP      TTGCCAGACACCACCTATCTTGGTCCTCTAAATTGTAAATCATGTTGGCAGAAATTTGAC    120
                     ************************************************************

LCMV-WE_ZP           AGCTTGGTTAGATGCCATGACCACTATCTTTGCAGACACTGTCTGAATCTCCTGCTGTCA    180
LCMV-P42_ZP          AGCTTGGTTAGATGCCATGACCACTATCTTTGCAGACACTGTCTGAATCTCCTGCTGTCA    180
LCMV-P52_ZP          AGCTTGGTTAGATGCCATGACCACTATCTTTGCAGACACTGTCTGAATCTCCTGCTGTCA    180
LCMV-P91_ZP          AGCTTGGTTAGATGCCATGACCACTATCTTTGCAGACACTGTCTGAATCTCCTGCTGTCA    180
LCMV-P52-1_ZP        AGCTTGGTTAGATGCCATGACCACTATCTTTGCAGACACTGTCTGAATCTCCTGCTGTCA    180
LCMV-P52-1.3_ZP      AGCTTGGTTAGATGCCATGACCACTATCTTTGCAGACACTGTCTGAATCTCCTGCTGTCA    180
LCMV-P52-2.1_ZP      AGCTTGGTTAGATGCCATGACCACTATCTTTGCAGACACTGTCTGAATCTCCTGCTGTCA    180
                     ************************************************************

LCMV-WE_ZP           GTTTCCGACAGATGTCCTCTCTGTAAGTATCCACTGCCAACCAAACTGAAGGTGTCAACA    240
LCMV-P42_ZP          GTTTCCGACAGATGTCCTCTCTGTAAGTATCCACTGCCAACCAAACTGAAGGTGTCAACA    240
LCMV-P52_ZP          GTTTCCGACAGATGTCCTCTCTGTAAGTATCCACTGCCAACCAAACTGAAGGTGTCAACA    240
LCMV-P91_ZP          GTTTCCGACAGATGTCCTCTCTGTAAGTATCCACTGCCAACCAAACTGAAGGTGTCAACA    240
LCMV-P52-1_ZP        GTTTCCGACAGATGTCCTCTCTGTAAGTATCCACTGCCAACCAAACTGAAGGTGTCAACA    240
LCMV-P52-1.3_ZP      GTTTCCGACAGATGTCCTCTCTGTAAGTATCCACTGCCAACCAAACTGAAGGTGTCAACA    240
LCMV-P52-2.1_ZP      GTTTCCGACAGATGTCCTCTCTGTAAGTATCCACTGCCAACCAAACTGAAGGTGTCAACA    240
                     ************************************************************

LCMV-WE_ZP           GTCCCAAGCTCCCCACCTCCCTATGAGGAGTGA    273
LCMV-P42_ZP          GTCCCAAGCTCCCCACCTCCCTATGAGGAGTGA    273
LCMV-P52_ZP          GTCCCAAGCTCCCCACCTCCCTATGAGGAGTGA    273
LCMV-P91_ZP          GTCCCAAGCTCCCCACCTCCCTATGAGGAGTGA    273
LCMV-P52-1_ZP        GTCCCAAGCTCCCCACCTCCCTATGAGGAGTGA    273
LCMV-P52-1.3_ZP      GTCCCAAGCTCCCCACCTCCCTATGAGGAGTGA    273
LCMV-P52-2.1_ZP      GTCCCAAGCTCCCCACCTCCCTATGAGGAGTGA    273
                     *********************************
```

LCMV-WE_ZP: SEQ ID NO: 13
LCMV-P42_ZP: SEQ ID NO: 21
LCMV-P52_ZP: SEQ ID NO: 29
LCMV-P91_ZP: SEQ ID NO: 37
LCMV-P52-1_ZP: SEQ ID NO: 45
LCMV-P52-1.3_ZP: SEQ ID NO: 53
LCMV-P52-2.1_ZP: SEQ ID NO: 61

Source: 1-7235 Segment = L
Protein: RING finger protein Z
Gene: ZP
Gene: 90-362
Sequence Alignment: Aminoacid

```
LCMV-WE_ZP          MGQGKSKEERDTSNTGRAELLPDTTYLGPLNCKSCWQKFDSLVRCHDHYLCRHCLNLLLS     60
LCMV-P42_ZP         MGQGKSKEERDTSNTGRAELLPDTTYLGPLNCKSCWQKFDSLVRCHDHYLCRHCLNLLLS     60
LCMV-P52_ZP         MGQGKSKEERDTSNTGRAELLPDTTYLGPLNCKSCWQKFDSLVRCHDHYLCRHCLNLLLS     60
LCMV-P91_ZP         MGQGKSKEERDTSNTGRAELLPDTTYLGPLNCKSCWQKFDSLVRCHDHYLCRHCLNLLLS     60
LCMV-P52-1_ZP       MGQGKSKEERDTSNTGRAELLPDTTYLGPLNCKSCWQKFDSLVRCHDHYLCRHCLNLLLS     60
LCMV-P52-1.3_ZP     MGQGKSKEERDTSNTGRAELLPDTTYLGPLNCKSCWQKFDSLVRCHDHYLCRHCLNLLLS     60
LCMV-P52-2.1_ZP     MGQGKSKEERDTSNTGRAELLPDTTYLGPLNCKSCWQKFDSLVRCHDHYLCRHCLNLLLS     60
                    ************************************************************

LCMV-WE_ZP          VSDRCPLCKYPLPTKLKVSTVPSSPPPYEE     90
LCMV-P42_ZP         VSDRCPLCKYPLPTKLKVSTVPSSPPPYEE     90
LCMV-P52_ZP         VSDRCPLCKYPLPTKLKVSTVPSSPPPYEE     90
LCMV-P91_ZP         VSDRCPLCKYPLPTKLKVSTVPSSPPPYEE     90
LCMV-P52-1_ZP       VSDRCPLCKYPLPTKLKVSTVPSSPPPYEE     90
LCMV-P52-1.3_ZP     VSDRCPLCKYPLPTKLKVSTVPSSPPPYEE     90
LCMV-P52-2.1_ZP     VSDRCPLCKYPLPTKLKVSTVPSSPPPYEE     90
                    ******************************
```

LCMV-WE_ZP: SEQ ID NO: 14
LCMV-P42_ZP: SEQ ID NO: 22
LCMV-P52_ZP: SEQ ID NO: 30
LCMV-P91_ZP: SEQ ID NO: 38
LCMV-P52-1_ZP: SEQ ID NO: 46
LCMV-P52-1.3_ZP: SEQ ID NO: 54
LCMV-P52-2.1_ZP: SEQ ID NO: 62

Source: 1-7235 Segment = L
Protein: RNA-directed RNA polymerase L
Gene: LP
Gene: 574-7203 complement
Sequence Alignment: Nucleotide

```
LCMV-WE_LP          ATGGATGAAACTATTGCAGATTTGAGAGAGTTGTGTCTAAATTACATAGAACAGGACGAG     60
LCMV-P42_LP         ATGGATGAAACTATTGCAGATTTGAGAGAGTTGTGTCTAAATTACATAGAACAGGACGAG     60
LCMV-P52_LP         ATGGATGAAACTATTGCAGATTTGAGAGAGTTGTGTCTAAATTACATAGAACAGGACGAG     60
LCMV-P91_LP         ATGGATGAAACTATTGCAGATTTGAGAGAGTTGTGTCTAAATTACATAGAACAGGACGAG     60
LCMV-P52-1_LP       ATGGATGAAACTATTGCAGATTTGAGAGAGTTGTGTCTAAATTACATAGAACAGGACGAG     60
LCMV-P52-1.3_LP     ATGGATGAAACTATTGCAGATTTGAGAGAGTTGTGTCTAAATTACATAGAACAGGACGAG     60
LCMV-P52-2.1_LP     ATGGATGAAACTATTGCAGATTTGAGAGAGTTGTGTCTAAATTACATAGAACAGGACGAA     60
                    *********************************************************** 

LCMV-WE_LP          AGGCTGTCAAGGCAAAAACTCAACTTCCTGGGACAAAGAGAACCCAGAATGGTGCTAATT     120
LCMV-P42_LP         AGGCTGTCAAGGCAAAAACTCAACTTCCTGGGACAAAGAGAACCCAGAATGGTGCTAATT     120
LCMV-P52_LP         AGGCTGTCAAGGCAAAAACTCAACTTCCTGGGACAAAGAGAACCCAGAATGGTGCTAATT     120
LCMV-P91_LP         AGGCTGTCAAGGCAAAAACTCAACTTCCTGGGACAAAGAGAACCCAGAATGGTGCTAATT     120
LCMV-P52-1_LP       AGGCTGTCAAGGCAAAAACTCAACTTCCTGGGACAAAGAGAACCCAGAATGGTGCTAATT     120
LCMV-P52-1.3_LP     AGGCTGTCAAGGCAAAAACTCAACTTCCTGGGACAAAGAGAACCCAGAATGGTGCTAATT     120
LCMV-P52-2.1_LP     AGGCTGTCAAGGCAAAAACTCAACTTCCTGGGACAAAGAGAACCCAGAATGGTGCTAATT     120
                    ************************************************************

LCMV-WE_LP          GAGGGACTCAAATTGTTATCACGCTGTATAGAGATAGACAGTGCAGACAAAAGTGGTTGC     180
LCMV-P42_LP         GAGGGACTCAAATTGTTATCACGCTGTATAGAGATAGACAGTGCAGACAAAAGTGGTTGC     180
LCMV-P52_LP         GAGGGACTCAAATTGTTATCACGCTGTATAGAGATAGACAGTGCAGACAAAAGTGGTTGC     180
LCMV-P91_LP         GAGGGACTCAAATTGTTATCACGCTGTATAGAGATAGACAGTGCAGACAAAAGTGGTTGC     180
LCMV-P52-1_LP       GAGGGACTCAAATTGTTATCACGCTGTATAGAGATAGACAGTGCAGACAAAAGTGGTTGC     180
LCMV-P52-1.3_LP     GAGGGACTCAAATTGTTATCACGCTGTATAGAGATAGACAGTGCAGACAAAAGTGGTTGC     180
LCMV-P52-2.1_LP     GAGGGACTCAAATTGTTATCACGCTGTATAGAGATAGACAGTGCAGACAAAAGTGGTTGC     180
                    ************************************************************

LCMV-WE_LP          ATACACAACCACGATGACAAATCTGTTGAAACAATCCTAATAGACTCTGGGATTGTGTGT     240
LCMV-P42_LP         ATACACAACCACGATGACAAATCTGTTGAAACAATCCTAATAGACTCTGGGATTGTGTGT     240
LCMV-P52_LP         ATACACAACCACGATGACAAATCTGTTGAAACAATCCTAATAGACTCTGGGATTGTGTGT     240
LCMV-P91_LP         ATACACAACCACGATGACAAATCTGTTGAAACAATCCTAATAGACTCTGGGATTGTGTGT     240
LCMV-P52-1_LP       ATACACAACCACGATGACAAATCTGTTGAAACAATCCTAATAGACTCTGGGATTGTGTGT     240
LCMV-P52-1.3_LP     ATACACAACCACGATGACAAATCTGTTGAAACAATCCTAATAGACTCTGGGATTGTGTGT     240
LCMV-P52-2.1_LP     ATACACAACCACGATGACAAATCTGTTGAAACAATCCTAATAGACTCTGGGATTGTGTGT     240
                    ************************************************************

LCMV-WE_LP          CCAGGACTGCCACTCATCATCCCTGATGGTTATAAGTTGATTGACAATTCCCTTATTCTT     300
LCMV-P42_LP         CCAGGACTGCCACTCATCATCCCTGATGGTTATAAGTTGATTGACAATTCCCTTATTCTT     300
LCMV-P52_LP         CCAGGACTGCCACTCATCATCCCTGATGGTTATAAGTTGATTGACAATTCCCTTATTCTT     300
LCMV-P91_LP         CCAGGACTGCCACTCATCATCCCTGATGGTTATAAGTTGATTGACAATTCCCTTATTCTT     300
LCMV-P52-1_LP       CCAGGACTGCCACTCATCATCCCTGATGGTTATAAGTTGATTGACAATTCCCTTATTCTT     300
LCMV-P52-1.3_LP     CCAGGACTGCCACTCATCATCCCTGATGGTTATAAGTTGATTGACAATTCCCTTATTCTT     300
LCMV-P52-2.1_LP     CCAGGACTGCCACTCATCATCCCTGATGGTTATAAGTTGATTGACAATTCCCTTATTCTT     300
                    ************************************************************

LCMV-WE_LP          CTTGAATGTTTTGTTAGAAGCACACCAGCTAGTTTTGAAAAGAAGTTCATTGAGGACACC     360
LCMV-P42_LP         CTTGAATGTTTTGTTAGAAGCACACCAGCTAGTTTTGAAAAGAAGTTCATTGAGGACACC     360
LCMV-P52_LP         CTTGAATGTTTTGTTAGAAGCACACCAGCTAGTTTTGAAAAGAAGTTCATTGAGGACACC     360
LCMV-P91_LP         CTTGAATGTTTTGTTAGAAGCACACCAGCTAGTTTTGAAAAGAAGTTCATTGAGGACACC     360
LCMV-P52-1_LP       CTTGAATGTTTTGTTAGAAGCACACCAGCTAGTTTTGAAAAGAAGTTCATTGAGGACACC     360
LCMV-P52-1.3_LP     CTTGAATGTTTTGTTAGAAGCACACCAGCTAGTTTTGAAAAGAAGTTCATTGAGGACACC     360
LCMV-P52-2.1_LP     CTTGAATGTTTTGTTAGAAGCACACCAGCTAGTTTTGAAAAGAAGTTCATTGAGGACACC     360
                    ************************************************************

LCMV-WE_LP          AACAAACTAGCATGCATCAAAGAAGATCTTGCTGTTGCAGGCATCACACTGGTTCCAATA     420
LCMV-P42_LP         AACAAACTAGCATGCATCAAAGAAGATCTTGCTGTTGCAGGCATCACACTGGTTCCAATA     420
LCMV-P52_LP         AACAAACTAGCATGCATCAAAGAAGATCTTGCTGTTGCAGGCATCACACTGGTTCCAATA     420
LCMV-P91_LP         AACAAACTAGCATGCATCAAAGAAGATCTTGCTGTTGCAGGCATCACACTGGTTCCAATA     420
LCMV-P52-1_LP       AACAAACTAGCATGCATCAAAGAAGATCTTGCTGTTGCAGGCATCACACTGGTTCCAATA     420
LCMV-P52-1.3_LP     AACAAACTAGCATGCATCAAAGAAGATCTTGCTGTTGCAGGCATCACACTGGTTCCAATA     420
LCMV-P52-2.1_LP     AACAAACTAGCATGCATCAAAGAAGATCTTGCTGTTGCAGGCATCACACTGGTTCCAATA     420
                    ************************************************************
```

Figure 26 (cont'd)

```
LCMV-WE_LP          GTGGATGGTCGTTGTGATTATGATAACAGTTTCATGCCAGAATGGGTGAATTTTAAGTTC    480
LCMV-P42_LP         GTGGATGGTCGTTGTGATTATGATAACAGTTTCATGCCAGAATGGGTGAATTTTAAGTTC    480
LCMV-P52_LP         GTGGATGGTCGTTGTGATTATGATAACAGTTTCATGCCAGAATGGGTGAATTTTAAGTTC    480
LCMV-P91_LP         GTGGATGGTCGTTGTGATTATGATAACAGTTTCATGCCAGAATGGGTGAATTTTAAGTTC    480
LCMV-P52-1_LP       GTGGATGGTCGTTGTGATTATGATAACAGTTTCATGCCAGAATGGGTGAATTTTAAGTTC    480
LCMV-P52-1.3_LP     GTGGATGGTCGTTGTGATTATGATAACAGTTTCATGCCAGAATGGGTGAATTTTAAGTTC    480
LCMV-P52-2.1_LP     GTGGATGGTCGTTGTGATTATGATAACAGTTTCATGCCAGAATGGGTGAATTTTAAGTTC    480
                    ************************************************************

LCMV-WE_LP          AGAGACCTCCTATTTAAACTCCTGGAGTATTCTAGTCAAGATGAGAAAGTTTTTGAGGAG    540
LCMV-P42_LP         AGAGACCTCCTATTTAAACTCCTGGAGTATTCTAGTCAAGATGAGAAAGTTTTTGAGGAG    540
LCMV-P52_LP         AGAGACCTCCTATTTAAACTCCTGGAGTATTCTAGTCAAGATGAGAAAGTTTTTGAGGAG    540
LCMV-P91_LP         AGAGACCTCCTATTTAAACTCCTGGAGTATTCTAGTCAAGATGAGAAAGTTTTTGAGGAG    540
LCMV-P52-1_LP       AGAGACCTCCTATTTAAACTCCTGGAGTATTCTAGTCAAGATGAGAAAGTTTTTGAGGAG    540
LCMV-P52-1.3_LP     AGAGACCTCCTATTTAAACTCCTGGAGTATTCTAGTCAAGATGAGAAAGTTTTTGAGGAG    540
LCMV-P52-2.1_LP     AGAGACCTCCTATTTAAACTCCTGGAGTATTCTAGTCAAGATGAGAAAGTTTTTGAGGAG    540
                    ************************************************************

LCMV-WE_LP          TCTGAATACTTCAGGCTCTGTGAGTCTCTTAAGACCACTGTTGACAAACGTTCCGGCATG    600
LCMV-P42_LP         TCTGAATACTTCAGGCTCTGTGAGTCTCTTAAGACCACTGTTGACAAACGTTCCGGCATG    600
LCMV-P52_LP         TCTGAATACTTCAGGCTCTGTGAGTCTCTTAAGACCACTGTTGACAAACGTTCCGGCATG    600
LCMV-P91_LP         TCTGAATACTTCAGGCTCTGTGAGTCTCTTAAGACCACTGTTGACAAACGTTCCGGCATG    600
LCMV-P52-1_LP       TCTGAATACTTCAGGCTCTGTGAGTCTCTTAAGACCACTGTTGACAAACGTTCCGGCATG    600
LCMV-P52-1.3_LP     TCTGAATACTTCAGGCTCTGTGAGTCTCTTAAGACCACTGTTGACAAACGTTCCGGCATG    600
LCMV-P52-2.1_LP     TCTGAATACTTCAGGCTCTGTGAGTCTCTTAAGACCACTGTTGACAAACGTTCCGGCATG    600
                    ************************************************************

LCMV-WE_LP          GACTCAATGAAAATTTTGAAAGACGCAAGATCATTTCATAACGATGAGATTATGAAAATG    660
LCMV-P42_LP         GACTCAATGAAAATTTTGAAAGACGCAAGATCATTTCATAACGATGAGATTATGAAAATG    660
LCMV-P52_LP         GACTCAATGAAAATTTTGAAAGACGCAAGATCATTTCATAACGATGAGATTATGAAAATG    660
LCMV-P91_LP         GACTCAATGAAAATTTTGAAAGACGCAAGATCATTTCATAACGATGAGATTATGAAAATG    660
LCMV-P52-1_LP       GACTCAATGAAAATTTTGAAAGACGCAAGATCATTTCATAACGATGAGATTATGAAAATG    660
LCMV-P52-1.3_LP     GACTCAATGAAAATTTTGAAAGACGCAAGATCATTTCATAACGATGAGATTATGAAAATG    660
LCMV-P52-2.1_LP     GACTCAATGAAAATTTTGAAAGACGCAAGATCATTTCATAACGATGAGATTATGAAAATG    660
                    ************************************************************

LCMV-WE_LP          TGCCACGATGGTGTCAACCCCAACATGAGTTGCGATGATGTGGTCTTTGGCATAAATTCC    720
LCMV-P42_LP         TGCCACGATGGTGTCAACCCCAACATGAGTTGCGATGATGTGGTCTTTGGCATAAATTCC    720
LCMV-P52_LP         TGCCACGATGGTGTCAACCCCAACATGAGTTGCGATGATGTGGTCTTTGGCATAAATTCC    720
LCMV-P91_LP         TGCCACGATGGTGTCAACCCCAACATGAGTTGCGATGATGTGGTCTTTGGCATAAATTCC    720
LCMV-P52-1_LP       TGCCACGATGGTGTCAACCCCAACATGAGTTGCGATGATGTGGTCTTTGGCATAAATTCC    720
LCMV-P52-1.3_LP     TGCCACGATGGTGTCAACCCCAACATGAGTTGCGATGATGTGGTCTTTGGCATAAATTCC    720
LCMV-P52-2.1_LP     TGCCACGATGGTGTCAACCCCAACATGAGTTGCGATGATGTGGTCTTTGGCATAAATTCC    720
                    ************************************************************

LCMV-WE_LP          TTTTTTGGCAGGTTTAGGAGGGACCTGTTAAATGGGAAACTCAAAAGGAATTTCCAAAAG    780
LCMV-P42_LP         TTTTTTGGCAGGTTTAGGAGGGACCTGTTAAATGGGAAACTCAAAAGGAATTTCCAAAAG    780
LCMV-P52_LP         TTTTTTGGCAGGTTTAGGAGGGACCTGTTAAATGGGAAACTCAAAAGGAATTTCCAAAAG    780
LCMV-P91_LP         TTTTTTGGCAGGTTTAGGAGGGACCTGTTAAATGGGAAACTCAAAAGGAATTTCCAAAAG    780
LCMV-P52-1_LP       TTTTTTGGCAGGTTTAGGAGGGACCTGTTAAATGGGAGACTCAAAAGGAATTTCCAAAAG    780
LCMV-P52-1.3_LP     TTTTTTGGCAGGTTTAGGAGGGACCTGTTAAATGGGAAACTCAAAAGGAATTTCCAAAAG    780
LCMV-P52-2.1_LP     TTTTTTGGCAGGTTTAGGAGGGACCTGTTAAATGGGAAACTCAAAAGGAATTTCCAAAAG    780
                    ************************************* **********************

LCMV-WE_LP          GTCAGCCCTGGGGGCTTAATCAAGGAATTCTCTGAACTTTATGAAACCCTTACTGATAAT    840
LCMV-P42_LP         GTCAGCCCTGGGGGCTTAATCAAGGAATTCTCTGAACTTTATGAAACCCTTACTGATAAT    840
LCMV-P52_LP         GTCAGCCCTGGGGGCTTAATCAAGGAATTCTCTGAACTTTATGAAACCCTTACTGATAAT    840
LCMV-P91_LP         GTCAGCCCTGGGGGCTTAATCAAGGAATTCTCTGAACTTTATGAAACCCTTACTGATAAT    840
LCMV-P52-1_LP       GTCAGCCCTGGGGGCTTAATCAAGGAATTCTCTGAACTTTATGAAACCCTTACTGATAAT    840
LCMV-P52-1.3_LP     GTCAGCCCTGGGGGCTTAATCAAGGAATTCTCTGAACTTTATGAAACCCTTACTGATAAT    840
LCMV-P52-2.1_LP     GTCAGCCCTGGGGGCTTAATCAAGGAATTCTCTGAACTTTATGAAACCCTTACTGATAAT    840
                    ************************************************************

LCMV-WE_LP          GATGACATATTAATGTTGAGCAAAGAGGCAGTTGAATCCTGCCCCTTAATGAGGTTCATT    900
LCMV-P42_LP         GATGACATATTAATGTTGAGCAAAGAGGCAGTTGAATCCTGCCCCTTAATGAGGTTCATT    900
LCMV-P52_LP         GATGACATATTAATGTTGAGCAAAGAGGCAGTTGAATCCTGCCCCTTAATGAGGTTCATT    900
LCMV-P91_LP         GATGACATATTAATGTTGAGCAAAGAGGCAGTTGAATCCTGCCCCTTAATGAGGTTCATT    900
LCMV-P52-1_LP       GATGACATATTAATGTTGAGCAAAGAGGCAGTTGAATCCTGCCCCTTAATGAGGTTCATT    900
LCMV-P52-1.3_LP     GATGACATATTAATGTTGAGCAAAGAGGCAGTTGAATCCTGCCCCTTAATGAGGTTCATT    900
LCMV-P52-2.1_LP     GATGACATATTAATGTTGAGCAAAGAGGCAGTTGAATCCTGCCCCTTAATGAGGTTCATT    900
                    ************************************************************
```

Figure 26 (cont'd)

```
LCMV-WE_LP      ACAGCAGAGACCCATGGGCATGAGAGAGGAAGCGATGCTAACACTGAGTATGAAAGGCTA      960
LCMV-P42_LP     ACAGCAGAGACCCATGGGCATGAGAGAGGAAGCGATGCTAACACTGAGTATGAAAGGCTA      960
LCMV-P52_LP     ACAGCAGAGACCCATGGGCATGAGAGAGGAAGCGATGCTAACACTGAGTATGAAAGGCTA      960
LCMV-P91_LP     ACAGCAGAGACCCATGGGCATGAGAGAGGAAGCGATGCTAACACTGAGTATGAAAGGCTA      960
LCMV-P52-1_LP   ACAGCAGAGACCCATGGGCATGAGAGAGGAAGCGATGCTAACACTGAGTATGAAAGGCTA      960
LCMV-P52-1.3_LP ACAGCAGAGACCCATGGGCATGAGAGAGGAAGCGATGCTAACACTGAGTATGAAAGGCTA      960
LCMV-P52-2.1_LP ACAGCAGAGACCCATGGGCATGAGAGAGGAAGCGATGCTAACACTGAGTATGAAAGGCTA      960
                ************************************************************

LCMV-WE_LP      CTCTCTATGTTGAACAAGGTGAAAAGTTTAAAATTATTAAACACTAGAAGGAGACAGCTG     1020
LCMV-P42_LP     CTCTCTATGTTGAACAAGGTGAAAAGTTTAAAATTATTAAACACTAGAAGGAGACAGCTG     1020
LCMV-P52_LP     CTCTCTATGTTGAACAAGGTGAAAAGTTTAAAATTATTAAACACTAGAAGGAGACAGCTG     1020
LCMV-P91_LP     CTCTCTATGTTGAACAAGGTGAAAAGTTTAAAATTATTAAACACTAGAAGGAGACAGCTG     1020
LCMV-P52-1_LP   CTCTCTATGTTGAACAAGGTGAAAAGTTTAAAATTATTAAACACTAGAAGGAGACAGCTG     1020
LCMV-P52-1.3_LP CTCTCTATGTTAAACAAGGTGAAAAGTTTAAAATTATTAAACACTAGAAGGAGACAGCTG     1020
LCMV-P52-2.1_LP CTCTCTATGTTGAACAAGGTGAAAAGTTTAAAATTATTAAACACTAGAAGGAGACAGCTG     1020
                *********** ************************************************

LCMV-WE_LP      CTGAACTTAGATGTCTTATGTCTTTCTTCACTTATTAAGCAGTCAATTTCCAAAGGGTTG     1080
LCMV-P42_LP     CTGAACTTAGATGTCTTATGTCTTTCTTCACTTATTAAGCAGTCAATTTCCAAAGGGTTG     1080
LCMV-P52_LP     CTGAACTTAGATGTCTTATGTCTTTCTTCACTTATTAAGCAGTCAATTTCCAAAGGGTTG     1080
LCMV-P91_LP     CTGAACTTAGATGTCTTATGTCTTTCTTCACTTATTAAGCAGTCAATTTCCAAAGGGTTG     1080
LCMV-P52-1_LP   CTGAACTTAGATGTCTTATGTCTTTCTTCACTTATTAAGCAGTCAATTTCCAAAGGGTTG     1080
LCMV-P52-1.3_LP CTGAACTTAGATGTCTTATGTCTTTCTTCACTTATTAAGCAGTCAATTTCCAAAGGGTTG     1080
LCMV-P52-2.1_LP CTGAACTTAGATGTCTTATGTCTTTCTTCACTTATTAAGCAGTCAATTTCCAAAGGGTTG     1080
                ************************************************************

LCMV-WE_LP      GAAAATGATAAACATTGGGTTGGTTGTTGCTACAGTAGTGTGAATGATAGGCTTGTGAGC     1140
LCMV-P42_LP     GAAAATGATAAACATTGGGTTGGTTGTTGCTACAGTAGTGTGAATGATAGGCTTGTGAGC     1140
LCMV-P52_LP     GAAAATGATAAACATTGGGTTGGTTGTTGCTACAGTAGTGTGAATGATAGGCTTGTGAGC     1140
LCMV-P91_LP     GAAAATGATAAACATTGGGTTGGTTGCTGCTACAGTAGTGTGAATGATAGGCTTGTGAGC     1140
LCMV-P52-1_LP   GAAAATGATAAACATTGGGTTGGTTGTTGCTACAGTAGTGTGAATGATAGGCTTGTGAGC     1140
LCMV-P52-1.3_LP GAAAATGATAAACATTGGGTTGGTTGTTGCTACAGTAGTGTGAATGATAGGCTTGTGAGC     1140
LCMV-P52-2.1_LP GAAAATGATAAACATTGGGTTGGTTGTTGCTACAGTAGTGTGAATGATAGGCTTGTGAGC     1140
                ************************** *********************************

LCMV-WE_LP      CTTCAAAGTACCAAAGAAGAATTCATGAGACTTTTGAAGAACAGAAGAAAATCAAGAGTG     1200
LCMV-P42_LP     CTTCAAAGTACCAAAGAAGAATTCATGAGACTTTTGAAGAACAGAAGAAAATCAAGAGTG     1200
LCMV-P52_LP     CTTCAAAGTACCAAAGAAGAATTCATGAGACTTTTGAAGAACAGAAGAAAATCAAGAGTG     1200
LCMV-P91_LP     CTTCAAAGTACCAAAGAAGAATTCATGAGACTTTTGAAGAACAGAAGAAAATCAAGAGTG     1200
LCMV-P52-1_LP   CTTCAAAGTACCAAAGAAGAATTCATGAGACTTTTGAAGAACAGAAGAAAATCAAGAGTG     1200
LCMV-P52-1.3_LP CTTCAAAGTACCAAAGAAGAATTCATGAGACTTTTGAAGAACAGAAGAAAATCAAGAGTG     1200
LCMV-P52-2.1_LP CTTCAAAGTACCAAAGAAGAATTCATGAGACTTTTGAAGAACAGAAGAAAATCAAGAGTG     1200
                ************************************************************

LCMV-WE_LP      CACAAAAAGGCATCTCTTGATGAGCTTTTTAGGGTATCCATAAATGAGTTCATAGCAAAA     1260
LCMV-P42_LP     CACAAAAAGGCATCTCTTGATGAGCTTTTTAGGGTATCCATAAATGAGTTCATAGCAAAA     1260
LCMV-P52_LP     CACAAAAAGGCATCTCTTGATGAGCTTTTTAGGGTATCCATAAATGAGTTCATAGCAAAA     1260
LCMV-P91_LP     CACAAAAAGGCATCTCTTGATGAGCTTTTTAGGGTATCCATAAATGAGTTCATAGCAAAA     1260
LCMV-P52-1_LP   CACAAAAAGGCATCTCTTGATGAGCTTTTTAGGGTATCCATAAATGAGTTCATAGCAAAA     1260
LCMV-P52-1.3_LP CACAAAAAGGCATCTCTTGATGAGCTTTTTAGGGTATCCATAAATGAGTTCATAGCAAAA     1260
LCMV-P52-2.1_LP CACAAAAAGGCATCTCTTGATGAGCTTTTTAGGGTATCCATAAATGAGTTCATAGCAAAA     1260
                ************************************************************

LCMV-WE_LP      ATCCAGAAATGCCTATCAACAGTGGGACTTAGTTTTGAGCATTACGGACTATCAGAATGC     1320
LCMV-P42_LP     ATCCAGAAATGCCTATCAACAGTGGGACTTAGTTTTGAGCATTACGGACTATCAGAATGC     1320
LCMV-P52_LP     ATCCAGAAATGCCTATCAACAGTGGGACTTAGTTTTGAGCATTACGGACTATCAGAATGC     1320
LCMV-P91_LP     ATCCAGAAATGCCTATCAACAGTGGGACTTAGTTTTGAGCATTACGGACTATCAGAATGC     1320
LCMV-P52-1_LP   ATCCAGAAATGCCTATCAACAGTGGGACTTAGTTTTGAGCATTACGGACTATCAGAATGC     1320
LCMV-P52-1.3_LP ATCCAGAAATGCCTATCAACAGTGGGACTTAGTTTTGAGCATTACGGACTATCAGAATGC     1320
LCMV-P52-2.1_LP ATCCAGAAATGCCTATCAACAGTGGGACTTAGTTTTGAGCATTACGGACTATCAGAATGC     1320
                ************************************************************

LCMV-WE_LP      CTCGTGCAAGAATGCCATATACCATTTGCTGAATTTGAGAACTTTATGAGAGCCGGGACT     1380
LCMV-P42_LP     CTCGTGCAAGAATGCCATATACCATTTGCTGAATTTGAGAACTTTATGAGAGCCGGGACT     1380
LCMV-P52_LP     CTCGTGCAAGAATGCCATATACCATTTGCTGAATTTGAGAACTTTATGAGAGCCGGGACT     1380
LCMV-P91_LP     CTCGTGCAAGAATGCCATATACCATTTGCTGAATTTGAGAACTTTATGAGAGCCGGGACT     1380
LCMV-P52-1_LP   CTCGTGCAAGAATGCCATATACCATTTGCTGAATTTGAGAACTTTATGAGAGCCGGGACT     1380
LCMV-P52-1.3_LP CTCGTGCAAGAATGCCATATACCATTTGCTGAATTTGAGAACTTTATGAGAGCCGGGACT     1380
LCMV-P52-2.1_LP CTCGTGCAAGAATGCCATATACCATTTGCTGAATTTGAGAACTTTATGAGAGCCGGGACT     1380
                ************************************************************
```

Figure 26 (cont'd)

```
LCMV-WE_LP          CATCCTGTAATGCATTACACAAAATTTGAAGATTACACTTTCCAGCCTAACATAGAGCAA    1440
LCMV-P42_LP         CATCCTGTAATGCATTACACAAAATTTGAAGATTACACTTTCCAGCCTAACATAGAGCAA    1440
LCMV-P52_LP         CATCCTGTAATGCATTACACAAAATTTGAAGATTACACTTTCCAGCCTAACATAGAGCAA    1440
LCMV-P91_LP         CATCCTGTAATGCATTACACAAAATTTGAAGATTACACTTTCCAGCCTAACATAGAGCAA    1440
LCMV-P52-1_LP       CATCCTGTAATGCATTACACAAAATTTGAAGATTACACTTTCCAGCCTAACATAGAGCAA    1440
LCMV-P52-1.3_LP     CATCCTGTAATGCATTACACAAAATTTGAAGATTACACTTTCCAGCCTAACATAGAGCAA    1440
LCMV-P52-2.1_LP     CATCCTGTAATGCATTACACAAAATTTGAAGATTACACTTTCCAGCCTAACATAGAGCAA    1440
                    ************************************************************

LCMV-WE_LP          TTGAGGGGTTTACAGAGTTTGAGAAAACTGTCATCTGTTTGTTTGGCTCTAACAAACAGC    1500
LCMV-P42_LP         TTGAGGGGTTTACAGAGTTTGAGAAAACTGTCATCTGTTTGTTTGGCTCTAACAAACAGC    1500
LCMV-P52_LP         TTGAGGGGTTTACAGAGTTTGAGAAAACTGTCATCTGTTTGTTTGGCTCTAACAAACAGC    1500
LCMV-P91_LP         TTGAGGGGTTTACAGAGTTTGAGAAAACTGTCATCTGTTTGTTTGGCTCTAACAAACAGC    1500
LCMV-P52-1_LP       TTGAGGGGTTTACAGAGTTTGAGAAAACTGTCATCTGTTTGTTTGGCTCTAACAAACAGC    1500
LCMV-P52-1.3_LP     TTGAGGGGTTTACAGAGTTTGAGAAAACTGTCATCTGTTTGTTTGGCTCTAACAAACAGC    1500
LCMV-P52-2.1_LP     TTGAGGGGTTTACAGAGTTTGAGAAAACTGTCATCTGTTTGTTTGGCTCTAACAAACAGC    1500
                    ************************************************************

LCMV-WE_LP          ATGAAAACAAGCTCAGTTGCAAGGTTGAGACAGAACCAACTGGGGTCTGTGAGATATCAA    1560
LCMV-P42_LP         ATGAAAACAAGCTCAGTTGCAAGGTTGAGACAGAACCAACTGGGGTCTGTGAGATATCAA    1560
LCMV-P52_LP         ATGAAAACAAGCTCAGTTGCAAGGTTGAGACAGAACCAACTGGGGTCTGTGAGATATCAA    1560
LCMV-P91_LP         ATGAAAACAAGCTCAGTTGCAAGGTTGAGACAGAACCAACTGGGGTCTGTGAGATATCAA    1560
LCMV-P52-1_LP       ATGAAAACAAGCTCAGTTGCAAGGTTGAGACAGAACCAACTGGGGTCTGTGAGATATCAA    1560
LCMV-P52-1.3_LP     ATGAAAACAAGCTCAGTTGCAAGGTTGAGACAGAACCAACTGGGGTCTGTGAGATATCAA    1560
LCMV-P52-2.1_LP     ATGAAAACAAGCTCAGTTGCAAGGTTGAGACAGAACCAACTGGGGTCTGTGAGATATCAA    1560
                    ************************************************************

LCMV-WE_LP          GTGGTGGAGTGCAAAGAGGTGTTTTGCCAGATAATAAAACTGGATTCCGAAGAGTATCAT    1620
LCMV-P42_LP         GTGGTGGAGTGCAAAGAGGTGTTTTGCCAGATAATAAAACTGGATTCCGAAGAGTATCAT    1620
LCMV-P52_LP         GTGGTGGAGTGCAAAGAGGTGTTTTGCCAGATAATAAAACTGGATTCCGAAGAGTATCAT    1620
LCMV-P91_LP         GTGGTGGAGTGCAAAGAGGTGTTTTGCCAGATAATAAAACTGGATTCCGAAGAGTATCAT    1620
LCMV-P52-1_LP       GTGGTGGAGTGCAAAGAGGTGTTTTGCCAGATAATAAAACTGGATTCCGAAGAGTATCAT    1620
LCMV-P52-1.3_LP     GTGGTGGAGTGCAAAGAGGTGTTTTGCCAGATAATAAAACTGGATTCCGAAGAGTATCAT    1620
LCMV-P52-2.1_LP     GTGGTGGAGTGCAAAGAGGTGTTTTGCCAGATAATAAAACTGGATTCCGAAGAGTATCAT    1620
                    ************************************************************

LCMV-WE_LP          CTACTATATCAGAAAACTGGAGAATCATCGAGGTGTTATTCCATACAAGGTCCGGATGGT    1680
LCMV-P42_LP         CTACTATATCAGAAAACTGGAGAATCATCGAGGTGTTATTCCATACAAGGTCCGGATGGT    1680
LCMV-P52_LP         CTACTATATCAGAAAACTGGAGAATCATCGAGGTGTTATTCCATACAAGGTCCGGATGGT    1680
LCMV-P91_LP         CTACTATATCAGAAAACTGGAGAATCATCGAGGTGTTATTCCATACAAGGTCCGGATGGT    1680
LCMV-P52-1_LP       CTACTATATCAGAAAACTGGAGAATCATCGAGGTGTTATTCCATACAAGGTCCGGATGGT    1680
LCMV-P52-1.3_LP     CTACTATATCAGAAAACTGGAGAATCATCGAGGTGTTATTCCATACAAGGTCCGGATGGT    1680
LCMV-P52-2.1_LP     CTACTATATCAGAAAACTGGAGAATCATCGAGGTGTTATTCCATACAAGGTCCGGATGGT    1680
                    ************************************************************

LCMV-WE_LP          CACTTGATTTCCTTTTACGCAGATCCAAAAAGGTTCTTTTTACCAATTTTTTCAGATGAG    1740
LCMV-P42_LP         CACTTGATTTCCTTTTACGCAGATCCAAAAAGGTTCTTTTTACCAATTTTTTCAGATGAG    1740
LCMV-P52_LP         CACTTGATTTCCTTTTACGCAGATCCAAAAAGGTTCTTTTTACCAATTTTTTCAGATGAG    1740
LCMV-P91_LP         CACTTGATTTCCTTTTACGCAGATCCAAAAAGGTTCTTTTTACCAATTTTTTCAGATGAG    1740
LCMV-P52-1_LP       CACTTGATTTCCTTTTACGCAGATCCAAAAAGGTTCTTTTTACCAATTTTTTCAGATGAG    1740
LCMV-P52-1.3_LP     CACTTGATTTCCTTTTACGCAGATCCAAAAAGGTTCTTTTTACCAATTTTTTCAGATGAG    1740
LCMV-P52-2.1_LP     CACTTGATTTCCTTTTACGCAGATCCAAAAAGGTTCTTTTTACCAATTTTTTCAGATGAG    1740
                    ************************************************************

LCMV-WE_LP          GTGTTGCACAACATGATAGACACAATGATTTCATGGATTAGGTCATGCCCTGACTTAAAA    1800
LCMV-P42_LP         GTGTTGCACAACATGATAGACACAATGATTTCATGGATTAGGTCATGCCCTGACTTAAAA    1800
LCMV-P52_LP         GTGTTGCACAACATGATAGACACAATGATTTCATGGATTAGGTCATGCCCTGACTTAAAA    1800
LCMV-P91_LP         GTGTTGCACAACATGATAGACACAATGATTTCATGGATTAGGTCATGCCCTGACTTAAAA    1800
LCMV-P52-1_LP       GTGTTGCACAACATGATAGACACAATGATTTCATGGATTAGGTCATGCCCTGACTTAAAA    1800
LCMV-P52-1.3_LP     GTGTTGCACAACATGATAGACACAATGATTTCATGGATTAGGTCATGCCCTGACTTAAAA    1800
LCMV-P52-2.1_LP     GTGTTGCACAACATGATAGACACAATGATTTCATGGATTAGGTCATGCCCTGACTTAAAA    1800
                    ************************************************************

LCMV-WE_LP          GATTCTCTTATTGACATTGAGACTGCACTAAGGACATTGATCCTACTGATGCTCACCAAC    1860
LCMV-P42_LP         GATTCTCTTATTGACATTGAGACTGCACTAAGGACATTGATCCTACTGATGCTCACCAAC    1860
LCMV-P52_LP         GATTCTCTTATTGACATTGAGACTGCACTAAGGACATTGATCCTACTGATGCTCACCAAC    1860
LCMV-P91_LP         GATTCTCTTATTGACATTGAGACTGCACTAAGGACATTGATCCTACTGATGCTCACCAAC    1860
LCMV-P52-1_LP       GATTCTCTTATTGACATTGAGACTGCACTAAGGACATTGATCCTACTGATGCTCACCAAC    1860
LCMV-P52-1.3_LP     GATTCTCTTATTGACATTGAGACTGCACTAAGGACATTGATCCTACTGATGCTCACCAAC    1860
LCMV-P52-2.1_LP     GATTCTCTTATTGACATTGAGACTGCACTAAGGACATTGATCCTACTGATGCTCACCAAC    1860
                    ************************************************************
```

Figure 26 (cont'd)

```
LCMV-WE_LP      CCAACAAAGAGAAATCAAAAGCAGGTTCAAAATATTAGGTATTTAGTGATGGCCATCGTC    1920
LCMV-P42_LP     CCAACAAAGAGAAATCAAAAGCAGGTTCAAAATATTAGGTATTTAGTGATGGCCATCGTC    1920
LCMV-P52_LP     CCAACAAAGAGAAATCAAAAGCAGGTTCAAAATATTAGGTATTTAGTGATGGCCATCGTC    1920
LCMV-P91_LP     CCAACAAAGAGAAATCAAAAGCAGGTTCAAAATATTAGGTATTTAGTGATGGCCATCGTC    1920
LCMV-P52-1_LP   CCAACAAAGAGAAATCAAAAGCAGGTTCAAAATATTAGGTATTTAGTGATGGCCATCGTC    1920
LCMV-P52-1.3_LP CCAACAAAGAGAAATCAAAAGCAGGTTCAAAATATTAGGTATTTAGTGATGGCCATCGTC    1920
LCMV-P52-2.1_LP CCAACAAAGAGAAATCAAAAGCAGGTTCAAAATATTAGGTATTTAGTGATGGCCATCGTC    1920
                ************************************************************

LCMV-WE_LP      TCAGACTTTTCATCGACCTCATTAATGGATAAGTTGAAGGAGGATCTAATCACACCTGCC    1980
LCMV-P42_LP     TCAGACTTTTCATCGACCTCATTAATGGATAAGTTGAAGGAGGATCTAATCACACCTGCC    1980
LCMV-P52_LP     TCAGACTTTTCATCGACCTCATTAATGGATAAGTTGAAGGAGGATCTAATCACACCTGCC    1980
LCMV-P91_LP     TCAGACTTTTCATCGACCTCATTAATGGATAAGTTGAAGGAGGATCTAATCACACCTGCC    1980
LCMV-P52-1_LP   TCAGACTTTTCATCGACCTCATTAATGGATAAGTTGAAGGAGGATCTAATCACACCTGCC    1980
LCMV-P52-1.3_LP TCAGACTTTTCATCGACCTCATTAATGGATAAGTTGAAGGAGGATCTAATCACACCTGCC    1980
LCMV-P52-2.1_LP TCAGACTTTTCATCGACCTCATTAATGGATAAGTTGAAGGAGGATCTAATCACACCTGCC    1980
                ************************************************************

LCMV-WE_LP      GAGAAAGTGGTGTACAGGCTGCTTCGGTTTTTGATTAGGACAATTTTTGGTACTGGTGAA    2040
LCMV-P42_LP     GAGAAAGTGGTGTACAGGCTGCTTCGGTTTTTGATTAGGACAATTTTTGGTACTGGTGAA    2040
LCMV-P52_LP     GAGAAAGTGGTGTACAGGCTGCTTCGGTTTTTGATTAGGACAATTTTTGGTACTGGTGAA    2040
LCMV-P91_LP     GAGAAAGTGGTGTACAGGCTGCTTCGGTTTTTGATTAGGACAATTTTTGGTACTGGTGAA    2040
LCMV-P52-1_LP   GAGAAAGTGGTGTACAGGCTGCTTCGGTTTTTGATTAGGACAATTTTTGGTACTGGTGAA    2040
LCMV-P52-1.3_LP GAGAAAGTGGTGTACAGGCTGCTTCGGTTTTTGATTAGGACAATTTTTGGTACTGGTGAA    2040
LCMV-P52-2.1_LP GAGAAAGTGGTGTACAGGCTGCTTCGGTTTTTGATTAGGACAATTTTTGGTACTGGTGAA    2040
                ************************************************************

LCMV-WE_LP      AAGGTGTTATTGAGTGCAAAATTCAAGTTTATGTTGAATGTGTCATACCTGTGTCATTTG    2100
LCMV-P42_LP     AAGGTGTTATTGAGTGCAAAATTCAAGTTTATGTTGAATGTGTCATACCTGTGTCATTTG    2100
LCMV-P52_LP     AAGGTGTTATTGAGTGCAAAATTCAAGTTTATGTTGAATGTRTCATACCTGTGTCATTTG    2100
LCMV-P91_LP     AAGGTGTTATTGAGTGCAAAATTCAAGTTTATGTTGAATGTGTCATACCTGTGTCATTTG    2100
LCMV-P52-1_LP   AAGGTGTTATTGAGTGCAAAATTCAAGTTTATGTTGAATGTGTCATACCTGTGTCATTTG    2100
LCMV-P52-1.3_LP AAGGTGTTATTGAGTGCAAAATTCAAGTTTATGTTGAATGTGTCATACCTGTGTCATTTG    2100
LCMV-P52-2.1_LP AAGGTGTTATTGAGTGCAAAATTTAAGTTTATGTTGAATGTGTCATACCTGTGTCATTTG    2100
                *********************** ***************** ******************

LCMV-WE_LP      ATCACAAAGGAGACCCCTGATAGATTGACAGATCAGATAAAATGTTTTGAAAAGTTCTTT    2160
LCMV-P42_LP     ATCACAAAGGAGACCCCTGATAGATTGACAGATCAGATAAAATGTTTTGAAAAGTTCTTT    2160
LCMV-P52_LP     ATCACAAAGGAGACCCCTGATAGATTGACAGATCAGATAAAATGTTTTGAAAAGTTCTTT    2160
LCMV-P91_LP     ATCACAAAGGAGACCCCTGATAGATTGACAGATCAGATAAAATGTTTTGAAAAGTTCTTT    2160
LCMV-P52-1_LP   ATCACAAAGGAGACCCCTGATAGATTGACAGATCAGATAAAATGTTTTGAAAAGTTCTTT    2160
LCMV-P52-1.3_LP ATCACAAAGGAGACCCCTGATAGATTGACAGATCAGATAAAATGTTTTGAAAAGTTCTTT    2160
LCMV-P52-2.1_LP ATCACAAAGGAGACCCCTGATAGATTGACAGATCAGATAAAATGTTTTGAAAAGTTCTTT    2160
                ************************************************************

LCMV-WE_LP      GAGCCCAAGAGTGAGTTTGGTTTCTTTGTCAACCCTAAGGAAACAATCACACCCGAAGAG    2220
LCMV-P42_LP     GAGCCCAAGAGTGAGTTTGGTTTCTTTGTCAACCCTAAGGAAACAATCACACCCGAAGAG    2220
LCMV-P52_LP     GAGCCCAAGAGTGAGTTTGGTTTCTTTGTCAACCCTAAGGAAACAATCACACCCGAAGAG    2220
LCMV-P91_LP     GAGCCCAAGAGTGAGTTTGGTTTCTTTGTCAACCCTAAGGAAACAATCACACCCGAAGAG    2220
LCMV-P52-1_LP   GAGCCCAAGAGTGAGTTTGGTTTCTTTGTCAACCCTAAGGAAACAATCACACCCGAAGAG    2220
LCMV-P52-1.3_LP GAGCCCAAGAGTGAGTTTGGTTTCTTTGTCAACCCTAAGGAAACAATCACACCCGAAGAG    2220
LCMV-P52-2.1_LP GAGCCCAAGAGTGAGTTTGGTTTCTTTGTCAACCCTAAGGAAACAATCACACCCGAAGAG    2220
                ************************************************************

LCMV-WE_LP      GAATGTGTTTTTTATGAACAAATGAAGAAGTTCACCGGTAAAGATATTGATTGTCAGCAT    2280
LCMV-P42_LP     GAATGTGTTTTTTATGAACAAATGAAGAAGTTCACCGGTAAAGATATTGATTGTCAGCAT    2280
LCMV-P52_LP     GAATGTGTTTTTTATGAACAAATGAAGAAGTTCACCGGTAAAGATATTGATTGTCAGCAT    2280
LCMV-P91_LP     GAATGTGTTTTTTATGAACAAATGAAGAAGTTCACCGGTAAAGATATTGATTGTCAGCAT    2280
LCMV-P52-1_LP   GAATGTGTTTTTTATGAACAAATGAAGAAGTTCACCGGTAAAGATATTGATTGTCAGCAT    2280
LCMV-P52-1.3_LP GAATGTGTTTTTTATGAACAAATGAAGAAGTTCACCGGTAAAGATATTGATTGTCAGCAT    2280
LCMV-P52-2.1_LP GAATGTGTTTTTTATGAACAAATGAAGAAGTTCACCGGTAAAGATATTGATTGTCAGCAT    2280
                ************************************************************

LCMV-WE_LP      TCAACCCCTGGTGTTAATTTAGAGATCTTTAGCATGATGGTATCTTCATTCAACAATGGC    2340
LCMV-P42_LP     TCAACCCCTGGTGTTAATTTAGAGATCTTTAGCATGATGGTATCTTCATTCAACAATGGC    2340
LCMV-P52_LP     TCAACCCCTGGTGTTAATTTAGAGATCTTTAGCATGATGGTATCTTCATTCAACAATGGC    2340
LCMV-P91_LP     TCAACCCCTGGTGTTAATTTAGAGATCTTTAGCATGATGGTATCTTCATTCAACAATGGC    2340
LCMV-P52-1_LP   TCAACCCCTGGTGTTAATTTAGAGATCTTTAGCATGATGGTATCTTCATTCAACAATGGC    2340
LCMV-P52-1.3_LP TCAACCCCTGGTGTTAATTTAGAGATCTTTAGCATGATGGTATCTTCATTCAACAATGGC    2340
LCMV-P52-2.1_LP TCAACCCCTGGTGTTAATTTAGAGATCTTTAGCATGATGGTATCTTCATTCAACAATGGC    2340
                ************************************************************
```

Figure 26 (cont'd)

```
LCMV-WE_LP          ACCTTAATTCTAAAAGGGGAGAAAAGGCTCAACAATCTGGACCCCATGACCAACTCTGGA    2400
LCMV-P42_LP         ACCTTAATTCTAAAAGGGGAGAAAAGGCTCAACAATCTGGACCCCATGACCAACTCTGGA    2400
LCMV-P52_LP         ACCTTAATTCTAAAAGGGGAGAAAAGGCTCAACAATCTGGACCCCATGACCAACTCTGGA    2400
LCMV-P91_LP         ACCTTAATTCTAAAAGGGGAGAAAAGGCTCAACAATCTGGACCCCATGACCAACTCTGGA    2400
LCMV-P52-1_LP       ACCTTAATTCTAAAAGGGGAGAAAAGGCTCAACAATCTGGACCCCATGACCAACTCTGGA    2400
LCMV-P52-1.3_LP     ACCTTAATTCTAAAAGGGGAGAAAAGGCTCAACAATCTGGACCCCATGACCAACTCTGGA    2400
LCMV-P52-2.1_LP     ACCTTAATTCTAAAAGGGGAGAAAAGGCTCAACAATCTGGACCCCATGACCAACTCTGGA    2400
                    ************************************************************

LCMV-WE_LP          TGTGCGACAGCATTAGATCTCGCAAGCAACAAAAGTGTGGTTGTCAATAAACATCTGAAT    2460
LCMV-P42_LP         TGTGCGACAGCATTAGATCTCGCAAGCAACAAAAGTGTGGTTGTCAATAAACATCTGAAT    2460
LCMV-P52_LP         TGTGCGACAGCATTAGATCTCGCAAGCAACAAAAGTGTGGTTGTCAATAAACATCTGAAT    2460
LCMV-P91_LP         TGTGCGACAGCATTAGATCTCGCAAGCAACAAAAGTGTGGTTGTCAATAAACATCTGAAT    2460
LCMV-P52-1_LP       TGTGCGACAGCATTAGATCTCGCAAGCAACAAAAGTGTGGTTGTCAATAAACATCTGAAT    2460
LCMV-P52-1.3_LP     TGTGCGACAGCATTAGATCTCGCAAGCAACAAAAGTGTGGTTGTCAATAAACATCTGAAT    2460
LCMV-P52-2.1_LP     TGTGCGACAGCATTAGATCTCGCAAGCAACAAAAGTGTGGTTGTCAATAAACATCTGAAT    2460
                    ************************************************************

LCMV-WE_LP          GGAGAACGGCTTTTGGAGTATGATTTTAACAAATTGCTTGTTAGTGCTGTGAGCCAAATT    2520
LCMV-P42_LP         GGAGAACGGCTTTTGGAGTATGATTTTAACAAATTGCTTGTTAGTGCTGTGAGCCAAATT    2520
LCMV-P52_LP         GGAGAACGGCTTTTGGAGTATGATTTTAACAAATTGCTTGTTAGTGCTGTGAGCCAAATT    2520
LCMV-P91_LP         GGAGAACGGCTTTTGGAGTATGATTTTAACAAATTGCTTGTTAGTGCTGTGAGCCAAATT    2520
LCMV-P52-1_LP       GGAGAACGGCTTTTGGAGTATGATTTTAACAAATTGCTTGTTAGTGCTGTGAGCCAAATT    2520
LCMV-P52-1.3_LP     GGAGAACGGCTTTTGGAGTATGATTTTAACAAATTGCTTGTTAGTGCTGTGAGCCAAATT    2520
LCMV-P52-2.1_LP     GGAGAACGGCTTTTGGAGTATGATTTTAACAAATTGCTTGTTAGTGCTGTGAGCCAAATT    2520
                    ************************************************************

LCMV-WE_LP          ACAGAGGGCTTCATGAGGAAACAAAAGTATAAGCTGAGACACTCAGATTACGAATATAAG    2580
LCMV-P42_LP         ACAGAGGGCTTCATGAGGAAACAAAAGTATAAGCTGAGACACTCAGATTACGAATATAAG    2580
LCMV-P52_LP         ACAGAGGGCTTCATGAGGAAACAAAAGTATAAGCTGAGACACTCAGATTACGAATATAAG    2580
LCMV-P91_LP         ACAGAGGGCTTCATGAGGAAACAAAAGTATAAGCTGAGACACTCAGATTACGAATATAAG    2580
LCMV-P52-1_LP       ACAGAGGGCTTCATGAGGAAACAAAAGTATAAGCTGAGACACTCAGATTACGAATATAAG    2580
LCMV-P52-1.3_LP     ACAGAGGGCTTCATGAGGAAACAAAAGTATAAGCTGAGACACTCAGATTACGAATATAAG    2580
LCMV-P52-2.1_LP     ACAGAGGGCTTCATGAGGAAACAAAAGTATAAGCTGAGACACTCAGATTACGAATATAAG    2580
                    ************************************************************

LCMV-WE_LP          GTCTCAAAGCTTGTCTCTAGATTAGTCATCGGTTCCAGGAAAACAGAAGTAGACAAATTG    2640
LCMV-P42_LP         GTCTCAAAGCTTGTCTCTAGATTAGTCATCGGTTCCAGGAAAACAGAAGTAGACAAATTG    2640
LCMV-P52_LP         GTCTCAAAGCTTGTCTCTAGATTAGTCATCGGTTCCAGGAAAACAGAAGTAGACAAATTG    2640
LCMV-P91_LP         GTCTCAAAGCTTGTCTCTAGATTAGTCATCGGTTCCAGGAAAACAGAAGTAGACAAATTG    2640
LCMV-P52-1_LP       GTCTCAAAGCTTGTCTCTAGATTAGTCATCGGTTCTAGGAAAACAGAAGTAGACAAATTG    2640
LCMV-P52-1.3_LP     GTCTCAAAGCTTGTCTCTAGATTAGTCATCGGTTCCAGGAAAACAGAAGTAGACAAATTA    2640
LCMV-P52-2.1_LP     GTCTCAAAGCTTGTCTCTAGATTAGTCATCGGTTCCAGGAAAACAGAAGTAGACAAATTG    2640
                    *********************************** *********************** 

LCMV-WE_LP          GAAGATGATCCGGTAGATGTGTGTTTCGAGGGGGAGGAGGAGACAAGTTTTTTCAGGAGT    2700
LCMV-P42_LP         GAAGATGATCCGGTAGATGTGTGTTTCGAGGGGGAGGAGGAGACAAGTTTTTTCAGGAGT    2700
LCMV-P52_LP         GAAGATGATCCGGTAGATGTGTGTTTCGAGGGGGAGGAGGAGACAAGTTTTTTCAGGAGT    2700
LCMV-P91_LP         GAAGATGATCCGGTAGATGTGTGTTTCGAGGGGGAGGAGGAGACAAGTTTTTTCAGGAGT    2700
LCMV-P52-1_LP       GAAGATGATCCGGTAGATGTGTGTTTCGAGGGGGAGGAGGAGACAAGTTTTTTCAGGAGT    2700
LCMV-P52-1.3_LP     GAAGATGATCCGGTAGATGTGTGTTTCGAGGGGGAGGAGGAGACAAGTTTTTTCAGGAGT    2700
LCMV-P52-2.1_LP     GAAGATGATCCGGTAGATGTGTGTTTCGAGGGGGAGGAGGAGACAAGTTTTTTCAGGAGT    2700
                    ************************************************************

LCMV-WE_LP          TTAGAAGATAAGGTCAGCTCCACAATAACACGGTATAATAGAGGCACTAGGCTTAATGAA    2760
LCMV-P42_LP         TTAGAAGATAAGGTCAGCTCCACAATAACACGGTATAATAGAGGCACTAGGCTTAATGAA    2760
LCMV-P52_LP         TTAGAAGATAAGGTCAGCTCCACAATAACACGGTATAATAGAGGCACTAGGCTTAATGAA    2760
LCMV-P91_LP         TTAGAAGATAAGGTCAGCTCCACAATAACACGGTATAATAGAGGCACTAGGCTTAATGAA    2760
LCMV-P52-1_LP       TTAGAAGATAAGGTCAGCTCCACAATAACACGGTATAATAGAGGCACTAGGCTTAATGAA    2760
LCMV-P52-1.3_LP     TTAGAAGATAAGGTCAGCTCCACAATAACACGGTATAATAGAGGCACTAGGCTTAATGAA    2760
LCMV-P52-2.1_LP     TTAGAAGATAAGGTCAGCTCCACAATAACACGGTATAATAGAGGCACTAGGCTTAATGAA    2760
                    ************************************************************

LCMV-WE_LP          GGGCAAGGGGAGGGAGAATTCAAGAACACAAAAGGACTACACCACCTTCAGATTATTTTG    2820
LCMV-P42_LP         GGGCAAGGGGAGGGAGAATTCAAGAACACAAAAGGACTACACCACCTTCAGATTATTTTG    2820
LCMV-P52_LP         GGGCAAGGGGAGGGAGAATTCAAGAACACAAAAGGACTACACCACCTTCAGATTATTTTG    2820
LCMV-P91_LP         GGGCAAGGGGAGGGAGAATTCAAGAACACAAAAGGACTACACCACCTTCAGATTATTTTG    2820
LCMV-P52-1_LP       GGGCAAGGGGAGGGAGAATTCAAGAACACAAAAGGACTACACCACCTTCAGATTATTTTG    2820
LCMV-P52-1.3_LP     GGGCAAGGGGAGGGAGAATTCAAGAACACAAAAGGACTACACCACCTTCAGATTATTTTG    2820
LCMV-P52-2.1_LP     GGGCAAGGGGAGGGAGAATTCAAGAACACAAAAGGACTACACCACCTTCAGATTATTTTG    2820
                    ************************************************************
```

Figure 26 (cont'd)

```
LCMV-WE_LP          TCAGGTAAAAGAGCTTATCTGAGGAAAGTCATTTTATCAGAAATTTCATTTCATCTAGTA     2880
LCMV-P42_LP         TCAGGTAAAAGAGCTTATCTGAGGAAAGTCATTTTATCAGAAATTTCATTTCATCTAGTA     2880
LCMV-P52_LP         TCAGGTAAAAGAGCTTATCTGAGGAAAGTCATTTTATCAGAAATTTCATTTCATCTAGTA     2880
LCMV-P91_LP         TCAGGTAAAAGAGCTTATCTGAGGAAAGTCATTTTATCAGAAATTTCATTTCATCTAGTA     2880
LCMV-P52-1_LP       TCAGGTAAAAGAGCTTATCTGAGGAAAGTCATTTTATCAGAAATTTCATTTCATCTAGTA     2880
LCMV-P52-1.3_LP     TCAGGTAAAAGAGCTTATCTGAGGAAAGTCATTTTATCAGAAATTTCATTTCATCTAGTA     2880
LCMV-P52-2.1_LP     TCAGGTAAAAGAGCTTATCTGAGGAAAGTCATTTTATCAGAAATTTCATTTCATCTAGTA     2880
                    ************************************************************

LCMV-WE_LP          GAGGACTTTGATCCATCCTGTCTCACCAATGACGACATGAGGTTTATTTGTGAGGCTGTT     2940
LCMV-P42_LP         GAGGACTTTGATCCATCCTGTCTCACCAATGACGACATGAGGTTTATTTGTGAGGCTGTT     2940
LCMV-P52_LP         GAGGACTTTGATCCATCCTGTCTCACCAATGACGACATGAGGTTTATTTGTGAGGCTGTT     2940
LCMV-P91_LP         GAGGACTTTGATCCATCCTGTCTCACCAATGACGACATGAGGTTTATTTGTGAGGCTGTT     2940
LCMV-P52-1_LP       GAGGACTTTGATCCATCCTGTCTCACCAATGACGACATGAGGTTTATTTGTGAGGCTGTT     2940
LCMV-P52-1.3_LP     GAGGACTTTGATCCATCCTGTCTCACCAATGACGACATGAGGTTTATTTGTGAGGCTGTT     2940
LCMV-P52-2.1_LP     GAGGACTTTGATCCATCCTGTCTCACCAATGACGACATGAGGTTTATTTGTGAGGCTGTT     2940
                    ************************************************************

LCMV-WE_LP          GAAGGTTCAACAGAACTGTCACCATTGTATTTTACATCAGCTGTCAAAGAACAATGTGGT     3000
LCMV-P42_LP         GAAGGTTCAACAGAACTGTCACCATTGTATTTTACATCAGCTGTCAAAGAACAATGTGGT     3000
LCMV-P52_LP         GAAGGTTCAACAGAACTGTCACCATTGTATTTTACATCAGCTGTCAAAGAACAATGTGGT     3000
LCMV-P91_LP         GAAGGTTCAACAGAACTGTCACCATTGTATTTTACATCAGCTGTCAAAGAACAATGTGGT     3000
LCMV-P52-1_LP       GAAGGTTCAACAGAACTGTCACCATTGTATTTTACATCAGCTGTCAAAGAACAATGTGGT     3000
LCMV-P52-1.3_LP     GAAGGTTCAACAGAACTGTCACCATTGTATTTTACATCAGCTGTCAAAGAACAATGTGGT     3000
LCMV-P52-2.1_LP     GAAGGTTCAACAGAACTGTCACCATTGTATTTTACATCAGCTGTCAAAGAACAATGTGGT     3000
                    ************************************************************

LCMV-WE_LP          CTGGATGAGATGGCAAGAAACCTCTGTAGAAAGTTCTTCTCAGAGGGTGATTGGTTCTCA     3060
LCMV-P42_LP         CTGGATGAGATGGCAAGAAACCTCTGTAGAAAGTTCTTCTCAGAGGGTGATTGGTTCTCA     3060
LCMV-P52_LP         CTGGATGAGATGGCAAGAAACCTCTGTAGAAAGTTCTTCTCAGAGGGTGATTGGTTCTCA     3060
LCMV-P91_LP         CTGGATGAGATGGCAAGAAACCTCTGTAGAAAGTTCTTCTCAGAGGGTGATTGGTTCTCA     3060
LCMV-P52-1_LP       CTGGATGAGATGGCAAGAAACCTCTGTAGAAAGTTCTTCTCAGAGGGTGATTGGTTCTCA     3060
LCMV-P52-1.3_LP     CTGGATGAGATGGCAAGAAACCTCTGTAGAAAGTTCTTCTCAGAGGGTGATTGGTTCTCA     3060
LCMV-P52-2.1_LP     CTGGATGAGATGGCAAGAAACCTCTGTAGAAAGTTCTTCTCAGAGGGTGATTGGTTCTCA     3060
                    ************************************************************

LCMV-WE_LP          TGTATGAAGATGATCTTGTTACAGATGAATGCAAATGCGTATTCAGGGAAGTACAGACAC     3120
LCMV-P42_LP         TGTATGAAGATGATCTTGTTACAGATGAATGCAAATGCGTATTCAGGGAAGTACAGACAC     3120
LCMV-P52_LP         TGTATGAAGATGATCTTGTTACAGATGAATGCAAATGCGTATTCAGGGAAGTACAGACAC     3120
LCMV-P91_LP         TGTATGAAGATGATCTTGTTACAGATGAATGCAAATGCGTATTCAGGGAAGTACAGACAC     3120
LCMV-P52-1_LP       TGTATGAAGATGATCTTGTTACAGATGAATGCAAATGCGTATTCAGGGAAGTACAGACAC     3120
LCMV-P52-1.3_LP     TGTATGAAGATGATCTTGTTACAGATGAATGCAAATGCGTATTCAGGGAAGTACAGACAC     3120
LCMV-P52-2.1_LP     TGTATGAAGATGATCTTGTTACAGATGAATGCAAATGCGTATTCAGGGAAGTACAGACAC     3120
                    ************************************************************

LCMV-WE_LP          ATGCAGAGGCAGAGCTTAAATTTTAAATTTGACTGGGACAAATTGGAAGAAGATGTAAGA     3180
LCMV-P42_LP         ATGCAGAGGCAGAGCTTAAATTTTAAATTTGACTGGGACAAATTGGAAGAAGATGTAAGA     3180
LCMV-P52_LP         ATGCAGAGGCAGAGCTTAAATTTTAAATTTGACTGGGACAAATTGGAAGAAGATGTAAGA     3180
LCMV-P91_LP         ATGCAGAGGCAGAGCTTAAATTTTAAATTTGACTGGGACAAATTGGAAGAAGATGTAAGA     3180
LCMV-P52-1_LP       ATGCAGAGGCAGAGTTTAAATTTTAAATTTGACTGGGACAAATTGGAAGAAGATGTAAGA     3180
LCMV-P52-1.3_LP     ATGCAGAGGCAGAGCTTAAATTTTAAATTTGACTGGGACAAATTGGAAGAAGATGTAAGA     3180
LCMV-P52-2.1_LP     ATGCAGAGGCAGAGCTTAAATTTTAAATTTGACTGGGACAAATTGGAAGAAGATGTAAGA     3180
                    ************** *********************************************

LCMV-WE_LP          ATTAGTGAAAGGGAAAGCAATTCTGAATCTCTAAGTAAGGCCCTTTCATTGACAAAATGC     3240
LCMV-P42_LP         ATTAGTGAAAGGGAAAGCAATTCTGAATCTCTAAGTAAGGCCCTTTCATTGACAAAATGC     3240
LCMV-P52_LP         ATTAGTGAAAGGGAAAGCAATTCTGAATCTCTAAGTAAGGCCCTTTCATTGACAAAATGC     3240
LCMV-P91_LP         ATTAGTGAAAGGGAAAGCAATTCTGAATCTCTAAGTAAGGCCCTTTCATTGACAAAATGC     3240
LCMV-P52-1_LP       ATTAGTGAAAGGGAAAGCAATTCTGAATCTCTAAGTAAGGCCCTTTCATTGACAAAATGC     3240
LCMV-P52-1.3_LP     ATTAGTGAAAGGGAAAGCAATTCTGAATCTCTAAGTAAGGCCCTTTCATTGACAAAATGC     3240
LCMV-P52-2.1_LP     ATTAGTGAAAGGGAAAGCAATTCTGAATCTCTAAGTAAGGCCCTTTCATTGACAAAATGC     3240
                    ************************************************************

LCMV-WE_LP          ATGAGTGCTGCTCTAAAGAATCTGTGTTTTTACTCAGAAGAATCACCAACATCATACACT     3300
LCMV-P42_LP         ATGAGTGCTGCTCTAAAGAATCTGTGTTTTTACTCAGAAGAATCACCAACATCATACACT     3300
LCMV-P52_LP         ATGAGTGCTGCTCTAAAGAATCTGTGTTTTTACTCAGAAGAATCACCAACATCATACACT     3300
LCMV-P91_LP         ATGAGTGCTGCTCTAAAGAATCTGTGTTTTTACTCAGAAGAATCACCAACATCATACACT     3300
LCMV-P52-1_LP       ATGAGTGCTGCTCTAAAGAATCTGTGTTTTTACTCAGAAGAATCACCAACATCATACACT     3300
LCMV-P52-1.3_LP     ATGAGTGCTGCTCTAAAGAATCTGTGTTTTTACTCAGAAGAATCACCAACATCATACACT     3300
LCMV-P52-2.1_LP     ATGAGTGCTGCTCTAAAGAATCTGTGTTTTTACTCAGAAGAATCACCAACATCATACACT     3300
                    ************************************************************
```

Figure 26 (cont'd)

```
LCMV-WE_LP          TCAGTTGGCCCTGACTCTGGGAGACTAAAATTTGCATTGTCATACAAAGAGCAGGTTGGG     3360
LCMV-P42_LP         TCAGTTGGCCCTGACTCTGGGAGACTAAAATTTGCATTGTCATACAAAGAGCAGGTTGGG     3360
LCMV-P52_LP         TCAGTTGGCCCTGACTCTGGGAGACTAAAATTTGCATTGTCATACAAAGAGCAGGTTGGG     3360
LCMV-P91_LP         TCAGTTGGCCCTGACTCTGGGAGACTAAAATTTGCATTGTCATACAAAGAGCAGGTTGGG     3360
LCMV-P52-1_LP       TCAGTTGGCCCTGACTCTGGGAGACTAAAATTTGCATTGTCATACAAAGAGCAGGTTGGG     3360
LCMV-P52-1.3_LP     TCAGTTGGCCCTGACTCTGGGAGACTAAAATTTGCATTGTCATACAAAGAGCAGGTTGGG     3360
LCMV-P52-2.1_LP     TCAGTTGGCCCTGACTCTGGGAGACTAAAATTTGCATTGTCATACAAAGAGCAGGTTGGG     3360
                    ************************************************************

LCMV-WE_LP          GGAAATAGAGAGCTTTACATTGGGGATTTGAGGACAAAAATGTTCACAAGATTGGTAGAA     3420
LCMV-P42_LP         GGAAATAGAGAGCTTTACATTGGGGATTTGAGGACAAAAATGTTCACAAGATTGGTAGAA     3420
LCMV-P52_LP         GGAAATAGAGAGCTTTACATTGGGGATTTGAGGACAAAAATGTTCACAAGATTGGTAGAA     3420
LCMV-P91_LP         GGAAATAGAGAGCTTTACATTGGGGATTTGAGGACAAAAATGTTCACAAGATTGGTAGAA     3420
LCMV-P52-1_LP       GGAAATAGAGAGCTTTACATTGGGGATTTGAGGACAAAAATGTTCACAAGATTGGTAGAA     3420
LCMV-P52-1.3_LP     GGAAATAGAGAGCTTTACATTGGGGATTTGAGGACAAAAATGTTCACAAGATTGGTAGAA     3420
LCMV-P52-2.1_LP     GGAAATAGAGAGCTTTACATTGGGGATTTGAGGACAAAAATGTTCACAAGATTGGTAGAA     3420
                    ************************************************************

LCMV-WE_LP          GATTATTTTGAATCCTTTTCTAGTTTCTTTTCAGGATCTTGTTTAAACAATGACAAAGAG     3480
LCMV-P42_LP         GATTATTTTGAATCCTTTTCTAGTTTCTTTTCAGGATCTTGTTTAAACAATGACAAAGAG     3480
LCMV-P52_LP         GATTATTTTGAATCCTTTTCTAGTTTCTTTTCAGGATCTTGTTTAAACAATGACAAAGAG     3480
LCMV-P91_LP         GATTATTTTGAATCCTTTTCTAGTTTCTTTTCAGGATCTTGTTTAAACAATGATAAAGAG     3480
LCMV-P52-1_LP       GATTATTTTGAATCCTTTTCTAGTTTCTTTTCAGGATCTTGTTTAAACAATGACAAAGAG     3480
LCMV-P52-1.3_LP     GATTACTTTGAATCCTTTTCTAGTTTCTTTTCAGGATCTTGTTTAAACAATGACAAAGAG     3480
LCMV-P52-2.1_LP     GATTATTTTGAATCCTTTTCTAGTTTCTTTTCAGGATCTTGTTTAAACAATGACAAAGAG     3480
                    ***** *********************************************** ******

LCMV-WE_LP          TTTGAAAATGCAATCTTGTCAATGACTATCAATGTGAGAGAAGGGTTGTTAAACTACAGC     3540
LCMV-P42_LP         TTTGAAAATGCAATCTTGTCAATGACTATCAATGTGAGAGAAGGGTTGTTAAACTACAGC     3540
LCMV-P52_LP         TTTGAAAATGCAATCTTGTCAATGACTATCAATGTGAGAGAAGGGTTGTTAAACTACAGC     3540
LCMV-P91_LP         TTTGAAAATGCAATCTTGTCAATGACTATCAATGTGAGAGAAGGGTTGTTAAACTACAGC     3540
LCMV-P52-1_LP       TTTGAAAATGCAATCTTGTCAATGACTATCAATGTGAGAGAAGGGTTGTTAAACTACAGC     3540
LCMV-P52-1.3_LP     TTTGAAAATGCAATCTTGTCAATGACTATCAATGTGAGAGAAGGGTTGTTAAACTACAGC     3540
LCMV-P52-2.1_LP     TTTGAAAATGCAATCTTGTCAATGACTATCAATGTGAGAGAAGGGTTGTTAAACTACAGC     3540
                    ************************************************************

LCMV-WE_LP          ATGGATCACAGCAAATGGGGACCAATGATGTGCCCATTCCTATTCTTAATGCTTCTCCAA     3600
LCMV-P42_LP         ATGGATCACAGCAAATGGGGACCAATGATGTGCCCATTCCTATTCTTAATGCTYCTCCAA     3600
LCMV-P52_LP         ATGGATCACAGCAAATGGGGACCAATGATGTGCCCATTCCTATTCTTAATGCTTCTCCAA     3600
LCMV-P91_LP         ATGGATCACAGCAAATGGGGACCAATGATGTGCCCATTCCTATTCTTAATGCTTCTCCAA     3600
LCMV-P52-1_LP       ATGGATCACAGCAAATGGGGACCAATGATGTGCCCATTCCTATTCTTAATGCTTCTCCAA     3600
LCMV-P52-1.3_LP     ATGGATCACAGCAAATGGGGACCAATGATGTGCCCATTCCTATTCTTAATGCTTCTCCAA     3600
LCMV-P52-2.1_LP     ATGGATCACAGCAAATGGGGACCAATGATGTGCCCATTCCTATTCTTAATGCTTCTCCAA     3600
                    ***************************************************** ******

LCMV-WE_LP          AATCTCAAACTGGGTGATGATCAGTACGTGCGTTCTGGAAAAGATCATGTTAGCACCTTG     3660
LCMV-P42_LP         AATCTCAAACTGGGTGATGATCAGTACGTGCGTTCTGGAAAAGATCATGTTAGCACCTTG     3660
LCMV-P52_LP         AATCTCAAACTGGGTGATGATCAGTACGTGCGTTCTGGAAAAGATCATGTTAGCACCTTG     3660
LCMV-P91_LP         AATCTCAAACTGGGTGATGATCAGTACGTGCGTTCTGGAAAAGATCATGTTAGCACCTTG     3660
LCMV-P52-1_LP       AATCTCAAACTGGGTGATGATCAGTACGTGCGTTCTGGGAAAGATCATGTTAGCACCTTG     3660
LCMV-P52-1.3_LP     AATCTCAAACTGGGTGATGATCAGTACGTGCGTTCTGGAAAAGATCATGTTAGCACCTTG     3660
LCMV-P52-2.1_LP     AATCTCAAACTGGGTGATGATCAGTACGTGCGTTCTGGAAAAGATCATGTTAGCACCTTG     3660
                    ************************************** *********************

LCMV-WE_LP          TTGACTTGGCATATGCATAAACTTGTTGAAGTCCCTTTCCCTGTTGTGAATGCAATGATG     3720
LCMV-P42_LP         TTGACTTGGCATATGCATAAACTTGTTGAAGTCCCTTTCCCTGTTGTGAATGCAATGATG     3720
LCMV-P52_LP         TTGACTTGGCATATGCATAAACTTGTTGAAGTCCCTTTCCCTGTTGTGAATGCAATGATG     3720
LCMV-P91_LP         TTGACTTGGCATATGCATAAACTTGTTGAAGTCCCTTTCCCTGTTGTGAATGCAATGATG     3720
LCMV-P52-1_LP       TTGACTTGGCATATGCATAAACTTGTTGAAGTCCCTTTCCCTGTTGTGAATGCAATGATG     3720
LCMV-P52-1.3_LP     TTGACTTGGCATATGCATAAACTTGTTGAAGTCCCTTTCCCTGTTGTGAATGCAATGATG     3720
LCMV-P52-2.1_LP     TTGACTTGGCATATGCATAAACTTGTTGAAGTCCCTTTCCCTGTTGTGAATGCAATGATG     3720
                    ************************************************************

LCMV-WE_LP          AAATCATATGTTAAATCAAAACTCAAGCTTCTCAAAGGGTCAGGAACGACTGTTACGGAG     3780
LCMV-P42_LP         AAATCATATGTTAAATCAAAACTCAAGCTTCTCAAAGGGTCAGGAACGACTGTTACGGAG     3780
LCMV-P52_LP         AAATCATATGTTAAATCAAAACTCAAGCTTCTCAAAGGGTCAGGAACGACTGTTACGGAG     3780
LCMV-P91_LP         AAATCATATGTTAAATCAAAACTCAAGCTTCTCAAAGGGTCAGGAACGACTGTTACGGAG     3780
LCMV-P52-1_LP       AAATCATATGTTAAATCAAAACTCAAGCTTCTCAAAGGGTCAGGAACGACTGTTACGGAG     3780
LCMV-P52-1.3_LP     AAATCATATGTTAAATCAAAACTCAAGCTTCTCAAAGGGTCAGGAACGACTGTTACGGAG     3780
LCMV-P52-2.1_LP     AAATCATATGTTAAATCAAAACTCAAGCTTCTCAAAGGGTCAGGAACGACTGTTACGGAG     3780
                    ************************************************************
```

Figure 26 (cont'd)

```
LCMV-WE_LP          AGAATCTTTAGAGAGTATTTTGAAATGGGGGTGGTGCCATCTCACATATCTAGTCTCATT   3840
LCMV-P42_LP         AGAATCTTTAGAGAGTATTTTGAAATGGGGGTGGTGCCATCTCACATATCTAGTCTCATT   3840
LCMV-P52_LP         AGAATCTTTAGAGAGTATTTTGAAATGGGGGTGGTGCCATCTCACATATCTAGTCTCATT   3840
LCMV-P91_LP         AGAATCTTTAGAGAGTATTTTGAAATGGGGGTGGTGCCATCTCACATATCTAGTCTCATT   3840
LCMV-P52-1_LP       AGAATCTTTAGAGAGTATTTTGAAATGGGGGTGGTGCCATCTCACATATCTAGTCTCATT   3840
LCMV-P52-1.3_LP     AGAATCTTTAGAGAGTATTTTGAAATGGGGGTGGTGCCATCTCACATATCTAGTCTCATT   3840
LCMV-P52-2.1_LP     AGAATCTTTAGAGAGTATTTTGAAATGGGGGTGGTGCCATCTCACATATCTAGTCTCATT   3840
                    ************************************************************

LCMV-WE_LP          GACATGGGACAGGGGATCCTACACAATGCTTCTGATTTTTACGGTTTAATTAGTGAAAGG   3900
LCMV-P42_LP         GACATGGGACAGGGGATCCTACACAATGCTTCTGATTTTTACGGTTTAATTAGTGAAAGG   3900
LCMV-P52_LP         GACATGGGACAGGGGATCCTACACAATGCTTCTGATTTTTACGGTTTAATTAGTGAAAGG   3900
LCMV-P91_LP         GACATGGGACAGGGGATCCTACACAATGCTTCTGATTTTTACGGTTTAATTAGTGAAAGG   3900
LCMV-P52-1_LP       GACATGGGACAGGGGATCCTACACAATGCTTCTGATTTTTACGGTTTAATTAGTGAAAGG   3900
LCMV-P52-1.3_LP     GACATGGGACAGGGGATCCTACACAATGCTTCTGATTTTTACGGTTTAATTAGTGAAAGG   3900
LCMV-P52-2.1_LP     GACATGGGACAGGGGATCCTACACAATGCTTCTGATTTTTACGGTTTAATTAGTGAAAGG   3900
                    ************************************************************

LCMV-WE_LP          TTTATCAATTATTGTATTGGTGTCATTTTTGGAGAGAGGCCAGAAGCCTATACATCAAGT   3960
LCMV-P42_LP         TTTATCAATTATTGTATTGGTGTCATTTTTGGAGAGAGGCCAGAAGCCTATACATCAAGT   3960
LCMV-P52_LP         TTTATCAATTATTGTATTGGTGTCATTTTTGGAGAGAGGCCAGAAGCCTATACATCAAGT   3960
LCMV-P91_LP         TTTATCAATTATTGTATTGGTGTCATTTTTGGAGAGAGGCCAGAAGCCTATACATCAAGT   3960
LCMV-P52-1_LP       TTTATCAATTATTGTATTGGTGTCATTTTTGGAGAGAGGCCAGAAGCCTATACATCAAGT   3960
LCMV-P52-1.3_LP     TTTATCAATTATTGTATTGGTGTCATTTTTGGAGAGAGGCCAGAAGCCTATACATCAAGT   3960
LCMV-P52-2.1_LP     TTTATCAATTATTGTATTGGTGTCATTTTTGGAGAGAGGCCAGAAGCCTATACATCAAGT   3960
                    ************************************************************

LCMV-WE_LP          GATGATCAGATCACTTTATTTGACAAGAGATTGAGTGACTTAGTTGATAGTGACCCAGAA   4020
LCMV-P42_LP         GATGATCAGATCACTTTATTTGACAAGAGATTGAGTGACTTAGTTGATAGTGACCCAGAA   4020
LCMV-P52_LP         GATGATCAGATCACTTTATTTGACAAGAGATTGAGTGACTTAGTTGATAGTGACCCAGAA   4020
LCMV-P91_LP         GATGATCAGATCACTTTATTTGACAAGAGATTGAGTGACTTAGTTGATAGTGACCCAGAA   4020
LCMV-P52-1_LP       GATGATCAGATCACTTTATTTGACAAGAGATTGAGTGACTTAGTTGATAGTGACCCAGAA   4020
LCMV-P52-1.3_LP     GATGATCAGATCACTTTATTTGACAAGAGATTGAGTGACTTAGTTGATAGTGACCCAGAA   4020
LCMV-P52-2.1_LP     GATGATCAGATCACTTTATTTGACAAGAGATTGAGTGACTTAGTTGATAGTGACCCAGAA   4020
                    ************************************************************

LCMV-WE_LP          GAAGTCCTTGTCTTGCTGGAATTCCACTCTCACTTAAGTGGTTTGTTGAACAAGTTCATC   4080
LCMV-P42_LP         GAAGTCCTTGTCTTGCTGGAATTCCACTCTCACTTAAGTGGTTTGTTGAACAAGTTCATC   4080
LCMV-P52_LP         GAAGTCCTTGTCTTGCTGGAATTCCACTCTCACTTAAGTGGTTTGTTGAACAAGTTCATC   4080
LCMV-P91_LP         GAAGTCCTTGTCTTGCTGGAATTCCACTCTCACTTAAGTGGTTTGTTGAACAAGTTCATC   4080
LCMV-P52-1_LP       GAAGTCCTTGTCTTGCTGGAATTCCACTCTCACTTAAGTGGTTTGTTGAACAAGTTCATC   4080
LCMV-P52-1.3_LP     GAAGTCCTTGTCTTGCTGGAATTCCACTCTCACTTAAGTGGTTTGTTGAACAAGTTCATC   4080
LCMV-P52-2.1_LP     GAAGTCCTTGTCTTGCTGGAATTCCACTCTCACTTAAGTGGTTTGTTGAACAAGTTCATC   4080
                    ************************************************************

LCMV-WE_LP          AGTCCAAAAAGTGTGGTTGGGCGGTTTGCAGCGGAATTCAAATCCAGATTTTATGTGTGG   4140
LCMV-P42_LP         AGTCCAAAAAGTGTGGTTGGGCGGTTTGCAGCGGAATTCAAATCCAGATTTTATGTGTGG   4140
LCMV-P52_LP         AGTCCAAAAAGTGTGGTTGGGCGGTTTGCAGCGGAATTCAAATCCAGATTTTATGTGTGG   4140
LCMV-P91_LP         AGTCCAAAAAGTGTGGTTGGGCGGTTTGCAGCGGAATTCAAATCCAGATTTTATGTGTGG   4140
LCMV-P52-1_LP       AGTCCAAAAAGTGTGGTTGGGCGGTTTGCAGCGGAATTCAAATCCAGATTTTATGTGTGG   4140
LCMV-P52-1.3_LP     AGTCCAAAAAGTGTGGTTGGGCGGTTTGCAGCGGAATTCAAATCCAGATTTTATGTGTGG   4140
LCMV-P52-2.1_LP     AGTCCAAAAAGTGTGGTTGGGCGGTTTGCAGCGGAATTCAAATCCAGATTTTATGTGTGG   4140
                    ************************************************************

LCMV-WE_LP          GGGGAGGAGGTCCCTCTCCTCACGAAATTTGTGTCTGCGGCACTACACAATGTTAAGTGT   4200
LCMV-P42_LP         GGGGAGGAGGTCCCTCTCCTCACGAAATTTGTGTCTGCGGCACTACACAATGTTAAGTGT   4200
LCMV-P52_LP         GGGGAGGAGGTCCCTCTCCTCACGAAATTTGTGTCTGCGGCACTACACAATGTTAAGTGT   4200
LCMV-P91_LP         GGGGAGGAGGTCCCTCTCCTCACGAAATTTGTGTCTGCGGCACTACACAATGTTAAGTGT   4200
LCMV-P52-1_LP       GGGGAGGAGGTCCCTCTCCTCACGAAATTTGTGTCTGCGGCACTACACAATGTTAAGTGT   4200
LCMV-P52-1.3_LP     GGGGAGGAGGTCCCTCTCCTCACGAAATTTGTGTCTGCGGCACTACACAATGTTAAGTGT   4200
LCMV-P52-2.1_LP     GGGGAGGAGGTCCCTCTCCTCACGAAATTTGTGTCTGCGGCACTACACAATGTTAAGTGT   4200
                    ************************************************************

LCMV-WE_LP          AAAGAACCGCATCAACTTTGTGAGACAATAGATACGATTGCTGATCAAGCTATAGCAAAT   4260
LCMV-P42_LP         AAAGAACCGCATCAACTTTGTGAGACAATAGATACGATTGCTGATCAAGCTATAGCAAAT   4260
LCMV-P52_LP         AAAGAACCGCATCAACTTTGTGAGACAATAGATACGATTGCTGATCAAGCTATAGCAAAT   4260
LCMV-P91_LP         AAAGAACCGCATCAACTTTGTGAGACAATAGATACGATTGCTGATCAAGCTATAGCAAAT   4260
LCMV-P52-1_LP       AAAGAACCGCATCAACTTTGTGAGACAATAGATACGATTGCTGATCAAGCTATAGCAAAT   4260
LCMV-P52-1.3_LP     AAAGAACCGCATCAACTTTGTGAGACAATAGATACGATTGCTGATCAAGCTATAGCAAAT   4260
LCMV-P52-2.1_LP     AAAGAACCGCATCAACTTTGTGAGACAATAGATACGATTGCTGATCAAGCTATAGCAAAT   4260
                    ************************************************************
```

Figure 26 (cont'd)

```
LCMV-WE_LP          GGAGTTCCAGTTTTTTTAGTAAACTGTATCCAGAGGAGGACACTGGATCTCTTGAAATAT   4320
LCMV-P42_LP         GGAGTTCCAGTTTTTTTAGTAAACTGTATCCAGAGGAGGACACTGGATCTCTTGAAATAT   4320
LCMV-P52_LP         GGAGTTCCAGTTTTTTTAGTAAACTGTATCCAGAGGAGGACACTGGATCTCTTGAAATAT   4320
LCMV-P91_LP         GGAGTTCCAGTTTTTTTAGTAAACTGTATCCAGAGGAGGACACTGGATCTCTTGAAATAT   4320
LCMV-P52-1_LP       GGAGTTCCAGTTTTTTTAGTAAACTGTATCCAGAGGAGGACACTGGATCTCTTGAAATAT   4320
LCMV-P52-1.3_LP     GGAGTTCCAGTTTTTTTAGTAAACTGTATCCAGAGGAGGACACTGGATCTCTTGAAATAT   4320
LCMV-P52-2.1_LP     GGAGTTCCAGTTTTTTTAGTAAACTGTATCCAGAGGAGGACACTGGATCTCTTGAAATAT   4320
                    ************************************************************

LCMV-WE_LP          GCTAATTTCCCTTTAGATCCATTCTTGTTAAACACTCACACTGATGTAAAGGATTGGTTA   4380
LCMV-P42_LP         GCTAATTTCCCTTTAGATCCATTCTTGTTAAACACTCACACTGATGTAAAGGATTGGTTA   4380
LCMV-P52_LP         GCTAATTTCCCTTTAGATCCATTCTTGTTAAACACTCACACTGATGTAAAGGATTGGTTA   4380
LCMV-P91_LP         GCTAATTTCCCTTTAGATCCATTCTTGTTAAACACTCACACTGATGTAAAGGATTGGTTA   4380
LCMV-P52-1_LP       GCTAATTTCCCTTTAGATCCATTCTTGTTAAACACTCACACTGATGTAAAGGATTGGTTA   4380
LCMV-P52-1.3_LP     GCTAATTTCCCTTTAGATCCATTCTTGTTAAACACTCACACTGATGTAAAGGATTGGTTA   4380
LCMV-P52-2.1_LP     GCTAATTTCCCTTTAGATCCATTCTTGTTAAACACTCACACTGATGTAAAGGATTGGTTA   4380
                    ************************************************************

LCMV-WE_LP          GATGGTTCTAGAGGTTATAGAATCCAAAGACTCATTGAAGAATTGTGTCCCAGTGAAACA   4440
LCMV-P42_LP         GATGGTTCTAGAGGTTATAGAATCCAAAGACTCATTGAAGAATTGTGTCCCAGTGAAACA   4440
LCMV-P52_LP         GATGGTTCTAGAGGTTATAGAATCCAAAGACTCATTGAAGAATTGTGTCCCAGTGAAACA   4440
LCMV-P91_LP         GATGGTTCTAGAGGTTATAGAATCCAAAGACTCATTGAAGAATTGTGTCCCAGTGAAACA   4440
LCMV-P52-1_LP       GATGGTTCTAGAGGTTATAGAATCCAAAGACTCATTGAAGAATTGTGTCCCAGTGAAACA   4440
LCMV-P52-1.3_LP     GATGGTTCTAGAGGTTATAGAATCCAAAGACTCATTGAAGAATTGTGTCCCAGTGAAACA   4440
LCMV-P52-2.1_LP     GATGGTTCTAGAGGTTATAGAATCCAAAGACTCATTGAAGAATTGTGTCCCAGTGAAACA   4440
                    ************************************************************

LCMV-WE_LP          AAGATCATGAGAAAACTTGTAAGAAGACTACATCACAAACTCAAGAACGGTGAATGTAAC   4500
LCMV-P42_LP         AAGATCATGAGAAAACTTGTAAGAAGACTACATCACAAACTCAAGAACGGTGAATGTAAC   4500
LCMV-P52_LP         AAGATCATGAGAAAACTTGTAAGAAGACTACATCACAAACTCAAGAACGGTGAATGTAAC   4500
LCMV-P91_LP         AAGATCATGAGAAAACTTGTAAGAAGACTACATCACAAACTCAAGAACGGTGAATGTAAC   4500
LCMV-P52-1_LP       AAGATCATGAGAAAACTTGTAAGAAGACTACATCACAAACTCAAGAACGGTGAATGTAAC   4500
LCMV-P52-1.3_LP     AAGATCATGAGAAAACTTGTAAGAAGACTACATCACAAACTCAAGAACGGTGAATGTAAC   4500
LCMV-P52-2.1_LP     AAGATCATGAGAAAACTTGTAAGAAGACTACATCACAAACTCAAGAACGGTGAATGTAAC   4500
                    ************************************************************

LCMV-WE_LP          GAGGAATTTTTTCTAGACCTCTTCAACAGGGAAAAGAAAGAGGCCATCCTTCAATTGGGA   4560
LCMV-P42_LP         GAGGAATTTTTTCTAGACCTCTTCAACAGGGAAAAGAAAGAGGCCATCCTTCAATTGGGA   4560
LCMV-P52_LP         GAGGAATTTTTTCTAGACCTCTTCAACAGGGAAAAGAAAGAGGCCATCCTTCAATTGGGA   4560
LCMV-P91_LP         GAGGAATTTTTTCTAGACCTCTTCAACAGGGAAAAGGAAGAGGCCATCCTTCAATTGGGA   4560
LCMV-P52-1_LP       GAGGAATTTTTTCTAGACCTCTTCAACAGGGAAATGAAAGAGGCCATCCTTCAATTGGGA   4560
LCMV-P52-1.3_LP     GAGGAATTTTTTCTAGACCTCTTCAACAGGGAAAAGAAAGAGGCCATCCTTCAATTGGGA   4560
LCMV-P52-2.1_LP     GAGGAATTTTTTCTAGACCTCTTCAACAGGGAAAAGAAAGAGGCCATCCTTCAATTGGGA   4560
                    ********************************** * ***********************

LCMV-WE_LP          GAGATTCTTGGTCTTGAGGATGATCTTAATGAGTTGGCAAGCATCAATTGGTTGAATCTG   4620
LCMV-P42_LP         GAGATTCTTGGTCTTGAGGATGATCTTAATGAGTTGGCAAGCATCAATTGGTTGAATCTG   4620
LCMV-P52_LP         GAGATTCTTGGTCTTGAGGATGATCTTAATGAGTTGGCAAGCATCAATTGGTTGAATCTG   4620
LCMV-P91_LP         GAGATTCTTGGTCTTGAGGATGATCTTAATGAGTTGGCAAGCATCAATTGGTTGAATCTG   4620
LCMV-P52-1_LP       GAGATTCTTGGTCTTGAGGATGATCTCAATGAGTTGGCAAGCATCAATTGGTTGAATCTG   4620
LCMV-P52-1.3_LP     GAGATTCTTGGTCTTGAGGATGATCTTAATGAGTTGGCAAGCATCAATTGGTTGAATCTG   4620
LCMV-P52-2.1_LP     GAGATTCTTGGTCTTGAGGATGATCTTAATGAGTTGGCAAGCATCAATTGGTTGAATCTG   4620
                    ************************** *********************************

LCMV-WE_LP          AATGAAATGTTCCCATTGAGGATGGTTCTGAGACAAAAAGTGGTTTACCCATCAGTAATG   4680
LCMV-P42_LP         AATGAAATGTTCCCATTGAGGATGGTTCTGAGACAAAAAGTGGTTTACCCATCAGTRATG   4680
LCMV-P52_LP         AATGAAATGTTCCCATTGAGGATGGTTCTGAGACAAAAAGTGGTTTACCCATCAGTAATG   4680
LCMV-P91_LP         AATGAAATGTTCCCATTGAGGATGGTTCTGAGACAAAAAGTGGTTTACCCATCAGTAATG   4680
LCMV-P52-1_LP       AATGAAATGTTCCCATTGAGGATGGTTCTGAGACAAAAAGTGGTTTACCCATCAGTAATG   4680
LCMV-P52-1.3_LP     AATGAAATGTTCCCATTGAGGATGGTTCTGAGACAAAAAGTGGTTTACCCATCAGTAATG   4680
LCMV-P52-2.1_LP     AATGAAATGTTCCCATTGAGGATGGTTCTGAGACAAAAAGTGGTTTACCCATCAGTAATG   4680
                    ******************************************************** ***

LCMV-WE_LP          ACCTTTCAAGAGGAAAAGATCCCCTCATTGATTAAAACACTCCAAAATAAGCTTTGTAGT   4740
LCMV-P42_LP         ACCTTTCAAGAGGAAAAGATCCCCTCATTGATTAAAACACTCCAAAATAAGCTTTGTAGT   4740
LCMV-P52_LP         ACCTTTCAAGAGGAAAAGATCCCCTCATTGATTAAAACACTCCAAAATAAGCTTTGTAGT   4740
LCMV-P91_LP         ACCTTTCAAGAGGAAAAGATCCCCTCATTGATTAAAACACTCCAAAATAAGCTTTGTAGT   4740
LCMV-P52-1_LP       ACCTTTCAAGAGGAAAAGATCCCCTCATTGATTAAAACACTCCAAAATAAGCTTTGTAGT   4740
LCMV-P52-1.3_LP     ACCTTTCAAGAGGAAAAGATCCCCTCATTGATTAAAACACTCCAAAATAAGCTTTGTAGT   4740
LCMV-P52-2.1_LP     ACCTTTCAAGAGGAAAAGATCCCCTCATTGATTAAAACACTCCAAAATAAGCTTTGTAGT   4740
                    ************************************************************
```

Figure 26 (cont'd)

```
LCMV-WE_LP          AAGTTCACAAGAGGTGCACAGAAGCTGTTGTCAGAGGCAATCAACAAATCAGCTTTTCAG    4800
LCMV-P42_LP         AAGTTCACAAGAGGTGCACAGAAGCTGTTGTCAGAGGCAATCAACAAATCAGCTTTTCAG    4800
LCMV-P52_LP         AAGTTCACAAGAGGTGCACAGAAGCTGTTGTCAGAGGCAATCAACAAATCAGCTTTTCAG    4800
LCMV-P91_LP         AAGTTCACAAGAGGTGCACAGAAGCTGTTGTCAGAGGCAATCAACAAATCAGCTTTTCAG    4800
LCMV-P52-1_LP       AAGTTCACAAGAGGTGCACAGAAGCTGTTGTCAGAGGCAATCAACAAATCAGCTTTTCAG    4800
LCMV-P52-1.3_LP     AAGTTCACAAGAGGTGCACAGAAGCTGTTGTCAGAGGCAATCAACAAATCAGCTTTTCAG    4800
LCMV-P52-2.1_LP     AAGTTCACAAGAGGTGCACAGAAGCTGTTGTCAGAGGCAATCAACAAATCAGCTTTTCAG    4800
                    ************************************************************

LCMV-WE_LP          AGTTGTGTCTCATCCGGCTTTATAGGTCTCTGTAAGACTTTAGGAAGTAGGTGTGTGAGA    4860
LCMV-P42_LP         AGTTGTGTCTCATCCGGCTTTATAGGTCTCTGTAAGACTTTAGGAAGTAGGTGTGTGAGA    4860
LCMV-P52_LP         AGTTGTGTCTCATCCGGCTTTATAGGTCTCTGTAAGACTTTAGGAAGTAGGTGTGTGAGA    4860
LCMV-P91_LP         AGTTGTGTCTCATCCGGCTTTATAGGTCTCTGTAAGACTTTAGGAAGTAGGTGTGTGAGA    4860
LCMV-P52-1_LP       AGTTGTGTCTCATCCGGCTTTATAGGTCTCTGTAAGACTTTAGGAAGTAGGTGTGTGAGA    4860
LCMV-P52-1.3_LP     AGTTGTGTCTCATCCGGCTTTATAGGTCTCTGTAAGACTTTAGGAAGTAGGTGTGTGAGA    4860
LCMV-P52-2.1_LP     AGTTGTGTCTCATCCGGCTTTATAGGTCTCTGTAAGACTTTAGGAAGTAGGTGTGTGAGA    4860
                    ************************************************************

LCMV-WE_LP          AATAAAAACAGGGAAAATATGTATATCAGAAAGGTGCTTGAAGATCTGACCATGGATGAA    4920
LCMV-P42_LP         AATAAAAACAGGGAAAATATGTATATCAGAAAGGTGCTTGAAGATCTGACCATGGATGAA    4920
LCMV-P52_LP         AATAAAAACAGGGAAAATATGTATATCAGAAAGGTGCTTGAAGATCTGACCATGGATGAA    4920
LCMV-P91_LP         AATAAAAACAGGGAAAATATGTATATCAGAAAGGTGCTTGAAGATCTGACCATGGATGAA    4920
LCMV-P52-1_LP       AATAAAAACAGGGAAAATATGTATATCAGAAAGGTGCTTGAAGATCTGACCATGGATGAA    4920
LCMV-P52-1.3_LP     AATAAAAACAGGGAAAATATGTATATCAGAAAGGTGCTTGAAGATCTGACCATGGATGAA    4920
LCMV-P52-2.1_LP     AATAAAAACAGGGAAAATATGTATATCAGAAAGGTGCTTGAAGATCTGACCATGGATGAA    4920
                    ************************************************************

LCMV-WE_LP          CATGTCACAAGGGTTCACAAACAAGATGGTGTGATGTTGTACATTTGCGACAAGCAGAGA    4980
LCMV-P42_LP         CATGTCACAAGGGTTCACAAACAAGATGGTGTGATGTTGTACATTTGCGACAAGCAGAGA    4980
LCMV-P52_LP         CATGTCACAAGGGTTCACAAACAAGATGGTGTGATGTTGTACATTTGCGACAAGCAGAGA    4980
LCMV-P91_LP         CATGTCACAAGGGTTCACAAACAAGATGGTGTGATGTTGTACATTTGCGACAAGCAGAGA    4980
LCMV-P52-1_LP       CATGTCACAAGGGTTCACAAACAAGATGGTGTGATGTTGTACATTTGCGACAAGCAGAGA    4980
LCMV-P52-1.3_LP     CATGTCACAAGGGTTCACAAACAAGATGGTGTGATGTTGTACATTTGCGACAAGCAGAGA    4980
LCMV-P52-2.1_LP     CATGTCACAAGGGTTCACAAACAAGATGGTGTGATGTTGTACATTTGCGACAAGCAGAGA    4980
                    ************************************************************

LCMV-WE_LP          CACCCAGAGGCTCACCGTGACCACATCAACCTTTTGAGGCCCCTTCTCTGGGACTACATT    5040
LCMV-P42_LP         CACCCAGAGGCTCACCGTGACCACATCAACCTTTTGAGGCCCCTTCTCTGGGACTACATT    5040
LCMV-P52_LP         CACCCAGAGGCTCACCGTGACCACATCAACCTTTTGAGGCCCCTTCTCTGGGACTACATT    5040
LCMV-P91_LP         CACCCAGAGGCTCACCGTGACCACATCAACCTTTTGAGGCCCCTTCTCTGGGACTACATT    5040
LCMV-P52-1_LP       CACCCAGAGGCTCACCGTGACCACATCAACCTTTTGAGGCCCCTTCTCTGGGACTACATT    5040
LCMV-P52-1.3_LP     CACCCAGAGGCTCACCGTGACCACATCAACCTTTTGAGGCCCCTTCTCTGGGACTACATT    5040
LCMV-P52-2.1_LP     CACCCAGAGGCTCACCGTGACCACATCAACCTTTTGAGGCCCCTTCTCTGGGACTACATT    5040
                    ************************************************************

LCMV-WE_LP          TGCATCTCATTGAGCAACTCTTTTGAGCTGGGTGTTTGGGTTTTAGCAGAACCTGTGAAA    5100
LCMV-P42_LP         TGCATCTCATTGAGCAACTCTTTTGAGCTGGGTGTTTGGGTTTTAGCAGAACCTGTGAAA    5100
LCMV-P52_LP         TGCATCTCATTGAGCAACTCTTTTGAGCTGGGTGTTTGGGTTTTAGCAGAACCTGTGAAA    5100
LCMV-P91_LP         TGCATCTCATTGAGCAACTCTTTTGAGCTGGGTGTTTGGGTTTTAGCAGAACCTGTGAAA    5100
LCMV-P52-1_LP       TGCATCTCATTGAGCAACTCTTTTGAGCTGGGTGTTTGGGTTTTAGCAGAACCTGTGAAA    5100
LCMV-P52-1.3_LP     TGCATCTCATTGAGCAACTCTTTTGAGCTGGGTGTTTGGGTTTTAGCAGAACCTGTGAAA    5100
LCMV-P52-2.1_LP     TGCATCTCATTGAGCAACTCTTTTGAGCTGGGTGTTTGGGTTTTAGCAGAACCTGTGAAA    5100
                    ************************************************************

LCMV-WE_LP          GGAAAGAACGAGAGTAATTCGGCTGTTAGGCACTTAAATCCATGTGATTATGTAGCAAGA    5160
LCMV-P42_LP         GGAAAGAACGAGAGTAATTCGGCTGTTAGGCACTTAAATCCATGTGATTATGTAGCAAGA    5160
LCMV-P52_LP         GGAAAGAACGAGAGTAATTCGGCTGTTAGGCACTTAAATCCATGTGATTATGTAGCAAGA    5160
LCMV-P91_LP         GGAAAGAACGAGAGTAATTCGGCTGTTAGGCACTTAAATCCATGTGATTATGTAGCAAGA    5160
LCMV-P52-1_LP       GGAAAGAACGAGAGTAATTCGGCTGTTAGGCACTTAAATCCATGTGATTATGTAGCAAGA    5160
LCMV-P52-1.3_LP     GGAAAGAACGAGAGTAATTCGGCTGTTAGGCACTTAAATCCATGTGATTATGTAGCAAGA    5160
LCMV-P52-2.1_LP     GGAAAGAACGAGAGTAATTCGGCTGTTAGGCACTTAAATCCATGTGATTATGTAGCAAGA    5160
                    ************************************************************

LCMV-WE_LP          AAACCTGAGAGTTCGAGACTACTAGAGGATAAAGTGAGTTTGAATCATGTAATTCAATCT    5220
LCMV-P42_LP         AAACCTGAGAGTTCGAGACTACTAGAGGATAAAGTGAGTTTGAATCATGTAATTCAATCT    5220
LCMV-P52_LP         AAACCTGAGAGTTCGAGACTACTAGAGGATAAAGTGAGTTTGAATCATGTAATTCAATCT    5220
LCMV-P91_LP         AAACCTGAGAGTTCGAGACTACTAGAGGATAAAGTGAGTTTGAATCATGTAATTCAATCT    5220
LCMV-P52-1_LP       AAACCTGAGAGTTCGAGACTACTAGAGGATAAAGTGAGTTTGAATCATGTAATTCAATCT    5220
LCMV-P52-1.3_LP     AAACCTGAGAGTTCGAGACTACTAGAGGATAAAGTGAGTTTGAATCATGTAATTCAATCT    5220
LCMV-P52-2.1_LP     AAACCTGAGAGTTCGAGACTACTAGAGGATAAAGTGAGTTTGAATCATGTAATTCAATCT    5220
                    ************************************************************
```

Figure 26 (cont'd)

```
LCMV-WE_LP          GTGAGGCGACTGTACCCCAAAATCTTTGAGGATCAGTTGCTCCCATTCATGTCTGATGTG   5280
LCMV-P42_LP         GTGAGGCGACTGTACCCCAAAATCTTTGAGGATCAGTTGCTCCCATTCATGTTTGATGTG   5280
LCMV-P52_LP         GTGAGGCGACTGTACCCCAAAATCTTTGAGGATCAGTTGCTCCCATTCATGTCTGATGTG   5280
LCMV-P91_LP         GTGAGGCGACTGTACCCCAAAATCTTTGAGGATCAGTTGCTCCCATTCATGTCTGATGTG   5280
LCMV-P52-1_LP       GTGAGGCGACTGTACCCCAAAATCTTTGAGGATCAGTTGCTCCCATTCATGTCTGATGTG   5280
LCMV-P52-1.3_LP     GTGAGGCGACTGTACCCCAAAATCTTTGAGGATCAGTTGCTCCCATTCATGTCTGATGTG   5280
LCMV-P52-2.1_LP     GTGAGGCGACTGTACCCCAAAATCTTTGAGGATCAGTTGCTCCCATTCATGTCTGATGTG   5280
                    ***************************************************** ******

LCMV-WE_LP          AGCTCAAAAAATATGAGATGGAGTCCCAGGATTAAATTCCTTGACCTTTGTGTGCTGATT   5340
LCMV-P42_LP         AGCTCAAAAAATATGAGATGGAGTCCCAGGATTAAATTCCTTGACCTTTGTGTGCTGATT   5340
LCMV-P52_LP         AGCTCAAAAAATATGAGATGGAGTCCCAGGATTAAATTCCTTGACCTTTGTGTGCTGATT   5340
LCMV-P91_LP         AGCTCAAAAAATATGAGATGGAGTCCCAGGATTAAATTCCTTGACCTTTGTGTGCTGATT   5340
LCMV-P52-1_LP       AGCTCAAAAAATATGAGATGGAGTCCCAGGATTAAATTCCTTGACCTTTGTGTGCTGATT   5340
LCMV-P52-1.3_LP     AGCTCAAAAAATATGAGATGGAGTCCCAGGATTAAATTCCTTGACCTTTGTGTGCTGATT   5340
LCMV-P52-2.1_LP     AGCTCAAAAAATATGAGATGGAGTCCCAGGATTAAATTCCTTGACCTTTGTGTGCTGATT   5340
                    ************************************************************

LCMV-WE_LP          GACATCAACTCAGAGTCTTTGTCACTCATTTCTCATGTTGTCAAATGGAAGAGGGACGAA   5400
LCMV-P42_LP         GACATCAACTCAGAGTCTTTGTCACTCATTTCTCATGTTGTCAAATGGAAGAGGGACGAA   5400
LCMV-P52_LP         GACATCAACTCAGAGTCTTTGTCACTCATTTCTCATGTTGTCAAATGGAAGAGGGACGAA   5400
LCMV-P91_LP         GACATCAACTCAGAGTCTTTGTCACTCATTTCTCATGTTGTCAAATGGAAGAGGGACGAA   5400
LCMV-P52-1_LP       GACATCAACTCAGAGTCTTTGTCACTCATTTCTCATGTTGTCAAATGGAAGAGGGACGAA   5400
LCMV-P52-1.3_LP     GACATCAACTCAGAGTCTTTGTCACTCATTTCTCATGTTGTCAAATGGAAGAGGGACGAA   5400
LCMV-P52-2.1_LP     GACATCAACTCAGAGTCTTTGTCACTCATTTCTCATGTTGTCAAATGGAAGAGGGACGAA   5400
                    ************************************************************

LCMV-WE_LP          CATTACACTGTGCTGTTTTCTGATCTCGTCAACTCTCACCAACGGTCAGACTCAAGTTTA   5460
LCMV-P42_LP         CATTACACTGTGCTGTTTTCTGATCTCGTCAACTCTCACCAACGGTCAGACTCAAGTTTA   5460
LCMV-P52_LP         CATTACACTGTGCTGTTTTCTGATCTCGTCAACTCTCACCAACGGTCAGACTCAAGTTTA   5460
LCMV-P91_LP         CATTACACTGTGCTGTTTTCTGATCTCGTCAACTCTCACCAACGGTCAGACTCAAGTTTA   5460
LCMV-P52-1_LP       CATTACACTGTGCTGTTTTCTGATCTCGTCAACTCTCACCAACGGTCAGACTCAAGTTTA   5460
LCMV-P52-1.3_LP     CATTACACTGTGCTGTTTTCTGATCTCGTCAACTCTCACCAACGGTCAGACTCAAGTTTA   5460
LCMV-P52-2.1_LP     CATTACACTGTGCTGTTTTCTGATCTCGTCAACTCTCACCAACGGTCAGACTCAAGTTTA   5460
                    ************************************************************

LCMV-WE_LP          GTTGATGAATTTGTTGTCAGCACAAGGGATGTCTGCAAGAACTTTTTGAAGCAAGTGTAT   5520
LCMV-P42_LP         GTTGATGAATTTGTTGTCAGCACAAGGGATGTCTGCAAGAACTTTTTGAAGCAAGTGTAT   5520
LCMV-P52_LP         GTTGATGAATTTGTTGTCAGCACAAGGGATGTCTGCAAGAACTTTTTGAAGCAAGTGTAT   5520
LCMV-P91_LP         GTTGATGAATTTGTTGTCAGCACAAGGGATGTCTGCAAGAACTTTTTGAAGCAAGTGTAT   5520
LCMV-P52-1_LP       GTTGATGAATTTGTTGTCAGCACAAGGGATGTCTGCAAGAACTTTTTGAAGCAAGTGTAT   5520
LCMV-P52-1.3_LP     GTTGATGAATTTGTTGTCAGCACAAGGGATGTCTGCAAGAACTTTTTGAAGCAAGTGTAT   5520
LCMV-P52-2.1_LP     GTTGATGAATTTGTTGTCAGCACAAGGGATGTCTGCAAGAACTTTTTGAAGCAAGTGTAT   5520
                    ************************************************************

LCMV-WE_LP          TTCGAATCATTTGTACGAGAGTTTGTTGCAACAGCTAGGACCTTAGGTAACTTTTCATGG   5580
LCMV-P42_LP         TTCGAATCATTTGTACGAGAGTTTGTTGCAACAGCTAGGACCTTAGGTAACTTTTCATGG   5580
LCMV-P52_LP         TTCGAATCATTTGTACGAGAGTTTGTTGCAACAGCTAGGACCTTAGGTAACTTTTCATGG   5580
LCMV-P91_LP         TTCGAATCATTTGTACGAGAGTTTGTTGCAACAGCTAGGACCTTAGGTAACTTTTCATGG   5580
LCMV-P52-1_LP       TTCGAATCATTTGTACGAGAGTTTGTTGCAACAGCTAGGACCTTAGGTAACTTTTCATGG   5580
LCMV-P52-1.3_LP     TTCGAATCATTTGTACGAGAGTTTGTTGCAACAGCTAGGACCTTAGGTAACTTTTCATGG   5580
LCMV-P52-2.1_LP     TTCGAATCATTTGTACGAGAGTTTGTTGCAACAGCTAGGACCTTAGGTAACTTTTCATGG   5580
                    ************************************************************

LCMV-WE_LP          TTCCCCCATAAGGACATGATGCCATCTGAAGATGGCGCTGAAGCACTGGGACCCTTCCAA   5640
LCMV-P42_LP         TTCCCCCATAAGGACATGATGCCATCTGAAGATGGCGCTGAAGCACTGGGACCCTTCCAA   5640
LCMV-P52_LP         TTCCCCCATAAGGACATGATGCCATCTGAAGATGGCGCTGAAGCACTGGGACCCTTCCAA   5640
LCMV-P91_LP         TTCCCCCATAAGGACATGATGCCATCTGAAGATGGCGCTGAAGCACTGGGACCCTTCCAA   5640
LCMV-P52-1_LP       TTCCCCCATAAGGACATGATGCCATCTGAAGATGGCGCTGAAGCACTGGGACCCTTCCAA   5640
LCMV-P52-1.3_LP     TTCCCCCATAAGGACATGATGCCATCTGAAGATGGCGCTGAAGCACTGGGACCCTTCCAA   5640
LCMV-P52-2.1_LP     TTCCCCCATAAGGACATGATGCCATCTGAAGATGGCGCTGAAGCACTGGGACCCTTCCAA   5640
                    ************************************************************

LCMV-WE_LP          TCATTTATTTTGAAAGTGGTGAACAAGAAAATAGAGAGGCCCATGTTTAGGAATGACTTG   5700
LCMV-P42_LP         TCATTTATTTTGAAAGTGGTGAACAAGAAAATAGAGAGGCCCATGTTTAGGAATGACTTG   5700
LCMV-P52_LP         TCATTTATTTTGAAAGTGGTGAACAAGAAAATAGAGAGGCCCATGTTTAGGAATGACTTG   5700
LCMV-P91_LP         TCATTTATTTTGAAAGTGGTGAACAAGAAAATAGAGAGGCCCATGTTTAGGAATGACTTG   5700
LCMV-P52-1_LP       TCATTTATTTTGAAAGTGGTGAACAAGAAAATAGAGAGGCCCATGTTTAGGAATGACTTG   5700
LCMV-P52-1.3_LP     TCATTTATTTTGAAAGTGGTGAACAAGAAAATAGAGAGGCCCATGTTTAGGAATGACTTG   5700
LCMV-P52-2.1_LP     TCATTTATTTTGAAAGTGGTGAACAAGAAAATAGAGAGGCCCATGTTTAGGAATGACTTG   5700
                    ************************************************************
```

Figure 26 (cont'd)

```
LCMV-WE_LP          CAGTTTGGTTTTGGTTGGTTCTCTTATCGTGTGGGGATGTTGTGTGTAATGCCGCTATG     5760
LCMV-P42_LP         CAGTTTGGTTTTGGTTGGTTCTCTTATCGTGTGGGGATGTTGTGTGTAATGCCGCTATG     5760
LCMV-P52_LP         CAGTTTGGTTTTGGTTGGTTCTCTTATCGTGTGGGGATGTTGTGTGTAATGCCGCTATG     5760
LCMV-P91_LP         CAGTTTGGTTTTGGTTGGTTCTCTTATCGTGTGGGGATGTTGTGTGTAATGCCGCTATG     5760
LCMV-P52-1_LP       CAGTTTGGTTTTGGTTGGTTCTCTTATCGTGTGGGGATGTTGTGTGTAATGCCGCTATG     5760
LCMV-P52-1.3_LP     CAGTTTGGTTTTGGTTGGTTCTCTTATCGTGTGGGGATGTTGTGTGTAATGCCGCTATG     5760
LCMV-P52-2.1_LP     CAGTTTGGTTTTGGTTGGTTCTCTTATCGTGTGGGGATGTTGTGTGTAATGCCGCTATG     5760
                    ************************************************************

LCMV-WE_LP          TTAATTAAGCAGGGTTTGACAGATCCAAAAGCATTTAAATCTTTAAGAGATTTGTGGGAT    5820
LCMV-P42_LP         TTAATTAAGCAGGGTTTGACAGATCCAAAAGCATTTAAATCTTTAAGAGATTTGTGGGAT    5820
LCMV-P52_LP         TTAATTAAGCAGGGTTTGACAGATCCAAAAGCATTTAAATCTTTAAGAGATTTGTGGGAT    5820
LCMV-P91_LP         TTAATTAAGCAGGGTTTGACAGATCCAAAAGCATTTAAATCTTTAAGAGATTTGTGGGAT    5820
LCMV-P52-1_LP       TTAATTAAGCAGGGTTTGACAGATCCAAAAGCATTTAAATCTTTAAGAGATTTGTGGGAT    5820
LCMV-P52-1.3_LP     TTAATTAAGCAGGGTTTGACAGATCCAAAAGCATTTAAATCTTTAAGAGATTTGTGGGAT    5820
LCMV-P52-2.1_LP     TTAATTAAGCAGGGTTTGACAGATCCAAAAGCATTTAAATCTTTAAGAGATTTGTGGGAT    5820
                    ************************************************************

LCMV-WE_LP          TACATGCTCAGCAGCACAGAGGGGATATTGGAGTTCTCAATCACAGTGGATTTCACACAC    5880
LCMV-P42_LP         TACATGCTCAGCAGCACAGAGGGGATATTGGAGTTCTCAATCACAGTGGATTTCACACAC    5880
LCMV-P52_LP         TACATGCTCAGCAGCACAGAGGGGATATTGGAGTTCTCAATCACAGTGGATTTCACACAC    5880
LCMV-P91_LP         TACATGCTCAGCAGCACAGAGGGGATATTGGAGTTCTCAATCACAGTGGATTTCACACAC    5880
LCMV-P52-1_LP       TACATGCTCAGCAGCACAGAGGGGATATTGGAGTTCTCAATCACAGTGGATTTCACACAC    5880
LCMV-P52-1.3_LP     TACATGCTCAGCAGCACAGAGGGGATATTGGAGTTCTCAATCACAGTGGATTTCACACAC    5880
LCMV-P52-2.1_LP     TACATGCTCAGCAGCACAGAGGGGATATTGGAGTTCTCAATCACAGTGGATTTCACACAC    5880
                    ************************************************************

LCMV-WE_LP          AACCAGAACAACACTGACTGCTTGAGGAAATTTTCATTGATCTTTGTGGTTAAATGCCAA    5940
LCMV-P42_LP         AACCAGAACAACACTGACTGCTTGAGGAAATTTTCATTGATCTTTGTGGTTAAATGCCAA    5940
LCMV-P52_LP         AACCAGAACAACACTGACTGCTTGAGGAAATTTTCATTGATCTTTGTGGTTAAATGCCAA    5940
LCMV-P91_LP         AACCAGAACAACACTGACTGCTTGAGGAAATTTTCATTGATCTTTGTGGTTAAATGCCAA    5940
LCMV-P52-1_LP       AACCAGAACAACACTGACTGCTTGAGGAAATTTTCATTGATCTTTGTGGTTAAATGCCAA    5940
LCMV-P52-1.3_LP     AACCAGAACAACACTGACTGCTTGAGGAAATTTTCATTGATCTTTGTGGTTAAATGCCAA    5940
LCMV-P52-2.1_LP     AACCAGAACAACACTGACTGCTTGAGGAAATTTTCATTGATCTTTGTGGTTAAATGCCAA    5940
                    ************************************************************

LCMV-WE_LP          TTACAGAGTCCAGGTGTAGCTGATTACTTATCGTGCTCTCATTTCTTCAAAGGTGAGGTT    6000
LCMV-P42_LP         TTACAGAGTCCAGGTGTAGCTGATTACTTATCGTGCTCTCATTTCTTCAAAGGTGAGGTT    6000
LCMV-P52_LP         TTACAGAGTCCAGGTGTAGCTGATTACTTATCGTGCTCTCATTCCTTCAAAGGTGAGGTT    6000
LCMV-P91_LP         TTACAGAGTCCAGGTGTAGCTGATTACTTATCGTGCTCTCATTCCTTCAAAGGTGAGGTT    6000
LCMV-P52-1_LP       TTACAGAGTCCAGGTGTAGCTGATTACTTATCGTGCTCTCATTTCTTCAAAGGTGAGGTT    6000
LCMV-P52-1.3_LP     TTACAGAGTCCAGGTGTAGCTGATTACTTATCGTGCTCTCATTCCTTCAAAGGTGAGGTT    6000
LCMV-P52-2.1_LP     TTACAGAGTCCAGGTGTAGCTGATTACTTATCGTGCTCTCATTTCTTCAAAGGTGAGGTT    6000
                    ******************************************* ****************

LCMV-WE_LP          GACAGGAGATTATTAGATGAGTGTCTCAATCTGTTGAGGACAGACCCCATCTTTAAAGCG    6060
LCMV-P42_LP         GACAGGAGATTATTAGATGAGTGTCTCAATCTGTTGAGGACAGACCCCATCTTTAAAGCG    6060
LCMV-P52_LP         GACAGGAGATTATTAGATGAGTGTCTCAATCTGTTGAGGACAGACCCCATCTTTAAAGCG    6060
LCMV-P91_LP         GACAGGAGATTATTAGATGAGTGTCTCAATCTGTTGAGGACAGACCCCATCTTTAAAGCG    6060
LCMV-P52-1_LP       GACAGGAGATTATTAGATGAGTGTCTCAATCTGTTGAGGACAGACCCCATCTTTAAAGCG    6060
LCMV-P52-1.3_LP     GACAGGAGATTATTAGATGAGTGTCTCAATCTGTTGAGGACAGACCCCATCTTTAAAGCG    6060
LCMV-P52-2.1_LP     GACAGGAGATTATTAGATGAGTGTCTCAATCTGTTGAGGACAGACCCCATCTTTAAAGCG    6060
                    ************************************************************

LCMV-WE_LP          AATGATGGAGTCTTTGACATTAGGTCTGAAGAGTTTGAAGATTACATGGAAGACCCTTTG    6120
LCMV-P42_LP         AATGATGGAGTCTTTGACATTAGGTCTGAAGAGTTTGAAGATTACATGGAAGACCCTTTG    6120
LCMV-P52_LP         AATGATGGAGTCTTTGACATTAGGTCTGAAGAGTTTGAAGATTACATGGAAGACCCTTTG    6120
LCMV-P91_LP         AATGATGGAGTCTTTGACATTAGGTCTGAAGAGTTTGAAGATTACATGGAAGACCCTTTG    6120
LCMV-P52-1_LP       AATGATGGAGTCTTTGACATTAGGTCTGAAGAGTTTGAAGATTACATGGAAGACCCTTTG    6120
LCMV-P52-1.3_LP     AATGATGGAGTCTTTGACATTAGGTCTGAAGAGTTTGAAGATTACATGGAAGACCCTTTG    6120
LCMV-P52-2.1_LP     AATGATGGAGTCTTTGACATTAGGTCTGAAGAGTTTGAAGATTACATGGAAGACCCTTTG    6120
                    ************************************************************

LCMV-WE_LP          ACACTTGGTGATTCACTAGAACTTGAACTAATAGGTTCTAGAAGGATTCTGAATGAGATC    6180
LCMV-P42_LP         ACACTTGGTGATTCACTAGAACTTGAACTAATAGGTTCTAGAAGGATTCTGAATGAGATC    6180
LCMV-P52_LP         ACACTTGGTGATTCACTAGAACTTGAACTAATAGGTTCTAGAAGGATTCTGAATGAGATC    6180
LCMV-P91_LP         ACACTTGGTGATTCACTAGAACTTGAACTAATAGGTTCTAGAAGGATTCTGAATGAGATC    6180
LCMV-P52-1_LP       ACACTTGGTGATTCACTAGAACTTGAACTAATAGGTTCTAGAAGGATTCTGAATGAGATC    6180
LCMV-P52-1.3_LP     ACACTTGGTGATTCACTAGAACTTGAACTAATAGGTTCTAGAAGGATTCTGAATGAGATC    6180
LCMV-P52-2.1_LP     ACACTTGGTGATTCACTAGAACTTGAACTAATAGGTTCTAGAAGGATTCTGAATGAGATC    6180
                    ************************************************************
```

Figure 26 (cont'd)

```
LCMV-WE_LP          AAATCTACTGACTTTGAGAGGATAGGGCCTGAGTGGGAACCTGTGCCTCTGACCATAAGG     6240
LCMV-P42_LP         AAATCTACTGACTTTGAGAGGATAGGGCCTGAGTGGGAACCTGTGCCTCTGACCATAAGG     6240
LCMV-P52_LP         AAATCTACTGACTTTGAGAGGATAGGGCCTGAGTGGGAACCTGTGCCTCTGACCATAAGG     6240
LCMV-P91_LP         AAATCTACTGACTTTGAGAGGATAGGGCCTGAGTGGGAACCTGTGCCTCTGACCATAAGG     6240
LCMV-P52-1_LP       AAATCTACTGACTTTGAGAGGATAGGGCCTGAGTGGGAACCTGTGCCTCTGACCATAAGG     6240
LCMV-P52-1.3_LP     AAATCTACTGACTTTGAGAGGATAGGGCCTGAGTGGGAACCTGTGCCTCTGACCATAAGG     6240
LCMV-P52-2.1_LP     AAATCTACTGACTTTGAGAGGATAGGGCCTGAGTGGGAACCTGTGCCTCTGACCATAAGG     6240
                    ************************************************************

LCMV-WE_LP          AAGGGTGCCCTCTTTGAGGGGAGGAACTTTGTTCAGAATATCTCTGTGAAATTGGAGACA     6300
LCMV-P42_LP         AAGGGTGCCCTCTTTGAGGGGAGGAACTTTGTTCAGAATATCTCTGTGAAATTGGAGACA     6300
LCMV-P52_LP         AAGGGTGCCCTCTTTGAGGGGAGGAACTTTGTTCAGAATRTCTCTGTGAAATTGGAGACA     6300
LCMV-P91_LP         AAGGGTGCCCTCTTTGAGGGGAGGAACTTTGTTCAGAATATCTCTGTGAAATTGGAGACA     6300
LCMV-P52-1_LP       AAGGGTGCCCTCTTTGAGGGGAGGAACTTTGTTCAGAATATCTCTGTGAAATTGGAGACA     6300
LCMV-P52-1.3_LP     AAGGGTGCCCTCTTTGAGGGGAGGAACTTTGTTCAGAATATCTCTGTGAAATTGGAGACA     6300
LCMV-P52-2.1_LP     AAGGGTGCCCTCTTTGAGGGGAGGAACTTTGTTCAGAATATCTCTGTGAAATTGGAGACA     6300
                    *************************************** ********************

LCMV-WE_LP          AAGGACATGAGGGTCTTTCTGGCAGAGCTCGAGGGCTGTGGAAAAATTGGTGATGTCCTC     6360
LCMV-P42_LP         AAGGACATGAGRGTCTTTCTGGCAGAGCTCGAGGGCTGTGGAAAAATTGGTGATGTCCTC     6360
LCMV-P52_LP         AAGGACATGAGGGTCTTTCTGGCAGAGCTCGAGGGCTGTGGAAAAATTGGTGATGTCCTC     6360
LCMV-P91_LP         AAGGACATGAGGGTCTTTCTGGCAGAGCTCGAGGGCTGTGGAAAAATTGGTGATGTCCTC     6360
LCMV-P52-1_LP       AAGGACATGAGGGTCTTTCTGGCAGAGCTCGAGGGCTGTGGAGAAATTGGTGATGTCCTC     6360
LCMV-P52-1.3_LP     AAGGACATGAGGGTCTTTCTGGCAGAGCTCGAGGGCTGTGGAAAAATTGGTGATGTCCTC     6360
LCMV-P52-2.1_LP     AAGGACATGAGGGTCTTTCTGGCAGAGCTCGAGGGCTGTGGAGAAATTGGTGATGTCCTC     6360
                    *********** ****************************** *****************

LCMV-WE_LP          GGCAGCCTCCTCCTGCACCGATTCAGAACTGGTGAGCACTTGATGGAGTCAGAAATAAGT     6420
LCMV-P42_LP         GGCAGCCTCCTCCTGCACCGATTCAGAACTGGTGAGCACTTGATGGAGTCAGAAATAAGT     6420
LCMV-P52_LP         GGCAGCCTCCTCCTGCACCGATTCAGAACTGGTGAGCACTTGATGGAGTCAGAAATAAGT     6420
LCMV-P91_LP         GGCAGCCTCCTCCTGCACCGATTCAGAACTGGTGAGCACTTGATGGAGTCAGAAATAAGT     6420
LCMV-P52-1_LP       GGCAGCCTCCTCCTGCACCGATTCAGAACTGGTGAGCACTTGATGGAGTCAGAAATAAGT     6420
LCMV-P52-1.3_LP     GGCAGCCTCCTCCTGCACCGATTCAGAACTGGTGAGCACTTGATGGAGTCAGAAATAAGT     6420
LCMV-P52-2.1_LP     GGCAGCCTCCTCCTGCACCGATTCAGAACTGGTGAGCACTTGATGGAGTCAGAAATAAGT     6420
                    ************************************************************

LCMV-WE_LP          ACAGTTCTTCAGGAGCTCTGCATGGACAGATCCGTCATGCTGACACCATTATCTTTTGTG     6480
LCMV-P42_LP         ACAGTTCTTCAGGAGCTCTGCATGGACAGATCCGTCATGCTGACACCATTATCTTTTGTG     6480
LCMV-P52_LP         RCAGTTCTTCAGGAGCTCTGCATGGACAGATCCGTCATGCTGACACCATTATCTTTTGTG     6480
LCMV-P91_LP         ACAGTTCTTCAGGAGCTCTGCATGGACAGATCCGTCATGCTGACACCATTATCTTTTGTG     6480
LCMV-P52-1_LP       RCAGTTCTTCAGGAGCTCTGCATGGACAGATCCGTCATGCTGACACCATTATCTTTTGTG     6480
LCMV-P52-1.3_LP     ACAGTTCTTCAGGAGCTCTGCATGGACAGATCCGTCATGCTGACACCATTATCTTTTGTG     6480
LCMV-P52-2.1_LP     ACAGTTCTTCAGGAGCTCTGCATGGACAGATCCGTCATGCTGACACCATTATCTTTTGTG     6480
                     ***********************************************************

LCMV-WE_LP          CCAGATTGGTTCACCTTCAGAGATTGTAGGCTCTGCTTCAGCAGGTCAAAGAACACTGTA     6540
LCMV-P42_LP         CCAGATTGGTTCACCTTCAGAGATTGTAGGCTCTGCTTCAGCAGGTCAAAGAACACTGTR     6540
LCMV-P52_LP         CCAGATTGGTTCACCTTCAGAGATTGTAGGCTCTGCTTCAGCAGGTCAAAGAACACTGTA     6540
LCMV-P91_LP         CCAGATTGGTTCACCTTCAGAGATTGTAGGCTCTGCTTCAGCARGTCAAAGAACACTGTA     6540
LCMV-P52-1_LP       CCAGATTGGTTCACCTTCAGAGATTGTAGGCTCTGCTTCAGCAGGTCAAAGAACACTGTA     6540
LCMV-P52-1.3_LP     CCAGATTGGTTCACCTTCAGAGATTGTAGGCTCTGCTTCAGCAGGTCAAAGAACACTGTA     6540
LCMV-P52-2.1_LP     CCAGATTGGTTCACCTTCAGAGATTGTAGGCTCTGCTTCAGCAGGTCAAAGAACACTGTA     6540
                    ******************************************* *************** 

LCMV-WE_LP          ATGTATGAGACAACTGGGGGCAGGTTCAGACTCAAGGGGAAATCCTGTGACGATTGGCTG     6600
LCMV-P42_LP         ATGTATGAGACAACTGGGGGCAGGTTCAGACTCAAGGGGAAATCCTGTGACGATTGGCTG     6600
LCMV-P52_LP         ATGTATGAGACAACTGGGGGCAGGTTCAGACTCAAGGGGAAATCCTGTGACGATTGGCTG     6600
LCMV-P91_LP         ATGTATGAGACAACTGGGGGCAGGTTCAGACTCAAGGGGAAATCCTGTGACGATTGGCTG     6600
LCMV-P52-1_LP       ATGTATGAGACAGCTGGGGGCAGGTTCAGACTCAAGGGGAAATCCTGTGACGATTGGCTG     6600
LCMV-P52-1.3_LP     ATGTATGAGACAACTGGGGGCAGGTTCAGACTCAAGGGGAAATCCTGTGACGATTGGCTG     6600
LCMV-P52-2.1_LP     ATGTATGAGACAACTGGGGGCAGGTTCAGACTCAAGGGGAAATCCTGTGACGATTGGCTG     6600
                    ************ ***********************************************

LCMV-WE_LP          GCGGAGCGGGTGGCCGAGGAGATCGACTAG   6630   LCMV-WE_LP:      SEQ ID NO: 15
LCMV-P42_LP         GCGGAGCGGGTGGCCGAGGAGATCGACTAG   6630   LCMV-P42_LP:     SEQ ID NO: 23
LCMV-P52_LP         GCGGAGCGGGTGGCCGAGGAGATCGACTAG   6630   LCMV-P52_LP:     SEQ ID NO: 31
LCMV-P91_LP         GCGGAGCGGGTGGCCGAGGAGATCGACTAG   6630   LCMV-P91_LP:     SEQ ID NO: 39
LCMV-P52-1_LP       GCGGAGCGGGTGGCCGAGGAGATCGACTAG   6630   LCMV-P52-1_LP:   SEQ ID NO: 47
LCMV-P52-1.3_LP     GCGGAGCGGGTGGCCGAGGAGATCGACTAG   6630   LCMV-P52-1.3_LP: SEQ ID NO: 55
LCMV-P52-2.1_LP     GCGGAGCGGGTGGCCGAGGAGATCGACTAG   6633   LCMV-P52-2.1_LP: SEQ ID NO: 63
                    ******************************
```

Source: 1-7235   Segment = L
Protein:        RNA-directed RNA polymerase L
Gene:   LP
Gene:   574-7203 complement
Sequence Alignment: Aminoacid

```
LCMV-WE_LP          MDETIADLRELCLNYIEQDERLSRQKLNFLGQREPRMVLIEGLKLLSRCIEIDSADKSGC   60
LCMV-P42_LP         MDETIADLRELCLNYIEQDERLSRQKLNFLGQREPRMVLIEGLKLLSRCIEIDSADKSGC   60
LCMV-P52_LP         MDETIADLRELCLNYIEQDERLSRQKLNFLGQREPRMVLIEGLKLLSRCIEIDSADKSGC   60
LCMV-P91_LP:        MDETIADLRELCLNYIEQDERLSRQKLNFLGQREPRMVLIEGLKLLSRCIEIDSADKSGC   60
LCMV-P52-1_LP       MDETIADLRELCLNYIEQDERLSRQKLNFLGQREPRMVLIEGLKLLSRCIEIDSADKSGC   60
LCMV-P52-1.3_LP     MDETIADLRELCLNYIEQDERLSRQKLNFLGQREPRMVLIEGLKLLSRCIEIDSADKSGC   60
LCMV-P52-2.1_LP     MDETIADLRELCLNYIEQDERLSRQKLNFLGQREPRMVLIEGLKLLSRCIEIDSADKSGC   60
                    ************************************************************

LCMV-WE_LP          IHNHDDKSVETILIDSGIVCPGLPLIIPDGYKLIDNSLILLECFVRSTPASFEKKFIEDT   120
LCMV-P42_LP         IHNHDDKSVETILIDSGIVCPGLPLIIPDGYKLIDNSLILLECFVRSTPASFEKKFIEDT   120
LCMV-P52_LP         IHNHDDKSVETILIDSGIVCPGLPLIIPDGYKLIDNSLILLECFVRSTPASFEKKFIEDT   120
LCMV-P91_LP:        IHNHDDKSVETILIDSGIVCPGLPLIIPDGYKLIDNSLILLECFVRSTPASFEKKFIEDT   120
LCMV-P52-1_LP       IHNHDDKSVETILIDSGIVCPGLPLIIPDGYKLIDNSLILLECFVRSTPASFEKKFIEDT   120
LCMV-P52-1.3_LP     IHNHDDKSVETILIDSGIVCPGLPLIIPDGYKLIDNSLILLECFVRSTPASFEKKFIEDT   120
LCMV-P52-2.1_LP     IHNHDDKSVETILIDSGIVCPGLPLIIPDGYKLIDNSLILLECFVRSTPASFEKKFIEDT   120
                    ************************************************************

LCMV-WE_LP          NKLACIKEDLAVAGITLVPIVDGRCDYDNSFMPEWVNFKFRDLLFKLLEYSSQDEKVFEE   180
LCMV-P42_LP         NKLACIKEDLAVAGITLVPIVDGRCDYDNSFMPEWVNFKFRDLLFKLLEYSSQDEKVFEE   180
LCMV-P52_LP         NKLACIKEDLAVAGITLVPIVDGRCDYDNSFMPEWVNFKFRDLLFKLLEYSSQDEKVFEE   180
LCMV-P91_LP:        NKLACIKEDLAVAGITLVPIVDGRCDYDNSFMPEWVNFKFRDLLFKLLEYSSQDEKVFEE   180
LCMV-P52-1_LP       NKLACIKEDLAVAGITLVPIVDGRCDYDNSFMPEWVNFKFRDLLFKLLEYSSQDEKVFEE   180
LCMV-P52-1.3_LP     NKLACIKEDLAVAGITLVPIVDGRCDYDNSFMPEWVNFKFRDLLFKLLEYSSQDEKVFEE   180
LCMV-P52-2.1_LP     NKLACIKEDLAVAGITLVPIVDGRCDYDNSFMPEWVNFKFRDLLFKLLEYSSQDEKVFEE   180
                    ************************************************************

LCMV-WE_LP          SEYFRLCESLKTTVDKRSGMDSMKILKDARSFHNDEIMKMCHDGVNPNMSCDDVVFGINS   240
LCMV-P42_LP         SEYFRLCESLKTTVDKRSGMDSMKILKDARSFHNDEIMKMCHDGVNPNMSCDDVVFGINS   240
LCMV-P52_LP         SEYFRLCESLKTTVDKRSGMDSMKILKDARSFHNDEIMKMCHDGVNPNMSCDDVVFGINS   240
LCMV-P91_LP:        SEYFRLCESLKTTVDKRSGMDSMKILKDARSFHNDEIMKMCHDGVNPNMSCDDVVFGINS   240
LCMV-P52-1_LP       SEYFRLCESLKTTVDKRSGMDSMKILKDARSFHNDEIMKMCHDGVNPNMSCDDVVFGINS   240
LCMV-P52-1.3_LP     SEYFRLCESLKTTVDKRSGMDSMKILKDARSFHNDEIMKMCHDGVNPNMSCDDVVFGINS   240
LCMV-P52-2.1_LP     SEYFRLCESLKTTVDKRSGMDSMKILKDARSFHNDEIMKMCHDGVNPNMSCDDVVFGINS   240
                    ************************************************************

LCMV-WE_LP          FFGRFRRDLLNGKLKRNFQKVSPGGLIKEFSELYETLTDNDDILMLSKEAVESCPLMRFI   300
LCMV-P42_LP         FFGRFRRDLLNGKLKRNFQKVSPGGLIKEFSELYETLTDNDDILMLSKEAVESCPLMRFI   300
LCMV-P52_LP         FFGRFRRDLLNGKLKRNFQKVSPGGLIKEFSELYETLTDNDDILMLSKEAVESCPLMRFI   300
LCMV-P91_LP:        FFGRFRRDLLNGKLKRNFQKVSPGGLIKEFSELYETLTDNDDILMLSKEAVESCPLMRFI   300
LCMV-P52-1_LP       FFGRFRRDLLNGRLKRNFQKVSPGGLIKEFSELYETLTDNDDILMLSKEAVESCPLMRFI   300
LCMV-P52-1.3_LP     FFGRFRRDLLNGKLKRNFQKVSPGGLIKEFSELYETLTDNDDILMLSKEAVESCPLMRFI   300
LCMV-P52-2.1_LP     FFGRFRRDLLNGKLKRNFQKVSPGGLIKEFSELYETLTDNDDILMLSKEAVESCPLMRFI   300
                    ************:***********************************************

LCMV-WE_LP          TAETHGHERGSDANTEYERLLSMLNKVKSLKLLNTRRRQLLNLDVLCLSSLIKQSISKGL   360
LCMV-P42_LP         TAETHGHERGSDANTEYERLLSMLNKVKSLKLLNTRRRQLLNLDVLCLSSLIKQSISKGL   360
LCMV-P52_LP         TAETHGHERGSDANTEYERLLSMLNKVKSLKLLNTRRRQLLNLDVLCLSSLIKQSISKGL   360
LCMV-P91_LP:        TAETHGHERGSDANTEYERLLSMLNKVKSLKLLNTRRRQLLNLDVLCLSSLIKQSISKGL   360
LCMV-P52-1_LP       TAETHGHERGSDANTEYERLLSMLNKVKSLKLLNTRRRQLLNLDVLCLSSLIKQSISKGL   360
LCMV-P52-1.3_LP     TAETHGHERGSDANTEYERLLSMLNKVKSLKLLNTRRRQLLNLDVLCLSSLIKQSISKGL   360
LCMV-P52-2.1_LP     TAETHGHERGSDANTEYERLLSMLNKVKSLKLLNTRRRQLLNLDVLCLSSLIKQSISKGL   360
                    ************************************************************

LCMV-WE_LP          ENDKHWVGCCYSSVNDRLVSLQSTKEEFMRLLKNRRKSRVHKKASLDELFRVSINEFIAK   420
LCMV-P42_LP         ENDKHWVGCCYSSVNDRLVSLQSTKEEFMRLLKNRRKSRVHKKASLDELFRVSINEFIAK   420
LCMV-P52_LP         ENDKHWVGCCYSSVNDRLVSLQSTKEEFMRLLKNRRKSRVHKKASLDELFRVSINEFIAK   420
LCMV-P91_LP:        ENDKHWVGCCYSSVNDRLVSLQSTKEEFMRLLKNRRKSRVHKKASLDELFRVSINEFIAK   420
LCMV-P52-1_LP       ENDKHWVGCCYSSVNDRLVSLQSTKEEFMRLLKNRRKSRVHKKASLDELFRVSINEFIAK   420
LCMV-P52-1.3_LP     ENDKHWVGCCYSSVNDRLVSLQSTKEEFMRLLKNRRKSRVHKKASLDELFRVSINEFIAK   420
LCMV-P52-2.1_LP     ENDKHWVGCCYSSVNDRLVSLQSTKEEFMRLLKNRRKSRVHKKASLDELFRVSINEFIAK   420
                    ************************************************************
```

Figure 26 (cont'd)

```
LCMV-WE_LP         IQKCLSTVGLSFEHYGLSECLVQECHIPFAEFENFMRAGTHPVMHYTKFEDYTFQPNIEQ    480
LCMV-P42_LP        IQKCLSTVGLSFEHYGLSECLVQECHIPFAEFENFMRAGTHPVMHYTKFEDYTFQPNIEQ    480
LCMV-P52_LP        IQKCLSTVGLSFEHYGLSECLVQECHIPFAEFENFMRAGTHPVMHYTKFEDYTFQPNIEQ    480
LCMV-P91_LP:       IQKCLSTVGLSFEHYGLSECLVQECHIPFAEFENFMRAGTHPVMHYTKFEDYTFQPNIEQ    480
LCMV-P52-1_LP      IQKCLSTVGLSFEHYGLSECLVQECHIPFAEFENFMRAGTHPVMHYTKFEDYTFQPNIEQ    480
LCMV-P52-1.3_LP    IQKCLSTVGLSFEHYGLSECLVQECHIPFAEFENFMRAGTHPVMHYTKFEDYTFQPNIEQ    480
LCMV-P52-2.1_LP    IQKCLSTVGLSFEHYGLSECLVQECHIPFAEFENFMRAGTHPVMHYTKFEDYTFQPNIEQ    480
                   ************************************************************

LCMV-WE_LP         LRGLQSLRKLSSVCLALTNSMKTSSVARLRQNQLGSVRYQVVECKEVFCQIIKLDSEEYH    540
LCMV-P42_LP        LRGLQSLRKLSSVCLALTNSMKTSSVARLRQNQLGSVRYQVVECKEVFCQIIKLDSEEYH    540
LCMV-P52_LP        LRGLQSLRKLSSVCLALTNSMKTSSVARLRQNQLGSVRYQVVECKEVFCQIIKLDSEEYH    540
LCMV-P91_LP:       LRGLQSLRKLSSVCLALTNSMKTSSVARLRQNQLGSVRYQVVECKEVFCQIIKLDSEEYH    540
LCMV-P52-1_LP      LRGLQSLRKLSSVCLALTNSMKTSSVARLRQNQLGSVRYQVVECKEVFCQIIKLDSEEYH    540
LCMV-P52-1.3_LP    LRGLQSLRKLSSVCLALTNSMKTSSVARLRQNQLGSVRYQVVECKEVFCQIIKLDSEEYH    540
LCMV-P52-2.1_LP    LRGLQSLRKLSSVCLALTNSMKTSSVARLRQNQLGSVRYQVVECKEVFCQIIKLDSEEYH    540
                   ************************************************************

LCMV-WE_LP         LLYQKTGESSRCYSIQGPDGHLISFYADPKRFFLPIFSDEVLHNMIDTMISWIRSCPDLK    600
LCMV-P42_LP        LLYQKTGESSRCYSIQGPDGHLISFYADPKRFFLPIFSDEVLHNMIDTMISWIRSCPDLK    600
LCMV-P52_LP        LLYQKTGESSRCYSIQGPDGHLISFYADPKRFFLPIFSDEVLHNMIDTMISWIRSCPDLK    600
LCMV-P91_LP:       LLYQKTGESSRCYSIQGPDGHLISFYADPKRFFLPIFSDEVLHNMIDTMISWIRSCPDLK    600
LCMV-P52-1_LP      LLYQKTGESSRCYSIQGPDGHLISFYADPKRFFLPIFSDEVLHNMIDTMISWIRSCPDLK    600
LCMV-P52-1.3_LP    LLYQKTGESSRCYSIQGPDGHLISFYADPKRFFLPIFSDEVLHNMIDTMISWIRSCPDLK    600
LCMV-P52-2.1_LP    LLYQKTGESSRCYSIQGPDGHLISFYADPKRFFLPIFSDEVLHNMIDTMISWIRSCPDLK    600
                   ************************************************************

LCMV-WE_LP         DSLIDIETALRTLILLMLTNPTKRNQKQVQNIRYLVMAIVSDFSSTSLMDKLKEDLITPA    660
LCMV-P42_LP        DSLIDIETALRTLILLMLTNPTKRNQKQVQNIRYLVMAIVSDFSSTSLMDKLKEDLITPA    660
LCMV-P52_LP        DSLIDIETALRTLILLMLTNPTKRNQKQVQNIRYLVMAIVSDFSSTSLMDKLKEDLITPA    660
LCMV-P91_LP:       DSLIDIETALRTLILLMLTNPTKRNQKQVQNIRYLVMAIVSDFSSTSLMDKLKEDLITPA    660
LCMV-P52-1_LP      DSLIDIETALRTLILLMLTNPTKRNQKQVQNIRYLVMAIVSDFSSTSLMDKLKEDLITPA    660
LCMV-P52-1.3_LP    DSLIDIETALRTLILLMLTNPTKRNQKQVQNIRYLVMAIVSDFSSTSLMDKLKEDLITPA    660
LCMV-P52-2.1_LP    DSLIDIETALRTLILLMLTNPTKRNQKQVQNIRYLVMAIVSDFSSTSLMDKLKEDLITPA    660
                   ************************************************************

LCMV-WE_LP         EKVVYRLLRFLIRTIFGTGEKVLLSAKFKFMLNVSYLCHLITKETPDRLTDQIKCFEKFF    720
LCMV-P42_LP        EKVVYRLLRFLIRTIFGTGEKVLLSAKFKFMLNVSYLCHLITKETPDRLTDQIKCFEKFF    720
LCMV-P52_LP        EKVVYRLLRFLIRTIFGTGEKVLLSAKFKFMLNVSYLCHLITKETPDRLTDQIKCFEKFF    720
LCMV-P91_LP:       EKVVYRLLRFLIRTIFGTGEKVLLSAKFKFMLNVSYLCHLITKETPDRLTDQIKCFEKFF    720
LCMV-P52-1_LP      EKVVYRLLRFLIRTIFGTGEKVLLSAKFKFMLNVSYLCHLITKETPDRLTDQIKCFEKFF    720
LCMV-P52-1.3_LP    EKVVYRLLRFLIRTIFGTGEKVLLSAKFKFMLNVSYLCHLITKETPDRLTDQIKCFEKFF    720
LCMV-P52-2.1_LP    EKVVYRLLRFLIRTIFGTGEKVLLSAKFKFMLNVSYLCHLITKETPDRLTDQIKCFEKFF    720
                   ************************************************************

LCMV-WE_LP         EPKSEFGFFVNPKETITPEEECVFYEQMKKFTGKDIDCQHSTPGVNLEIFSMMVSSFNNG    780
LCMV-P42_LP        EPKSEFGFFVNPKETITPEEECVFYEQMKKFTGKDIDCQHSTPGVNLEIFSMMVSSFNNG    780
LCMV-P52_LP        EPKSEFGFFVNPKETITPEEECVFYEQMKKFTGKDIDCQHSTPGVNLEIFSMMVSSFNNG    780
LCMV-P91_LP:       EPKSEFGFFVNPKETITPEEECVFYEQMKKFTGKDIDCQHSTPGVNLEIFSMMVSSFNNG    780
LCMV-P52-1_LP      EPKSEFGFFVNPKETITPEEECVFYEQMKKFTGKDIDCQHSTPGVNLEIFSMMVSSFNNG    780
LCMV-P52-1.3_LP    EPKSEFGFFVNPKETITPEEECVFYEQMKKFTGKDIDCQHSTPGVNLEIFSMMVSSFNNG    780
LCMV-P52-2.1_LP    EPKSEFGFFVNPKETITPEEECVFYEQMKKFTGKDIDCQHSTPGVNLEIFSMMVSSFNNG    780
                   ************************************************************

LCMV-WE_LP         TLILKGEKRLNNLDPMTNSGCATALDLASNKSVVVNKHLNGERLLEYDFNKLLVSAVSQI    840
LCMV-P42_LP        TLILKGEKRLNNLDPMTNSGCATALDLASNKSVVVNKHLNGERLLEYDFNKLLVSAVSQI    840
LCMV-P52_LP        TLILKGEKRLNNLDPMTNSGCATALDLASNKSVVVNKHLNGERLLEYDFNKLLVSAVSQI    840
LCMV-P91_LP:       TLILKGEKRLNNLDPMTNSGCATALDLASNKSVVVNKHLNGERLLEYDFNKLLVSAVSQI    840
LCMV-P52-1_LP      TLILKGEKRLNNLDPMTNSGCATALDLASNKSVVVNKHLNGERLLEYDFNKLLVSAVSQI    840
LCMV-P52-1.3_LP    TLILKGEKRLNNLDPMTNSGCATALDLASNKSVVVNKHLNGERLLEYDFNKLLVSAVSQI    840
LCMV-P52-2.1_LP    TLILKGEKRLNNLDPMTNSGCATALDLASNKSVVVNKHLNGERLLEYDFNKLLVSAVSQI    840
                   ************************************************************

LCMV-WE_LP         TEGFMRKQKYKLRHSDYEYKVSKLVSRLVIGSRKTEVDKLEDDPVDVCFEGEEETSFFRS    900
LCMV-P42_LP        TEGFMRKQKYKLRHSDYEYKVSKLVSRLVIGSRKTEVDKLEDDPVDVCFEGEEETSFFRS    900
LCMV-P52_LP        TEGFMRKQKYKLRHSDYEYKVSKLVSRLVIGSRKTEVDKLEDDPVDVCFEGEEETSFFRS    900
LCMV-P91_LP:       TEGFMRKQKYKLRHSDYEYKVSKLVSRLVIGSRKTEVDKLEDDPVDVCFEGEEETSFFRS    900
LCMV-P52-1_LP      TEGFMRKQKYKLRHSDYEYKVSKLVSRLVIGSRKTEVDKLEDDPVDVCFEGEEETSFFRS    900
LCMV-P52-1.3_LP    TEGFMRKQKYKLRHSDYEYKVSKLVSRLVIGSRKTEVDKLEDDPVDVCFEGEEETSFFRS    900
LCMV-P52-2.1_LP    TEGFMRKQKYKLRHSDYEYKVSKLVSRLVIGSRKTEVDKLEDDPVDVCFEGEEETSFFRS    900
                   ************************************************************
```

Figure 26 (cont'd)

```
LCMV-WE_LP         LEDKVSSTITRYNRGTRLNEGQGEGEFKNTKGLHHLQIILSGKRAYLRKVILSEISFHLV    960
LCMV-P42_LP        LEDKVSSTITRYNRGTRLNEGQGEGEFKNTKGLHHLQIILSGKRAYLRKVILSEISFHLV    960
LCMV-P52_LP        LEDKVSSTITRYNRGTRLNEGQGEGEFKNTKGLHHLQIILSGKRAYLRKVILSEISFHLV    960
LCMV-P91_LP:       LEDKVSSTITRYNRGTRLNEGQGEGEFKNTKGLHHLQIILSGKRAYLRKVILSEISFHLV    960
LCMV-P52-1_LP      LEDKVSSTITRYNRGTRLNEGQGEGEFKNTKGLHHLQIILSGKRAYLRKVILSEISFHLV    960
LCMV-P52-1.3_LP    LEDKVSSTITRYNRGTRLNEGQGEGEFKNTKGLHHLQIILSGKRAYLRKVILSEISFHLV    960
LCMV-P52-2.1_LP    LEDKVSSTITRYNRGTRLNEGQGEGEFKNTKGLHHLQIILSGKRAYLRKVILSEISFHLV    960
                   ************************************************************

LCMV-WE_LP         EDFDPSCLTNDDMRFICEAVEGSTELSPLYFTSAVKEQCGLDEMARNLCRKFFSEGDWFS    1020
LCMV-P42_LP        EDFDPSCLTNDDMRFICEAVEGSTELSPLYFTSAVKEQCGLDEMARNLCRKFFSEGDWFS    1020
LCMV-P52_LP        EDFDPSCLTNDDMRFICEAVEGSTELSPLYFTSAVKEQCGLDEMARNLCRKFFSEGDWFS    1020
LCMV-P91_LP:       EDFDPSCLTNDDMRFICEAVEGSTELSPLYFTSAVKEQCGLDEMARNLCRKFFSEGDWFS    1020
LCMV-P52-1_LP      EDFDPSCLTNDDMRFICEAVEGSTELSPLYFTSAVKEQCGLDEMARNLCRKFFSEGDWFS    1020
LCMV-P52-1.3_LP    EDFDPSCLTNDDMRFICEAVEGSTELSPLYFTSAVKEQCGLDEMARNLCRKFFSEGDWFS    1020
LCMV-P52-2.1_LP    EDFDPSCLTNDDMRFICEAVEGSTELSPLYFTSAVKEQCGLDEMARNLCRKFFSEGDWFS    1020
                   ************************************************************

LCMV-WE_LP         CMKMILLQMNANAYSGKYRHMQRQSLNFKFDWDKLEEDVRISERESNSESLSKALSLTKC    1080
LCMV-P42_LP        CMKMILLQMNANAYSGKYRHMQRQSLNFKFDWDKLEEDVRISERESNSESLSKALSLTKC    1080
LCMV-P52_LP        CMKMILLQMNANAYSGKYRHMQRQSLNFKFDWDKLEEDVRISERESNSESLSKALSLTKC    1080
LCMV-P91_LP:       CMKMILLQMNANAYSGKYRHMQRQSLNFKFDWDKLEEDVRISERESNSESLSKALSLTKC    1080
LCMV-P52-1_LP      CMKMILLQMNANAYSGKYRHMQRQSLNFKFDWDKLEEDVRISERESNSESLSKALSLTKC    1080
LCMV-P52-1.3_LP    CMKMILLQMNANAYSGKYRHMQRQSLNFKFDWDKLEEDVRISERESNSESLSKALSLTKC    1080
LCMV-P52-2.1_LP    CMKMILLQMNANAYSGKYRHMQRQSLNFKFDWDKLEEDVRISERESNSESLSKALSLTKC    1080
                   ************************************************************

LCMV-WE_LP         MSAALKNLCFYSEESPTSYTSVGPDSGRLKFALSYKEQVGGNRELYIGDLRTKMFTRLVE    1140
LCMV-P42_LP        MSAALKNLCFYSEESPTSYTSVGPDSGRLKFALSYKEQVGGNRELYIGDLRTKMFTRLVE    1140
LCMV-P52_LP        MSAALKNLCFYSEESPTSYTSVGPDSGRLKFALSYKEQVGGNRELYIGDLRTKMFTRLVE    1140
LCMV-P91_LP:       MSAALKNLCFYSEESPTSYTSVGPDSGRLKFALSYKEQVGGNRELYIGDLRTKMFTRLVE    1140
LCMV-P52-1_LP      MSAALKNLCFYSEESPTSYTSVGPDSGRLKFALSYKEQVGGNRELYIGDLRTKMFTRLVE    1140
LCMV-P52-1.3_LP    MSAALKNLCFYSEESPTSYTSVGPDSGRLKFALSYKEQVGGNRELYIGDLRTKMFTRLVE    1140
LCMV-P52-2.1_LP    MSAALKNLCFYSEESPTSYTSVGPDSGRLKFALSYKEQVGGNRELYIGDLRTKMFTRLVE    1140
                   ************************************************************

LCMV-WE_LP         DYFESFSSFFSGSCLNNDKEFENAILSMTINVREGLLNYSMDHSKWGPMMCPFLFLMLLQ    1200
LCMV-P42_LP        DYFESFSSFFSGSCLNNDKEFENAILSMTINVREGLLNYSMDHSKWGPMMCPFLFLMLLQ    1200
LCMV-P52_LP        DYFESFSSFFSGSCLNNDKEFENAILSMTINVREGLLNYSMDHSKWGPMMCPFLFLMLLQ    1200
LCMV-P91_LP:       DYFESFSSFFSGSCLNNDKEFENAILSMTINVREGLLNYSMDHSKWGPMMCPFLFLMLLQ    1200
LCMV-P52-1_LP      DYFESFSSFFSGSCLNNDKEFENAILSMTINVREGLLNYSMDHSKWGPMMCPFLFLMLLQ    1200
LCMV-P52-1.3_LP    DYFESFSSFFSGSCLNNDKEFENAILSMTINVREGLLNYSMDHSKWGPMMCPFLFLMLLQ    1200
LCMV-P52-2.1_LP    DYFESFSSFFSGSCLNNDKEFENAILSMTINVREGLLNYSMDHSKWGPMMCPFLFLMLLQ    1200
                   ************************************************************

LCMV-WE_LP         NLKLGDDQYVRSGKDHVSTLLTWHMHKLVEVPFPVVNAMMKSYVKSKLKLLKGSGTTVTE    1260
LCMV-P42_LP        NLKLGDDQYVRSGKDHVSTLLTWHMHKLVEVPFPVVNAMMKSYVKSKLKLLKGSGTTVTE    1260
LCMV-P52_LP        NLKLGDDQYVRSGKDHVSTLLTWHMHKLVEVPFPVVNAMMKSYVKSKLKLLKGSGTTVTE    1260
LCMV-P91_LP:       NLKLGDDQYVRSGKDHVSTLLTWHMHKLVEVPFPVVNAMMKSYVKSKLKLLKGSGTTVTE    1260
LCMV-P52-1_LP      NLKLGDDQYVRSGKDHVSTLLTWHMHKLVEVPFPVVNAMMKSYVKSKLKLLKGSGTTVTE    1260
LCMV-P52-1.3_LP    NLKLGDDQYVRSGKDHVSTLLTWHMHKLVEVPFPVVNAMMKSYVKSKLKLLKGSGTTVTE    1260
LCMV-P52-2.1_LP    NLKLGDDQYVRSGKDHVSTLLTWHMHKLVEVPFPVVNAMMKSYVKSKLKLLKGSGTTVTE    1260
                   ************************************************************

LCMV-WE_LP         RIFREYFEMGVVPSHISSLIDMGQGILHNASDFYGLISERFINYCIGVIFGERPEAYTSS    1320
LCMV-P42_LP        RIFREYFEMGVVPSHISSLIDMGQGILHNASDFYGLISERFINYCIGVIFGERPEAYTSS    1320
LCMV-P52_LP        RIFREYFEMGVVPSHISSLIDMGQGILHNASDFYGLISERFINYCIGVIFGERPEAYTSS    1320
LCMV-P91_LP:       RIFREYFEMGVVPSHISSLIDMGQGILHNASDFYGLISERFINYCIGVIFGERPEAYTSS    1320
LCMV-P52-1_LP      RIFREYFEMGVVPSHISSLIDMGQGILHNASDFYGLISERFINYCIGVIFGERPEAYTSS    1320
LCMV-P52-1.3_LP    RIFREYFEMGVVPSHISSLIDMGQGILHNASDFYGLISERFINYCIGVIFGERPEAYTSS    1320
LCMV-P52-2.1_LP    RIFREYFEMGVVPSHISSLIDMGQGILHNASDFYGLISERFINYCIGVIFGERPEAYTSS    1320
                   ************************************************************

LCMV-WE_LP         DDQITLFDKRLSDLVDSDPEEVLVLLEFHSHLSGLLNKFISPKSVVGRFAAEFKSRFYVW    1380
LCMV-P42_LP        DDQITLFDKRLSDLVDSDPEEVLVLLEFHSHLSGLLNKFISPKSVVGRFAAEFKSRFYVW    1380
LCMV-P52_LP        DDQITLFDKRLSDLVDSDPEEVLVLLEFHSHLSGLLNKFISPKSVVGRFAAEFKSRFYVW    1380
LCMV-P91_LP:       DDQITLFDKRLSDLVDSDPEEVLVLLEFHSHLSGLLNKFISPKSVVGRFAAEFKSRFYVW    1380
LCMV-P52-1_LP      DDQITLFDKRLSDLVDSDPEEVLVLLEFHSHLSGLLNKFISPKSVVGRFAAEFKSRFYVW    1380
LCMV-P52-1.3_LP    DDQITLFDKRLSDLVDSDPEEVLVLLEFHSHLSGLLNKFISPKSVVGRFAAEFKSRFYVW    1380
LCMV-P52-2.1_LP    DDQITLFDKRLSDLVDSDPEEVLVLLEFHSHLSGLLNKFISPKSVVGRFAAEFKSRFYVW    1380
                   ************************************************************
```

Figure 26 (cont'd)

```
LCMV-WE_LP          GEEVPLLTKFVSAALHNVKCKEPHQLCETIDTIADQAIANGVPVFLVNCIQRRTLDLLKY   1440
LCMV-P42_LP         GEEVPLLTKFVSAALHNVKCKEPHQLCETIDTIADQAIANGVPVFLVNCIQRRTLDLLKY   1440
LCMV-P52_LP         GEEVPLLTKFVSAALHNVKCKEPHQLCETIDTIADQAIANGVPVFLVNCIQRRTLDLLKY   1440
LCMV-P91_LP:        GEEVPLLTKFVSAALHNVKCKEPHQLCETIDTIADQAIANGVPVFLVNCIQRRTLDLLKY   1440
LCMV-P52-1_LP       GEEVPLLTKFVSAALHNVKCKEPHQLCETIDTIADQAIANGVPVFLVNCIQRRTLDLLKY   1440
LCMV-P52-1.3_LP     GEEVPLLTKFVSAALHNVKCKEPHQLCETIDTIADQAIANGVPVFLVNCIQRRTLDLLKY   1440
LCMV-P52-2.1_LP     GEEVPLLTKFVSAALHNVKCKEPHQLCETIDTIADQAIANGVPVFLVNCIQRRTLDLLKY   1440
                    ************************************************************

LCMV-WE_LP          ANFPLDPFLLNTHTDVKDWLDGSRGYRIQRLIEELCPSETKIMRKLVRRLHHKLKNGECN   1500
LCMV-P42_LP         ANFPLDPFLLNTHTDVKDWLDGSRGYRIQRLIEELCPSETKIMRKLVRRLHHKLKNGECN   1500
LCMV-P52_LP         ANFPLDPFLLNTHTDVKDWLDGSRGYRIQRLIEELCPSETKIMRKLVRRLHHKLKNGECN   1500
LCMV-P91_LP:        ANFPLDPFLLNTHTDVKDWLDGSRGYRIQRLIEELCPSETKIMRKLVRRLHHKLKNGECN   1500
LCMV-P52-1_LP       ANFPLDPFLLNTHTDVKDWLDGSRGYRIQRLIEELCPSETKIMRKLVRRLHHKLKNGECN   1500
LCMV-P52-1.3_LP     ANFPLDPFLLNTHTDVKDWLDGSRGYRIQRLIEELCPSETKIMRKLVRRLHHKLKNGECN   1500
LCMV-P52-2.1_LP     ANFPLDPFLLNTHTDVKDWLDGSRGYRIQRLIEELCPSETKIMRKLVRRLHHKLKNGECN   1500
                    ************************************************************

LCMV-WE_LP          EEFFLDLFNREKKEAILQLGEILGLEDDLNELASINWLNLNEMFPLRMVLRQKVVYPSVM   1560
LCMV-P42_LP         EEFFLDLFNREKKEAILQLGEILGLEDDLNELASINWLNLNEMFPLRMVLRQKVVYPSVM   1560
LCMV-P52_LP         EEFFLDLFNREKKEAILQLGEILGLEDDLNELASINWLNLNEMFPLRMVLRQKVVYPSVM   1560
LCMV-P91_LP:        EEFFLDLFNREKEEAILQLGEILGLEDDLNELASINWLNLNEMFPLRMVLRQKVVYPSVM   1560
LCMV-P52-1_LP       EEFFLDLFNREMKEAILQLGEILGLEDDLNELASINWLNLNEMFPLRMVLRQKVVYPSVM   1560
LCMV-P52-1.3_LP     EEFFLDLFNREKKEAILQLGEILGLEDDLNELASINWLNLNEMFPLRMVLRQKVVYPSVM   1560
LCMV-P52-2.1_LP     EEFFLDLFNREKKEAILQLGEILGLEDDLNELASINWLNLNEMFPLRMVLRQKVVYPSVM   1560
                    *********** :***********************************************

LCMV-WE_LP          TFQEEKIPSLIKTLQNKLCSKFTRGAQKLLSEAINKSAFQSCVSSGFIGLCKTLGSRCVR   1620
LCMV-P42_LP         TFQEEKIPSLIKTLQNKLCSKFTRGAQKLLSEAINKSAFQSCVSSGFIGLCKTLGSRCVR   1620
LCMV-P52_LP         TFQEEKIPSLIKTLQNKLCSKFTRGAQKLLSEAINKSAFQSCVSSGFIGLCKTLGSRCVR   1620
LCMV-P91_LP:        TFQEEKIPSLIKTLQNKLCSKFTRGAQKLLSEAINKSAFQSCVSSGFIGLCKTLGSRCVR   1620
LCMV-P52-1_LP       TFQEEKIPSLIKTLQNKLCSKFTRGAQKLLSEAINKSAFQSCVSSGFIGLCKTLGSRCVR   1620
LCMV-P52-1.3_LP     TFQEEKIPSLIKTLQNKLCSKFTRGAQKLLSEAINKSAFQSCVSSGFIGLCKTLGSRCVR   1620
LCMV-P52-2.1_LP     TFQEEKIPSLIKTLQNKLCSKFTRGAQKLLSEAINKSAFQSCVSSGFIGLCKTLGSRCVR   1620
                    ************************************************************

LCMV-WE_LP          NKNRENMYIRKVLEDLTMDEHVTRVHKQDGVMLYICDKQRHPEAHRDHINLLRPLLWDYI   1680
LCMV-P42_LP         NKNRENMYIRKVLEDLTMDEHVTRVHKQDGVMLYICDKQRHPEAHRDHINLLRPLLWDYI   1680
LCMV-P52_LP         NKNRENMYIRKVLEDLTMDEHVTRVHKQDGVMLYICDKQRHPEAHRDHINLLRPLLWDYI   1680
LCMV-P91_LP:        NKNRENMYIRKVLEDLTMDEHVTRVHKQDGVMLYICDKQRHPEAHRDHINLLRPLLWDYI   1680
LCMV-P52-1_LP       NKNRENMYIRKVLEDLTMDEHVTRVHKQDGVMLYICDKQRHPEAHRDHINLLRPLLWDYI   1680
LCMV-P52-1.3_LP     NKNRENMYIRKVLEDLTMDEHVTRVHKQDGVMLYICDKQRHPEAHRDHINLLRPLLWDYI   1680
LCMV-P52-2.1_LP     NKNRENMYIRKVLEDLTMDEHVTRVHKQDGVMLYICDKQRHPEAHRDHINLLRPLLWDYI   1680
                    ************************************************************

LCMV-WE_LP          CISLSNSFELGVWVLAEPVKGKNESNSAVRHLNPCDYVARKPESSRLLEDKVSLNHVIQS   1740
LCMV-P42_LP         CISLSNSFELGVWVLAEPVKGKNESNSAVRHLNPCDYVARKPESSRLLEDKVSLNHVIQS   1740
LCMV-P52_LP         CISLSNSFELGVWVLAEPVKGKNESNSAVRHLNPCDYVARKPESSRLLEDKVSLNHVIQS   1740
LCMV-P91_LP:        CISLSNSFELGVWVLAEPVKGKNESNSAVRHLNPCDYVARKPESSRLLEDKVSLNHVIQS   1740
LCMV-P52-1_LP       CISLSNSFELGVWVLAEPVKGKNESNSAVRHLNPCDYVARKPESSRLLEDKVSLNHVIQS   1740
LCMV-P52-1.3_LP     CISLSNSFELGVWVLAEPVKGKNESNSAVRHLNPCDYVARKPESSRLLEDKVSLNHVIQS   1740
LCMV-P52-2.1_LP     CISLSNSFELGVWVLAEPVKGKNESNSAVRHLNPCDYVARKPESSRLLEDKVSLNHVIQS   1740
                    ************************************************************

LCMV-WE_LP          VRRLYPKIFEDQLLPFMSDVSSKNMRWSPRIKFLDLCVLIDINSESLSLISHVVKWKRDE   1800
LCMV-P42_LP         VRRLYPKIFEDQLLPFMFDVSSKNMRWSPRIKFLDLCVLIDINSESLSLISHVVKWKRDE   1800
LCMV-P52_LP         VRRLYPKIFEDQLLPFMSDVSSKNMRWSPRIKFLDLCVLIDINSESLSLISHVVKWKRDE   1800
LCMV-P91_LP:        VRRLYPKIFEDQLLPFMSDVSSKNMRWSPRIKFLDLCVLIDINSESLSLISHVVKWKRDE   1800
LCMV-P52-1_LP       VRRLYPKIFEDQLLPFMSDVSSKNMRWSPRIKFLDLCVLIDINSESLSLISHVVKWKRDE   1800
LCMV-P52-1.3_LP     VRRLYPKIFEDQLLPFMSDVSSKNMRWSPRIKFLDLCVLIDINSESLSLISHVVKWKRDE   1800
LCMV-P52-2.1_LP     VRRLYPKIFEDQLLPFMSDVSSKNMRWSPRIKFLDLCVLIDINSESLSLISHVVKWKRDE   1800
                    ***************** ******************************************

LCMV-WE_LP          HYTVLFSDLVNSHQRSDSSLVDEFVVSTRDVCKNFLKQVYFESFVREFVATARTLGNFSW   1860
LCMV-P42_LP         HYTVLFSDLVNSHQRSDSSLVDEFVVSTRDVCKNFLKQVYFESFVREFVATARTLGNFSW   1860
LCMV-P52_LP         HYTVLFSDLVNSHQRSDSSLVDEFVVSTRDVCKNFLKQVYFESFVREFVATARTLGNFSW   1860
LCMV-P91_LP:        HYTVLFSDLVNSHQRSDSSLVDEFVVSTRDVCKNFLKQVYFESFVREFVATARTLGNFSW   1860
LCMV-P52-1_LP       HYTVLFSDLVNSHQRSDSSLVDEFVVSTRDVCKNFLKQVYFESFVREFVATARTLGNFSW   1860
LCMV-P52-1.3_LP     HYTVLFSDLVNSHQRSDSSLVDEFVVSTRDVCKNFLKQVYFESFVREFVATARTLGNFSW   1860
LCMV-P52-2.1_LP     HYTVLFSDLVNSHQRSDSSLVDEFVVSTRDVCKNFLKQVYFESFVREFVATARTLGNFSW   1860
                    ************************************************************
```

Figure 26 (cont'd)

```
LCMV-WE_LP           FPHKDMMPSEDGAEALGPFQSFILKVVNKKIERPMFRNDLQFGFGWFSYRVGDVVCNAAM    1920
LCMV-P42_LP          FPHKDMMPSEDGAEALGPFQSFILKVVNKKIERPMFRNDLQFGFGWFSYRVGDVVCNAAM    1920
LCMV-P52_LP          FPHKDMMPSEDGAEALGPFQSFILKVVNKKIERPMFRNDLQFGFGWFSYRVGDVVCNAAM    1920
LCMV-P91_LP:         FPHKDMMPSEDGAEALGPFQSFILKVVNKKIERPMFRNDLQFGFGWFSYRVGDVVCNAAM    1920
LCMV-P52-1_LP        FPHKDMMPSEDGAEALGPFQSFILKVVNKKIERPMFRNDLQFGFGWFSYRVGDVVCNAAM    1920
LCMV-P52-1.3_LP      FPHKDMMPSEDGAEALGPFQSFILKVVNKKIERPMFRNDLQFGFGWFSYRVGDVVCNAAM    1920
LCMV-P52-2.1_LP      FPHKDMMPSEDGAEALGPFQSFILKVVNKKIERPMFRNDLQFGFGWFSYRVGDVVCNAAM    1920
                     ************************************************************

LCMV-WE_LP           LIKQGLTDPKAFKSLRDLWDYMLSSTEGILEFSITVDFTHNQNNTDCLRKFSLIFVVKCQ    1980
LCMV-P42_LP          LIKQGLTDPKAFKSLRDLWDYMLSSTEGILEFSITVDFTHNQNNTDCLRKFSLIFVVKCQ    1980
LCMV-P52_LP          LIKQGLTDPKAFKSLRDLWDYMLSSTEGILEFSITVDFTHNQNNTDCLRKFSLIFVVKCQ    1980
LCMV-P91_LP:         LIKQGLTDPKAFKSLRDLWDYMLSSTEGILEFSITVDFTHNQNNTDCLRKFSLIFVVKCQ    1980
LCMV-P52-1_LP        LIKQGLTDPKAFKSLRDLWDYMLSSTEGILEFSITVDFTHNQNNTDCLRKFSLIFVVKCQ    1980
LCMV-P52-1.3_LP      LIKQGLTDPKAFKSLRDLWDYMLSSTEGILEFSITVDFTHNQNNTDCLRKFSLIFVVKCQ    1980
LCMV-P52-2.1_LP      LIKQGLTDPKAFKSLRDLWDYMLSSTEGILEFSITVDFTHNQNNTDCLRKFSLIFVVKCQ    1980
                     ************************************************************

LCMV-WE_LP           LQSPGVADYLSCSHFFKGEVDRRLLDECLNLLRTDPIFKANDGVFDIRSEEFEDYMEDPL    2040
LCMV-P42_LP          LQSPGVADYLSCSHFFKGEVDRRLLDECLNLLRTDPIFKANDGVFDIRSEEFEDYMEDPL    2040
LCMV-P52_LP          LQSPGVADYLSCSHSFKGEVDRRLLDECLNLLRTDPIFKANDGVFDIRSEEFEDYMEDPL    2040
LCMV-P91_LP:         LQSPGVADYLSCSHSFKGEVDRRLLDECLNLLRTDPIFKANDGVFDIRSEEFEDYMEDPL    2040
LCMV-P52-1_LP        LQSPGVADYLSCSHFFKGEVDRRLLDECLNLLRTDPIFKANDGVFDIRSEEFEDYMEDPL    2040
LCMV-P52-1.3_LP      LQSPGVADYLSCSHSFKGEVDRRLLDECLNLLRTDPIFKANDGVFDIRSEEFEDYMEDPL    2040
LCMV-P52-2.1_LP      LQSPGVADYLSCSHFFKGEVDRRLLDECLNLLRTDPIFKANDGVFDIRSEEFEDYMEDPL    2040
                     ************** *********************************************
                                                                           X=I/V
LCMV-WE_LP           TLGDSLELELIGSRRILNEIKSTDFERIGPEWEPVPLTIRKGALFEGRNFVQNISVKLET    2100
LCMV-P42_LP          TLGDSLELELIGSRRILNEIKSTDFERIGPEWEPVPLTIRKGALFEGRNFVQNISVKLET    2100
LCMV-P52_LP          TLGDSLELELIGSRRILNEIKSTDFERIGPEWEPVPLTIRKGALFEGRNFVQNXSVKLET    2100
LCMV-P91_LP:         TLGDSLELELIGSRRILNEIKSTDFERIGPEWEPVPLTIRKGALFEGRNFVQNISVKLET    2100
LCMV-P52-1_LP        TLGDSLELELIGSRRILNEIKSTDFERIGPEWEPVPLTIRKGALFEGRNFVQNISVKLET    2100
LCMV-P52-1.3_LP      TLGDSLELELIGSRRILNEIKSTDFERIGPEWEPVPLTIRKGALFEGRNFVQNISVKLET    2100
LCMV-P52-2.1_LP      TLGDSLELELIGSRRILNEIKSTDFERIGPEWEPVPLTIRKGALFEGRNFVQNISVKLET    2100
                     ***************************************************** ******

                                                             X=T/A
LCMV-WE_LP           KDMRVFLAELEGCGKIGDVLGSLLLHRFRTGEHLMESEISTVLQELCMDRSVMLTPLSFV    2160
LCMV-P42_LP          KDMRVFLAELEGCGKIGDVLGSLLLHRFRTGEHLMESEISTVLQELCMDRSVMLTPLSFV    2160
LCMV-P52_LP          KDMRVFLAELEGCGKIGDVLGSLLLHRFRTGEHLMESEISXVLQELCMDRSVMLTPLSFV    2160
LCMV-P91_LP:         KDMRVFLAELEGCGKIGDVLGSLLLHRFRTGEHLMESEISTVLQELCMDRSVMLTPLSFV    2160
LCMV-P52-1_LP        KDMRVFLAELEGCGEIGDVLGSLLLHRFRTGEHLMESEISTVLQELCMDRSVMLTPLSFV    2160
LCMV-P52-1.3_LP      KDMRVFLAELEGCGKIGDVLGSLLLHRFRTGEHLMESEISTVLQELCMDRSVMLTPLSFV    2160
LCMV-P52-2.1_LP      KDMRVFLAELEGCGEIGDVLGSLLLHRFRTGEHLMESEISTVLQELCMDRSVMLTPLSFV    2160
                     **************:************************* *******************

                                  X=R/K
LCMV-WE_LP           PDWFTFRDCRLCFSRSKNTVMYETTGGRFRLKGKSCDDWLAERVAEEID    2209
LCMV-P42_LP          PDWFTFRDCRLCFSRSKNTVMYETTGGRFRLKGKSCDDWLAERVAEEID    2209
LCMV-P52_LP          PDWFTFRDCRLCFSRSKNTVMYETTGGRFRLKGKSCDDWLAERVAEEID    2209
LCMV-P91_LP:         PDWFTFRDCRLCFSXSKNTVMYETTGGRFRLKGKSCDDWLAERVAEEID    2209
LCMV-P52-1_LP        PDWFTFRDCRLCFSRSKNTVMYETAGGRFRLKGKSCDDWLAERVAEEID    2209
LCMV-P52-1.3_LP      PDWFTFRDCRLCFSRSKNTVMYETTGGRFRLKGKSCDDWLAERVAEEID    2209
LCMV-P52-2.1_LP      PDWFTFRDCRLCFSRSKNTVMYETTGGRFRLKGKSCDDWLAERVAEEID    2209
                     ************** *********:************************

LCMV-WE_LP:      SEQ ID NO: 16
LCMV-P42_LP:     SEQ ID NO: 24
LCMV-P52_LP:     SEQ ID NO: 32
LCMV-P91_LP:     SEQ ID NO: 40
LCMV-P52-1_LP:   SEQ ID NO: 48
LCMV-P52-1.3_LP: SEQ ID NO: 56
LCMV-P52-2.1_LP: SEQ ID NO: 64
LCMV-P52-1.3_LP: SEQ ID NO: 56
```

METHOD FOR PRODUCING AN ANTITUMORAL ARENAVIRUS AS WELL AS ARENAVIRUS MUTANTS

CROSS REFERENCE TO RELATED APPLICATIONS

The present invention is filed under 35 U.S.C. § 371 as the U.S. national phase of International Application No. PCT/EP2019/074307, filed 12 Sep. 2019, which designated the U.S. and claims the benefit of priority of German Patent Application DE 10 2018 215 551.8 filed on 12 Sep. 2018, the contents of each of which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Mar. 12, 2021, is named SCH-6900-US SeqListing.txt and is 365 kilobytes in size.

FIELD OF THE INVENTION AND BACKGROUND

The invention relates to a method for the preparation of an antitumoral arenavirus, arenavirus mutants, isolated proteins or peptides, in particular isolated glycoproteins, an arenavirus and nucleic acids encoding for corresponding proteins or peptides.

Arenaviruses belong to the family of human pathogenic pleomorphic RNA viruses. Diseases with these viruses belong to the zoonoses due to their natural reservoir in animals, predominantly rodents. Zoonoses are diseases that can be transmitted from animals to humans and vice versa from humans to animals.

At least eight arenaviruses are known to cause a disease in humans, typically aseptic meningitis and haemorrhagic fever. Known viruses that can cause a disease in humans are the lymphocytic choriomeningitis virus (LCMV), guanarito virus (GTOV), junin virus (JUNV), lassa virus (LASV), lujo virus (LUJV), machupo virus (MACV), sabia virus (SABV) and whitewater arroyo virus (WWAV).

Arenaviruses with the genus mammarenavirus are divided into two groups, the Old World Arenaviruses and the New World Arenaviruses. These groups differ geographically and genetically. Old World Arenaviruses, such as the lymphocytic choriomeningitis virus, were found mainly in countries of the Eastern Hemisphere, such as European, Asian and African countries. In contrast, New World Arenaviruses have been found in Western Hemisphere countries such as Argentina, Bolivia, Venezuela, Brazil and the United States of America.

Arenaviruses replicate in the cell and enter the extracellular space as virions (infectious particles). Virions have a pleomorphic, often round shape with a diameter of mostly 110 nm to 130 nm up to 50 nm to 300 nm. The capsid of the virion is surrounded by an envelope protein consisting of a double lipid membrane and homotrimers of glycoproteins (GP1 and GP2) that protrude in the shape of spikes. GP1 is directed outwards and binds to the cellular receptor during infection. GP2 is directed in the opposite direction and mediates fusion with the cell. The Z-proteins lay like a ring below the lipid layer, located inside the nucleocapsid the ribonucleoprotein (RNP)-complexes each consists of the shorter RNA segment (S segment 3.5 kb) respectively the longer RNA segment (L segment 7.2 kb) and the nucleoproteins. The L-protein, the viral polymerase, is associated with the RNP complexes. L- and S-segments carry the genetic information and code for two proteins each. The single-stranded RNAs have a mixed (i.e. ambisense polarity), at their 3' untranslated ends the sequences (approx. 19-30 bp) are conserved, also within the virus family. First, the mRNAs of nucleoprotein and L-protein are transcribed, followed by replication and mRNA transcription of Z-protein and the glycoprotein precursor, and finally followed by translation and modification of the viral proteins.

The use of arenaviruses as vaccination vectors is well known. A prominent example is the vaccination virus Candid #1 used against Argentine haemorrhagic fever. This is a vaccination variant of the Junin virus.

From WO 2009/083210 A1, the use of replication defective, i.e. genetically modified arenavirus particles (virions) inter alia for the treatment of neoplastic diseases such as melanoma, prostate carcinoma, breast carcinoma and lung carcinoma is known. The publication "Development of replication-defective lymphocytic choriomeningitis virus vectors for the induction of potent CD8+ T cell immunity" (Nature Medicine, vol. 16, no. 3, March 2010, p. 339-345; doi: 10.1038/nm.2104) mentions as a potential application area for such virus particles cancer immunotherapy.

Further from WO 2006/008074 A1 the use of packaging cells which produce both retroviral and with arenavirus-glycoprotein pseudotyped virions for gene therapy of solid tumors is known.

The above described state-of-the-art methods for the treatment of tumors are based on the use of virus particles that are very complicated to generate by means of genetic engineering. In addition, in case of gene therapy treatment methods a sufficient, therapeutically effective transduction of the tumor tissue with genetically engineered virions or packaging cells which produce virions is often not achievable.

From WO 2016/166285 A1, however, arenaviruses for the treatment and/or prevention of tumors are known, whereat said arenaviruses are free of genomic foreign RNA. Additionally, from WO 2016/166285 A1 a method for the production of arenaviruses with tumor regressive properties is known.

Nevertheless, there is still a need for specific and in particular therapeutically effective arenaviruses for use in the treatment and/or prevention of tumors.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIGS. 25A-E show nucleic acid and amino acid sequences of LCMV-WE (FIG. 25A), LCMV mutant P42 (FIG. 25B), LCMV mutant P52 (FIG. 25C), LCMV mutant P91 (FIG. 25D), LCMV mutant P52-1 (FIG. 25E), LCMV mutant P52-1.3 (FIG. 25F), and LCMV mutant P52-2.1 (FIG. 25G).

FIGS. 26A-H show alignments of nucleic acid and amino acid sequences LCMV-WE and mutants P42, P52, P92, P52-1, P52-1.3, and P52-2.1 pre-glycoprotein polyprotein GP complex (FIG. 26A and FIG. 26B), nucleoprotein (FIG. 26C and FIG. 26D), and ring finger protein Z (FIG. 26E and FIG. 26F), RNA-directed RNA polymerase L (FIG. 26G and FIG. 26H).

Object and Solution

Figure 1:
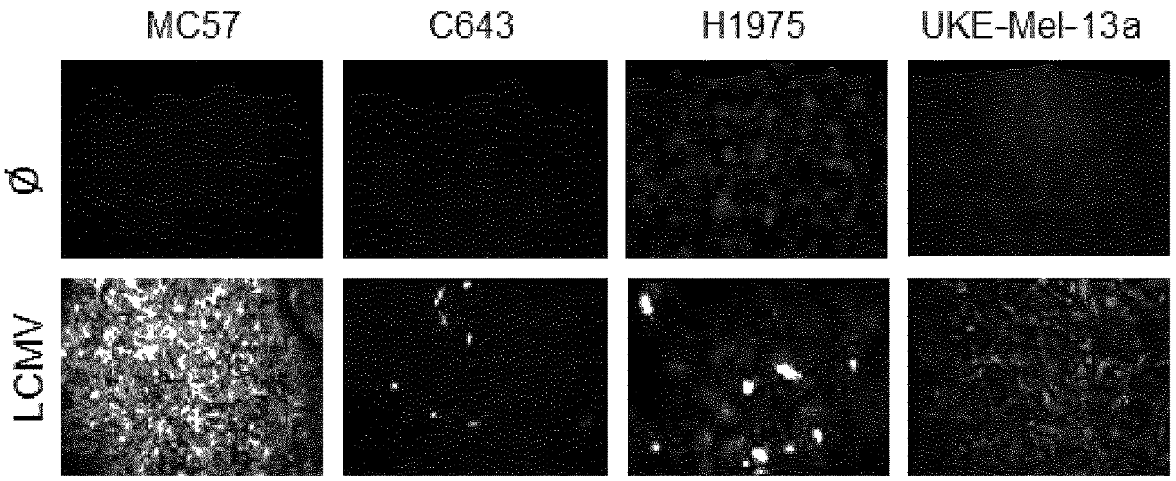
FIG. 1 shows LCMV spread in MC57, C643, H1975 and UKE-Mel-13a cells. Ø=without infection, LCMV=LCMV infected.

The underlying object of the present invention is to produce arenaviruses with antitumor properties and/or improved antitumor properties. Furthermore, the underlying object of the invention is to provide corresponding arenavirus mutants, isolated proteins or peptides, in particular glycoproteins and/or L-proteins, of arenaviruses as well as nucleic acids coding for them.

The above objects are solved by a lymphocytic choriomeningitis virus mutant according to independent claim 1, a method according to independent claim 15, as well as a lymphocytic choriomeningitis virus mutant according to claim 22. Preferred embodiments of the method and the lymphocytic choriomeningitis virus mutant are subject of the dependent claims and to the present description. Additional aspects of the present invention are disclosed in the description. The wording of all claims is hereby incorporated by explicit reference to the content of the present description.

The present invention is based on the surprising finding that certain mutants of an arenavirus, in particular lymphocytic choriomeningitis virus (LCMV) may have improved antitumoral activities as compared to a wild type virus.

Accordingly, the present invention generally relates to a mutant of lymphocytic choriomeningitis virus, preferably a mutant of strain WE.

The mutant may be capable of undergoing a stronger propagation in a tumor cell, such as a H1975 cell, a HCC1954 cell, a murine pancreatic cancer cell, or a human melanoma cell, as compared to the wild type lymphocytic choriomeningitis virus strain WE. The mutant may also be capable of inducing a stronger innate immune activation than LCMV-WE wild type in vivo. The mutant may also be capable of having a stronger antitumoral effect in vivo than LCMV-WE wild type. The mutant may also be capable of increasing expansion of tumor-specific CD8+ T cells as compared to LCMV-WE wild type. The mutant may also be capable of increasing the function of tumor-specific CD8+ T cells. The mutant may also have a higher capacity to stimulate tumor specific T cells as compared to the LCMV-WE wild type.

The mutant a of lymphocytic choriomeningitis virus of the invention preferably comprises a nucleic acid encoding a glycoprotein, wherein said glycoprotein comprises at least one mutation at positions corresponding to positions 181 and 185 of the wild type glycoprotein sequence set forth in SEQ ID NO: 10. The preferred mutations are Arg 185→Trp and/or Ile 181→Met (such as Arg 185→Trp only, Ile 181→Met only, or Arg 185→Trp and Ile 181→Met) as compared to the wild type glycoprotein sequence set forth in SEQ ID NO: 10 and/or (a) respective protein(s) encoded by the nucleic acid. While the examples of the present application demonstrate that the presence of either one of the mutations may already be sufficient in order to provide an improved function over a wild type lymphocytic choriomeningitis virus, the presence of both of the recited mutations will further improve the function of the LCMV, which may be additively or even synergistically. Accordingly, in a preferred embodiment, both mutations are present in the LCMV of the invention.

Without wishing to be bound by theory, it is further believed that the presence of the one or two above-mentioned mutations in the glycoprotein can improve the function of the LCMV (e.g. replication or propagation in a tumor cell, anti-tumoral activities, and/or immune system stimulation as described above), independent from the presence of other mutations, in particular of other mutations in other genes or proteins of LCMV. The assumption is based on the finding that the mutations Arg 185→Trp and Ile 181→Met in the glycoprotein remain conserved while some other mutations appear and disappear during serial passages, and/or are not conserved among different mutant strains. The assumption is further based on the fact that the glycoprotein(s) of LCMV form the spikes on the virion envelope, and are thus believed to play a predominant role in the virus's ability to infect a tumor cell.

The LCMV mutant of the invention may comprise a nucleic acid encoding a glycoprotein, wherein the glycoprotein has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.5%, preferably at least about 99.7% sequence identity, to the wild type glycoprotein sequence set forth in SEQ ID NO: 10, and/or may comprise (a) respective protein(s) encoded by the nucleic acid.

The LCMV mutant of the invention may comprises a nucleic acid encoding a glycoprotein, wherein the glycoprotein comprises the mutations Arg 185→Trp and Ile 181→Met as compared to the wild type glycoprotein set forth in SEQ ID NO: 10.

The LCMV mutant of the invention may comprise a nucleic acid encoding a glycoprotein, wherein said glycoprotein has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.5%, preferably at least about 99.7% sequence identity, or is preferably identical, to a sequence set forth in any one of SEQ ID NOs: 18, 26, 34, 42, 50, and 58, and/or may comprise (a) respective protein(s) encoded by the nucleic acid.

The LCMV mutant of the invention may comprise a nucleic acid encoding a glycoprotein, wherein said nucleic acid comprises a sequence that has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, or is preferably identical, to a sequence set forth in SEQ ID NOs: 17, 25, 33, 41, 49, and 57, and/or may comprise (a) respective protein(s) encoded by the nucleic acid.

As already indicated above, it is believed that the glycoprotein(s) of LCMV, which form the spikes on the virion envelope, play a predominant role in the virus's ability to infect tumor cells. However, further proteins are preferably present in an LCMV.

The LCMV mutant of the invention may comprise a nucleic acid encoding a L-protein that has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity to the wild type L-protein sequence set forth in SEQ ID NO: 16, and/or may comprise a respective protein encoded by the nucleic acid.

The LCMV mutant of the invention may comprise a nucleic acid encoding a L-protein, wherein said L-protein has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, preferably at least about 99.8%, preferably at least about 99.9% sequence identity, or is preferably identical, to a sequence set forth in any one of SEQ ID NOs: 24, 32, 40, 48, 56, and 64, and/or may comprise a respective protein encoded by the nucleic acid.

The LCMV mutant of the invention may comprise a nucleic acid encoding a L-protein, wherein said L-protein comprises 1, 2, 3, 4, 5, 6, 7, 8, 9, or 10 mutations at positions corresponding to positions 253, 1512, 1513, 1758, 1995, 2094, 2115, 2141, 2175, and 2185 of the wild type L-protein sequence set forth in SEQ ID NO: 16. Preferred embodiments of mutations at these positions are: Lys 253→Arg; Lys 1512→Met; Lys 1513→Glu; Ser 1758→Phe; Phe 1995→Ser; Ile 2094→Val; Lys 2115→Glu; Thr 2141>Ala; Arg 2175→Lys; Thr 2185→Ala as compared to the wild type L-protein sequence set forth in SEQ ID NO: 16, and/or may comprise a respective protein encoded by the nucleic acid. Preferably, the LCMV mutein comprises 1, 2, 3, 4, or 5 of the aforementioned mutations.

The LCMV mutant of the invention may comprise a nucleic acid encoding a L-protein, wherein said L-protein comprises as compared to the wild type L-protein sequence set forth in SEQ ID NO: 16 one of the following sets of mutations: Ser 1758→Phe (corresponding to the mutations of mutant strain P42); Phe 1995→Ser, optionally Ile 2094→Val, and optionally Thr 2141→Ala (corresponding to the mutations of mutant strain P52, which is oligoclonal for positions 2094 and 2141); Lys 1513→Glu, Phe 1995→Ser, and optionally Arg 2175→Lys (corresponding to the mutations of mutant strain P91, which is oligoclonal for position 2175); Lys 253→Arg; Lys 1512→Met; Lys 2115→Glu; Thr 2185→Ala (corresponding to the mutations of mutant strain P52-1); Phe 1995→Ser (corresponding to the mutations of mutant strain P52-1.3); or Lys 2115→Glu (corresponding to the mutations of mutant strain P52-2.1), and/or may comprise a respective protein encoded by the nucleic acid.

The LCMV mutant of the invention may comprise a nucleic acid encoding an L-protein, wherein said nucleic acid has or—is preferably complementary to a sequence that has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, preferably at least about 99.8%, preferably at least about 99.9% sequence identity, or is preferably identical, to a sequence set forth in SEQ ID NOs:

17, 25, 33, 41, 49, and 57, and/or may comprise a respective protein encoded by the nucleic acid.

The LCMV mutant of the invention may comprise a nucleic acid encoding an nucleoprotein, wherein said nucleoprotein has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or is identical, to a nucleoprotein set forth in any one of SEQ ID NOs: 12, 20, 28, 36, 44, 52, and 60, and/or may comprise a respective protein encoded by the nucleic acid.

The LCMV mutant of the invention may comprise a nucleic acid encoding an nucleoprotein, wherein said nucleic acid has or—is preferably complementary to a sequence that has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or is identical, to a nucleoprotein set forth in any one of SEQ ID NOs: 11, 19, 27, 35, 43, 51, and 59, and/or may comprise a respective protein encoded by the nucleic acid.

The LCMV mutant of the invention may comprise a nucleic acid encoding a Z-protein, wherein said Z-protein has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or is identical, to a sequence set forth in any one of SEQ ID NOs: 14, 22, 30, 38, 46, 54, and 62, and/or may comprise a respective protein encoded by the nucleic acid.

The LCMV mutant of the invention may comprise a nucleic acid encoding a Z-protein, whrein said nucleic acid comprises a sequence that has at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or is identical, to a sequence set forth in any one of SEQ ID NOs: 13, 21, 29, 37, 45, 53, and 61, and/or may comprise a respective protein encoded by the nucleic acid.

A LCMV mutant of the invention may comprise (a) glycoprotein(s) preferably as defined herein, an L protein preferably as defined herein, a Z protein preferably as defined herein, and a nucleoprotein preferably as defined herein. A LCMV mutant of the invention may comprise (a) nucleic acid(s) that encode a) glycoprotein(s) preferably as defined herein, an L protein preferably as defined herein, an Z protein preferably as defined herein, and a nucleoprotein preferably as defined herein.

A LCMV mutant of the invention may comprise (a) nucleic acid(s) that encode the proteins of SEQ ID NOs: 18, 20, 22, and 24, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. The glycoprotein may comprise a Ile 181→Met mutation. The L-protein may comprise a Ser 1758→Phe mutation. A LCMV mutant of the invention may comprise (a) nucleic acid(s) that comprise(s) a sequence set forth in SEQ ID NOs: 17 and 21 and that comprise(s) a sequence that is complementary to the sequence set forth in SEQ ID NOs: 19 and 23.

A LCMV mutant of the invention may comprise (a) nucleic acid(s) that encode the proteins of SEQ ID NOs: 26, 28, 30, and 32, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. The glycoprotein may comprise a Ile 181→Met and a Arg 185→Trp mutation. The L protein may comprise following mutations Phe 1995→Ser, optionally Ile 2094→Val, and optionally Thr 2141>Ala. A LCMV mutant of the invention may comprise (a) nucleic acid(s) that comprise(s) a sequence set forth in SEQ ID NOs: 25 and 29 and that comprise(s) a sequence that is complementary to the sequence set forth in SEQ ID NOs: 27 and 31.

A LCMV mutant of the invention may comprise (a) nucleic acid(s) that encode the proteins of SEQ ID NOs: 34, 36, 38, and 40, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. The glycoprotein may comprise a Ile 181→Met and a Arg 185→Trp mutation. The L protein may comprise following mutations Lys 1513→Glu, Phe 1995→Ser, and optionally Arg 2175→Lys. A LCMV mutant of the invention may comprise (a) nucleic acid(s) that comprise(s) a sequence set forth in SEQ ID NOs: 33 and 37 and that comprise(s) a sequence that is complementary to the sequence set forth in SEQ ID NOs: 35 and 39.

A LCMV mutant of the invention may comprise (a) nucleic acid(s) that encode the proteins of SEQ ID NOs: 50, 52, 54, and 56, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. The glycoprotein may comprise a Ile 181→Met and a Arg 185→Trp mutation. The L protein may comprise following mutations Lys 253→Arg; Lys 1512→Met; Lys 2115→Glu; Thr 2185→Ala. A LCMV mutant of the invention may comprise (a) nucleic acid(s) that comprise(s) a sequence set forth in SEQ ID NOs: 41 and 45 and that comprise(s) a sequence that is complementary to the sequence set forth in SEQ ID NOs: 43 and 47.

A LCMV mutant of the invention may comprise (a) nucleic acid(s) that encode the proteins of SEQ ID NOs: 58, 60, 62, and 64, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. The glycoprotein may comprise a Arg 185→Trp mutation. The L protein may comprise a Phe 1995→Ser mutation.

A LCMV mutant of the invention may comprise (a) nucleic acid(s) that comprise(s) a sequence set forth in SEQ ID NOs: 49 and 53 and that comprise(s) a sequence that is complementary to the sequence set forth in SEQ ID NOs: 51 and 55.

A LCMV mutant of the invention may comprise (a) nucleic acid(s) that encode the proteins of SEQ ID NOs: 66, 68, 70, and 72, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. The glycoprotein may comprise a Ile 181→Met mutation. The L protein may comprise a Lys 2115→Glu mutation. A LCMV mutant of the invention may comprise (a) nucleic acid(s) that comprise(s) a sequence set forth in SEQ ID NOs: 57 and 61 and that comprise(s) a sequence that is complementary to the sequence set forth in SEQ ID NOs: 59 and 63.

A LCMV of the disclosure may comprise (a) nucleic acid(s) that encode the proteins of SEQ ID NOs: 10, 12, 14, and 18, or proteins having at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity to these sequences. A LCMV of the disclosure may comprise (a) nucleic acid(s) that comprise(s) a sequence set forth in SEQ ID NOs: 10 and 14 and that comprise(s) a sequence that is complementary to the sequence set forth in SEQ ID NOs: 12 and 16.

The present invention also generally relates to a LCMV of the disclosure, in particular of an LCMV mutant of the disclosure, for use in therapy.

In particular when a LCMV mutant of the disclosure is used, such use may comprise a stronger propagation of the LCMV mutant in a tumor (cell), as compared to the use wild type lymphocytic choriomeningitis virus strain WE. Such use may also comprise inducing a stronger innate immune activation as compared to the use of LCMV-WE wild type in vivo. Such use may also comprise promoting a stronger antitumoral effect in vivo as compared to the use of LCMV-WE wild type. Such use may also comprise increasing expansion of tumor-specific CD8+ T cells as compared to the use of LCMV-WE wild type. The use may also comprise increasing the function of tumor-specific CD8+ T cells. The use may also comprise stimulating tumor specific T cells to a larger extent as compared to the LCMV-WE wild type.

The LCMV (mutant) of the disclosure may be for use in the treatment and/or prevention of a tumor. The tumor may be any tumor disclosed herein. The tumor is preferably selected from the group consisting of carcinoma, melanoma, blastoma, lymphoma and sarcoma.

According to a first aspect, the invention relates to a method for the production of an antitumor arenavirus, i.e. a tumor-fighting or -repulsive arenavirus (so-called tumor regressive arenavirus), in particular an arenavirus which has in comparison to an original arenavirus improved antitumor properties, i.e. improved tumor-fighting or -repulsive properties.

The method comprises the following steps:

a) plating primary tumor cells in a nutrient medium, preferably liquid nutrient medium, or plating cells of the cell line H1975, C643 or Tramp-C2 onto and/or into a nutrient medium, preferably liquid nutrient medium, b) inoculation of the plated primary tumor cells with an original arenavirus or inoculation of the plated cells of the cell line H1975, C643 or Tramp-C2 with an original arenavirus, c) incubating the inoculated primary tumor cells or incubating the inoculated cells of the cell line H1975, C643 or Tramp-C2, i.e. incubating the primary tumor cells and the original arenavirus or incubating the cells of the cell line H1975, C643 or Tramp-C2 and the original arenavirus under conditions suitable for causing at least a portion of the inoculated primary tumor cells or at least a portion of the inoculated cells of the cell line H1975, C643 or Tramp-C2, in particular only part of the inoculated primary tumor cells or only part of the inoculated cells of the cell line H1975, C643 or Tramp-C2 or all inoculated primary tumor cells or all inoculated cells of the cell line H1975, C643 or Tramp-C2, to be infected with the original arenavirus, d) extracting an arenavirus-containing cell culture supernatant from an incubated primary tumor cell culture, or extracting an arenavirus-containing cell culture supernatant from the incubated cells of the cell line H1975, C643 or Tramp-C2 containing cell culture, wherein the step sequence a) to d) is repeated a plurality of times, wherein the primary tumor cells or the cells of the cell line H1975, C643 or Tramp-C2 when performing the first repetition of step sequence a) to d), for performing step b) is inoculated with the arenavirus-containing cell culture supernatant or a part thereof extracted when performing step d) before the first repetition of the step sequence a) to d, and wherein the primary tumor cells or the cells of cell line H1975, C643 or Tramp-C2 when performing each further repetition of the step sequence a) to d), for performing step b) is inoculated with the arenavirus-containing cell culture supernatant or a part thereof extracted when performing step d) of a previous repetition of the step sequence a) to d).

The first conduct of step sequence a) to d) can also be referred to as the “first passage” within the meaning of the present invention. The first passage is therefore performed with the original arenavirus as inoculum. Each further passage is then performed with an arenavirus-containing cell culture supernatant or part thereof extracted in step d) of a preceding preferably immediately preceding passage. From performing a second passage onwards said passage can be referred to as “repeated passage”, within the meaning of the present invention.

The term “original arenavirus” in the context of the present invention can be understood to mean an arenavirus which is used before the first repetition of step sequence a) to d), i.e. before the first passage for inoculation of the primary tumor cells or the cells of the cell line H1975, C643 or Tramp-C2 (step b)). The “original arenavirus” may refer to, which is described in more detail below, a wildtype arenavirus or a mutant thereof. In particular, the term may refer to an original arenavirus without antitumor properties or with antitumor properties.

The term "wild-type arenavirus" within the in the context of the present invention should be understood to mean an arenavirus with a genome which occurs in nature in its genetically normal form.

The term "primary tumor cells" in the context of the present invention should be understood to mean unpassaged or non-passaged tumor cells, i.e. tumor cells isolated directly from a tumor tissue or tumor cells isolated directly from a tumor tissue, which have been passaged before performing step a) a maximum of 1000 times, in particular a maximum of 100 times, preferably a maximum of 10 times, or primary tumor cells which are characterized by having different cell clones. In the case of the latter, heterogeneity can be demonstrated by different protein expression and by different DNA sequences (genetic fingerprinting).

The term "cell line H1975" in the context of the present invention should be understood to mean a cell line which has been isolated from a human adenocarcinoma and is deposited at ATCC (American Type Culture Collection) under the designation NCI-H1975 (ATCC® CRL-5908@) and under the accession or deposit number CVCL-1511.

The term "cell line C643" in the context of the present invention should be understood to mean a cell line which has been isolated from human anaplastic thyroid carcinoma deposited under the designation C643 and under the accession or deposit number CVCL-5969 (ExPASy Cellosaurus).

The term "cell line Tramp-C2" in the context of the present invention should be understood to mean a cell line isolated from a murine adenocarcinoma and deposited under the designation Tramp-C2 and under the accession or deposit number CVCL-3615 (ExPASy Cellosaurus).

The term "plating out" in the context of the present invention should be understood to mean the seeding or introduction of primary tumor cells or cells of the cell line H1975, C643 or Tramp-C2 onto and/or into a culture medium, preferably a liquid culture medium. In other words, the term "plating" in the sense of this invention should be understood to mean the cultivation, in particular initial cultivation, of primary tumor cells or cells of the cell line H1975, C643 or Tramp-C2 on and/or in a culture medium, preferably liquid culture medium.

The term "lymphocytic choriomeningitis virus WE strain" may refer to the LCMV-WE strain that has been described by Seiler, P., et al., J. Immunol. 162 (8), 4536-4541 (1999). The term "lymphocytic choriomeningitis virus WE strain" as used herein preferably refers to a LCMV that comprises glycoproteins having the sequence of positions 59-265 and 266-498 of SEQ ID NO: 10, a nucleoprotein having the sequence of SEQ ID NO: 12; a Z-protein having the sequence of SEQ ID NO: 14; and/or a L-protein having the sequence of SEQ ID NO: 16. The term "lymphocytic choriomeningitis virus WE strain" as used herein also preferably refers to a LCMV that comprises one ore more, preferably two nucleic acid molecules, which comprise sequences that are or are complementary to the sequences of SEQ ID NOs: 9, 11, 13, and/or 15.

The term "arenavirus mutant" or "mutant of an arenavirus" in the context of the present invention should be understood to mean an arenavirus whose genome and/or proteome has at least one mutation, in particular at least one point mutation, with respect to the genome and/or proteome of its wild type. Preferably, The term "arenavirus mutant" or "mutant of an arenavirus" should be understood as an arenavirus with a protein, in particular glycoprotein and/or L-protein, which has with respect to a corresponding protein, in particular glycoprotein and/or L-protein of a corresponding wildtype arenavirus, at least one mutation, preferably in the form of an amino acid substitution.

Accordingly, the term "lymphocytic choriomeningitis virus mutant" should be understood as a mutant of the lymphocytic choriomeningitis virus, whose genome and/or proteome has with respect to the genome and/or proteome of the wild-type lymphocytic choriomeningitis virus at least one mutation, in particular at least one point mutation. Preferably, the term "lymphocytic choriomeningitis virus mutant" should be understood to mean an arenavirus with a protein, in particular glycoprotein and/or L-protein, which has with respect to a corresponding protein, in particular glycoprotein and/or L-protein, of the wild-type lymphocytic choriomeningitis virus at least one mutation, preferably in the form of an amino acid substitution.

The term "glycoprotein" in the context of the present invention should be understood to mean a macromolecule which consists of a protein, which in a certain context can also be refered to as a protein moiety, or protein component and one or more covalently bound carbohydrate groups (sugar groups), in particular mono- and/or oligo- and/or polysaccharide groups.

The term "repeated passage" or "repeated passaging" in the context of the present invention, unless otherwise stated, should be understood as a single or repeated process in which primary tumor cells or cells of the cell line H1975, C643 or Tramp-C2 are treated with arenavirus produced from primary tumor cells or cells of the cell line H1975, C643 or Tramp-C2. Therefor a culture medium for primary tumor cells or cells of the cell line H1975 C643 or Tramp-C2, such as DMEM (Dulbecco's Modified Eagle's Medium) with 10% Fetal Calf Serum (FKS) and 1% penicillin/streptomycin/glutamine (equivalent to 1 unit/ml penicillin, 100 microg/ml streptomycin and 2 mM L-glutamine), must be used. Non-infected primary tumor cells or non-infected cells of the cell line H1975, C643 or Tramp-C2 are preferably plated 0 to 7 days, in particular 1 to 7 days, prior to the inoculation step (step b). Preferably, a culture medium used for cell plating is replaced prior to the inoculation step by a fresh culture medium. In some cases, the culture medium may be extracted 1, 10 or 100 minutes after the inoculation step (step b) and replaced with a fresh culture medium. After an incubation period of 24, 48, 72 or 96 hours, a cell culture supernatant containing an accumulation of mutated arenaviruses is extracted. Part of this supernatant is added to new, uninfected primary tumor cells or cells of the cell lines H1975, C643 or Tramp-C2.

The term "nucleic acid" as used herein may generally refers to DNA or RNA. DNA and RNA differ—among others—in their nucleobases. The complementary base to adenine in DNA is thymine, whereas in RNA, it is uracil. For the sake of simplification, the corresponding base to adenine is denoted as "t" throughout the application, which—depending on its context—may refer to thymine (in DNA) or uracil (in RNA).

The term "encoding" or "encode(s)" as used herein in the context of a nucleic acid, relates to a nucleic acid having a sequence that can be translated into a particular amino acid sequence that is encoded by the nucleic acid. The nucleic acid sequence may encompass the sequence of a coding strand, and may also encompass the sequence of a strand that is complementary to the coding strand.

"Percent (%) sequence identity" with respect to sequences disclosed herein is defined as the percentage of amino acid residues or nucleotides in a candidate sequence that are pair-wise identical with the amino acid residues or nucleotides in a reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein. For determining sequence identity, uracil (e.g. in RNA) may be considered to be identical to thymine (e.g. in DNA).

The invention is also based on the surprising finding that through passaging of primary tumor cells or cells of the cell line H1975, C643 or Tramp-C2 infected with an arenavirus, an arenavirus with antitumor properties, in particular an arenavirus with improved antitumor properties compared to the arenavirus that was used can be produced. The production of such an arenavirus is based on the fact that the original arenavirus, usually a wild-type arenavirus, is difficultly able to proliferate in the primary tumor cells or the cells of the cell line H1975. An equally limited proliferation was observed in the cell lines C643 and Tramp-C2. The limited proliferation triggers an increased selection or adaptation pressure in the arenavirus during infection and replication in the primary tumor cells or in the cells of the cell line H1975, C643 or Tramp-C2. Randomly emerged virus mutants, which were able to proliferate in the primary tumor cells or the cells of the cell line H1975, C643 or Tramp-C2, overgrow the original arenavirus, usually the wild type arenavirus. Through passaging, in particular a repeated passaging (multiple repetition of the step sequence a) to d)), preferably results in an enrichment of an arenavirus, which has an antitumoral effect with respect to the primary tumor cells or cells of the cell line H1975, C643 or Tramp-C2 or which has improved antitumoral properties as compared to the original arenavirus. The antitumoral effect of the arenavirus mutant is based on the fact that it can infect the cells better and replicates better within the cells. In doing so, the arenavirus mutant can spread more successfully in the cells used as compared to the original arenavirus and, in particular, promote enhanced immune activation. Since many tumor cells do not have any antiviral factors and therefore show a limited viral resistance, the method according to the invention can be particularly advantageous not only for the production of an antitumoral arenavirus, but also for the production of a tumor-specific arenavirus, i.e. for the production of an antitumoral and tumor-specific arenavirus.

The primary tumor cells as well as the cells of the cell lines H1975, C643 and Tramp-C2 were identified by the inventors as cells which surprisingly allow only a reduced replication of arenaviruses and which in the course of passing trigger a particularly high selection pressure or adaptation compulsion in arenaviruses.

In an embodiment of the invention, the primary tumor cells are passaged before performing step a) at most 1000 times, in particular at most 100 times, preferably at most 10 times. The term "passaging" shall in this context be understood as the dilution of the cells in a cell culture, thus the uptake of the cells into a suspension and plating of a part of the cells (e.g. 50%, 10% or 1%) in a new nutrient medium. The less the primary tumor cells are passaged before step a), the more the cells correspond to the properties of the tumor cells of a patient. In particular, large differences (heterogeneity) between individual primary tumor cells in morphology, RNA expression pattern, protein expression and DNA sequence map tumor cells in vivo. Thereby an arenavirus can be produced in an advantageous way, which is particularly suitable for a therapeutic treatment of respective tumor patients, in particular patient groups of it.

In particular, the primary tumor cells can prior to step a) be subjected to no passage. In other words, to perform step a) unpassaged, i.e. not passaged primary tumor cells can be used. Thereby the original arenavirus or the arenavirus contained in the extracted cell culture supernatant or a part thereof is forced to adapt to cells that represent the tumor cells of a patient particularly well. In doing so, it is possible to generate particularly suited arenaviruses for the therapeutic treatment of respective tumor patients, in particular patient groups thereof.

The already often passaged cells of the cell lines H1975, C643 and Tramp-C2, were identified by the inventors as equally suitable cells, although they have already been passaged in vitro for years.

In a further embodiment of the invention, step c) is performed during a period of 1 hour to 1000 hours, in particular 3 hours to 300 hours, preferably 12 hours to 96 hours. The time periods disclosed in this paragraph have been shown to be particularly beneficial for efficient incubation and consequently infecting of the inoculated primary tumor cells or the inoculated cells of the cell line H1975, C643 or Tramp-C2 with the original arenavirus or the arenavirus contained in the extracted cell culture supernatant or part thereof.

In a further embodiment of the invention, step (b) and/or step (c) is performed at a temperature of 4° C. to 50° C., in particular 20° C. to 42° C., preferably 34° C. to 39° C. The temperature ranges disclosed in this paragraph have been found to be particularly advantageous for efficient inoculation and/or incubation (and consequently infection) of the primary tumor cells or cells of the cell line H1975, C643 or Tramp-C2 with the original arenavirus or the arenavirus contained in the extracted cell culture supernatant or part thereof.

In a further embodiment of the invention, step a) and/or step b) and/or step c) and/or step d) is performed in a nutrient medium preferably selected from the group consisting of RPMI-1640 (Roswell Park Memorial Institute), DMEM (Dulbecco's Modified Eagle's Medium) and IMDM (Iscove's Modified Dulbecco's Medium). The nutrient medium may additionally contain serum (0.1-20%), such as fetal calf serum and/or human serum, and/or amino acids, such as glutamate and/or glutamine, and/or antibiotics. A culture medium enables the cultivation of the primary tumor cells or the cells of cell line H1975, C643 or Tramp-C2. In particular, a culture medium favours with particular advantage the growth and/or cell division of the primary tumor cells or cells of the cell line H1975, C643 or Tramp-C2. The culture media mentioned in this paragraph are particularly suitable for the cultivation of primary tumor cells or cells of the cell line H1975, C643 or Tramp-C2.

In a further embodiment of the invention, step a) and/or step b) and/or step c) are performed under a carbon dioxide atmosphere (CO2 atmosphere) of 0% to 20%, in particular 0.1% to 20%, preferably 2% to 10%, more preferably 4% to 6%. This allows the pH of a nutrient medium used for step a) and/or step b) and/or step c) to be kept constant. This allows efficient plating and/or inoculation and/or incubation (and consequently infection) of the primary tumor cells or the cells of the cell line H1975, C643 or Tramp-C2 with the original arenavirus respectively the arenavirus contained in the extracted cell culture supernatant or part thereof.

Preferably step a) and/or step b) and/or step c) is performed in an incubator, by means of which controlled external conditions for growth and/or cell division of the primary tumor cells or the cells of cell line H1975, C643 or Tramp-C2 can be created.

In the further embodiment of the invention, the sequence of steps a) to d) is repeated 3 times to 1000 times, in particular 10 times to 100 times, preferably 20 times to 50 times. A multiple repetition of the step sequence a) to d), in particular as disclosed in this paragraph, has been shown to be particularly beneficial in view of the development of beneficial mutations with regard to antitumoral properties, in particular point mutations, and consequently to the production of an antitumoral arenavirus.

In the further embodiment of the invention, the nutrient medium is replaced by a fresh or new nutrient medium before performing step b). Through this step the conditions of infection can advantageously be standardized.

In a further embodiment of the invention, the culture medium is replaced by a fresh or new culture medium within a period of 0.1 minutes to 600 minutes, in particular 1 minute to 30 minutes, preferably 5 minutes to 15 minutes after step b). This step advantageously increases the selection pressure of the infection, as the time of infection is limited.

In a further embodiment of the invention multiple nutrient medium changes are performed. For example, the nutrient medium can be replaced by a fresh or new nutrient medium before step b) and the latter can be replaced by a fresh or new nutrient medium within a period of 0.1 minutes to 600 minutes, in particular 1 minute to 30 minutes, preferably 5 minutes to 15 minutes after performing step b).

In a further embodiment of the invention, the primary tumor cells or the cells of the cell line H1975, C643 or Tramp-C2 and/or the original arenavirus and/or the arenavirus contained in the extracted cell culture supernatant or part thereof are treated with at least one chemotherapeutic agent before performing step d), in particular before performing step c), in particular before performing step b), in particular before performing step a). Thereby tumor cells can be simulated which have already been chemotherapeutically treated. This advantageously allows the production of an arenavirus which is particularly suited for the treatment of tumor patients who have already been treated with chemotherapy and/or who are considered to have undergone all therapy options already.

In the further embodiment of the invention, the original arenavirus and/or the arenavirus contained in the extracted cell culture supernatant or a part thereof is before performing step b) treated with at least one chemotherapeutic agent. Thereby the natural mutation rate in the arenavirus can advantageously be increased and thus accelerating its adaptation to the primary tumor cells or cells of the cell line H1975, C643 or Tramp-C2.

The at least one chemotherapeutic agent may in particular be selected from the group consisting of alkylants, topoisomerase inhibitors, mitotic inhibitors, antimetabolites, antibiotics, kinase inhibitors, thalidomide derivatives, cell apoptosis inducers, biological therapeutics such as biological cytostatics, isotope-containing compounds, hormones, hormone antagonists, histone deacetylase inhibitors and other cytostatic agents.

The alkylating agents may be selected from the group consisting of oxazaphosphorins, N-lost derivatives, alkyl sulfonates, hydrazines, platinum-containing substances, anthracyclines and mixtures of at least two of the above alkylating agents.

The oxazaphosphorins may, for example, be selected from the group consisting of cyclophosphamide, ifosfamide and mixtures thereof.

The N-lost derivatives may be selected from the group consisting of chlorambucil, melphalan and mixtures thereof.

The alkyl sulfonates may, for example, be husulfan.

The hydrazines may, for example, be selected from the group consisting of temozolomide, dacarbazine, procarbazine and mixtures of at least two of the above hydrazines.

The platinum-containing substances may, for example, be selected from the group consisting of cisplatin, carboplatin, oxaliplatin and mixtures of at least two of said platinum-containing substances.

The anthracyclines may, for example, be selected from the group consisting of doxorubicin, daunorubicin, idarubicin, elirubicin and mixtures of at least two of said anthracyclines.

The above-mentioned topoisomerase inhibitors may be selected from the group consisting of topoisomerase I inhibitors, topoisomerase II inhibitors (etoposide) and mixtures thereof.

For example, the topoisomerase I inhibitors may be selected from the group consisting of irinotecan, topotecan and mixtures thereof.

Topoisomerase II inhibitors may be etoposide, for example.

The above-mentioned mitosis inhibitors or antimetabolites may be selected from the group consisting of *vinca* alkaloids, taxanes, folic acid antagonists, pyrimidine antagonists, purine antagonists, ribonucleotide reductase inhibitors and mixtures of at least two of the above-mentioned mitosis inhibitors or antimetabolites.

For example, the *vinca* alkaloids may be selected from the group consisting of vincristine, vinblastine and mixtures thereof.

Taxanes may be selected from the group consisting of docetaxel, paclitaxel and mixtures thereof.

For example, the folic acid antagonists may be selected from the group consisting of methotrexate, pemetrexed and mixtures thereof.

The pyrimidine antagonists may, for example, be selected from the group consisting of cytarabine, 5-fluorouracil, gemcitabine, capecitabine and mixtures of at least two of said pyrimidine antagonists.

The purine antagonists may, for example, be selected from the group consisting of 5-azacytidine, azathioprine, 6-mercaptopurine, fludarabine and mixtures of at least two of said purine antagonists.

For example, the ribonucleotide reductase inhibitor may be hydroxyurea.

The above antibiotics may be selected from the group consisting of bleomycin, actinomycin D, mitomycin and mixtures of at least two of the above antibiotics.

The above mentioned kinase inhibitors may be selected from the group consisting of afatinib, alectinib, axitinib, crizotinib, cobimetinib, dasatinib, dabrafenib, erlotinib, gefitinib, imatinib, Ixazomib, lenvatinib, nilotinib, osimertinib, palbociclib, pazopanib, ponatinib, regorafenib, sunitinib, vemurafenib, trametinib, everolimus and mixtures of at least two of said kinase inhibitors.

The above mentioned thalidomide derivatives may be selected from the group consisting of lenalidomide, pomalidomide and mixtures thereof.

The cell apoptosis inducers mentioned above may be selected from the group consisting of methoxals, venetoclax and mixtures thereof.

The above mentioned biological therapeutics may be selected from the group consisting of rituximab, trastuzumab, cetuximab, panitumumab, ipilimumab, pembrolizumab, nivolumab, atezolizumab, avelumab, nivolumab, olaratumab, ramucirumab and mixtures of at least two of the above mentioned biological therapeutics.

The above-mentioned hormones and/or hormone antagonists may be selected from the group consisting of buserelin, goserelin, leuprorelin, triptorelin, estramustin, tamoxifen, aromatase inhibitors such as anastrozole, Antiandrogens such as enzalutamide, flutamide, bica-lutamide, progestins such as megestrol acetate and medroxyprogesterone acetate, glucocorticoids and mixtures of at least two of the aforementioned hormones and/or hormone antagonists.

The other cytostatic agents mentioned above may be selected from the group consisting of bexarotene, afatinib, crizotinib erlotinib, gefitinib, lapatinib, dasatinib, imatinib, nilotinib, ponatinib, regorafenib, sonidegib, hydroxycarbamide, trametinib, tretininoin, isotretinoin, alitretinoin, MAOP (5-amino-4-oxopentanoic acid methyl ester) and mixtures of at least two of the foregoing other cytostatic agents.

Furthermore, the primary tumor cells or the cells of the cell line H1975, C643 or Tramp-C2 and/or the original arenavirus and/or the arenavirus contained in the extracted cell culture supernatant or a part thereof, before performing step d), in particular before performing step c), in particular before performing step b), in particular before performing step a), may be treated with radiation, in particular selected from the group consisting of ultraviolet (UV) rays, in particular UVA rays and/or UVB rays, alpha rays, beta rays, gamma rays and X-rays. Thereby, tumor cells can advantageously be simulated which have already been subjected to therapeutic radiation. This advantageously allows the production of an arenavirus, which can be used especially for the treatment of tumor patients who have already been treated with radiation therapy.

Furthermore, the original arenavirus and/or the arenavirus contained in the extracted cell culture supernatant or part thereof before performing step b) be treated with radiation, in particular selected from the group consisting of ultraviolet (UV) rays, in particular UVA rays and/or UVB rays, alpha rays, beta rays, gamma rays and X-rays. Thereby the natural mutation rate in the arenavirus and thus its adaptation to the primary tumor cells or cells of the cell line H1975, C643 or Tramp-C2 can advantageously be increased.

In another embodiment of the invention primary tumor cells or cells of the cell line H1975, C643 or Tramp-C2 are used which are resistant to at least one chemotherapeutic agent. For example, primary tumor cells resistant to paclitaxel and/or trametinib may be used. Thereby, tumor cells of a patient can advantageously be simulated, which are resistant to at least one chemotherapeutic agent during tumor treatment. The embodiments of the invention described in this paragraph thus represent further possibilities for the production of a powerful antitumoral arenavirus.

In a further embodiment of the invention, the primary tumor cells or the cells of the cell line H1975, C643 or Tramp-C2 and/or the original arenavirus and/or the arenavirus contained in the extracted cell culture supernatant or a part thereof are before performing step d), in particular before performing step c), in particular before performing step b), in particular before performing step a) treated with at least one antiviral compound, in particular with alpha-interferon and/or gamma-interferon. Thereby original arenavirus or the arenavirus contained in the cell culture supernatant extracted or in a part thereof can advantageously be forced to adapt in an antiviral environment, whereby an antitumoral arenavirus exhibiting resistance at the same time can be produced. Such an arenavirus is particularly effective from a therapeutic point of view, as it can also be used to combat tumor tissue that may exhibit viral resistance.

Furthermore, the method may comprise a further step e) isolating and/or identifying an antitumoral arenavirus, in particular an arenavirus, which has improved antitumoral properties with respect to the original arenavirus, from the cell culture supernatant extracted or a part thereof by means of cloning and/or PCR (polymerase chain reaction) and/or sequencing.

Primary tumor cells preferably used are primary malignant tumor cells, in particular primary carcinoma cells, primary melanoma cells, primary blastoma cells, primary lymphoma cells or primary sarcoma cells.

In a further embodiment of the invention, primary tumor cells are primary choroidal melanoma cells, primary anal carcinoma cells, primary angiosarcoma cells, primary astrocytoma cells, primary basal cell carcinoma cells, primary cervical carcinoma cells, primary chondrosarcoma cells, primary chorionic carcinoma cells, primary dermal squamous cell carcinoma cells, primary small intestine carcinoma cells, primary endometrial carcinoma cells, primary Ewing sarcoma cells, primary fibrosarcoma cells, primary gallbladder carcinoma cells, primary bile duct carcinoma cells, primary glioblastoma cells, primary bladder carcinoma cells, primary ureter carcinoma cells, primary urethral carcinoma cells, primary hepatocellular carcinoma cells, primary testicular tumor cells, primary hypopharyngeal carcinoma cells, primary pituitary carcinoma cells, primary Kaposi sarcoma cells, primary small cell bronchial carcinoma cells, primary colon carcinoma cells, primary colorectal carcinoma cells, primary laryngeal carcinoma cells, primary leiomyosarcoma cells, primary liposarcoma cells, primary gastric carcinoma cells, primary malignant fibrous histiocytoma cells, primary breast carcinoma cells, primary medulloblastoma cells, primary melanoma cells, primary oral floor carcinoma cells, primary sinus carcinoma cells, primary nasopharyngeal carcinoma cells, primary adrenal cortex carcinoma cells, primary parathyroid carcinoma cells, primary neurogenic sarcoma cells, primary non-small-cell bronchial carcinoma cells, primary renal carcinoma cells, primary oropharyngeal carcinoma cells, primary osteosarcoma cells, primary ovarian carcinoma cells, primary pancreatic tumor cells, primary penis carcinoma cells, primary pheochromocytoma cells, primary pleural mesothelioma cells, primary prostate carcinoma cells, primary rectal carcinoma cells, primary retinoblastoma cells, primary rhabdomyosarcoma cells, primary thyroid carcinoma cells, primary salivary gland carcinoma cells, primary esophageal carcinoma cells, primary tonsil carcinoma cells, primary vaginal carcinoma cells, primary vulvar carcinoma cells, primary Wilms tumor cells, primary cells of neuroendocrine tumors or primary tongue carcinoma cells.

Particularly preferred are primary melanoma cells, primary lung carcinoma cells, primary pancreatic carcinoma cells, primary colon carcinoma cells, primary gastric carcinoma cells, primary pharyngeal carcinoma cells, primary laryngeal carcinoma cells, primary renal cell carcinoma cells are particularly preferred as primary tumor cells, primary ovarian carcinoma cells, primary endometrial carcinoma cells, primary thyroid carcinoma cells, primary prostate carcinoma cells, primary liver carcinoma cells or primary sarcoma cells, such as primary neurogenic sarcoma cells, primary osteosarcoma cells or primary rhabdomyosarcoma cells.

In a further embodiment of the invention, a wild type arenavirus, i.e. a so-called wild type arenavirus, is used as the original arenavirus.

In a further embodiment of the invention, an old world arenavirus is used as the original arenavirus. The old world arenavirus is preferably selected from the group consisting of Catarina Virus, Danfenong Virus, Ippy Virus (IP-PYV), Kodoko Virus, Lassa Virus (LASV), Lymphocytic Choriomeningitis Virus (LCMV), Morogoro Virus, Mobala Virus (MOBV), Gairo Virus and Mopeia Virus (MOPV), Pinhal Virus, Skinner Tank Virus.

Prefered is as original arenavirus the lymphocytic choriomeningitis virus, in particular a wild type of the lymphocytic choriomeningitis virus. For example, a strain of the lymphocytic choriomeningitis virus, in particular selected from the group consisting of WE, Armstrong, Clone 13 (Clone 13) and Docile, can be used as the original arenavirus.

Particularly preferred is the wild-type lymphocytic choriomeningitis virus, i.e. a wild-type lymphocytic choriomeningitis virus comprising an L-protein comprising or consisting of an amino acid sequence according to SEQ ID NO: 7, and/or a nucleic acid, in particular ribonucleic acid, preferably L-ribonucleic acid, comprising or consisting of a nucleic acid sequence, in particular ribonucleic acid sequence, preferably L-ribonucleic acid sequence, which is complementary to a nucleic acid sequence pursuant to SEQ ID NO: 8.

Furthermore, a new world arenavirus can be used as original arenavirus. The new world arenavirus is preferably selected from the group consisting of Allpahuayo Virus (ALLV), Amapari Virus (AMAV), Bear Canyon Virus (BCNV), Chapare Virus, Cupixi Virus (CPXV), Flexal Virus (FLEV), Guanarito Virus (GTOV), Junin Virus (JUNV), Candid #1 (Candid No. 1), Latino virus (LATV), Machupo virus (MACV), Oliveros virus (OLVV), Parana virus (PARV), Pichinide virus (PICV), Pirital virus (PIRV), Sabia virus (SABV), Tacaribe virus (TCRV), Tamiami virus (TAMV) and Whitewater arroyo virus (WWAV).

Furthermore, an arenavirus without antitumoral properties can be used as the original arenavirus.

Alternatively, an original arenavirus with antitumoral properties can be used.

According to a second aspect, the invention relates to a lymphocytic choriomeningitis virus mutant, i.e. a mutant of the lymphocytic choriomeningitis virus.

The lymphocytic choriomeningitis virus mutant comprises a protein or peptide, in particular a glycoprotein. The protein or peptide comprises a mutation, in particular a point mutation. The mutation, in particular point mutation, is preferably different from the sequences AJ297484, AJ233196 and the reference sequence LCMV, (strain WE-Essen).

Preferably the lymphocytic choriomeningitis virus mutant has a glycoprotein, in particular a protein component or a protein moiety of a glycoprotein, with at least one mutation, wherein the at least one mutation is an amino acid substitution of the isoleucine at position 181 of the glycoprotein by another amino acid, preferably methionine, and/or an amino acid substitution of the arginine at position 185 of the glycoprotein by another amino acid, preferably tryptophan.

Alternatively or in combination, the lymphocytic choriomeningitis virus mutant preferably comprises an L-protein with at least one mutation, wherein the at least one mutation is an amino acid substitution of the lysine at position 1513 of the L-protein by another amino acid, preferably glutamate, and/or an amino acid substitution of the phenylalanine at position 1995 of the L-protein by another amino acid, preferably serine, and/or an amino acid substitution of isoleucine at position 2094 of the L-protein by another amino acid, preferably valine, and/or an amino acid substitution of threonine at position 2141 of the L-protein by another amino acid, preferably alanine, and/or an amino acid substitution of arginine at position 2175 of the L-protein by another amino acid, preferably lysine.

Alternatively or in combination, the lymphocytic choriomeningitis virus mutant preferably comprises a protein or peptide, in particular a glycoprotein, in particular a protein component or a protein moiety of a glycoprotein, or an L-protein, comprising or consisting of an amino acid sequence pursuant to SEQ ID NO: 1, SEQ ID NO: 3, SEQ ID NO: 5, SEQ ID NO: 18, SEQ ID NO: 26, SEQ ID NO: 34, SEQ ID NO: 42, SEQ ID NO: 50, SEQ ID NO: 58, SEQ ID NO: 24, SEQ ID NO: 32, SEQ ID NO: 40, SEQ ID NO: 48, SEQ ID NO: 56, and SEQ ID NO: 64. The amino acid sequences according to SEQ ID NO: 1, SEQ ID NO: 3, SEQ ID NO: 18, SEQ ID NO: 26, SEQ ID NO: 34, SEQ ID NO: 42, SEQ ID NO: 50, and SEQ ID NO: 58 are preferably amino acid sequences of a glycoprotein of the lymphocytic choriomeningitis virus mutant. The amino acid sequence of SEQ ID NO: 5, SEQ ID NO: 24, SEQ ID NO: 32, SEQ ID NO: 40, SEQ ID NO: 48, SEQ ID NO: 56, and SEQ ID NO: 64 are preferably the amino acid sequence of an L-protein of the lymphocytic choriomeningitis virus mutant.

Alternatively or in combination, the lymphocytic choriomeningitis virus mutant preferably comprises a nucleic acid, in particular ribonucleic acid, which encodes a protein or peptide, in particular a glycoprotein or L-protein, comprising or consisting of an amino acid sequence according to SEQ ID NO: 1, SEQ ID NO: 3, SEQ ID NO: 5, SEQ ID NO: 18, SEQ ID NO: 26, SEQ ID NO: 34, SEQ ID NO: 42, SEQ ID NO: 50, SEQ ID NO: 58, SEQ ID NO: 24, SEQ ID NO: 32, SEQ ID NO: 40, SEQ ID NO: 48, SEQ ID NO: 56, or SEQ ID NO: 64.

Alternatively or in combination, the lymphocytic choriomeningitis virus mutant preferably comprises a nucleic acid, in particular ribonucleic acid, which comprises a nucleic acid sequence, in particular ribonucleic acid sequence, or consists of a nucleic acid sequence, in particular ribonucleic acid sequence, which is complementary to a nucleic acid sequence pursuant to SEQ ID No. 2, SEQ ID No. 4, SEQ ID No. 6, SEQ ID NO: 17, SEQ ID NO: 25, SEQ ID NO: 33, SEQ ID NO: 41, SEQ ID NO: 49, SEQ ID NO: 57, SEQ ID NO: 23, SEQ ID NO: 31, SEQ ID NO: 39, SEQ ID NO: 47, SEQ ID NO: 55, or SEQ ID NO: 63.

It was surprisingly found out that a respective mutant/respective mutants of the lymphocytic choriomeningitis virus—as described in the previous paragraphs—has/have improved replication competence in primary tumor cells or cells of the cell line H1975 as well as antitumoral or improved antitumoral properties, in particular with respect to the wild type of the lymphocytic choriomeningitis virus.

Furthermore, it is preferred that the codon for isoleucine at position 181 of the glycoprotein is replaced by another codon, preferably by a codon for methionine.

Furthermore, it is preferred that the codon for arginine at position 185 of the glycoprotein is replaced by another codon, preferably by a codon for tryptophan.

Furthermore, it is preferred that the codon for histidine at position 155 of the glycoprotein is replaced by another codon, preferably a codon for tyrosine.

Furthermore, it is preferred that the codon for arginine at position 358 of the glycoprotein is replaced by another codon, preferably by a codon for lysine.

Furthermore, it is also preferred that the lymphocytic choriomeningitis virus mutant comprises a nucleic acid, in particular ribonucleic acid, preferably L-ribonucleic acid, comprising a mutation, wherein the mutation is a nucleotide substitution of adenine at position 4537 of the nucleic acid, in particular ribonucleic acid, preferably L-ribonucleic acid, by guanine.

Furthermore, it is preferred that the lymphocytic choriomeningitis virus mutant comprises a nucleic acid, in particular ribonucleic acid, preferably L-ribonucleic acid, encoding an L-protein comprising a mutation, wherein the mutation is an amino acid substitution of the lysine at position 1513 of the L-protein, by another amino acid, preferably by glutamate.

Furthermore, it is preferred that the lymphocytic choriomeningitis virus mutant comprises a nucleic acid, in particular a ribonucleic acid, preferably L-ribonucleic acid, encoding an L-protein comprising a mutation, wherein the mutation is an amino acid substitution of the phenylalanine at position 1995 of the L-protein, by another amino acid, preferably by a serine.

Furthermore, it is also preferred that the lymphocytic choriomeningitis virus mutant comprises a nucleic acid, in particular ribonucleic acid, preferably L-ribonucleic acid, comprising a mutation, wherein the mutation is a nucleotide substitution of thymine at position 5984 of the nucleic acid, in particular ribonucleic acid, preferably L-ribonucleic acid, preferably by the nucleotide cytosine.

Furthermore, it is also preferred that the lymphocytic choriomeningitis virus mutant comprises a nucleic acid, in particular ribonucleic acid, preferably L-ribonucleic acid, which encodes an L-protein comprising a mutation, wherein the mutation is an amino acid substitution of the isoleucine at position 2094 of the L-protein, by another amino acid, preferably by valine.

Furthermore, it is preferred that the lymphocytic choriomeningitis virus mutant comprises a nucleic acid, in particular ribonucleic acid, preferably L-ribonucleic acid, comprising a mutation, wherein the mutation is a nucleotide substitution of adenine at nucleotide position 6280 of the nucleic acid, in particular ribonucleic acid, preferably L-ribonucleic acid, by another nucleotide, preferably guanine.

Furthermore, it is preferred that the lymphocytic choriomeningitis virus mutant comprises a nucleic acid, in particular ribonucleic acid, preferably L-ribonucleic acid, encoding an L-protein comprising a mutation, wherein the mutation is an amino acid substitution of the threonine at position 2141 of the L-protein, by another amino acid, preferably by alanine.

Furthermore, it is also preferred that the lymphocytic choriomeningitis virus mutant comprises a nucleic acid, in particular ribonucleic acid, preferably L-ribonucleic acid, comprising a mutation, wherein the mutation is a nucleotide substitution of adenine at position 6421 of the nucleic acid, in particular ribonucleic acid, preferably L-ribonucleic acid, preferably by another nucleotide, preferably guanine.

Furthermore, it is also preferred that the lymphocytic choriomeningitis virus mutant comprises a nucleic acid, in particular ribonucleic acid, preferably L-ribonucleic acid, encoding an L-protein comprising a mutation, wherein the mutation is an amino acid substitution of arginine at position 2175 of the L-protein, preferably by lysine.

Furthermore, it is also preferred that the lymphocytic choriomeningitis virus mutant comprises a nucleic acid, in particular ribonucleic acid, preferably L-ribonucleic acid, comprising a mutation, wherein the mutation is a nucleotide substitution of guanine at position 6524 of the nucleic acid, in particular ribonucleic acid, preferably L-ribonucleic acid, by the nucleotide adenine.

In another embodiment of the invention the lymphocytic choriomeningitis virus mutant is a lymphocytic choriomeningitis virus mutant, including any lymphocytic choriomeningitis virus mutant of the disclosure, for application or use in medicine.

Preferably the lymphocytic choriomeningitis virus mutant is a lymphocytic choriomeningitis virus mutant for application or use in the treatment and/or prevention of a tumor.

The tumor is preferably selected from the group consisting of carcinoma, melanoma, blastoma, lymphoma and sarcoma.

The term "carcinoma" in the context of the present invention should be understood to mean a malignant neoplasia of epithelial origin.

The term "sarcoma" in the context of the present invention should be understood to mean a malignant neoplasia of mesodermal origin.

The term "melanoma" in the context of the present invention should be understood to mean a malignant neoplasia of melanocytic origin.

The term "lymphoma" in the context of the present invention should be understood to mean a malignant neoplasia of lymphocytic origin.

The term "blastoma" in the context of the present invention should be understood to mean a malignant neoplasia of embryonic origin.

The carcinoma is preferably selected from the group consisting of anal carcinoma, bronchial carcinoma, lung carcinoma, endometrial carcinoma, gallbladder carcinoma, bladder carcinoma, hepatocellular carcinoma, testicular carcinoma, colon carcinoma, colorectal carcinoma, rectal carcinoma, laryngeal carcinoma, esophageal carcinoma, gastric carcinoma, breast carcinoma, renal carcinoma, ovarian carcinoma, pancreatic carcinoma, pharyngeal carcinoma, oropharyngeal carcinoma, prostate carcinoma, thyroid carcinoma and cervical carcinoma.

The sarcoma can be selected from the group consisting of angiosarcoma, chondrosarcoma, Ewing sarcoma, fibrosarcoma, Kaposi sarcoma, liposarcoma, leiomyosarcoma, malignant fibrous histiocytoma, neurogenic sarcoma, osteosarcoma and rhabdomyosarcoma.

Further, the lymphocytic choriomeningitis virus mutant can be prepared or used for local, in particular intramuscular, intraperitoneal, or subcutaneous administration.

Alternatively, the lymphocytic choriomeningitis virus mutant can be prepared or used for systemic, in particular intravenous, administration.

For further characteristics and benefits of the lymphocytic choriomeningitis virus mutant, full reference is made to the previous and the following description.

According to a third aspect, the invention relates a lymphocytic choriomeningitis virus mutant comprising or consisting of a protein or peptide, in particular glycoprotein or L protein, comprising or consisting of an amino acid sequence pursuant to SEQ ID NO: 1, SEQ ID NO: 3, SEQ ID NO: 5, SEQ ID NO: 18, SEQ ID NO: 26, SEQ ID NO: 34, SEQ ID NO: 42, SEQ ID NO: 50, SEQ ID NO: 58, SEQ ID NO: 66, SEQ ID NO: 24, SEQ ID NO: 32, SEQ ID NO: 40, SEQ ID NO: 48, SEQ ID NO: 56, or SEQ ID NO: 64.

Alternatively or in combination, the lymphocytic choriomeningitis virus mutant comprises a nucleic acid, in particular ribonucleic acid, wherein the nucleic acid, in particular ribonucleic acid, comprises a nucleic acid sequence, in particular ribonucleic acid sequence, or consists of a nucleic acid sequence, in particular ribonucleic acid sequence, which is or is complementary to a nucleic acid sequence pursuant to SEQ ID NO: 2, SEQ ID NO: 4, SEQ ID NO: 6, SEQ ID NO: 17, SEQ ID NO: 25, SEQ ID NO: 33, SEQ ID NO: 41, SEQ ID NO: 49, SEQ ID NO: 57, SEQ ID NO: 65, SEQ ID NO: 23, SEQ ID NO: 31, SEQ ID NO: 39, SEQ ID NO: 47, SEQ ID NO: 55, or SEQ ID NO: 63.

Preferably the lymphocytic choriomeningitis virus mutant is a lymphocytic choriomeningitis virus mutant for application or use in medicine.

The lymphocytic choriomeningitis virus mutant is particular preferably a lymphocytic choriomeningitis virus mutant for use or application in the treatment and/or prevention of a tumor.

The tumor is preferably selected from the group consisting of carcinoma, melanoma, blastoma, lymphoma and sarcoma.

The term "carcinoma" in the context of the present invention should be understood to mean a malignant neoplasia of epithelial origin.

The term "sarcoma" in the context of the present invention should be understood to mean a malignant neoplasia of mesodermal origin.

The term "melanoma" in the context of the present invention should be understood to mean a malignant neoplasia of melanocytic origin.

The term "lymphoma" in the context of the present invention should be understood to mean a malignant neoplasia of lymphocytic origin.

The term "blastoma" in the context of the present invention should be understood to mean a malignant neoplasia of embryonic origin.

The carcinoma is preferably selected from the group consisting of anal carcinoma, bronchial carcinoma, lung carcinoma, endometrial carcinoma, gallbladder carcinoma, bladder carcinoma, hepatocellular carcinoma, testicular carcinoma, colon carcinoma, colorectal carcinoma, rectal carcinoma, laryngeal carcinoma, esophageal carcinoma, gastric carcinoma, breast carcinoma, renal carcinoma, ovarian carcinoma, pancreatic carcinoma, pharyngeal carcinoma, oropharyngeal carcinoma, prostate carcinoma, thyroid carcinoma and cervical carcinoma.

The sarcoma can be selected from the group consisting of angiosarcoma, chondrosarcoma, Ewing's sarcoma, fibrosarcoma, Kaposi's sarcoma, liposarcoma, leiomyosarcoma, malignant fibrous histiocytoma, neurogenic sarcoma, osteosarcoma and rhabdomyosarcoma.

Further, the lymphocytic choriomeningitis virus mutant can be prepared or used for local, in particular intramuscular, intraperitoneal, or subcutaneous administration.

Alternatively, the lymphocytic choriomeningitis virus mutant can be prepared or used for systemic, in particular intravenous, administration.

With regard to other characteristics and advantages of the lymphocytic choriomeningitis virus mutant, in order to avoid repetitions, full reference is also made to the previous description, in particular to the statements made in the context of the second aspect of the invention. The features and advantages described therein, in particular with regard to the lymphocytic choriomeningitis virus mutant, the protein or peptide, in particular glycoprotein, and the nucleic acid, in particular ribonucleic acid, also apply mutatis mutandis to the lymphocytic choriomeningitis virus mutant according to the third aspect of the invention.

According to a fourth aspect, the invention relates to a drug or medicament which comprises a lymphocytic choriomeningitis virus mutant according to the second or third aspect of the invention.

The drug or medicament can further comprise a checkpoint blocker, such as PD-1 (Programmed Cell Death Protein 1), and/or an apoptosis modulator, in particular an apoptosis inhibitor, such as SMAC-mimeticum (LCL-161).

The drug or medicament preferably further comprises a pharmaceutically acceptable carrier. The carrier may be selected from the group consisting of water, aqueous saline solution, aqueous buffer solution, cell culture medium and combinations of at least two of the foregoing carriers.

With regard to further features and advantages of the drug or medicament, in order to avoid repetitions, full reference is made to the previous description, in particular to the statements made in the context of the second and third aspects of the invention. The features and advantages described therein, in particular with respect to the lymphocytic choriomeningitis virus mutant, also apply mutatis mutandis to the drug or medicament referred to in the fourth aspect of the invention.

According to a fifth aspect, the invention relates an protein or peptide, which is preferably an isolated protein or peptide, in particular a glycoprotein or an L-protein, comprising or consisting of an amino acid sequence according to SEQ ID NO: 1, SEQ ID NO: 3, SEQ ID NO: 5, SEQ ID NO: 7, SEQ ID NO: 10, SEQ ID NO: 18, SEQ ID NO: 26, SEQ ID NO: 34, SEQ ID NO: 42, SEQ ID NO: 50, SEQ ID NO: 58, SEQ ID NO: 24, SEQ ID NO: 32, SEQ ID NO: 40, SEQ ID NO: 48, SEQ ID NO: 56, or SEQ ID NO: 64. The invention also relates to an isolated protein or peptide having at least at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity to SEQ ID NO: 1, SEQ ID NO: 3, SEQ ID NO: 5, SEQ ID NO: 7, SEQ ID NO: 10, SEQ ID NO: 18, SEQ ID NO: 26, SEQ ID NO: 34, SEQ ID NO: 42, SEQ ID NO: 50, SEQ ID NO: 58, SEQ ID NO: 24, SEQ ID NO: 32, SEQ ID NO: 40, SEQ ID NO: 48, SEQ ID NO: 56, or SEQ ID NO: 64.

The amino acid sequences according to SEQ ID NO: 1 and SEQ ID NO: 3 are preferably the amino acid sequence of a glycoprotein, in particular a protein component or a protein moiety of a glycoprotein, of a lymphocytic choriomeningitis virus mutant. The amino acid sequence according to SEQ ID NO: 5 is preferably the amino acid sequence of an L-protein of a lymphocytic choriomeningitis virus mutant. The amino acid sequence of SEQ ID NO: 7 is preferably the amino acid sequence of an L-protein of a wild type lymphocytic choriomeningitis virus.

The invention also relates an protein or peptide, which is preferably an isolated protein or peptide, in particular a nucleoprotein or a Z-protein, comprising or consisting of an amino acid sequence according to SEQ ID NO: 12, SEQ ID NO: 20, SEQ ID NO: 28, SEQ ID NO: 36, SEQ ID NO: 44, SEQ ID NO: 52, SEQ ID NO: 60, SEQ ID NO: 14, SEQ ID NO: 22, SEQ ID NO: 30, SEQ ID NO: 38, SEQ ID NO: 46, SEQ ID NO: 54, or SEQ ID NO: 62. The invention also relates to an isolated protein or peptide having at least at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity to SEQ ID NO: 12, SEQ ID NO: 20, SEQ ID NO: 28, SEQ ID NO: 36, SEQ ID NO: 44, SEQ ID NO: 52, SEQ ID NO: 60, SEQ ID NO: 14, SEQ ID NO: 22, SEQ ID NO: 30, SEQ ID NO: 38, SEQ ID NO: 46, SEQ ID NO: 54, or SEQ ID NO: 62.

With regard to other features and advantages of the protein or peptide, in order to avoid repetitions, full reference is also made to the previous description, in particular to the statements made in the second and third aspects of the invention. The advantages and features described therein, in particular with respect to the protein or peptide, in particular glycoprotein, also apply mutatis mutandis to the isolated protein or peptide according to the fifth aspect of the invention.

According to a sixth aspect, the invention relates to an nucleic acid, which is preferably an isolated nucleic acid, in particular ribonucleic acid, comprising or consisting of a nucleic acid sequence, in particular ribonucleic acid sequence, according to or complementary to SEQ ID NO: 2, SEQ ID NO: 4, SEQ ID NO: 6, SEQ ID NO: 8 SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 23, SEQ ID NO: 31, SEQ ID NO: 39, SEQ ID NO: 47, SEQ ID NO: 55, or SEQ ID NO: 63. The invention also relates to an isolated protein or peptide having at least at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity to SEQ ID NO: 2, SEQ ID NO: 4, SEQ ID NO: 6, SEQ ID NO: 8 SEQ ID NO: 9, SEQ ID NO: 17, SEQ ID NO: 25, SEQ ID NO: 33, SEQ ID NO: 41, SEQ ID NO: 49, SEQ ID NO: 57, SEQ ID NO: 23, SEQ ID NO: 31, SEQ ID NO: 39, SEQ ID NO: 47, SEQ ID NO: 55, or SEQ ID NO: 63 or a respective complementary sequence.

The invention also relates to a nucleic acid, which is preferably an isolated nucleic acid, in particular ribonucleic acid, comprising or consisting of a nucleic acid sequence, in particular ribonucleic acid sequence, according to or complementary to SEQ ID NO: 11, SEQ ID NO: 19, SEQ ID NO: 27, SEQ ID NO: 35, SEQ ID NO: 43, SEQ ID NO: 51, SEQ ID NO: 59, SEQ ID NO: 13, SEQ ID NO: 21, SEQ ID NO: 29, SEQ ID NO: 37, SEQ ID NO: 45, SEQ ID NO: 53, or SEQ ID NO: 61. The invention also relates to an isolated protein or peptide having at least at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least SEQ ID NO: 11, SEQ ID NO: 19, SEQ ID NO: 27, SEQ ID NO: 35, SEQ ID NO: 43, SEQ ID NO: 51, SEQ ID NO: 59, SEQ ID NO: 13, SEQ ID NO: 21, SEQ ID NO: 29, SEQ ID NO: 37, SEQ ID NO: 45, SEQ ID NO: 53, or SEQ ID NO: 61 or a respective complementary sequence.

The nucleic acid sequences according to SEQ ID NO: 2 and SEQ ID NO: 4 each preferably encode for a glycoprotein, in particular for a protein component or a protein moiety of a glycoprotein, of a lymphocytic choriomeningitis virus mutant.

The nucleic acid sequence according to SEQ ID NO: 6 preferably encodes for an L-protein of a lymphocytic choriomeningitis virus mutant.

The nucleic acid sequence of SEQ ID NO: 8 preferably encodes for an L-protein of a wild type lymphocytic choriomeningitis virus.

With regard to further features and advantages of the isolated nucleic acid, in order to avoid repetitions, full reference is also made to the previous description, in particular to the statements made in the context of the second and third aspects of the invention. The features and advantages described therein, in particular with regard to nucleic acid, in particular ribonucleic acid, also apply mutatis mutandis to the isolated nucleic acid according to the sixth aspect of the invention.

According to a seventh aspect, the invention relates to an isolated gene cluster or operon containing at least one nucleic acid, in particular ribonucleic acid, according to the fifth aspect of the invention.

With regard to further features and advantages of the gene cluster or operon, in order to avoid repetitions, full reference is also made to the previous description, in particular to the statements made in the context of the sixth aspect of the invention. The features and advantages described therein, in particular with regard to nucleic acid, in particular ribonucleic acid, also apply mutatis mutandis to the isolated gene cluster or operon according to the seventh aspect of the invention.

According to an eighth aspect, the invention relates to an expression vector containing at least one nucleic acid according to the sixth aspect of the invention or a gene cluster or operon according to the seventh aspect of the invention.

With regard to further features and advantages of the expression vector, in order to avoid repetitions, full reference is also made to the description, in particular to the statments made under the sixth and seventh aspects of the invention. The features and advantages described therein, in particular with respect to nucleic acid and gene cluster or operon, also apply mutatis mutandis to the expression vector according to the eighth aspect of the invention.

According to a ninth aspect, the invention relates to an organism, a virus, a vector or a plasmid which expresses or contains a protein or peptide according to the fifth aspect of the invention and/or which contains a nucleic acid, in particular ribonucleic acid, according to the sixth aspect of the invention.

The organism can be a host cell, a fungus or a bacterium.

The host cell can, for example, be a eukaryotic or prokaryotic cell. Furthermore, the host cell can be a cell that can be used for the production of organisms and/or vectors and/or plasmids.

The bacterium can for example be a vaccine vector or another therapeutic bacterium.

The virus can for example be a vaccine vector or another therapeutic virus.

With regard to further features and advantages of the host cell, in order to avoid repetitions, full reference is also made to the description, in particular to the statements made in the fifth and sixth aspects of the invention. The features and advantages described there, in particular with regard to the protein or peptide, in particular glycoprotein, and the nucleic acid, in particular ribonucleic acid, also apply mutatis mutandis to the host cell according to the ninth aspect of the invention.

Further features and advantages of the invention result from the following description of preferred embodiments in the form of examples, the corresponding figures and the claims. The embodiments described in the following are only intended to provide further description and a better understanding of the invention and should by no means be construed as limiting.

The present invention also relates to a pharmaceutical composition comprising a LCMV of the disclosure, preferably a LCMV mutant of the disclosure. The composition may further comprise pharmaceutically acceptable excipient. The pharmaceutical composition can further comprise a checkpoint blocker, such as PD-1 (Programmed Cell Death Protein 1), and/or an apoptosis modulator, in particular an apoptosis inhibitor, such as SMAC-mimeticum (LCL-161).

The pharmaceutical composition may further comprises a pharmaceutically acceptable carrier. The carrier may be selected from the group consisting of water, aqueous saline solution, aqueous buffer solution, cell culture medium and combinations of at least two of the foregoing carriers.

The present disclosure also relates to the use of a LCMV of the disclosure, preferably a LCMV mutant of the disclosure for the manufacture of a medicament. The medicament may be for the treatment a tumor. The medicament may be a medicament according to the fourth aspect of the invention.

The present disclosure also relates to a method of treating a tumor, comprising administering to a subject in need thereof an effective amount of an LCMV of the disclosure, preferably an LCMV mutant of the disclosure, or a medicament of the disclosure or a pharmaceutical composition of the disclosure.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms. E.g. the term "comprising" is meant to provide explicit support also for "consisting essentially of" and "consisting of", the term "consisting essentially of" is meant to provide explicit support also for "comprising" and "consisting of", the term "consisting of" is meant to provide explicit support also for "consisting essentially of" and "comprising", It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent applications, scientific publications, manufacturer's specifications, instructions, etc.) are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

EXAMPLES

1. Methods and Materials 1.1 Mice

For in vivo anti-tumoral analyses WT animals (on C57BL/6 background) or NOD.SCID mice without an adaptive immune systrain WEre used. OT-1 mice carry an ovalbumin-specific MHC-I restricted T cell receptor as transgene.

1.2 Cell Lines

MC57 (CVCL_4985) is a murine fibroblast cell line in which the arenavirus LCMV can multiply well. C643 (CVCL_5969) is a human anaplastic thyroid carcinoma cell line. H1975 is a human lung carcinoma cell line (CVCL_1511, ATCC, CRL-5908, adenocarcinoma). TrampC2 is a murine adenocarcinoma cell line (CVCL_3615). MOPC is a murine oropharyngeal cell line. CMT167 (CVCL_2405) is a murine lung carcinoma cell line. B16F10-OVA is a murine melanoma cell line (CVCL_0159) expressing ovalbumin as a model antigen. UKE-Mel-13a are primary tumor cells isolated from a human melanoma metastasis and have been passeged less than 100×. 511950 are primary tumor cells isolated from a transgenic murine pancreatic carcinoma (Mazur P K et al Nat Med. 2015 October;21(10):1163-71) and have been passaged less than 20×. 511950R originate from 511950 cells and have been passaged less than 100× under treatment with the MEK inhibitor trametinib.

1.3 Viruses

The LCMV strain WE was obtained from the laboratory of Prof. Zinkernagel (Experimental Immunology, Zurich, Switzerland) and has been propagated in L929 cells or BHK cells since 2008. The clones LCMV-P42, LCMV-P52 and LCMV-P91 were isolated and sequenced after different passages.

1.4 Reagents

LCL161 (Selleckchem) and anti-PD1 (BioXcell) were tested in combination with LCMV and LCMV-P52, respectively, for their anti-tumor activity.

1.5 Determination of LCMV Infected Cells by Immunofluorescence

Immunofluorescence was used to detect LCMV in cells. Cells were seeded in 24 well plates, each containing a cover glass. After 24 hours the cells were infected with LCMV and stained 24 hours later with a fluorochrome-labelled anti-LCMV-NP antibody (clone VL4), visualized with a fluorescence microscope and photographed with an integrated CCD camera.

1.6 Determination of LCMV in Supernatant by Plaque Assay

To determine the LCMV production of cells, cells were sown in 24-well plates and infected with LCMV after 24 hours. The supernatant was extracted after 24 hours. The supernatant was titrated in 24-well plates and MC57 cells (150,000 cells/hole) were added. Methyl cellulose was added after 4 hours. After another 48 hours, the cell lawn was analyzed for LCMV plaques with anti-LCMV-NP antibodies (clone KL53). The plaques were counted to determine the number of infectious particles/ml in the supernatant.

1.7 Passages of Viruses

In order to adapt viruses to tumors, different primary tumor cells or tumor cell lines were infected with LCMV-WE. Cells were plated in 24-well plates (approx. 100,000 cells/well in 1 mL medium). After 24 hours viruses with a Multiplicity of Infection (MOI)==1 in 100 μL were added. Depending on the setup, the initial inoculum was removed between 1-30 minutes and new medium was added. After 24 or 48 or 72 hours the cell culture supernatant was extracted and frozen for further analysis. Newly plated cells were infected with 100 microL of the extracted supernatant. This procedure was repeated between 30 and 100 times.

1.8 Sequencing

After reverse transcription of the viral RNA, the cDNA was amplified with sequence specific primer pairs (oligonucleotides) in the polymerase chain reaction (PCR). The PCR products were purified, sequenced by cycle sequencing (modified singer method), the products separated by capillary electrophoresis and the sequence recorded as an electropherogram. The nucleic acid sequence was translated to obtain the protein sequence.

1.9 Innate Immune Activation

The ability of LCMV to activate the innate immune system was determined by the biomarker IFN-alpha using murine IFN-alpha ELISA (ThermoFisher).

1.10 Adaptive Immune Activation

The ability of LCMV to activate the adaptive immune system was tested by tetramer staining (NIH, Tetramer Facility) of activated lymphocytes.

1.11 Tumor Growth and Treatments

To measure the anti-tumoral effect, C57BL/6 or NOD-.SCID mice (6-12 weeks old) $5\times10^5$ tumor cells (in 100 μL) were injected subcutaneously into the right or left flank. After a visible tumor was formed, the animals were treated and the mean tumor diameter or tumor volume was determined. For a metastasis model, B16F10-OVA cells were applied intravenously.

1.12 Isolation and Transfer of Ovalbumin (Tumor)-Specific CD8+ T Cells

For the analysis of tumor-specific CD8+ T cells, cells from the spleen of OT-1 mice were transferred into C57BL/6 mice carrying ovalbumin-expressing tumor (B16F10-OVA) cells. Spleens were mechanically crushed. After filtration, $10^7$ spleen cells per mouse were injected intravenously.

1.13 Measurement of Tumor-Specific CD8+ T Cells

To analyze the number of tumor-specific CD8+ T cells, cells from the blood were incubated with fluorescent ovalbumin tetramers (four coupled H-2 Kb MHC-I molecules carrying the peptide SIINFEKL, NIH Tetramer Facility) and fluorochrome-coupled anti-CD8 antibodies (eBioscience) and analyzed after washing in a flow cytometer. For the analysis of T cell function, spleen cells were mechanically crushed and incubated after filtration with Brefeldin A and with or without SIINFEKL peptide. After six hours the cells were fixed, permeabilized and stained with fluorescent antibodies specific for CD8 (anti-CD8, eBioscience) and intracellular interferon-gamma (anti-interferon-gamma, eBioscience). The frequency of IFN-gamma producing cells was analyzed by flow cytometry.

1.14 Statistical Analysis

The mean values were compared using an unpaired two-sample Student's t-test. The data are presented as mean f SEM. The level of statistical significance was determined to be p<0.05.

1.15 Generation of LCMV-P42:

LCMV-WE was passaged 42 times in primary tumor cell cultures (UKE-Mel-13a). After 42 passages, a functional mutation was detected in the new virus (LCMV-P42). Nucleic acid and amino acid sequences of LCMV-WE and mutant P42 are shown in FIGS. 25(A and B).

1.16 Generation of LCMV-P91, LCMV-P52 and It's Subclones:

LCMV-WE was passaged 52 times in the tumor cell lines H1975. After 52 passages, the mutations I181M, R185W were detected in the glycoprotein of the new virus. In addition some, most likely irrelevant and/or oligoclonal mutations (quasispecies) were found. This virus is named: "LCMV-P52". To determine the stability and importance of the mutations I181M and Ri85W, the supernatant of passage P52 was passaged 39 more times. The virus derived from this passage is named: "LCMV-P91" and still contained the mutations I181M and R185W. The virus LCMV-P52 was subcloned by limiting dilution. This clonal virus is named: "LCMV-P52.1". The mutations I181M, R185W remained stable. The as irrelevant considered and/or oligoclonal mutations (quasispecies) showed some changes. To determine the role of the single mutations I181M and R185W some earlier passages were analyzed. The passage P29 contained viruses with individual I181M and R185W mutations. Viruses from passage P29 were subcloned by limiting dilution. One subclone with the singular mutation R185W was named: "LCMV-P52-1.3"; one subclone with the singular mutation I181M was named: "LCMV-P52-2.1". Nucleic acid and amino acid sequences of LCMV mutants P52, P92, P52-1, P52-1.3, and P52-2.1 are shown in FIGS. 25(C-G). Alignments of nucleic acid and amino acid sequences LCMV-WE and mutants P42, P52, P92, P52-1, P52-1.3, and P52-2.1 are shown in FIGS. 26(A-H).

2. Investigations 2.1 Tumor cell lines MC57, C643, H1975 and primary tumor cell cultures (UKE Mel-13a) were infected with LCMV (strain WE, MOI 1). Replication was measured after 24 hours (n=3).

Thereby it was proven that LCMV (strain WE) spread differently. In comparison to the tumor cell line MC57, the spread was reduced in the cell lines C643 and H1975 as well as in primary tumor cell cultures (UKE-Mel-13a). The obtained results are shown graphically in FIG. 1.

In white the LCMV infected cells in the cultures with MC57, C643, H1975 and UKE-Mel-13a can be seen. Ø=without infection, LCMV=LCMV infected.

2.2 Tumor cell line MC57 and primary tumor cell cultures 511950 were infected with LCMV (strain WE, MOI 0, 1) (left graph). Tumor cell lines MC57, Tramp-C2 and primary tumor cell cultures (511950 and 511950R) were infected with LCMV (strain WE, MOI 1) (right graph).

The number of infectious virus particles was measured after 24 hours in the supernatant.

Thereby it was proven that LCMV (strain WE) proliferate less in comparison to the MC57 tumor cell line in the Tramp-C2 cell line as well as in the primary tumor cell cultures (511950 and 511950R). The results are shown in FIG. 2.

Figure 2:
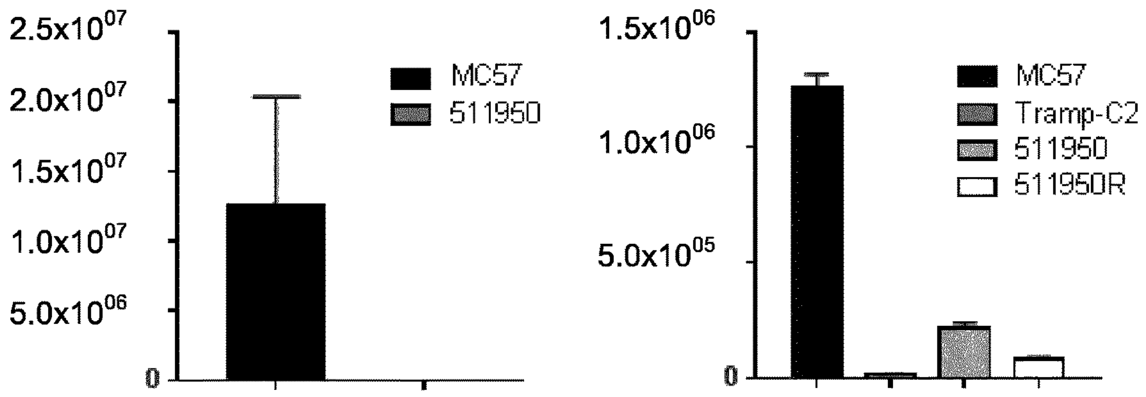
FIG. 2 shows the number of infectious virus particles measured in the supernatant after 24 hours of infection in MC57 cells, Tramp-C2 cells, and primary tumor cell cultures 511950 and 511950R.

FIG. 2 has the following legend:

Ordinate: Infectious LCMV particles in supernatant (PFU/mL),

Abscissa: Treatment groups; MC57, Tramp-C2, 511950, 511950R.

2.3 LCMV-WE was passaged 42 times in primary tumor cell cultures (UKE-Mel-13a). After 42 passages, a functional mutation was detected in the new virus (LCMV-P42).

Figure 3:
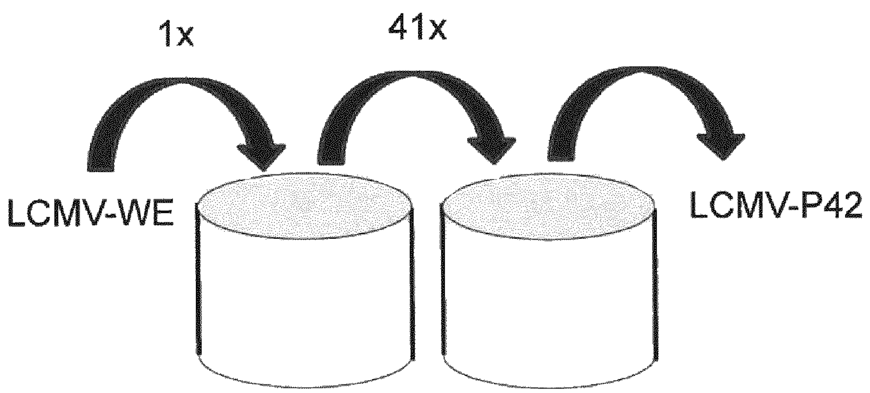
FIG. 3 shows an exemplary passaging protocol for LCMV-WE in UKE-Mel-13a cell cultures.

Thereby it could be proven that primary tumor cells are suitable for modifying arenaviruses by passaging. The experimental procedure is shown in FIG. 3.

2.4 LCMV-WE was passaged 52 times in tumor cell lines H1975. After 52 passages, functional mutations were detected in the new virus LCMV-P52.

Figure 4:
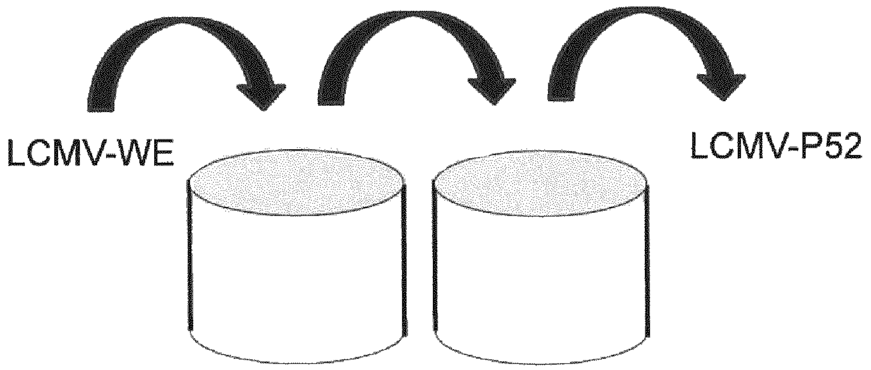
FIG. 4 shows an exemplary passaging protocol for LCMV-WE in H1975 cell cultures.

Thereby, using the example of H1975, it was proven that that tumor cell lines with reduced LCMV replication (compared to cell line MC57) are suitable for altering arenaviruses by passaging. The experimental procedure is illustrated in FIG. 4.

2.5 LCMV-P52 was passaged 39 times in tumor cell lines H1975. After 39 passages further functional mutations were detected in the new virus LCMV-P91.

Figure 5:
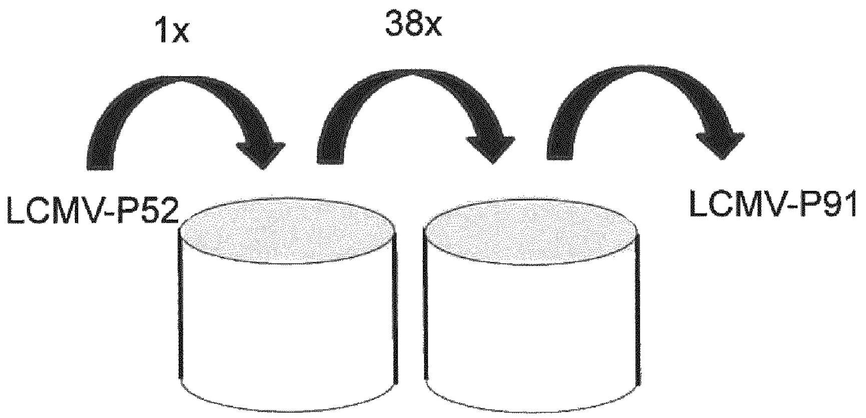
FIG. 5 shows an exemplary passaging protocol for LCMV-WE in H1975 cell cultures.

Thereby it was proven that H1975 cells are capable of altering arenaviruses by passaging. The experimental procedure is shown graphically in FIG. 5.

2.6 Cell lines H1975 were infected with LCMV-WE and LCMV-P52 (MOI 1). Virus was determined after 12 hours in the supernatant (n=6).

Thereby it was proven that LCMV-P52 replicate better than LCMV-WE in H1975 cells. The results obtained are shown graphically in FIG. 6.

Figure 6:
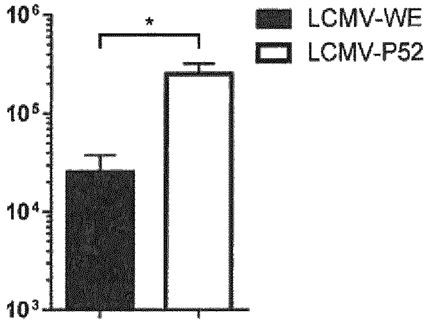
FIG. 6 shows the number of infectious virus particles measured in the supernatant after 12 hours of infection with LCMV-P52 and LCMV-WE in H1975 cells.

FIG. 6 has the following legend:

Ordinate: Infectious LCMV particles in the supernatant (PFU/mL),

Abscissa: Treatment groups; LCMV-WE or LCMV-P52

2.7 Murine bone marrow-derived dendritic cells were infected with LCMV-WE and LCMV-P52 (MOI 1). Virus was determined after 24 hours in supernatant (n=3).

Thereby it was proven that LCMV-P52 replicate better than LCMV-WE in antigen-presenting cells. The results obtained are shown graphically in FIG. 7.

Figure 7:
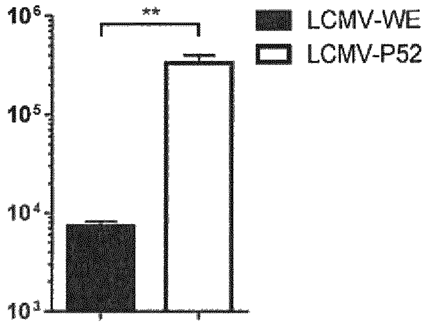
FIG. 7 shows the number of infectious virus particles measured in the supernatant after 24 hours of infection with LCMV-P52 and LCMV-WE in murine bone marrow-derived dendritic cells.

FIG. 7 has the following legend:

Ordinate: Infectious LCMV particles in the supernatant (PFU/mL),

Abscissa: Treatment groups; LCMV-WE or LCMV-P52

2.8 Tumor cell line H1975 was infected with LCMV-WE or LCMV-P52 (MOI 1). Virus spread was measured by immunofluorescence after 24 hours.

Figure 8:
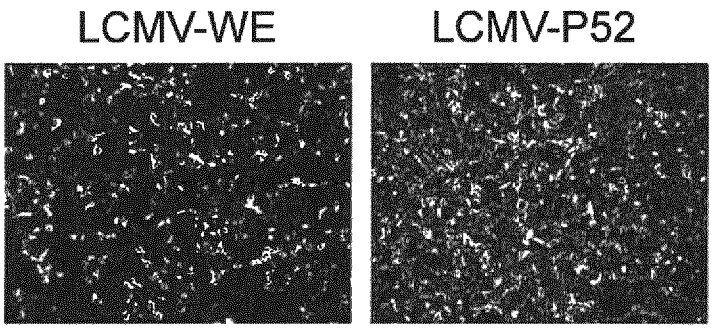
FIG. 8 shows LCMV-P52 and LCMV WE spread in H1975 cells.

Thereby it was proven that LCMV-P52 can spread better in tumor cell lines compared to LCMV WE using the example of H1975. The results obtained are shown graphically in FIG. 8.

Shown in white are the LCMV infected cells for a culture infected with LCMV-WE or LCMV-P52.

2.9 Primary tumor cells (UKE-Mel-13a) were infected with LCMV-WE or LCMV-P52 (MOI 1). The spread of the viruses was measured by immunofluorescence after 24 hours.

Figure 9:
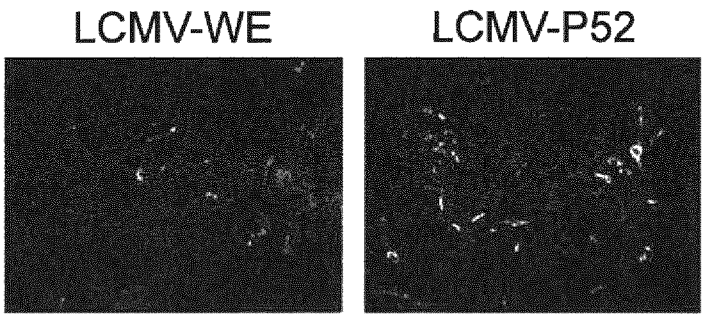
FIG. 9 shows LCMV-P52 and LCMV WE spread in UKE-Mel-13a cells

Thereby it was proven that LCMV-P52 can spread better in primary tumor cells compared to LCMV-WE. The obtained results are shown graphically in FIG. 9.

The LCMV infected cells for cultures infected with LCMV-WE or LCMV-P52 are shown in white.

2.10 C57BL/6 mice were infected with LCMV-WE or LCMV-P52 ($2\times10^4$ PFU intravenously). One day after infection the activation of the innate immune system was determined by measuring IFN-alpha in serum.

Thereby it was proven that LCMV-P52 causes a stronger innate immune activation than LCMV-WE. The obtained results are shown graphically in FIG. 10.

Figure 10:
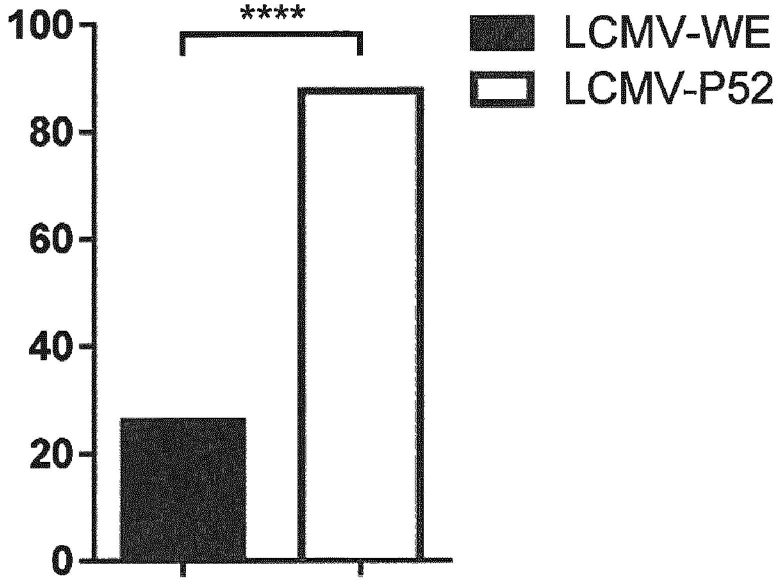
FIG. 10 shows activation of the innate immune system as determined by measuring IFN-alpha in serum from C57BL/6 mice following infection with LCMV-WE or LCMV-P52.

FIG. 10 has the following legend:

Ordinate: IFN-alpha concentration (ng/mL serum)

Abscissa: Treatment groups; LCMV-WE or LCMV-P52 infected animals.

2.11 C57BL/6 mice were infected with LCMV-WE or LCMV-P52 ($2\times10^4$ PFU intravenously). Activation of the adaptive immune system was determined by flow cytometry using tetramer (measures virus-specific CD8+ T cells).

Thereby it was proven that LCMV-P52 induces a stronger adaptive immune activation than LCMV-WE. The obtained results are shown graphically in FIG. 11.

Figure 11:
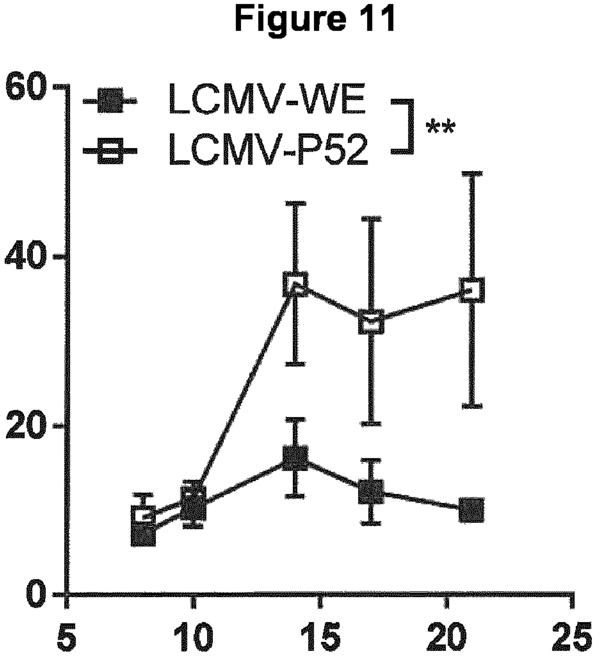
FIG. 11 shows a time course of activation of the adaptive immune system as determined by measuring virus-specific CD8+ T cells in C57BL/6 mice following infection with LCMV-WE or LCMV-P52.

FIG. 11 has the following legend:

Ordinate: Virus-specific CD8+ T cells (% of total CD8+ T cells in blood),

Abscissa: Time (days after infection)

2.12 NOD.SCID mice were subcutaneously treated with $5\times10^5$ H1975 cells (day −7). The mice were additionally infected with $2\times10^4$ PFU LCMV-WE or LCMV-P52 intratumorally (day 0). Tumor growth was analyzed.

Thereby it was proven that treatment with LCMV-P52 had a stronger anti-tumoral effect than treatment with LCMV-WE. The results obtained are shown graphically in FIG. 12.

Figure 12:
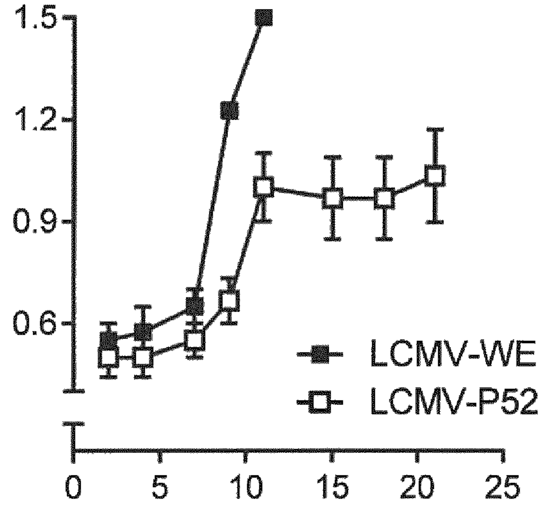
FIG. 12 shows a time course of MOPC tumor growth in NOD.SCID mice following infection with LCMV-WE or LCMV-P52.

FIG. 12 has the following legend:

Ordinate: mean tumor diameter (cm),

Abscissa: Time (days after LCMV treatment)

2.13 C57BL/6 mice were subcutaneously treated with $5\times10^5$ MOPC cells (day −7). A group of mice was additionally infected with $2\times10^4$ PFU LCMV-P52 intravenously (n=3, day 0). Tumor growth was analyzed.

Thereby it was proven that treatment with LCMV-P52 had a strong anti-tumoral effect. The results are shown graphically in FIG. 13.

Figure 13:
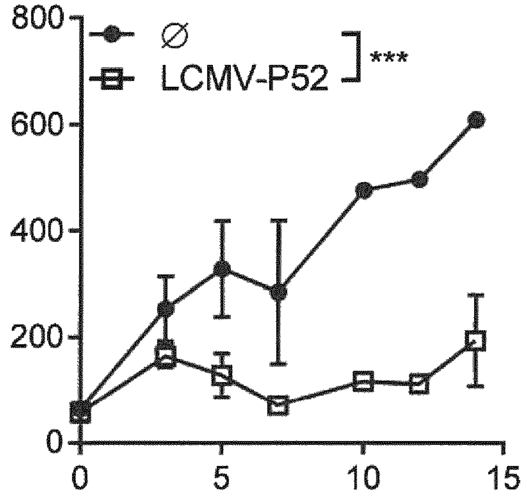
FIG. 13 shows a time course of MOPC tumor growth in C57BL/6 mice following infection with LCMV-P52.

FIG. 13 has the following legend:

Ordinate: tumor volume ($mm^3$),

Abscissa: Time (days after LCMV treatment)

2.14 C57BL/6 mice were subcutaneously treated with $5\times10^5$ CMT167 cells (day −7). One group of mice was additionally infected with $2\times10^4$ PFU LCMV-P52 intravenously (n=3, day 0). Tumor growth was analyzed.

Thereby it was proven that treatment with LCMV-P52 had a strong anti-tumoral effect. The results are shown in FIG. 14.

Figure 14:
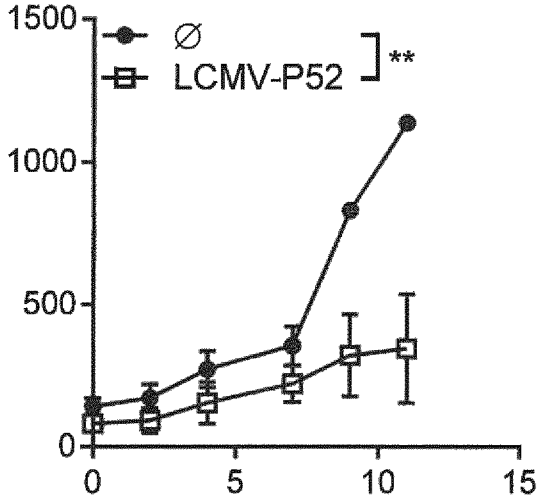
FIG. 14 shows a time course of CMT167 tumor growth in C57BL/6 mice following infection with LCMV-P52.

FIG. 14 has the following legend:

Ordinate: tumor volume ($mm^3$),

Abscissa: Time (days after LCMV treatment)

Figure 15:
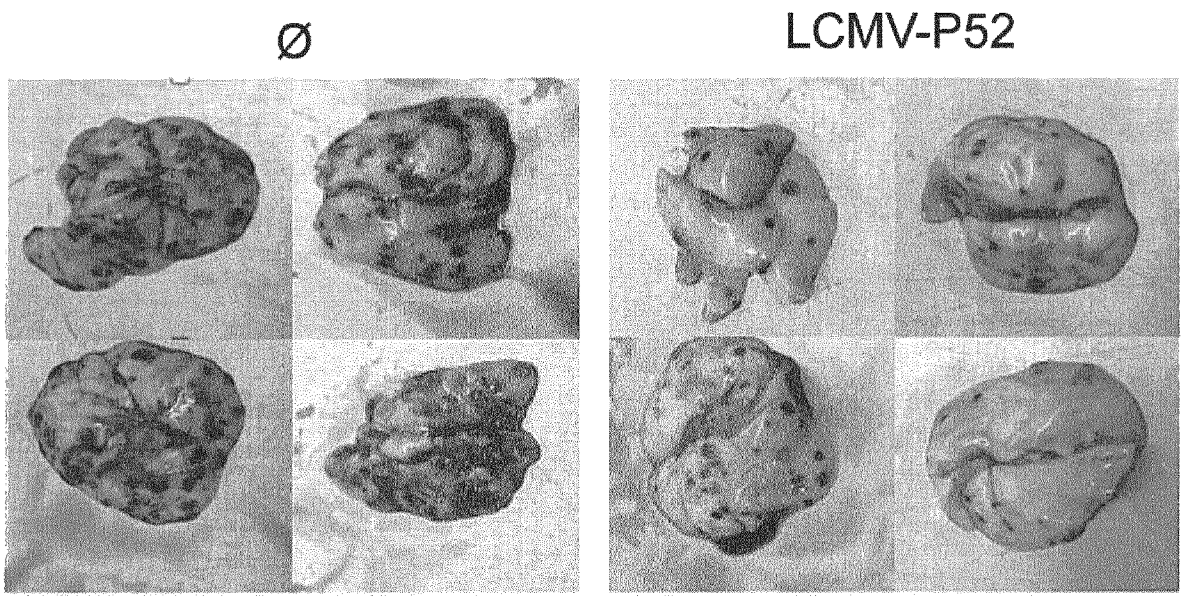
FIG. 15 shows CMT167 tumor growth in lung tissue of control C57BL/6 mice and mice infected with LCMV-P52.

Thereby it was proven that treatment with LCMV-P52 had a strong anti-tumoral effect. The results obtained are shown graphically in FIG. 15.

In black tumor cells in the lung are shown; Ø=without infection 2.15 C57BL/6 mice were treated intravenously with $5\times10^5$ Bl6F10-OVA cells (day −7). Tumor-specific CD8+ T cells isolated from the spleen of an OT-1 mouse were transferred (day −4). A group of animals were additionally treated with LCMV-P52 intravenously ($2\times10^4$ PFU, n=4). On day 9 the lungs were removed and photographed.

Ø=Control animals, 4 lungs each; LCMV-P52=treated with LCMV-P52, 4 lungs each.

2.16 C57BL/6 mice were treated intravenously with $5\times10^5$ B16F10-OVA cells (day −7). Tumor-specific CD8+ T cells isolated from the spleen of an OT-1 mouse were transferred (day −4). One group of animals were additionally treated with LCMV-P52 intravenously ($2\times10^4$ PFU, n=4). On day 3, the frequency of tumor-specific CD8+ T cells in the blood was determined.

Thereby it was proven that treatment with LCMV-P52 increases the expansion of tumor-specific CD8+ T cells. The results obtained are shown graphically in FIG. 16.

Figure 16:
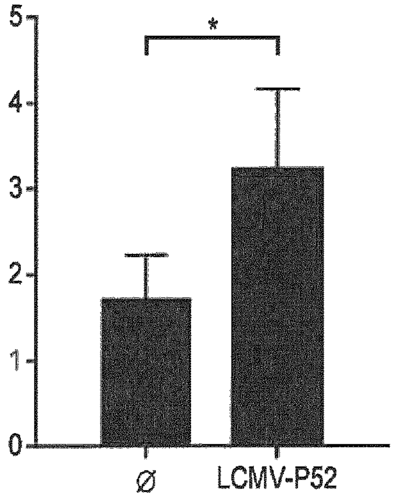
FIG. 16 shows measurement of CD8+ T cells in the blood of control OY-1 mice and mice infected with LCMV-P52 following administration of B16F10-OVA cells.

FIG. 16 has the following legend:

Ordinate: Frequency of tumor-specific CD8+ T cells in the blood (% of total CD8+ T cells), Abscissa: Treatment groups Ø=without infection LCMV-P52=treated with LCMV-P52

2.17 C57BL/6 mice were intravenously treated with $5\times10^5$ B16F10-OVA cells (day −7). Tumor-specific CD8+ T cells isolated from the spleen of an OT-1 mouse were transferred (day −4). One group of animals were additionally treated with LCMV-P52 intravenously ($2\times10^4$ PFU, n=4). On day 9, the function of tumor-specific CD8+ T cells in the spleen was determined by in vitro restimulation.

Thereby it was proven that treatment with LCMV-P52 increases the function of tumor-specific CD8+ T cells. The obtained results are shown graphically in FIG. 17.

Figure 17:
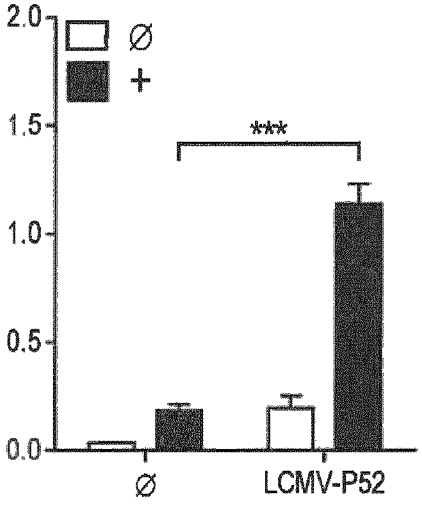
FIG. 17 shows measurement of CD8+ T cells in the spleen of control OY-1 mice and mice infected with LCMV-P52 following administration of B16F10-OVA cells.

FIG. 17 has the following legend:

Ordinate: Frequency of IFN-gamma-producing tumor-specific CD8+ T cells (% of total CD8+ T cells), Abscissa: Treatment groups; Ø: Without LCMV-P52 treatment; LCMV-P52: Treatment with LCMV-P52; Legend: −: Without antigen; +: Restimulation with antigen (SIINFEKL peptide).

2.18 C57BL/6 mice were subcutaneously treated with $5\times10^5$ B16F10-OVA cells (day −7). One group of animals was not further treated (n=3). One group of animals was treated with the inhibitor LCL-161 (oral 50 mg/kg body weight) twice a week from day 0. One group was treated intratumorally with LCMV-WE on day 0 ($2\times10^4$ PFU, n=4). One group was treated with LCL-161 and LCMV. Tumor growth was analyzed.

Thereby it was proven that treatment with LCMV-WE has a synergistic effect with LCL-161. The obtained results are shown graphically in FIG. 18.

Figure 18:
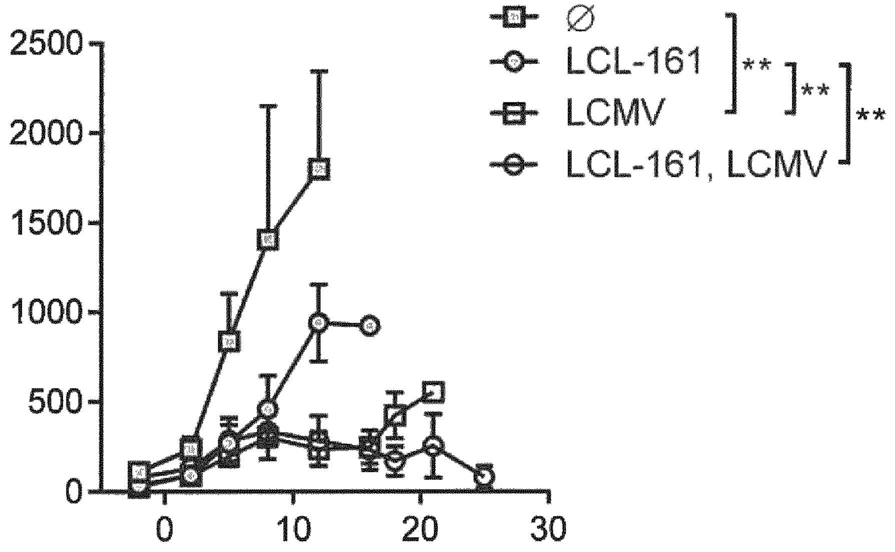
FIG. 18 shows a time course of B16F10-OVA tumor growth in C57BL/6 mice following infection with LCMV-WE, treatment with LCL-161, or co-treatment with both.

FIG. 18 has the following legend:

Ordinate: Tumor volume ($mm^3$),

Abscissa: Time (days after LCMV administration)

2.19 C57BL/6 mice were subcutaneously treated with $5\times10^5$ B16F10-OVA cells (day −7). One group of animals was not further treated (n=3). One group of animals was treated with the inhibitor LCL-161 (oral 50 mg/kg body weight) twice a week from day 0. One group was treated intratumorally with LCMV-WE on day 0 ($2\times10^4$ PFU, n=4). One group was treated with LCL-161 and LCMV. Survival of the animals was analyzed.

It could be shown that the treatment with LCMV-WE has a synergistic effect with LCL-161. The results obtained are shown graphically in FIG. 19.

Figure 19:
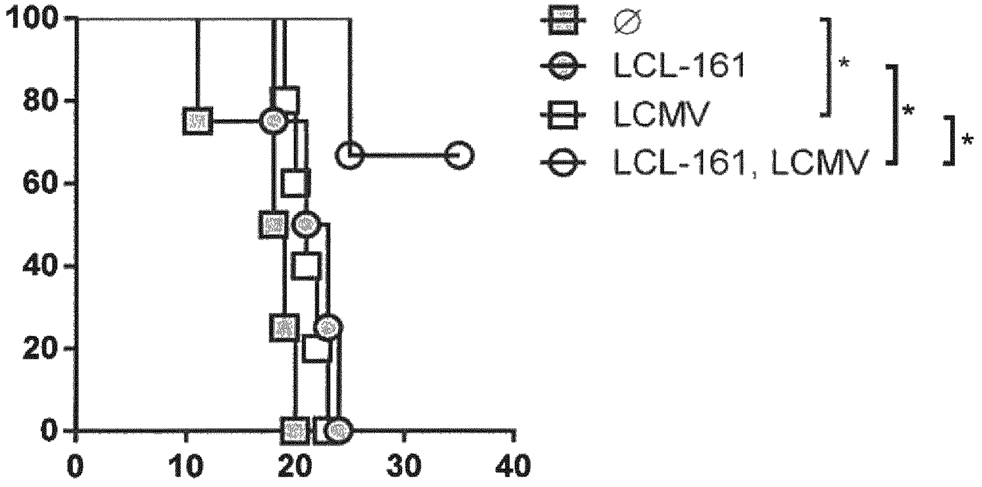
FIG. 19 shows a time course of B16F10-OVA tumor growth in C57BL/6 mice following infection with LCMV-WE, treatment with LCL-161, or co-treatment with both.

FIG. 19 has the following legend:

Ordinate: survival of animals (%),

Abscissa: Time (days after LCMV administration)

2.20 C57BL/6 mice were subcutaneously treated with $5\times10^5$ B16F10-OVA cells (day −9). One group of animals was not further treated (n=3). One group was treated intratumorally with LCMV-P52 on day 0 ($2\times10^4$ PFU, n=6-8). A group of animals was treated with the checkpoint blocker anti-PD-1 (200 μg. intraperitoneal) on days 1, 5 and 8. One group was treated with checkpoint blocker anti-PD-1 and LCMV-P52. Tumor growth was analyzed.

Thereby it was proven that the treatment with LCMV-P52 has a synergistic effect with checkpoint blockers (e.g. anti-PD-1). The results obtained are shown graphically in FIG. 20.

Figure 20:
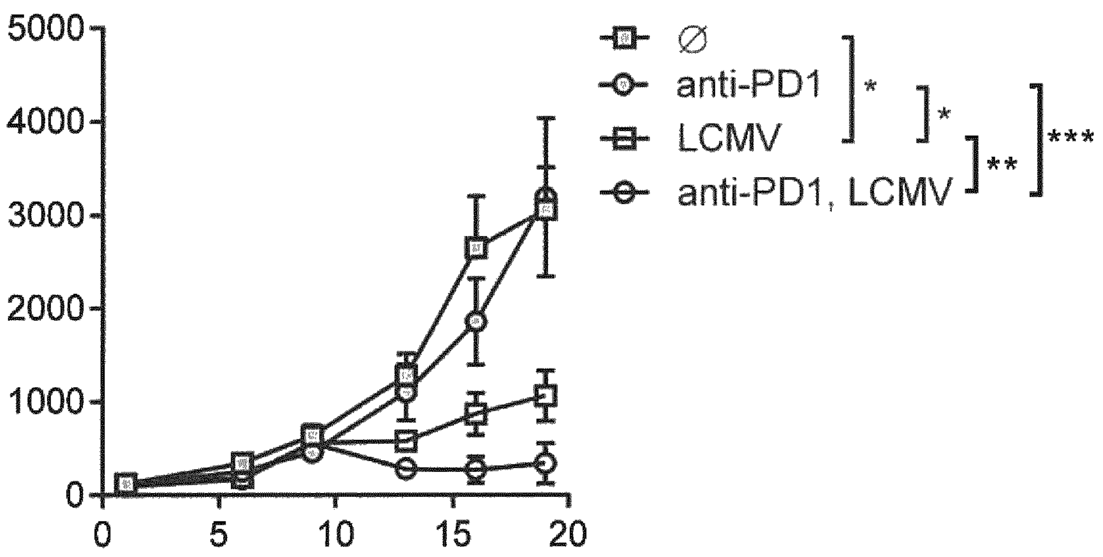
FIG. 20 shows a time course of B16F10-OVA tumor growth in C57BL/6 mice following infection with LCMV-P52, treatment with anti-PD-1, or co-treatment with both.

FIG. 20 has the following legend:

Ordinate: tumor volume ($mm^3$),

Abscissa: Time (days after LCMV treatment)

The amino acid and nucleic acid sequences mentioned in the present description correspond to the amino acid and nucleic acid sequences disclosed in the following sequence listing.

2.21 $10^5$ H1975 cells were seeded in 24 well plates. After 24 hours cells were infected with the viruses LCMV-WE, LCMV-P52.1 (I181M, R185W), LCMV-P52-1.3 (R185W) and LCMV-P52-2.1 (I181M) with a multiplicity of infection (MOI) of 0.1. Virus was analyzed in the supernatant after 24 hours. The results are shown in FIG. 21 (mean+SEM, n=6, *$p<0.05$, t-test).

The data show that the mutations I181M and R185W increase the viral propagation in tumor cells separately.

Figure 21:
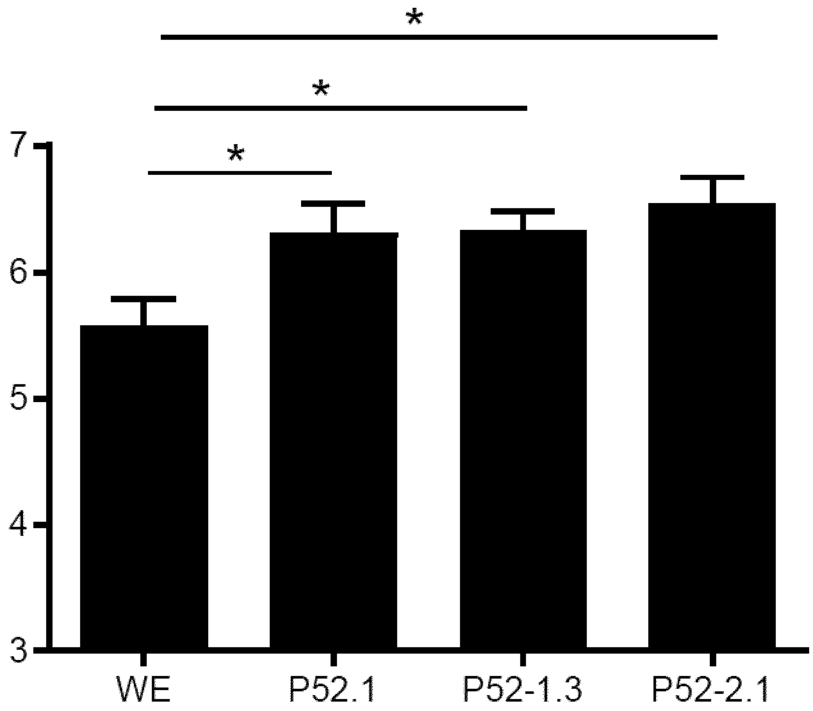
FIG. 21 shows the number of infectious virus particles measured in the supernatant after 24 hours of infection of H1975 cells with LCMV-WE, LCMV-P52.1 (I181M, R185W), LCMV-P52-1.3 (R185W) and LCMV-P52-2.1 (I181M).

FIG. 21 has the following legend:

X-axis: Different viruses

Y-axis: LCMV in the supernatant ($\log_{10}$ PFU/ml)

2.22 $2.5\times10^5$ HCC1954 cells were seeded in 24 well plates, followed by infection of LCMV-WE, LCMV-P52.1 (I181M, R185W), LCMV-P52-1.3 (R185W) and LCMV-P52-2.1 (I181M) with a multiplicity of infection (MOI) of 0.001. Virus was analyzed in the supernatant after 48 hours. The results are shown in FIG. 22 (error bars show SEM, n=4, **$p<0.001$, n.s. indicates not significant, one-way ANOVA with an additional Tukey post-test was used).

The data show that either the mutation I181M or the mutation 185W increase viral propagation in HCC1954 tumor cells.

Figure 22:
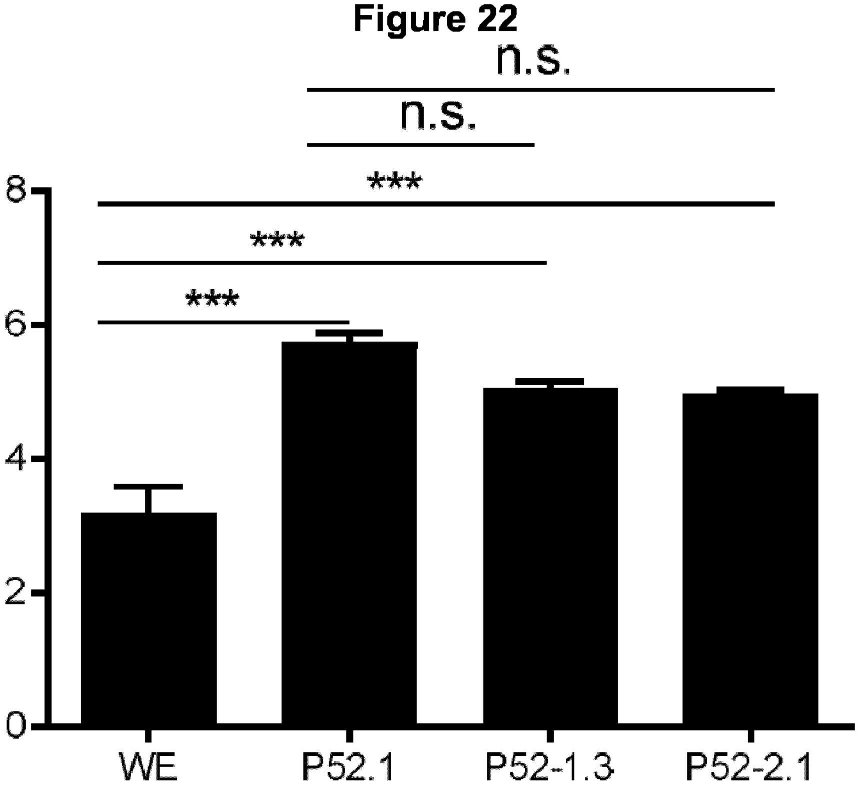
FIG. 22 shows the number of infectious virus particles measured in the supernatant after 24 hours of infection of HCC1954 cells with LCMV-WE, LCMV-P52.1 (I181M, R185W), LCMV-P52-1.3 (R185W) and LCMV-P52-2.1 (I181M).

FIG. 22 has the following legend:

X-axis: Different viruses

Y-axis: LCMV in the supernatant ($\log_{10}$ PFU/ml)

2.23 Murine Pancreatic cancer cells (511950, $4\times10^5$ cells), human Melanoma cells (UKE118b, $4\times10^5$ cells) or (UKE118c, $4\times10^5$ cells) were seeded in 24 well plates, followed by infection with LCMV-WE (white bars) or LCMV-P42 (I181M, black bars) with a multiplicity of infection (MOI) of 0.1. Virus was analyzed in the supernatant after 24 hours. The results are shown in FIG. 23 (mean+SEM, n=3, *$p<0.05$, t-test).

The data show that the mutation I181M leads to increase viral propagation in tumor cells.

Figure 23:
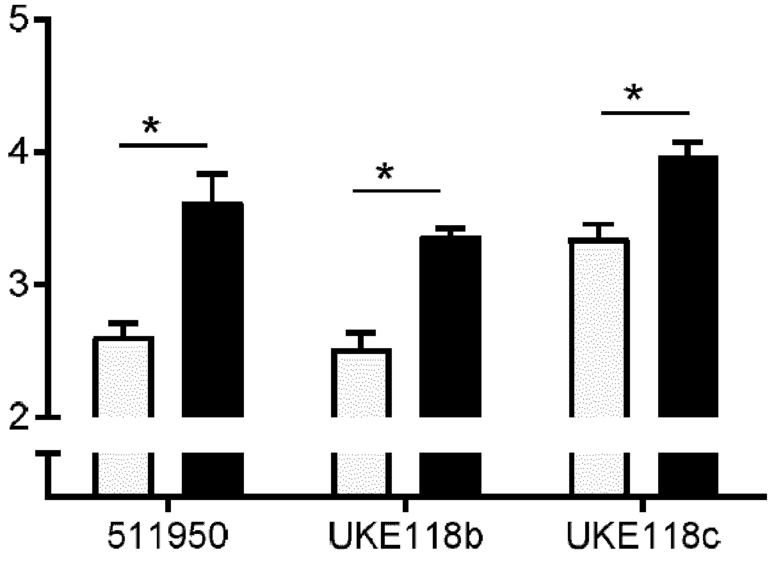
FIG. 23 shows the number of infectious virus particles measured in the supernatant after 24 hours of infection of Murine Pancreatic cancer (511950) cells, human Melanoma (UKE118b) cells, or human Melanoma (UKE118c) cells with LCMV-WE or LCMV-42 (I181M).

FIG. 23 has the following legend:

X-axis: Different cell types

Y-axis: LCMV in the supernatant ($\log_{10}$ PFU/ml)

2.24 C57BL/6 mice were infected intravenously with $2\times10^4$ PFU of either LCMV-WE, LCMV-P52.1 (I181M, RI85W), LCMV-P52-1.3 (RI85W) and LCMV-P52-2.1 (I181M). On day 8 (white bars) and day 10 (black bars) blood was analyzed for the frequencies of LCMV-GP33-specific $CD8^+$ T cells by using tetramers in flow cytometry. The results are shown in FIG. 24 (mean+SEM, n=6-12, pooled from four separate experiments, *$p<0.05$, t-test).

The data show that the mutations I181M and R185W increase the capacity of LCMV to stimulate specific T cells. The combination of the mutations I181M and R185W might have synergistic properties on early T cell stimulation.

Figure 24:
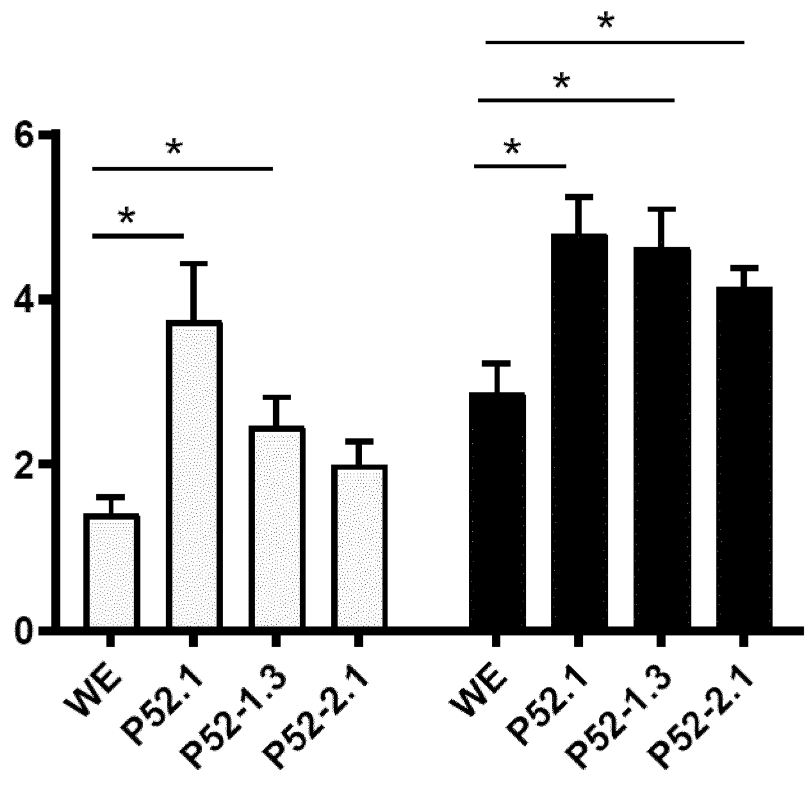
FIG. 24 shows measurement of LCMV-GP33-specific CD8+ T cells in the blood of C57BL/6 mice infected with LCMV-WE, LCMV-P52.1 (I181M, R185W), LCMV-P52-1.3 (R185W) and LCMV-P52-2.1 (I181M).

FIG. 24 has the following legend:

X-axis: Different viruses

Y-axis: Frequency of tetramer-GP33-binding $CD8^+$ T cells (% of total $CD8^+$ T cells).

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A mutant of lymphocytic choriomeningitis virus, wherein the mutant comprises a nucleic acid encoding a glycoprotein comprising a sequence that is at least 95% identical to residues 59-265 of SEQ ID NO: 10 and comprises Arg 185→Trp and Ile 181→Met amino acid substitutions as compared to the wild type glycoprotein sequence set forth in SEQ ID NO: 10.

2. The mutant of claim 1, wherein the glycoprotein has at least about 97% sequence identity to the wild type glycoprotein sequence set forth in SEQ ID NO: 10.

3. The mutant of claim 1, wherein the glycoprotein has at least about 95% sequence identity or is identical to a glycoprotein selected from the group consisting of SEQ ID NOs: 26, 34, and 42.

4. The mutant of claim 1, wherein the nucleic acid comprises a sequence that has at least about 95% sequence identity or is identical to a sequence selected from the group consisting of SEQ ID NOs: 25, 33, and 41.

5. The mutant of claim 1, wherein the mutant comprises a nucleic acid encoding a L-protein, wherein said L-protein has at least about 95% sequence identity to the wild type L-protein sequence set forth in SEQ ID NO: 16.

6. The mutant of claim 1, wherein the mutant comprises a nucleic acid encoding a L-protein, wherein said L-protein has at least about 95% sequence identity or is identical to a sequence selected from the group consisting of SEQ ID NOs: 24, 32, 40, 48, 56, and 64.

7. The mutant of claim 1, wherein the mutant comprises a nucleic acid encoding a L-protein, wherein said L-protein comprises 1, 2, 3, 4, 5, 6, 7, 8, 9, or 10 of the following amino acid substitutions: Lys 253→Arg, Lys 1512→Met, Lys 1513→Glu, Ser 1758→Phe, Phe 1995→Ser, Ile 2094→Val, Lys 2115→Glu, Thr 2141→Ala, Arg 2175→Lys, or Thr 2185→Ala, as compared to the wild type L-protein sequence set forth in SEQ ID NO: 16.

8. The mutant of claim 1, wherein the mutant comprises a nucleic acid encoding a L-protein, wherein said L-protein comprises one of the following sets of mutations:

(a) Ser 1758→Phe;

(b) Phe 1995→Ser; optionally Ile 2094→Val; and optionally Thr 2141→Ala;

(c) Lys 1513→Glu; Phe 1995→Ser; and optionally Arg 2175→Lys;

(d) Lys 253→Arg; Lys 1512→Met; Lys 2115→Glu; optionally Thr 2141→Ala; Thr 2185→Ala (e) Phe 1995→Ser; or (f) Lys 2115→Glu, as compared to the wild type L-protein sequence set forth in SEQ ID NO: 16.

9. The mutant of claim 1, wherein the mutant comprises a nucleic acid encoding an L-protein, wherein said nucleic acid is complementary to a sequence that has at least about 95% sequence identity or that is preferably identical to a sequence selected from the group consisting of SEQ ID NOs: 17, 25, 33, 41, 49, and 57.

10. The mutant claim 1, wherein the mutant comprises a nucleic acid encoding a nucleoprotein, wherein said nucleoprotein has at least about 95% sequence identity or that is identical to a nucleoprotein selected from the group consisting of SEQ ID NOs: 12, 20, 28, 36, 44, 52, and 60.

11. The mutant claim 1, wherein the mutant comprises a nucleic acid encoding a nucleoprotein, wherein said nucleic acid is complementary to a sequence that has at least about 95% sequence identity or that is identical to a sequence selected from the group consisting of SEQ ID NOs: 11, 19, 27, 35, 43, 51, and 59.

12. The mutant of claim 1, wherein the mutant comprises a nucleic acid encoding a Z-protein, wherein said Z-protein has at least about 95% sequence identity or that is identical to a sequence selected from the group consisting of SEQ ID NOs: 14, 22, 30, 38, 46, 54, and 62.

13. The mutant of claim 1, wherein the mutant comprises a nucleic acid encoding a Z-protein, wherein said nucleic acid comprises a sequence that has at least about 95% sequence identity or that is identical to a sequence selected from the group consisting of SEQ ID NOs: 13, 21, 29, 37, 45, 53, and 61.

14. A pharmaceutical composition comprising a lymphocytic choriomeningitis virus mutant of claim 1.

15. The pharmaceutical composition of claim 2, wherein the pharmaceutical composition further comprises a checkpoint blocker and/or an apoptosis modulator.

16. An A protein comprising:

(i) an amino acid sequence having at least 95% sequence identity to a sequence selected from the group consisting of SEQ ID NO: 26, SEQ ID NO: 34, SEQ ID NO: 42, and SEQ ID NO: 50, wherein the protein comprises Arg 185→Trp and Ile 181→Met amino acid substitutions as compared to the wild type glycoprotein sequence set forth in SEQ ID NO: 10; or (ii) an amino acid sequence having at least 95% sequence identity to the sequence of SEQ ID NO: 50, wherein the protein comprises an Arg 185→Trp amino acid substitution as compared to the wild type glycoprotein sequence set forth in SEQ ID NO: 10.

17. A nucleic acid, wherein the nucleic acid encodes a protein comprising an amino acid sequence (i) having at least 95% sequence identity to a sequence selected from the group consisting of SEQ ID NO: 26, SEQ ID NO: 34, and SEQ ID NO: 42, wherein the protein comprises Arg 185→Trp and Ile 181→Met amino acid substitutions as compared to the wild type glycoprotein sequence set forth in SEQ ID NO: 10; or (ii) having at least 95% sequence identity to the sequence of SEQ ID NO: 50, wherein the protein comprises an Arg 185→Trp amino acid substitution as compared to the wild type glycoprotein sequence set forth in SEQ ID NO: 10.

18. The mutant of claim 1, wherein the mutant is capable of undergoing a stronger propagation in a tumor cell as compared to the wild type lymphocytic choriomeningitis virus strain WE.

19. The nucleic acid of claim 17, wherein the nucleic acid is a ribonucleic acid.

20. The nucleic acid of claim 17, wherein the nucleic acid is comprised in an expression vector.

21. The protein of claim 16, wherein the protein is comprised in a virus.

22. A mutant of lymphocytic choriomeningitis virus, wherein the mutant comprises a nucleic acid encoding a glycoprotein comprising a sequence that is at least 95% identical to residues 59-265 of SEQ ID NO: 10, wherein the protein comprises an Arg 185→Trp amino acid substitution as compared to the wild type glycoprotein sequence set forth in SEQ ID NO: 10.

* * * * *

UNITED STATES PATENT AND TRADEMARK OFFICE

CERTIFICATE OF CORRECTION

PATENT NO. : 12,129,281 B2
APPLICATION NO. : 17/275967
DATED : October 29, 2024
INVENTOR(S) : Lang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this
Twentieth Day of May, 2025

Coke Morgan Stewart
*Acting Director of the United States Patent and Trademark Office*

SEQUENCE LISTING

<160> NUMBER OF SEQ ID NOS: 64

<210> SEQ ID NO 1
<211> LENGTH: 498
<212> TYPE: PRT
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Mutant p52
Glycoprotein; ssrna ambisense-strand viruses; arenaviridae;
arenavirus; old world arenaviruses

<400> SEQUENCE: 1

Met Gly Gln Ile Val Thr Met Phe Glu Ala Leu Pro His Ile Ile Asp
1 5 10 15

Glu Val Ile Asn Ile Val Ile Ile Val Leu Ile Ile Ile Thr Ser Ile
20 25 30

Lys Ala Val Tyr Asn Phe Ala Thr Cys Gly Ile Leu Ala Leu Val Ser
35 40 45

Phe Leu Phe Leu Ala Gly Arg Ser Cys Gly Met Tyr Gly Leu Asn Gly
50 55 60

Pro Asp Ile Tyr Lys Gly Val Tyr Gln Phe Lys Ser Val Glu Phe Asp
65 70 75 80

Met Ser His Leu Asn Leu Thr Met Pro Asn Ala Cys Ser Ala Asn Asn
85 90 95

Ser His His Tyr Ile Ser Met Gly Ser Ser Gly Leu Glu Leu Thr Phe
100 105 110

Thr Asn Asp Ser Ile Leu Asn His Asn Phe Cys Asn Leu Thr Ser Ala
115 120 125

Phe Asn Lys Lys Thr Phe Asp His Thr Leu Met Ser Ile Val Ser Ser
130 135 140

Leu His Leu Ser Ile Arg Gly Asn Ser Asn His Lys Ala Val Ser Cys
145 150 155 160

Asp Phe Asn Asn Gly Ile Thr Ile Gln Tyr Asn Leu Ser Phe Ser Asp
165 170 175

Pro Gln Ser Ala Met Ser Gln Cys Trp Thr Phe Arg Gly Arg Val Leu
180 185 190

Asp Met Phe Arg Thr Ala Phe Gly Gly Lys Tyr Met Arg Ser Gly Trp
195 200 205

Gly Trp Ala Gly Ser Asp Gly Lys Thr Thr Trp Cys Ser Gln Thr Ser
210 215 220

Tyr Gln Tyr Leu Ile Ile Gln Asn Arg Thr Trp Glu Asn His Cys Arg
225 230 235 240

Tyr Ala Gly Pro Phe Gly Met Ser Arg Ile Leu Phe Ala Gln Glu Lys
245 250 255

-continued

```
Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg


<210> SEQ ID NO 2
<211> LENGTH: 1497
<212> TYPE: DNA
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Mutant p52
      Glycoprotein; ssrna ambisense-strand viruses; arenaviridae;
      arenavirus; old world arenaviruses

<400> SEQUENCE: 2

atgggtcaga ttgtgacaat gtttgaggct ttgcctcaca tcattgatga ggtcatcaac      60

attgtcatta ttgtgctcat tataatcacg agcatcaaag ctgtgtacaa tttcgccacc     120

tgtgggatat tagcactggt cagcttcctt tttttggctg gtaggtcctg tggcatgtac     180

ggccttaatg gtcccgacat ctataaaggg gtttaccagt tcaaatcagt ggagtttgat     240

atgtctcact taaatctgac gatgcccaat gcgtgctcag ccaacaactc tcatcactac     300

atcagtatgg gaagctctgg actggagcta actttcacta acgactccat ccttaatcac     360

aatttttgca acttaacctc cgctttcaac aaaaagactt ttgaccatac actcatgagt     420

atagtctcga gtctgcacct cagtattaga gggaattcca accacaaagc agtgtcttgt     480

gattttaaca atggcatcac cattcaatac aacttgtcat tttcggaccc acagagcgct     540

atgagccagt gttggacttt cagaggtaga gtcttggaca tgtttagaac tgcctttgga     600
```

-continued

```
ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aatacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140

gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497
```

```
<210> SEQ ID NO 3
<211> LENGTH: 498
<212> TYPE: PRT
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Mutant p42
      Glycoprotein; ssrna ambisense-strand viruses; arenaviridae;
      arenavirus; old world arenaviruses

<400> SEQUENCE: 3

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Met Ser Gln Cys Arg Thr Phe Arg Gly Arg Val Leu
            180                 185                 190
```

-continued

```
Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg
```

<210> SEQ ID NO 4
<211> LENGTH: 1497
<212> TYPE: DNA
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Mutant p42 Glycoprotein; ssrna ambisense-strand viruses; arenaviridae; arenavirus; old world arenaviruses

<400> SEQUENCE: 4

```
atgggtcaga ttgtgacaat gtttgaggct ttgcctcaca tcattgatga ggtcatcaac      60

attgtcatta ttgtgctcat tataatcacg agcatcaaag ctgtgtacaa tttcgccacc     120

tgtgggatat tagcactggt cagcttcctt tttttggctg gtaggtcctg tggcatgtac     180
```

```
ggccttaatg gtcccgacat ctataaaggg gtttaccagt tcaaatcagt ggagtttgat    240

atgtctcact taaatctgac gatgcccaat gcgtgctcag ccaacaactc tcatcactac    300

atcagtatgg gaagctctgg actggagcta actttcacta acgactccat ccttaatcac    360

aatttttgca acttaacctc cgctttcaac aaaaagactt ttgaccatac actcatgagt    420

atagtctcga gtctgcacct cagtattaga gggaattcca accacaaagc agtgtcttgt    480

gattttaaca atggcatcac cattcaatac aacttgtcat tttcggaccc acagagcgct    540

atgagccagt gtaggacttt cagaggtaga gtcttggaca tgtttagaac tgcctttgga    600

ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aatacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140

gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497
```

<210> SEQ ID NO 5
<211> LENGTH: 2209
<212> TYPE: PRT
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Mutant
L-Protein; ssrna ambisense-strand viruses; arenaviridae;
arenavirus; old world arenaviruses

<400> SEQUENCE: 5

```
Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
```

-continued

```
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540
```

-continued

```
Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960
```

-continued

```
Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                 1005

Cys Arg  Lys Phe Phe Ser Glu  Gly Asp Trp Phe Ser  Cys Met Lys
    1010                 1015                 1020

Met Ile  Leu Leu Gln Met Asn  Ala Asn Ala Tyr Ser  Gly Lys Tyr
    1025                 1030                 1035

Arg His  Met Gln Arg Gln Ser  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125

Asp Leu  Arg Thr Lys Met Phe  Thr Arg Leu Val Glu  Asp Tyr Phe
    1130                 1135                 1140

Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260

Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
```

-continued

```
    1355                1360                1365

Phe Ala  Ala Glu Phe Lys Ser  Arg Phe Tyr Val Trp  Gly Glu Glu
    1370                1375                1380

Val Pro  Leu Leu Thr Lys Phe  Val Ser Ala Ala Leu  His Asn Val
    1385                1390                1395

Lys Cys  Lys Glu Pro His Gln  Leu Cys Glu Thr Ile  Asp Thr Ile
    1400                1405                1410

Ala Asp  Gln Ala Ile Ala Asn  Gly Val Pro Val Phe  Leu Val Asn
    1415                1420                1425

Cys Ile  Gln Arg Arg Thr Leu  Asp Leu Leu Lys Tyr  Ala Asn Phe
    1430                1435                1440

Pro Leu  Asp Pro Phe Leu Leu  Asn Thr His Thr Asp  Val Lys Asp
    1445                1450                1455

Trp Leu  Asp Gly Ser Arg Gly  Tyr Arg Ile Gln Arg  Leu Ile Glu
    1460                1465                1470

Glu Leu  Cys Pro Ser Glu Thr  Lys Ile Met Arg Lys  Leu Val Arg
    1475                1480                1485

Arg Leu  His His Lys Leu Lys  Asn Gly Glu Cys Asn  Glu Glu Phe
    1490                1495                1500

Phe Leu  Asp Leu Phe Asn Arg  Glu Lys Glu Glu Ala  Ile Leu Gln
    1505                1510                1515

Leu Gly  Glu Ile Leu Gly Leu  Glu Asp Asp Leu Asn  Glu Leu Ala
    1520                1525                1530

Ser Ile  Asn Trp Leu Asn Leu  Asn Glu Met Phe Pro  Leu Arg Met
    1535                1540                1545

Val Leu  Arg Gln Lys Val Val  Tyr Pro Ser Val Met  Thr Phe Gln
    1550                1555                1560

Glu Glu  Lys Ile Pro Ser Leu  Ile Lys Thr Leu Gln  Asn Lys Leu
    1565                1570                1575

Cys Ser  Lys Phe Thr Arg Gly  Ala Gln Lys Leu Leu  Ser Glu Ala
    1580                1585                1590

Ile Asn  Lys Ser Ala Phe Gln  Ser Cys Val Ser Ser  Gly Phe Ile
    1595                1600                1605

Gly Leu  Cys Lys Thr Leu Gly  Ser Arg Cys Val Arg  Asn Lys Asn
    1610                1615                1620

Arg Glu  Asn Met Tyr Ile Arg  Lys Val Leu Glu Asp  Leu Thr Met
    1625                1630                1635

Asp Glu  His Val Thr Arg Val  His Lys Gln Asp Gly  Val Met Leu
    1640                1645                1650

Tyr Ile  Cys Asp Lys Gln Arg  His Pro Glu Ala His  Arg Asp His
    1655                1660                1665

Ile Asn  Leu Leu Arg Pro Leu  Leu Trp Asp Tyr Ile  Cys Ile Ser
    1670                1675                1680

Leu Ser  Asn Ser Phe Glu Leu  Gly Val Trp Val Leu  Ala Glu Pro
    1685                1690                1695

Val Lys  Gly Lys Asn Glu Ser  Asn Ser Ala Val Arg  His Leu Asn
    1700                1705                1710

Pro Cys  Asp Tyr Val Ala Arg  Lys Pro Glu Ser Ser  Arg Leu Leu
    1715                1720                1725

Glu Asp  Lys Val Ser Leu Asn  His Val Ile Gln Ser  Val Arg Arg
    1730                1735                1740

Leu Tyr  Pro Lys Ile Phe Glu  Asp Gln Leu Leu Pro  Phe Met Ser
    1745                1750                1755
```

-continued

```
Asp Val  Ser Ser Lys Asn Met  Arg Trp Ser Pro Arg  Ile Lys Phe
    1760                 1765                 1770

Leu Asp  Leu Cys Val Leu Ile  Asp Ile Asn Ser Glu  Ser Leu Ser
    1775                 1780                 1785

Leu Ile  Ser His Val Val Lys  Trp Lys Arg Asp Glu  His Tyr Thr
    1790                 1795                 1800

Val Leu  Phe Ser Asp Leu Val  Asn Ser His Gln Arg  Ser Asp Ser
    1805                 1810                 1815

Ser Leu  Val Asp Glu Phe Val  Val Ser Thr Arg Asp  Val Cys Lys
    1820                 1825                 1830

Asn Phe  Leu Lys Gln Val Tyr  Phe Glu Ser Phe Val  Arg Glu Phe
    1835                 1840                 1845

Val Ala  Thr Ala Arg Thr Leu  Gly Asn Phe Ser Trp  Phe Pro His
    1850                 1855                 1860

Lys Asp  Met Met Pro Ser Glu  Asp Gly Ala Glu Ala  Leu Gly Pro
    1865                 1870                 1875

Phe Gln  Ser Phe Ile Leu Lys  Val Val Asn Lys Lys  Ile Glu Arg
    1880                 1885                 1890

Pro Met  Phe Arg Asn Asp Leu  Gln Phe Gly Phe Gly  Trp Phe Ser
    1895                 1900                 1905

Tyr Arg  Val Gly Asp Val Val  Cys Asn Ala Ala Met  Leu Ile Lys
    1910                 1915                 1920

Gln Gly  Leu Thr Asp Pro Lys  Ala Phe Lys Ser Leu  Arg Asp Leu
    1925                 1930                 1935

Trp Asp  Tyr Met Leu Ser Ser  Thr Glu Gly Ile Leu  Glu Phe Ser
    1940                 1945                 1950

Ile Thr  Val Asp Phe Thr His  Asn Gln Asn Asn Thr  Asp Cys Leu
    1955                 1960                 1965

Arg Lys  Phe Ser Leu Ile Phe  Val Val Lys Cys Gln  Leu Gln Ser
    1970                 1975                 1980

Pro Gly  Val Ala Asp Tyr Leu  Ser Cys Ser His Ser  Phe Lys Gly
    1985                 1990                 1995

Glu Val  Asp Arg Arg Leu Leu  Asp Glu Cys Leu Asn  Leu Leu Arg
    2000                 2005                 2010

Thr Asp  Pro Ile Phe Lys Ala  Asn Asp Gly Val Phe  Asp Ile Arg
    2015                 2020                 2025

Ser Glu  Glu Phe Glu Asp Tyr  Met Glu Asp Pro Leu  Thr Leu Gly
    2030                 2035                 2040

Asp Ser  Leu Glu Leu Glu Leu  Ile Gly Ser Arg Arg  Ile Leu Asn
    2045                 2050                 2055

Glu Ile  Lys Ser Thr Asp Phe  Glu Arg Ile Gly Pro  Glu Trp Glu
    2060                 2065                 2070

Pro Val  Pro Leu Thr Ile Arg  Lys Gly Ala Leu Phe  Glu Gly Arg
    2075                 2080                 2085

Asn Phe  Val Gln Asn Ile Ser  Val Lys Leu Glu Thr  Lys Asp Met
    2090                 2095                 2100

Arg Val  Phe Leu Ala Glu Leu  Glu Gly Cys Gly Lys  Ile Gly Asp
    2105                 2110                 2115

Val Leu  Gly Ser Leu Leu Leu  His Arg Phe Arg Thr  Gly Glu His
    2120                 2125                 2130

Leu Met  Glu Ser Glu Ile Ser  Thr Val Leu Gln Glu  Leu Cys Met
    2135                 2140                 2145
```

-continued

```
Asp Arg  Ser Val Met Leu Thr  Pro Leu Ser Phe Val  Pro Asp Trp
    2150                 2155                 2160

Phe Thr  Phe Arg Asp Cys Arg  Leu Cys Phe Ser Lys  Ser Lys Asn
    2165                 2170                 2175

Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp


<210> SEQ ID NO 6
<211> LENGTH: 6630
<212> TYPE: DNA
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Mutant
      L-Protein; ssrna ambisense-strand viruses; arenaviridae;
      arenavirus; old world arenaviruses

<400> SEQUENCE: 6

atggatgaaa ctattgcaga tttgagagag ttgtgtctaa attacataga acaggacgag     60

aggctgtcaa ggcaaaaact caacttcctg ggacaaagag aacccagaat ggtgctaatt    120

gagggactca aattgttatc acgctgtata gagatagaca gtgcagacaa aagtggttgc    180

atacacaacc acgatgacaa atctgttgaa acaatcctaa tagactctgg gattgtgtgt    240

ccaggactgc cactcatcat ccctgatggt tataagttga ttgacaattc ccttattctt    300

cttgaatgtt ttgttagaag cacaccagct agttttgaaa agaagttcat tgaggacacc    360

aacaaactag catgcatcaa agaagatctt gctgttgcag gcatcacact ggttccaata    420

gtggatggtc gttgtgatta tgataacagt ttcatgccag aatgggtgaa ttttaagttc    480

agagacctcc tatttaaact cctggagtat tctagtcaag atgagaaagt ttttgaggag    540

tctgaatact tcaggctctg tgagtctctt aagaccactg ttgacaaacg ttccggcatg    600

gactcaatga aaattttgaa agacgcaaga tcatttcata acgatgagat tatgaaaatg    660

tgccacgatg gtgtcaaccc caacatgagt tgcgatgatg tggtctttgg cataaattcc    720

ttttttggca ggtttaggag ggacctgtta aatgggaaac tcaaaaggaa tttccaaaag    780

gtcagccctg gggcttaat caaggaattc tctgaacttt atgaaaccct tactgataat     840

gatgacatat taatgttgag caaagaggca gttgaatcct gcccccttaat gaggttcatt    900

acagcagaga cccatgggca tgagagagga agcgatgcta acactgagta tgaaaggcta    960

ctctctatgt tgaacaaggt gaaaagttta aaattattaa acactagaag gagacagctg   1020

ctgaacttag atgtcttatg tctttcttca cttattaagc agtcaatttc caaagggttg   1080

gaaaatgata aacattgggt tggttgctgc tacagtagtg tgaatgatag gcttgtgagc   1140

cttcaaagta ccaaagaaga attcatgaga cttttgaaga acagaagaaa atcaagagtg   1200

cacaaaaagg catctcttga tgagcttttt agggtatcca taaatgagtt catagcaaaa   1260

atccagaaat gcctatcaac agtgggactt agttttgagc attacggact atcagaatgc   1320

ctcgtgcaag aatgccatat accatttgct gaatttgaga actttatgag agccgggact   1380

catcctgtaa tgcattacac aaaatttgaa gattacactt tccagcctaa catagagcaa   1440

ttgaggggtt tacagagttt gagaaaactg tcatctgttt gtttggctct aacaaacagc   1500

atgaaaacaa gctcagttgc aaggttgaga cagaaccaac tggggtctgt gagatatcaa   1560
```

-continued

```
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaacccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgataaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
```

-continued

```
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag tttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaaggaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
ttcccccata aggacatgat gccatctgaa gatggcgctg aagcactggg acccttccaa   5640
tcatttattt tgaaagtggt gaacaagaaa atagagaggc ccatgtttag gaatgacttg   5700
cagtttggtt ttggttggtt ctcttatcgt gtgggggatg ttgtgtgtaa tgccgctatg   5760
ttaattaagc agggtttgac agatccaaaa gcatttaaat ctttaagaga tttgtgggat   5820
tacatgctca gcagcacaga ggggatattg gagttctcaa tcacagtgga tttcacacac   5880
aaccagaaca acactgactg cttgaggaaa ttttcattga tctttgtggt taaatgccaa   5940
ttacagagtc caggtgtagc tgattactta tcgtgctctc attccttcaa aggtgaggtt   6000
gacaggagat tattagatga gtgtctcaat ctgttgagga cagaccccat ctttaaagcg   6060
aatgatggag tctttgacat taggtctgaa gagtttgaag attacatgga agaccctttg   6120
acacttggtg attcactaga acttgaacta ataggttcta gaaggattct gaatgagatc   6180
aaatctactg actttgagag gatagggcct gagtgggaac ctgtgcctct gaccataagg   6240
aagggtgccc tctttgaggg gaggaacttt gttcagaata tctctgtgaa attggagaca   6300
```

aggacatga gggtctttct ggcagagctc gagggctgtg gaaaaattgg tgatgtcctc 6360
ggcagcctcc tcctgcaccg attcagaact ggtgagcact tgatggagtc agaaataagt 6420
acagttcttc aggagctctg catggacaga tccgtcatgc tgacaccatt atcttttgtg 6480
ccagattggt tcaccttcag agattgtagg ctctgcttca gcaagtcaaa gaacactgta 6540
atgtatgaga caactggggg caggttcaga ctcaagggga aatcctgtga cgattggctg 6600
gcggagcggg tggccgagga gatcgactag 6630

<210> SEQ ID NO 7
<211> LENGTH: 2209
<212> TYPE: PRT
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Wildtype L-Protein; ssrna ambisense-strand viruses; arenaviridae; arenavirus; old world arenaviruses

<400> SEQUENCE: 7

Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

-continued

```
Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
```

-continued

```
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
    1010                1015                1020

Met Ile  Leu Leu Gln Met Asn  Ala Asn Ala Tyr Ser  Gly Lys Tyr
    1025                1030                1035

Arg His  Met Gln Arg Gln Ser  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Lys Cys  Met Ser Ala
    1070                1075                1080

Ala Leu  Lys Asn Leu Cys Phe  Tyr Ser Glu Glu Ser  Pro Thr Ser
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125
```

-continued

Asp Leu Arg Thr Lys Met Phe Thr Arg Leu Val Glu Asp Tyr Phe
1130 1135 1140

Glu Ser Phe Ser Ser Phe Phe Ser Gly Ser Cys Leu Asn Asn Asp
1145 1150 1155

Lys Glu Phe Glu Asn Ala Ile Leu Ser Met Thr Ile Asn Val Arg
1160 1165 1170

Glu Gly Leu Leu Asn Tyr Ser Met Asp His Ser Lys Trp Gly Pro
1175 1180 1185

Met Met Cys Pro Phe Leu Phe Leu Met Leu Leu Gln Asn Leu Lys
1190 1195 1200

Leu Gly Asp Asp Gln Tyr Val Arg Ser Gly Lys Asp His Val Ser
1205 1210 1215

Thr Leu Leu Thr Trp His Met His Lys Leu Val Glu Val Pro Phe
1220 1225 1230

Pro Val Val Asn Ala Met Met Lys Ser Tyr Val Lys Ser Lys Leu
1235 1240 1245

Lys Leu Leu Lys Gly Ser Gly Thr Thr Val Thr Glu Arg Ile Phe
1250 1255 1260

Arg Glu Tyr Phe Glu Met Gly Val Val Pro Ser His Ile Ser Ser
1265 1270 1275

Leu Ile Asp Met Gly Gln Gly Ile Leu His Asn Ala Ser Asp Phe
1280 1285 1290

Tyr Gly Leu Ile Ser Glu Arg Phe Ile Asn Tyr Cys Ile Gly Val
1295 1300 1305

Ile Phe Gly Glu Arg Pro Glu Ala Tyr Thr Ser Ser Asp Asp Gln
1310 1315 1320

Ile Thr Leu Phe Asp Lys Arg Leu Ser Asp Leu Val Asp Ser Asp
1325 1330 1335

Pro Glu Glu Val Leu Val Leu Leu Glu Phe His Ser His Leu Ser
1340 1345 1350

Gly Leu Leu Asn Lys Phe Ile Ser Pro Lys Ser Val Val Gly Arg
1355 1360 1365

Phe Ala Ala Glu Phe Lys Ser Arg Phe Tyr Val Trp Gly Glu Glu
1370 1375 1380

Val Pro Leu Leu Thr Lys Phe Val Ser Ala Ala Leu His Asn Val
1385 1390 1395

Lys Cys Lys Glu Pro His Gln Leu Cys Glu Thr Ile Asp Thr Ile
1400 1405 1410

Ala Asp Gln Ala Ile Ala Asn Gly Val Pro Val Phe Leu Val Asn
1415 1420 1425

Cys Ile Gln Arg Arg Thr Leu Asp Leu Leu Lys Tyr Ala Asn Phe
1430 1435 1440

Pro Leu Asp Pro Phe Leu Leu Asn Thr His Thr Asp Val Lys Asp
1445 1450 1455

Trp Leu Asp Gly Ser Arg Gly Tyr Arg Ile Gln Arg Leu Ile Glu
1460 1465 1470

Glu Leu Cys Pro Ser Glu Thr Lys Ile Met Arg Lys Leu Val Arg
1475 1480 1485

Arg Leu His His Lys Leu Lys Asn Gly Glu Cys Asn Glu Glu Phe
1490 1495 1500

Phe Leu Asp Leu Phe Asn Arg Glu Lys Lys Glu Ala Ile Leu Gln
1505 1510 1515

```
Leu Gly  Glu Ile Leu Gly Leu  Glu Asp Asp Leu Asn  Glu Leu Ala
    1520                 1525                 1530

Ser Ile  Asn Trp Leu Asn Leu  Asn Glu Met Phe Pro  Leu Arg Met
    1535                 1540                 1545

Val Leu  Arg Gln Lys Val Val  Tyr Pro Ser Val Met  Thr Phe Gln
    1550                 1555                 1560

Glu Glu  Lys Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Val Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Met Tyr Ile Arg  Lys Val Leu Glu Asp  Leu Thr Met
    1625                 1630                 1635

Asp Glu  His Val Thr Arg Val  His Lys Gln Asp Gly  Val Met Leu
    1640                 1645                 1650

Tyr Ile  Cys Asp Lys Gln Arg  His Pro Glu Ala His  Arg Asp His
    1655                 1660                 1665

Ile Asn  Leu Leu Arg Pro Leu  Leu Trp Asp Tyr Ile  Cys Ile Ser
    1670                 1675                 1680

Leu Ser  Asn Ser Phe Glu Leu  Gly Val Trp Val Leu  Ala Glu Pro
    1685                 1690                 1695

Val Lys  Gly Lys Asn Glu Ser  Asn Ser Ala Val Arg  His Leu Asn
    1700                 1705                 1710

Pro Cys  Asp Tyr Val Ala Arg  Lys Pro Glu Ser Ser  Arg Leu Leu
    1715                 1720                 1725

Glu Asp  Lys Val Ser Leu Asn  His Val Ile Gln Ser  Val Arg Arg
    1730                 1735                 1740

Leu Tyr  Pro Lys Ile Phe Glu  Asp Gln Leu Leu Pro  Phe Met Phe
    1745                 1750                 1755

Asp Val  Ser Ser Lys Asn Met  Arg Trp Ser Pro Arg  Ile Lys Phe
    1760                 1765                 1770

Leu Asp  Leu Cys Val Leu Ile  Asp Ile Asn Ser Glu  Ser Leu Ser
    1775                 1780                 1785

Leu Ile  Ser His Val Val Lys  Trp Lys Arg Asp Glu  His Tyr Thr
    1790                 1795                 1800

Val Leu  Phe Ser Asp Leu Val  Asn Ser His Gln Arg  Ser Asp Ser
    1805                 1810                 1815

Ser Leu  Val Asp Glu Phe Val  Val Ser Thr Arg Asp  Val Cys Lys
    1820                 1825                 1830

Asn Phe  Leu Lys Gln Val Tyr  Phe Glu Ser Phe Val  Arg Glu Phe
    1835                 1840                 1845

Val Ala  Thr Ala Arg Thr Leu  Gly Asn Phe Ser Trp  Phe Pro His
    1850                 1855                 1860

Lys Asp  Met Met Pro Ser Glu  Asp Gly Ala Glu Ala  Leu Gly Pro
    1865                 1870                 1875

Phe Gln  Ser Phe Ile Leu Lys  Val Val Asn Lys Lys  Ile Glu Arg
    1880                 1885                 1890

Pro Met  Phe Arg Asn Asp Leu  Gln Phe Gly Phe Gly  Trp Phe Ser
    1895                 1900                 1905

Tyr Arg  Val Gly Asp Val Val  Cys Asn Ala Ala Met  Leu Ile Lys
```

```
    1910                1915                1920

Gln Gly  Leu Thr Asp Pro Lys  Ala Phe Lys Ser Leu  Arg Asp Leu
    1925                1930                1935

Trp Asp  Tyr Met Leu Ser Ser  Thr Glu Gly Ile Leu  Glu Phe Ser
    1940                1945                1950

Ile Thr  Val Asp Phe Thr His  Asn Gln Asn Asn Thr  Asp Cys Leu
    1955                1960                1965

Arg Lys  Phe Ser Leu Ile Phe  Val Val Lys Cys Gln  Leu Gln Ser
    1970                1975                1980

Pro Gly  Val Ala Asp Tyr Leu  Ser Cys Ser His Phe  Phe Lys Gly
    1985                1990                1995

Glu Val  Asp Arg Arg Leu Leu  Asp Glu Cys Leu Asn  Leu Leu Arg
    2000                2005                2010

Thr Asp  Pro Ile Phe Lys Ala  Asn Asp Gly Val Phe  Asp Ile Arg
    2015                2020                2025

Ser Glu  Glu Phe Glu Asp Tyr  Met Glu Asp Pro Leu  Thr Leu Gly
    2030                2035                2040

Asp Ser  Leu Glu Leu Glu Leu  Ile Gly Ser Arg Arg  Ile Leu Asn
    2045                2050                2055

Glu Ile  Lys Ser Thr Asp Phe  Glu Arg Ile Gly Pro  Glu Trp Glu
    2060                2065                2070

Pro Val  Pro Leu Thr Ile Arg  Lys Gly Ala Leu Phe  Glu Gly Arg
    2075                2080                2085

Asn Phe  Val Gln Asn Ile Ser  Val Lys Leu Glu Thr  Lys Asp Met
    2090                2095                2100

Arg Val  Phe Leu Ala Glu Leu  Glu Gly Cys Gly Lys  Ile Gly Asp
    2105                2110                2115

Val Leu  Gly Ser Leu Leu Leu  His Arg Phe Arg Thr  Gly Glu His
    2120                2125                2130

Leu Met  Glu Ser Glu Ile Ser  Thr Val Leu Gln Glu  Leu Cys Met
    2135                2140                2145

Asp Arg  Ser Val Met Leu Thr  Pro Leu Ser Phe Val  Pro Asp Trp
    2150                2155                2160

Phe Thr  Phe Arg Asp Cys Arg  Leu Cys Phe Ser Arg  Ser Lys Asn
    2165                2170                2175

Thr Val  Met Tyr Glu Thr Thr  Gly Gly Arg Phe Arg  Leu Lys Gly
    2180                2185                2190

Lys Ser  Cys Asp Asp Trp Leu  Ala Glu Arg Val Ala  Glu Glu Ile
    2195                2200                2205

Asp
```

<210> SEQ ID NO 8
<211> LENGTH: 6630
<212> TYPE: DNA
<213> ORGANISM: Lymphocytic choriomeningitis virus
<220> FEATURE:
<221> NAME/KEY: MISC_FEATURE
<223> OTHER INFORMATION: Lymphocytic choriomeningitis virus Wildtype
L-Protein; ssrna ambisense-strand viruses; arenaviridae;
arenavirus; old world arenaviruses

<400> SEQUENCE: 8

```
atggatgaaa ctattgcaga tttgagagag ttgtgtctaa attacataga acaggacgag     60

aggctgtcaa ggcaaaaact caacttcctg ggacaaagag aacccagaat ggtgctaatt    120

gagggactca aattgttatc acgctgtata gagatagaca gtgcagacaa aagtggttgc    180
```

-continued

```
atacacaacc acgatgacaa atctgttgaa acaatcctaa tagactctgg gattgtgtgt    240
ccaggactgc cactcatcat ccctgatggt tataagttga ttgacaattc ccttattctt    300
cttgaatgtt ttgttagaag cacaccagct agttttgaaa agaagttcat tgaggacacc    360
aacaaactag catgcatcaa agaagatctt gctgttgcag gcatcacact ggttccaata    420
gtggatggtc gttgtgatta tgataacagt ttcatgccag aatgggtgaa ttttaagttc    480
agagacctcc tatttaaact cctggagtat tctagtcaag atgagaaagt tttgaggag     540
tctgaatact tcaggctctg tgagtctctt aagaccactg ttgacaaacg ttccggcatg    600
gactcaatga aaattttgaa agacgcaaga tcatttcata acgatgagat tatgaaaatg    660
tgccacgatg gtgtcaaccc caacatgagt tgcgatgatg tggtctttgg cataaattcc    720
ttttttggca ggtttaggag ggacctgtta aatgggaaac tcaaaaggaa tttccaaaag    780
gtcagccctg gggcttaat caaggaattc tctgaacttt atgaaaccct tactgataat     840
gatgacatat taatgttgag caaagaggca gttgaatcct gccccttaat gaggttcatt    900
acagcagaga cccatgggca tgagagagga agcgatgcta acactgagta tgaaaggcta    960
ctctctatgt tgaacaaggt gaaaagttta aaattattaa acactagaag gagacagctg   1020
ctgaacttag atgtcttatg tctttcttca cttattaagc agtcaatttc caaagggttg   1080
gaaaatgata aacattgggt tggttgttgc tacagtagtg tgaatgatag gcttgtgagc   1140
cttcaaagta ccaaagaaga attcatgaga cttttgaaga acagaagaaa atcaagagtg   1200
cacaaaaagg catctcttga tgagcttttt agggtatcca taaatgagtt catagcaaaa   1260
atccagaaat gcctatcaac agtgggactt agttttgagc attacggact atcagaatgc   1320
ctcgtgcaag aatgccatat accatttgct gaatttgaga actttatgag agccgggact   1380
catcctgtaa tgcattacac aaaatttgaa gattacactt tccagcctaa catagagcaa   1440
ttgaggggtt tacagagttt gagaaaactg tcatctgttt gtttggctct aacaaacagc   1500
atgaaaacaa gctcagttgc aaggttgaga cagaaccaac tggggtctgt gagatatcaa   1560
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacacaaaga gaaatcaaaa gcaggttcaa aatattaggt atttagtgat ggccatcgtc  1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaaccccctg gtgttaattt agagatcttt agcatgatgg tatcttcatt caacaatggc  2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
```

-continued

```
acagagggct tcatgaggaa acaaaagtat aagctgagac actcagatta cgaatataag   2580
gtctcaaagc ttgtctctag attagtcatc ggttccagga aaacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag ttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
```

```
catgtcacaa gggttcacaa acaagatggt gtgatgttgt acatttgcga caagcagaga   4980

cacccagagg ctcaccgtga ccacatcaac cttttgaggc cccttctctg ggactacatt   5040

tgcatctcat tgagcaactc ttttgagctg ggtgtttggg ttttagcaga acctgtgaaa   5100

ggaaagaacg agagtaattc ggctgttagg cacttaaatc catgtgatta tgtagcaaga   5160

aaacctgaga gttcgagact actagaggat aaagtgagtt tgaatcatgt aattcaatct   5220

gtgaggcgac tgtaccccaa aatctttgag gatcagttgc tcccattcat gtctgatgtg   5280

agctcaaaaa atatgagatg gagtcccagg attaaattcc ttgacctttg tgtgctgatt   5340

gacatcaact cagagtcttt gtcactcatt tctcatgttg tcaaatggaa gagggacgaa   5400

cattacactg tgctgttttc tgatctcgtc aactctcacc aacggtcaga ctcaagttta   5460

gttgatgaat ttgttgtcag cacaagggat gtctgcaaga actttttgaa gcaagtgtat   5520

ttcgaatcat ttgtacgaga gtttgttgca acagctagga ccttaggtaa cttttcatgg   5580

ttcccccata aggacatgat gccatctgaa gatggcgctg aagcactggg acccttccaa   5640

tcatttattt tgaaagtggt gaacaagaaa atagagaggc ccatgtttag gaatgacttg   5700

cagtttggtt ttggttggtt ctcttatcgt gtggggggatg ttgtgtgtaa tgccgctatg   5760

ttaattaagc agggtttgac agatccaaaa gcatttaaat ctttaagaga tttgtgggat   5820

tacatgctca gcagcacaga ggggatattg gagttctcaa tcacagtgga tttcacacac   5880

aaccagaaca acactgactg cttgaggaaa ttttcattga tctttgtggt taaatgccaa   5940

ttacagagtc caggtgtagc tgattactta tcgtgctctc atttcttcaa aggtgaggtt   6000

gacaggagat tattagatga gtgtctcaat ctgttgagga cagaccccat ctttaaagcg   6060

aatgatggag tctttgacat taggtctgaa gagtttgaag attacatgga agaccctttg   6120

acacttggtg attcactaga acttgaacta ataggttcta gaaggattct gaatgagatc   6180

aaatctactg actttgagag gatagggcct gagtgggaac ctgtgcctct gaccataagg   6240

aagggtgccc tctttgaggg gaggaacttt gttcagaata tctctgtgaa attggagaca   6300

aaggacatga gggtctttct ggcagagctc gagggctgtg gaaaaattgg tgatgtcctc   6360

ggcagcctcc tcctgcaccg attcagaact ggtgagcact tgatggagtc agaaataagt   6420

acagttcttc aggagctctg catggacaga tccgtcatgc tgacaccatt atcttttgtg   6480

ccagattggt tcaccttcag agattgtagg ctctgcttca gcaggtcaaa gaacactgta   6540

atgtatgaga caactggggg caggttcaga ctcaagggga aatcctgtga cgattggctg   6600

gcggagcggg tggccgagga gatcgactag                                    6630
```

<210> SEQ ID NO 9
<211> LENGTH: 1497
<212> TYPE: DNA
<213> ORGANISM: Lymphocytic choriomeningitis virus (strain WE)

<400> SEQUENCE: 9

```
atgggtcaga ttgtgacaat gtttgaggct ttgcctcaca tcattgatga ggtcatcaac     60

attgtcatta ttgtgctcat tataatcacg agcatcaaag ctgtgtacaa tttcgccacc    120

tgtgggatat tagcactggt cagcttcctt tttttggctg gtaggtcctg tggcatgtac    180

ggccttaatg gtcccgacat ctataaaggg gtttaccagt tcaaatcagt ggagtttgat    240

atgtctcact taaatctgac gatgcccaat gcgtgctcag ccaacaactc tcatcactac    300

atcagtatgg gaagctctgg actggagcta actttcacta acgactccat ccttaatcac    360
```

-continued aatttttgca acttaacctc cgctttcaac aaaaagactt ttgaccatac actcatgagt 420
atagtctcga gtctgcacct cagtattaga gggaattcca accacaaagc agtgtcttgt 480
gattttaaca atggcatcac cattcaatac aacttgtcat tttcggaccc acagagcgct 540
ataagccagt gtaggacttt cagaggtaga gtcttggaca tgtttagaac tgcctttgga 600
ggaaaataca tgagaagtgg ctggggctgg gcaggttcag atggcaagac cacttggtgc 660
agccaaacaa gctatcagta cctaatcata caaaacagga cttgggaaaa ccactgtaga 720
tatgcaggcc cttttgggat gtctagaatc ctctttgctc aggaaaagac aaagtttctc 780
actaggagac ttgcaggcac attcacctgg accctgtcag actcctcagg agtagaaaat 840
ccaggtggtt attgcctgac caaatggatg atccttgctg cagagctcaa atgttttggg 900
aatacagctg ttgcaaaatg taatgtcaat catgatgaag agttctgtga catgctacga 960
ctaattgatt acaacaaggc cgccctgagt aagttcaagc aagatgtaga gtctgccttg 1020
catgtattca aaacaacagt aaattctctg atttccgatc agctgttgat gaggaatcat 1080
ctaagagatc taatgggggt accatactgt aattactcaa agttctggta tctggaacat 1140
gctaagactg gtgagactag tgtacccaag tgctggcttg tcactaatgg ctcctacttg 1200
aatgagaccc actttagtga tcaaatcgaa caagaagcag ataacatgat cacagagatg 1260
ttgaggaagg actacataaa aagacaaggg agtactcctt tagccttaat ggatcttttg 1320
atgttttcaa catcagcata tctaatcagc atctttctgc atcttgtgaa gataccaaca 1380
catagacaca taaagggcgg ttcatgtcca aagccacacc gcttgaccaa caaggggatc 1440
tgtagttgtg gtgcattcaa ggtgcctggt gtaaaaacta tctggaaaag acgctga 1497

<210> SEQ ID NO 10
<211> LENGTH: 498
<212> TYPE: PRT
<213> ORGANISM: Lymphocytic choriomeningitis virus (strain WE)

<400> SEQUENCE: 10

Met Gly Gln Ile Val Thr Met Phe Glu Ala Leu Pro His Ile Ile Asp
1 5 10 15

Glu Val Ile Asn Ile Val Ile Ile Val Leu Ile Ile Ile Thr Ser Ile
20 25 30

Lys Ala Val Tyr Asn Phe Ala Thr Cys Gly Ile Leu Ala Leu Val Ser
35 40 45

Phe Leu Phe Leu Ala Gly Arg Ser Cys Gly Met Tyr Gly Leu Asn Gly
50 55 60

Pro Asp Ile Tyr Lys Gly Val Tyr Gln Phe Lys Ser Val Glu Phe Asp
65 70 75 80

Met Ser His Leu Asn Leu Thr Met Pro Asn Ala Cys Ser Ala Asn Asn
85 90 95

Ser His His Tyr Ile Ser Met Gly Ser Ser Gly Leu Glu Leu Thr Phe
100 105 110

Thr Asn Asp Ser Ile Leu Asn His Asn Phe Cys Asn Leu Thr Ser Ala
115 120 125

Phe Asn Lys Lys Thr Phe Asp His Thr Leu Met Ser Ile Val Ser Ser
130 135 140

Leu His Leu Ser Ile Arg Gly Asn Ser Asn His Lys Ala Val Ser Cys
145 150 155 160

Asp Phe Asn Asn Gly Ile Thr Ile Gln Tyr Asn Leu Ser Phe Ser Asp
165 170 175

-continued

```
Pro Gln Ser Ala Ile Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg


<210> SEQ ID NO 11
<211> LENGTH: 1677
<212> TYPE: DNA
<213> ORGANISM: Lymphocytic choriomeningitis virus (strain WE)

<400> SEQUENCE: 11

atgtctttgt ccaaagaagt caaaagcttt cagtggacac aggcgttgag gagggagttg      60

cagagtttta catcagatgt aaaggctgcc gtcatcaagg acgcaaccag tcttctaaat     120

gggttggact ttctgaagt cagcaacgtt cagaggatca tgagaaagga aaggagggat     180

gataaagact tgcagagact caggagtctt aaccagactg tgcattctct tgttgatctg     240

aagtctacat caaagaaaaa tgttctgaaa gtgggaagac ttagtgcaga ggaattgatg     300
```

-continued

```
accettgcag ctgatcttga gaagctgaag gccaaaatta tgagaactga gaggcctcaa    360

gcttctggag tctacatggg aaatttgaca gcacaacaac ttgatcaaag atcccaaata    420

ctgcaaatgg ttgggatgag aagacctcag cagggtgcaa gtggtgtagt aagggtttgg    480

gatgtgaagg actcatcact tctgaacaat cagttcggca caatgccaag cctgacaatg    540

gcttgcatgg caaaacagtc acagacccca ctcaatgatg ttgtgcaggc actcacagac    600

cttggcttac tttacacagt caaatacccg aatctcagtg atcttgaaag gctaaaggat    660

aaacacccag ttctgggggt cattactgaa cagcaatcta gtatcaatat ctctggttat    720

aatttcagtc ttggtgcagc tgtgaaagcg ggggcagctc tgctagatgg agggaacatg    780

ctggaatcta tcttgatcaa accgagcaac agtgaggatc tcctaaaagc agtcctcggg    840

gccaagaaga aactcaacat gtttgtctca gatcaagttg gagatagaaa tccctatgaa    900

aacatccttt ataaagtctg tctttcaggt gaaggatggc catacatagc ctgtagaacg    960

tcagttgtgg ggagagcatg ggagaacaca acaattgatc tcacaaatga aaaacttgtt   1020

gccaactcat ctaggccagt gcctggagca gcaggcccac ctcaggtggg cttgagttac   1080

agtcagacaa tgctgttgaa agacttgatg ggagggattg atcccaatgc tcccacatgg   1140

attgacattg agggcaggtt caatgatcca gtggagatag caatattcca accacaaaat   1200

gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaatagaagg gacataaaac tcattgatgt tgagatgacc   1440

aaggaggcct caagagaata tgaagataaa gtgtgggaca aatatggctg gctatgcaaa   1500

atgcacactg ggggtagtgag agacaaaaag aagaaagaga tcaccccaca ctgtgcactc   1560

atggactgca tcatttttga gagtgcttcc aaggcaagac tccctgatct aaaaaccgtt   1620

cacaacatcc tgccacatga tttaatcttc agaggaccca atgttgtgac actctaa      1677
```

```
<210> SEQ ID NO 12
<211> LENGTH: 558
<212> TYPE: PRT
<213> ORGANISM: Lymphocytic choriomeningitis virus (strain WE)

<400> SEQUENCE: 12

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125
```

-continued

```
Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
```

-continued 545 550 555

<210> SEQ ID NO 13
<211> LENGTH: 273
<212> TYPE: DNA
<213> ORGANISM: Lymphocytic choriomeningitis virus (strain WE)

<400> SEQUENCE: 13
atgggccaag gcaagtccaa agaagaaagg gacaccagca atacaggcag agcagagctt 60
ttgccagaca ccacctatct tggtcctcta aattgtaaat catgttggca gaaatttgac 120
agcttggtta gatgccatga ccactatctt tgcagacact gtctgaatct cctgctgtca 180
gtttccgaca gatgtcctct ctgtaagtat ccactgccaa ccaaactgaa ggtgtcaaca 240
gtcccaagct ccccacctcc ctatgaggag tga 273

<210> SEQ ID NO 14
<211> LENGTH: 90
<212> TYPE: PRT
<213> ORGANISM: Lymphocytic choriomeningitis virus (strain WE)

<400> SEQUENCE: 14

Met Gly Gln Gly Lys Ser Lys Glu Glu Arg Asp Thr Ser Asn Thr Gly
1 5 10 15

Arg Ala Glu Leu Leu Pro Asp Thr Thr Tyr Leu Gly Pro Leu Asn Cys
20 25 30

Lys Ser Cys Trp Gln Lys Phe Asp Ser Leu Val Arg Cys His Asp His
35 40 45

Tyr Leu Cys Arg His Cys Leu Asn Leu Leu Leu Ser Val Ser Asp Arg
50 55 60

Cys Pro Leu Cys Lys Tyr Pro Leu Pro Thr Lys Leu Lys Val Ser Thr
65 70 75 80

Val Pro Ser Ser Pro Pro Pro Tyr Glu Glu
85 90

<210> SEQ ID NO 15
<211> LENGTH: 6630
<212> TYPE: DNA
<213> ORGANISM: Lymphocytic choriomeningitis virus (strain WE)

<400> SEQUENCE: 15
atggatgaaa ctattgcaga tttgagagag ttgtgtctaa attacataga acaggacgag 60
aggctgtcaa ggcaaaaact caacttcctg ggacaaagag aacccagaat ggtgctaatt 120
gagggactca aattgttatc acgctgtata gagatagaca gtgcagacaa aagtggttgc 180
atacacaacc acgatgacaa atctgttgaa acaatcctaa tagactctgg gattgtgtgt 240
ccaggactgc cactcatcat ccctgatggt tataagttga ttgacaattc ccttattctt 300
cttgaatgtt ttgttagaag cacaccagct agttttgaaa agaagttcat tgaggacacc 360
aacaaactag catgcatcaa agaagatctt gctgttgcag gcatcacact ggttccaata 420
gtggatggtc gttgtgatta tgataacagt ttcatgccag aatgggtgaa ttttaagttc 480
agagacctcc tatttaaact cctggagtat tctagtcaag atgagaaagt ttttgaggag 540
tctgaatact tcaggctctg tgagtctctt aagaccactg ttgacaaacg ttccggcatg 600
gactcaatga aaattttgaa agacgcaaga tcatttcata acgatgagat tatgaaaatg 660
tgccacgatg gtgtcaaccc caacatgagt tgcgatgatg tggtctttgg cataaattcc 720
ttttttggca ggtttaggag ggacctgtta aatgggaaac tcaaaaggaa tttccaaaag 780

-continued

```
gtcagccctg ggggcttaat caaggaattc tctgaacttt atgaaaccct tactgataat    840
gatgacatat taatgttgag caaagaggca gttgaatcct gccccttaat gaggttcatt    900
acagcagaga cccatgggca tgagagagga agcgatgcta acactgagta tgaaaggcta    960
ctctctatgt tgaacaaggt gaaaagttta aaattattaa acactagaag gagacagctg   1020
ctgaacttag atgtcttatg tctttcttca cttattaagc agtcaatttc caaagggttg   1080
gaaaatgata aacattgggt tggttgttgc tacagtagtg tgaatgatag gcttgtgagc   1140
cttcaaagta ccaaagaaga attcatgaga cttttgaaga acagaagaaa atcaagagtg   1200
cacaaaaagg catctcttga tgagcttttt agggtatcca taaatgagtt catagcaaaa   1260
atccagaaat gcctatcaac agtgggactt agttttgagc attacggact atcagaatgc   1320
ctcgtgcaag aatgccatat accatttgct gaatttgaga actttatgag agccgggact   1380
catcctgtaa tgcattacac aaaatttgaa gattacactt tccagcctaa catagagcaa   1440
ttgaggggtt tacagagttt gagaaaactg tcatctgttt gtttggctct aacaaacagc   1500
atgaaaacaa gctcagttgc aaggttgaga cagaaccaac tggggtctgt gagatatcaa   1560
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaaccccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
```

-continued

```
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag tttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
```

```
ttcgaatcat ttgtacgaga gtttgttgca acagctagga ccttaggtaa cttttcatgg   5580

ttcccccata aggacatgat gccatctgaa gatggcgctg aagcactggg acccttccaa   5640

tcatttattt tgaaagtggt gaacaagaaa atagagaggc ccatgtttag gaatgacttg   5700

cagtttggtt ttggttggtt ctcttatcgt gtgggggatg ttgtgtgtaa tgccgctatg   5760

ttaattaagc agggtttgac agatccaaaa gcatttaaat ctttaagaga tttgtgggat   5820

tacatgctca gcagcacaga ggggatattg gagttctcaa tcacagtgga tttcacacac   5880

aaccagaaca acactgactg cttgaggaaa ttttcattga tctttgtggt taaatgccaa   5940

ttacagagtc caggtgtagc tgattactta tcgtgctctc atttcttcaa aggtgaggtt   6000

gacaggagat tattagatga gtgtctcaat ctgttgagga cagaccccat ctttaaagcg   6060

aatgatggag tctttgacat taggtctgaa gagtttgaag attacatgga agaccctttg   6120

acacttggtg attcactaga acttgaacta ataggttcta gaaggattct gaatgagatc   6180

aaatctactg actttgagag gatagggcct gagtgggaac ctgtgcctct gaccataagg   6240

aagggtgccc tctttgaggg gaggaacttt gttcagaata tctctgtgaa attggagaca   6300

aaggacatga gggtctttct ggcagagctc gagggctgtg gaaaaattgg tgatgtcctc   6360

ggcagcctcc tcctgcaccg attcagaact ggtgagcact tgatggagtc agaaataagt   6420

acagttcttc aggagctctg catggacaga tccgtcatgc tgacaccatt atcttttgtg   6480

ccagattggt tcaccttcag agattgtagg ctctgcttca gcaggtcaaa gaacactgta   6540

atgtatgaga caactggggg caggttcaga ctcaagggga aatcctgtga cgattggctg   6600

gcggagcggg tggccgagga gatcgactag                                     6630
```

<210> SEQ ID NO 16
<211> LENGTH: 2209
<212> TYPE: PRT
<213> ORGANISM: Lymphocytic choriomeningitis virus (strain WE)

<400> SEQUENCE: 16

```
Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175
```

-continued

```
Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590
```

-continued

```
Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
```

-continued

```
    1010                1015                1020

Met Ile  Leu Leu Gln Met Asn  Ala Asn Ala Tyr Ser  Gly Lys Tyr
    1025                1030                1035

Arg His  Met Gln Arg Gln Ser  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Lys Cys  Met Ser Ala
    1070                1075                1080

Ala Leu  Lys Asn Leu Cys Phe  Tyr Ser Glu Glu Ser  Pro Thr Ser
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125

Asp Leu  Arg Thr Lys Met Phe  Thr Arg Leu Val Glu  Asp Tyr Phe
    1130                1135                1140

Glu Ser  Phe Ser Ser Phe Phe  Ser Gly Ser Cys Leu  Asn Asn Asp
    1145                1150                1155

Lys Glu  Phe Glu Asn Ala Ile  Leu Ser Met Thr Ile  Asn Val Arg
    1160                1165                1170

Glu Gly  Leu Leu Asn Tyr Ser  Met Asp His Ser Lys  Trp Gly Pro
    1175                1180                1185

Met Met  Cys Pro Phe Leu Phe  Leu Met Leu Leu Gln  Asn Leu Lys
    1190                1195                1200

Leu Gly  Asp Asp Gln Tyr Val  Arg Ser Gly Lys Asp  His Val Ser
    1205                1210                1215

Thr Leu  Leu Thr Trp His Met  His Lys Leu Val Glu  Val Pro Phe
    1220                1225                1230

Pro Val  Val Asn Ala Met Met  Lys Ser Tyr Val Lys  Ser Lys Leu
    1235                1240                1245

Lys Leu  Leu Lys Gly Ser Gly  Thr Thr Val Thr Glu  Arg Ile Phe
    1250                1255                1260

Arg Glu  Tyr Phe Glu Met Gly  Val Val Pro Ser His  Ile Ser Ser
    1265                1270                1275

Leu Ile  Asp Met Gly Gln Gly  Ile Leu His Asn Ala  Ser Asp Phe
    1280                1285                1290

Tyr Gly  Leu Ile Ser Glu Arg  Phe Ile Asn Tyr Cys  Ile Gly Val
    1295                1300                1305

Ile Phe  Gly Glu Arg Pro Glu  Ala Tyr Thr Ser Ser  Asp Asp Gln
    1310                1315                1320

Ile Thr  Leu Phe Asp Lys Arg  Leu Ser Asp Leu Val  Asp Ser Asp
    1325                1330                1335

Pro Glu  Glu Val Leu Val Leu  Leu Glu Phe His Ser  His Leu Ser
    1340                1345                1350

Gly Leu  Leu Asn Lys Phe Ile  Ser Pro Lys Ser Val  Val Gly Arg
    1355                1360                1365

Phe Ala  Ala Glu Phe Lys Ser  Arg Phe Tyr Val Trp  Gly Glu Glu
    1370                1375                1380

Val Pro  Leu Leu Thr Lys Phe  Val Ser Ala Ala Leu  His Asn Val
    1385                1390                1395

Lys Cys  Lys Glu Pro His Gln  Leu Cys Glu Thr Ile  Asp Thr Ile
    1400                1405                1410
```

Ala Asp Gln Ala Ile Ala Asn Gly Val Pro Val Phe Leu Val Asn
1415 1420 1425

Cys Ile Gln Arg Arg Thr Leu Asp Leu Leu Lys Tyr Ala Asn Phe
1430 1435 1440

Pro Leu Asp Pro Phe Leu Leu Asn Thr His Thr Asp Val Lys Asp
1445 1450 1455

Trp Leu Asp Gly Ser Arg Gly Tyr Arg Ile Gln Arg Leu Ile Glu
1460 1465 1470

Glu Leu Cys Pro Ser Glu Thr Lys Ile Met Arg Lys Leu Val Arg
1475 1480 1485

Arg Leu His His Lys Leu Lys Asn Gly Glu Cys Asn Glu Glu Phe
1490 1495 1500

Phe Leu Asp Leu Phe Asn Arg Glu Lys Lys Glu Ala Ile Leu Gln
1505 1510 1515

Leu Gly Glu Ile Leu Gly Leu Glu Asp Asp Leu Asn Glu Leu Ala
1520 1525 1530

Ser Ile Asn Trp Leu Asn Leu Asn Glu Met Phe Pro Leu Arg Met
1535 1540 1545

Val Leu Arg Gln Lys Val Val Tyr Pro Ser Val Met Thr Phe Gln
1550 1555 1560

Glu Glu Lys Ile Pro Ser Leu Ile Lys Thr Leu Gln Asn Lys Leu
1565 1570 1575

Cys Ser Lys Phe Thr Arg Gly Ala Gln Lys Leu Leu Ser Glu Ala
1580 1585 1590

Ile Asn Lys Ser Ala Phe Gln Ser Cys Val Ser Ser Gly Phe Ile
1595 1600 1605

Gly Leu Cys Lys Thr Leu Gly Ser Arg Cys Val Arg Asn Lys Asn
1610 1615 1620

Arg Glu Asn Met Tyr Ile Arg Lys Val Leu Glu Asp Leu Thr Met
1625 1630 1635

Asp Glu His Val Thr Arg Val His Lys Gln Asp Gly Val Met Leu
1640 1645 1650

Tyr Ile Cys Asp Lys Gln Arg His Pro Glu Ala His Arg Asp His
1655 1660 1665

Ile Asn Leu Leu Arg Pro Leu Leu Trp Asp Tyr Ile Cys Ile Ser
1670 1675 1680

Leu Ser Asn Ser Phe Glu Leu Gly Val Trp Val Leu Ala Glu Pro
1685 1690 1695

Val Lys Gly Lys Asn Glu Ser Asn Ser Ala Val Arg His Leu Asn
1700 1705 1710

Pro Cys Asp Tyr Val Ala Arg Lys Pro Glu Ser Ser Arg Leu Leu
1715 1720 1725

Glu Asp Lys Val Ser Leu Asn His Val Ile Gln Ser Val Arg Arg
1730 1735 1740

Leu Tyr Pro Lys Ile Phe Glu Asp Gln Leu Leu Pro Phe Met Ser
1745 1750 1755

Asp Val Ser Ser Lys Asn Met Arg Trp Ser Pro Arg Ile Lys Phe
1760 1765 1770

Leu Asp Leu Cys Val Leu Ile Asp Ile Asn Ser Glu Ser Leu Ser
1775 1780 1785

Leu Ile Ser His Val Val Lys Trp Lys Arg Asp Glu His Tyr Thr
1790 1795 1800

-continued

```
Val Leu  Phe Ser Asp Leu Val  Asn Ser His Gln Arg  Ser Asp Ser
    1805                 1810                 1815

Ser Leu  Val Asp Glu Phe Val  Val Ser Thr Arg Asp  Val Cys Lys
    1820                 1825                 1830

Asn Phe  Leu Lys Gln Val Tyr  Phe Glu Ser Phe Val  Arg Glu Phe
    1835                 1840                 1845

Val Ala  Thr Ala Arg Thr Leu  Gly Asn Phe Ser Trp  Phe Pro His
    1850                 1855                 1860

Lys Asp  Met Met Pro Ser Glu  Asp Gly Ala Glu Ala  Leu Gly Pro
    1865                 1870                 1875

Phe Gln  Ser Phe Ile Leu Lys  Val Val Asn Lys Lys  Ile Glu Arg
    1880                 1885                 1890

Pro Met  Phe Arg Asn Asp Leu  Gln Phe Gly Phe Gly  Trp Phe Ser
    1895                 1900                 1905

Tyr Arg  Val Gly Asp Val Val  Cys Asn Ala Ala Met  Leu Ile Lys
    1910                 1915                 1920

Gln Gly  Leu Thr Asp Pro Lys  Ala Phe Lys Ser Leu  Arg Asp Leu
    1925                 1930                 1935

Trp Asp  Tyr Met Leu Ser Ser  Thr Glu Gly Ile Leu  Glu Phe Ser
    1940                 1945                 1950

Ile Thr  Val Asp Phe Thr His  Asn Gln Asn Asn Thr  Asp Cys Leu
    1955                 1960                 1965

Arg Lys  Phe Ser Leu Ile Phe  Val Val Lys Cys Gln  Leu Gln Ser
    1970                 1975                 1980

Pro Gly  Val Ala Asp Tyr Leu  Ser Cys Ser His Phe  Phe Lys Gly
    1985                 1990                 1995

Glu Val  Asp Arg Arg Leu Leu  Asp Glu Cys Leu Asn  Leu Leu Arg
    2000                 2005                 2010

Thr Asp  Pro Ile Phe Lys Ala  Asn Asp Gly Val Phe  Asp Ile Arg
    2015                 2020                 2025

Ser Glu  Glu Phe Glu Asp Tyr  Met Glu Asp Pro Leu  Thr Leu Gly
    2030                 2035                 2040

Asp Ser  Leu Glu Leu Glu Leu  Ile Gly Ser Arg Arg  Ile Leu Asn
    2045                 2050                 2055

Glu Ile  Lys Ser Thr Asp Phe  Glu Arg Ile Gly Pro  Glu Trp Glu
    2060                 2065                 2070

Pro Val  Pro Leu Thr Ile Arg  Lys Gly Ala Leu Phe  Glu Gly Arg
    2075                 2080                 2085

Asn Phe  Val Gln Asn Ile Ser  Val Lys Leu Glu Thr  Lys Asp Met
    2090                 2095                 2100

Arg Val  Phe Leu Ala Glu Leu  Glu Gly Cys Gly Lys  Ile Gly Asp
    2105                 2110                 2115

Val Leu  Gly Ser Leu Leu Leu  His Arg Phe Arg Thr  Gly Glu His
    2120                 2125                 2130

Leu Met  Glu Ser Glu Ile Ser  Thr Val Leu Gln Glu  Leu Cys Met
    2135                 2140                 2145

Asp Arg  Ser Val Met Leu Thr  Pro Leu Ser Phe Val  Pro Asp Trp
    2150                 2155                 2160

Phe Thr  Phe Arg Asp Cys Arg  Leu Cys Phe Ser Arg  Ser Lys Asn
    2165                 2170                 2175

Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
```

2195 2200 2205

Asp

<210> SEQ ID NO 17
<211> LENGTH: 1497
<212> TYPE: DNA
<213> ORGANISM: Lymphocytic choriomeningitis virus (mutant P42)

<400> SEQUENCE: 17
atgggtcaga ttgtgacaat gtttgaggct ttgcctcaca tcattgatga ggtcatcaac 60
attgtcatta ttgtgctcat tataatcacg agcatcaaag ctgtgtacaa tttcgccacc 120
tgtgggatat tagcactggt cagcttcctt tttttggctg gtaggtcctg tggcatgtac 180
ggccttaatg gtcccgacat ctataaaggg gtttaccagt tcaaatcagt ggagtttgat 240
atgtctcact taaatctgac gatgcccaat gcgtgctcag ccaacaactc tcatcactac 300
atcagtatgg gaagctctgg actggagcta actttcacta acgactccat ccttaatcac 360
aatttttgca acttaacctc cgctttcaac aaaaagactt ttgaccatac actcatgagt 420
atagtctcga gtctgcacct cagtattaga gggaattcca accacaaagc agtgtcttgt 480
gattttaaca atggcatcac cattcaatac aacttgtcat tttcggaccc acagagcgct 540
atgagccagt gtaggacttt cagaggtaga gtcttggaca tgtttagaac tgcctttgga 600
ggaaaataca tgagaagtgg ctggggctgg gcaggttcag atggcaagac cacttggtgc 660
agccaaacaa gctatcagta cctaatcata caaaacagga cttgggaaaa ccactgtaga 720
tatgcaggcc cttttgggat gtctagaatc ctctttgctc aggaaaagac aaagtttctc 780
actaggagac ttgcaggcac attcacctgg accctgtcag actcctcagg agtagaaaat 840
ccaggtggtt attgcctgac caaatggatg atccttgctg cagagctcaa atgttttggg 900
aatacagctg ttgcaaaatg taatgtcaat catgatgaag agttctgtga catgctacga 960
ctaattgatt acaacaaggc cgccctgagt aagttcaagc aagatgtaga gtctgccttg 1020
catgtattca aaacaacagt aaattctctg atttccgatc agctgttgat gaggaatcat 1080
ctaagagatc taatgggggt accatactgt aattactcaa agttctggta tctggaacat 1140
gctaagactg gtgagactag tgtacccaag tgctggcttg tcactaatgg ctcctacttg 1200
aatgagaccc actttagtga tcaaatcgaa caagaagcag ataacatgat cacagagatg 1260
ttgaggaagg actacataaa aagacaaggg agtactcctt tagccttaat ggatcttttg 1320
atgttttcaa catcagcata tctaatcagc atctttctgc atcttgtgaa gataccaaca 1380
catagacaca taaagggcgg ttcatgtcca aagccacacc gcttgaccaa caaggggatc 1440
tgtagttgtg gtgcattcaa ggtgcctggt gtaaaaacta tctggaaaag acgctga 1497

<210> SEQ ID NO 18
<211> LENGTH: 498
<212> TYPE: PRT
<213> ORGANISM: Lymphocytic choriomeningitis virus (mutant P42)

<400> SEQUENCE: 18

Met Gly Gln Ile Val Thr Met Phe Glu Ala Leu Pro His Ile Ile Asp
1 5 10 15

Glu Val Ile Asn Ile Val Ile Ile Val Leu Ile Ile Ile Thr Ser Ile
20 25 30

Lys Ala Val Tyr Asn Phe Ala Thr Cys Gly Ile Leu Ala Leu Val Ser
35 40 45

-continued

```
Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Met Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
```

465 470 475 480

Cys Ser Cys Gly Ala Phe Lys Val Pro Gly Val Lys Thr Ile Trp Lys
485 490 495

Arg Arg

<210> SEQ ID NO 19
<211> LENGTH: 1677
<212> TYPE: DNA
<213> ORGANISM: Lymphocytic choriomeningitis virus (mutant P42)

<400> SEQUENCE: 19
atgtctttgt ccaaagaagt caaaagcttt cagtggacac aggcgttgag gagggagttg 60
cagagtttta catcagatgt aaaggctgcc gtcatcaagg acgcaaccag tcttctaaat 120
gggttggact tttctgaagt cagcaacgtt cagaggatca tgagaaagga aaggagggat 180
gataaagact tgcagagact caggagtctt aaccagactg tgcattctct tgttgatctg 240
aagtctacat caaagaaaaa tgttctgaaa gtgggaagac ttagtgcaga ggaattgatg 300
acccttgcag ctgatcttga gaagctgaag gccaaaatta tgagaactga gaggcctcaa 360
gcttctggag tctacatggg aaatttgaca gcacaacaac ttgatcaaag atcccaaata 420
ctgcaaatgg ttgggatgag aagacctcag cagggtgcaa gtggtgtagt aagggtttgg 480
gatgtgaagg actcatcact tctgaacaat cagttcggca caatgccaag cctgacaatg 540
gcttgcatgg caaaacagtc acagacccca ctcaatgatg ttgtgcaggc actcacagac 600
cttggcttac tttacacagt caaatacccg aatctcagtg atcttgaaag gctaaaggat 660
aaacacccag ttctgggggt cattactgaa cagcaatcta gtatcaatat ctctggttat 720
aatttcagtc ttggtgcagc tgtgaaagcg ggggcagctc tgctagatgg agggaacatg 780
ctggaatcta tcttgatcaa accgagcaac agtgaggatc tcctaaaagc agtcctcggg 840
gccaagaaga aactcaacat gtttgtctca gatcaagttg gagatagaaa tccctatgaa 900
aacatccttt ataaagtctg tctttcaggt gaaggatggc catacatagc ctgtagaacg 960
tcagttgtgg ggagagcatg ggagaacaca acaattgatc tcacaaatga aaaacttgtt 1020
gccaactcat ctaggccagt gcctggagca gcaggcccac ctcaggtggg cttgagttac 1080
agtcagacaa tgctgttgaa agacttgatg ggagggattg atcccaatgc tcccacatgg 1140
attgacattg agggcaggtt caatgatcca gtggagatag caatattcca accacaaaat 1200
gggcaattca tacattttta cagggaacct acggaccaga agcaattcaa gcaggactca 1260
aagtattcac acggcatgga tcttgctgat ctcttcaatg cacagcctgg gctgacctca 1320
tcagttatag gtgctctccc acaagggatg gttttgagct gtcaaggttc tgatgacatc 1380
agaaagcttc tggactcaca aaatagaagg gacataaaac tcattgatgt tgagatgacc 1440
aaggaggcct caagagaata tgaagataaa gtgtgggaca aatatggctg gctatgcaaa 1500
atgcacactg ggtagtgag agacaaaaag aagaaagaga tcaccccaca ctgtgcactc 1560
atggactgca tcatttttga gagtgcttcc aaggcaagac tccctgatct aaaaaccgtt 1620
cacaacatcc tgccacatga tttaatcttc agaggaccca atgttgtgac actctaa 1677

<210> SEQ ID NO 20
<211> LENGTH: 558
<212> TYPE: PRT
<213> ORGANISM: Lymphocytic choriomeningitis virus (mutant P42)

<400> SEQUENCE: 20

-continued

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
```

```
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555


<210> SEQ ID NO 21
<211> LENGTH: 273
<212> TYPE: DNA
<213> ORGANISM: Lymphocytic choriomeningitis virus (mutant P42)

<400> SEQUENCE: 21

atgggccaag gcaagtccaa agaagaaagg gacaccagca atacaggcag agcagagctt      60

ttgccagaca ccacctatct tggtcctcta aattgtaaat catgttggca gaaatttgac     120

agcttggtta gatgccatga ccactatctt tgcagacact gtctgaatct cctgctgtca     180

gtttccgaca gatgtcctct ctgtaagtat ccactgccaa ccaaactgaa ggtgtcaaca     240

gtcccaagct ccccacctcc ctatgaggag tga                                  273


<210> SEQ ID NO 22
<211> LENGTH: 90
<212> TYPE: PRT
<213> ORGANISM: Lymphocytic choriomeningitis virus (mutant P42)

<400> SEQUENCE: 22

Met Gly Gln Gly Lys Ser Lys Glu Glu Arg Asp Thr Ser Asn Thr Gly
1               5                   10                  15

Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Pro Pro Pro Tyr Glu Glu
                85                  90


<210> SEQ ID NO 23
<211> LENGTH: 6630
<212> TYPE: DNA
<213> ORGANISM: Lymphocytic choriomeningitis virus (mutant P42)

<400> SEQUENCE: 23

atggatgaaa ctattgcaga tttgagagag ttgtgtctaa attacataga acaggacgag      60
```

-continued

```
aggctgtcaa ggcaaaaact caacttcctg ggacaaagag aacccagaat ggtgctaatt    120
gagggactca aattgttatc acgctgtata gagatagaca gtgcagacaa aagtggttgc    180
atacacaacc acgatgacaa atctgttgaa acaatcctaa tagactctgg gattgtgtgt    240
ccaggactgc cactcatcat ccctgatggt tataagttga ttgacaattc ccttattctt    300
cttgaatgtt ttgttagaag cacaccagct agttttgaaa agaagttcat tgaggacacc    360
aacaaactag catgcatcaa agaagatctt gctgttgcag gcatcacact ggttccaata    420
gtggatggtc gttgtgatta tgataacagt ttcatgccag aatgggtgaa ttttaagttc    480
agagacctcc tatttaaact cctggagtat tctagtcaag atgagaaagt tttgaggag     540
tctgaatact tcaggctctg tgagtctctt aagaccactg ttgacaaacg ttccggcatg    600
gactcaatga aaattttgaa agacgcaaga tcatttcata acgatgagat tatgaaaatg    660
tgccacgatg gtgtcaaccc caacatgagt tgcgatgatg tggtctttgg cataaattcc    720
tttttggca ggtttaggag ggacctgtta aatgggaaac tcaaaaggaa tttccaaaag     780
gtcagccctg gggcttaat caaggaattc tctgaacttt atgaaaccct tactgataat     840
gatgacatat taatgttgag caaagaggca gttgaatcct gcccccttaat gaggttcatt   900
acagcagaga cccatgggca tgagagagga agcgatgcta acactgagta tgaaaggcta    960
ctctctatgt tgaacaaggt gaaaagttta aaattattaa acactagaag gagacagctg   1020
ctgaacttag atgtcttatg tctttcttca cttattaagc agtcaatttc caaagggttg   1080
gaaaatgata aacattgggt tggttgttgc tacagtagtg tgaatgatag gcttgtgagc   1140
cttcaaagta ccaaagaaga attcatgaga cttttgaaga acagaagaaa atcaagagtg   1200
cacaaaaagg catctcttga tgagcttttt agggtatcca taaatgagtt catagcaaaa   1260
atccagaaat gcctatcaac agtgggactt agttttgagc attacggact atcagaatgc   1320
ctcgtgcaag aatgccatat accatttgct gaatttgaga actttatgag agccgggact   1380
catcctgtaa tgcattacac aaaatttgaa gattacactt tccagcctaa catagagcaa   1440
ttgaggggtt tacagagttt gagaaaactg tcatctgttt gtttggctct aacaaacagc   1500
atgaaaacaa gctcagttgc aaggttgaga cagaaccaac tggggtctgt gagatatcaa   1560
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaacccctg gtgttaattt agagatcttt agcatgatgg tatcttcatt caacaatggc   2340
accttaattc taaaagggga gaaaaggctc aacaatctgg accccatgac caactctgga   2400
```

-continued tgtgcgacag cattagatct cgcaagcaac aaaagtgtgg ttgtcaataa acatctgaat 2460
ggagaacggc ttttggagta tgattttaac aaattgcttg ttagtgctgt gagccaaatt 2520
acagagggct tcatgaggaa acaaaagtat aagctgagac actcagatta cgaatataag 2580
gtctcaaagc ttgtctctag attagtcatc ggttccagga aacagaagt agacaaattg 2640
gaagatgatc cggtagatgt gtgtttcgag ggggaggagg agacaagttt tttcaggagt 2700
ttagaagata aggtcagctc cacaataaca cggtataata gaggcactag gcttaatgaa 2760
gggcaagggg agggagaatt caagaacaca aaaggactac accaccttca gattattttg 2820
tcaggtaaaa gagcttatct gaggaaagtc attttatcag aaatttcatt tcatctagta 2880
gaggactttg atccatcctg tctcaccaat gacgacatga ggtttatttg tgaggctgtt 2940
gaaggttcaa cagaactgtc accattgtat tttacatcag ctgtcaaaga acaatgtggt 3000
ctggatgaga tggcaagaaa cctctgtaga aagttcttct cagagggtga ttggttctca 3060
tgtatgaaga tgatcttgtt acagatgaat gcaaatgcgt attcagggaa gtacagacac 3120
atgcagaggc agagcttaaa ttttaaattt gactgggaca aattggaaga agatgtaaga 3180
attagtgaaa gggaaagcaa ttctgaatct ctaagtaagg ccctttcatt gacaaaatgc 3240
atgagtgctg ctctaaagaa tctgtgtttt tactcagaag aatcaccaac atcatacact 3300
tcagttggcc ctgactctgg gagactaaaa tttgcattgt catacaaaga gcaggttggg 3360
ggaaatagag agctttacat tggggatttg aggacaaaaa tgttcacaag attggtagaa 3420
gattattttg aatccttttc tagtttcttt tcaggatctt gtttaaacaa tgacaaagag 3480
tttgaaaatg caatcttgtc aatgactatc aatgtgagag aagggttgtt aaactacagc 3540
atggatcaca gcaaatgggg accaatgatg tgcccattcc tattcttaat gctyctccaa 3600
aatctcaaac tgggtgatga tcagtacgtg cgttctggaa aagatcatgt tagcaccttg 3660
ttgacttggc atatgcataa acttgttgaa gtccctttcc ctgttgtgaa tgcaatgatg 3720
aaatcatatg ttaaatcaaa actcaagctt ctcaaagggt caggaacgac tgttacggag 3780
agaatcttta gagagtattt tgaaatgggg gtggtgccat ctcacatatc tagtctcatt 3840
gacatgggac aggggatcct acacaatgct tctgattttt acggtttaat tagtgaaagg 3900
tttatcaatt attgtattgg tgtcattttt ggagagaggc cagaagccta tacatcaagt 3960
gatgatcaga tcactttatt tgacaagaga ttgagtgact tagttgatag tgacccagaa 4020
gaagtccttg tcttgctgga attccactct cacttaagtg gtttgttgaa caagttcatc 4080
agtccaaaaa gtgtggttgg gcggtttgca gcggaattca aatccagatt ttatgtgtgg 4140
ggggaggagg tccctctcct cacgaaattt gtgtctgcgg cactacacaa tgttaagtgt 4200
aaagaaccgc atcaactttg tgagacaata gatacgattg ctgatcaagc tatagcaaat 4260
ggagttccag ttttttagt aaactgtatc cagaggagga cactggatct cttgaaatat 4320
gctaatttcc ctttagatcc attcttgtta aacactcaca ctgatgtaaa ggattggtta 4380
gatggttcta gaggttatag aatccaaaga ctcattgaag aattgtgtcc cagtgaaaca 4440
aagatcatga gaaaacttgt aagaagacta catcacaaac tcaagaacgg tgaatgtaac 4500
gaggaatttt ttctagacct cttcaacagg gaaaagaaag aggccatcct tcaattggga 4560
gagattcttg gtcttgagga tgatcttaat gagttggcaa gcatcaattg gttgaatctg 4620
aatgaaatgt tcccattgag gatggttctg agacaaaaag tggtttaccc atcagtratg 4680
acctttcaag aggaaaagat cccctcattg attaaaacac tccaaaataa gctttgtagt 4740
aagttcacaa gaggtgcaca gaagctgttg tcagaggcaa tcaacaaatc agcttttcag 4800

```
agttgtgtct catccggctt tataggtctc tgtaagactt taggaagtag gtgtgtgaga   4860

aataaaaaca gggaaaatat gtatatcaga aaggtgcttg aagatctgac catggatgaa   4920

catgtcacaa gggttcacaa acaagatggt gtgatgttgt acatttgcga caagcagaga   4980

cacccagagg ctcaccgtga ccacatcaac cttttgaggc cccttctctg ggactacatt   5040

tgcatctcat tgagcaactc ttttgagctg ggtgtttggg ttttagcaga acctgtgaaa   5100

ggaaagaacg agagtaattc ggctgttagg cacttaaatc catgtgatta tgtagcaaga   5160

aaacctgaga gttcgagact actagaggat aaagtgagtt tgaatcatgt aattcaatct   5220

gtgaggcgac tgtaccccaa aatctttgag gatcagttgc tcccattcat gtttgatgtg   5280

agctcaaaaa atatgagatg gagtcccagg attaaattcc ttgacctttg tgtgctgatt   5340

gacatcaact cagagtcttt gtcactcatt tctcatgttg tcaaatggaa gagggacgaa   5400

cattacactg tgctgttttc tgatctcgtc aactctcacc aacggtcaga ctcaagttta   5460

gttgatgaat ttgttgtcag cacaagggat gtctgcaaga actttttgaa gcaagtgtat   5520

ttcgaatcat ttgtacgaga gtttgttgca acagctagga ccttaggtaa cttttcatgg   5580

ttcccccata aggacatgat gccatctgaa gatggcgctg aagcactggg acccttccaa   5640

tcatttattt tgaaagtggt gaacaagaaa atagagaggc ccatgtttag gaatgacttg   5700

cagtttggtt ttggttggtt ctcttatcgt gtgggggatg ttgtgtgtaa tgccgctatg   5760

ttaattaagc agggtttgac agatccaaaa gcatttaaat ctttaagaga tttgtgggat   5820

tacatgctca gcagcacaga ggggatattg gagttctcaa tcacagtgga tttcacacac   5880

aaccagaaca acactgactg cttgaggaaa ttttcattga tctttgtggt taaatgccaa   5940

ttacagagtc caggtgtagc tgattactta tcgtgctctc atttcttcaa aggtgaggtt   6000

gacaggagat tattagatga gtgtctcaat ctgttgagga cagaccccat ctttaaagcg   6060

aatgatggag tctttgacat taggtctgaa gagtttgaag attacatgga agaccctttg   6120

acacttggtg attcactaga acttgaacta ataggttcta gaaggattct gaatgagatc   6180

aaatctactg actttgagag gatagggcct gagtgggaac ctgtgcctct gaccataagg   6240

aagggtgccc tctttgaggg gaggaacttt gttcagaata tctctgtgaa attggagaca   6300

aaggacatga grgtctttct ggcagagctc gagggctgtg gaaaaattgg tgatgtcctc   6360

ggcagcctcc tcctgcaccg attcagaact ggtgagcact tgatggagtc agaaataagt   6420

acagttcttc aggagctctg catggacaga tccgtcatgc tgacaccatt atcttttgtg   6480

ccagattggt tcaccttcag agattgtagg ctctgcttca gcaggtcaaa gaacactgtr   6540

atgtatgaga caactggggg caggttcaga ctcaagggga aatcctgtga cgattggctg   6600

gcggagcggg tggccgagga gatcgactag                                    6630
```

<210> SEQ ID NO 24
<211> LENGTH: 2209
<212> TYPE: PRT
<213> ORGANISM: Lymphocytic choriomeningitis virus (mutant P42)

<400> SEQUENCE: 24

```
Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45
```

```
Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460
```

-continued

```
His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
```

-continued

```
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
    1010                1015                1020

Met Ile  Leu Leu Gln Met Asn  Ala Asn Ala Tyr Ser  Gly Lys Tyr
    1025                1030                1035

Arg His  Met Gln Arg Gln Ser  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Lys Cys  Met Ser Ala
    1070                1075                1080

Ala Leu  Lys Asn Leu Cys Phe  Tyr Ser Glu Glu Ser  Pro Thr Ser
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125

Asp Leu  Arg Thr Lys Met Phe  Thr Arg Leu Val Glu  Asp Tyr Phe
    1130                1135                1140

Glu Ser  Phe Ser Ser Phe Phe  Ser Gly Ser Cys Leu  Asn Asn Asp
    1145                1150                1155

Lys Glu  Phe Glu Asn Ala Ile  Leu Ser Met Thr Ile  Asn Val Arg
    1160                1165                1170

Glu Gly  Leu Leu Asn Tyr Ser  Met Asp His Ser Lys  Trp Gly Pro
    1175                1180                1185

Met Met  Cys Pro Phe Leu Phe  Leu Met Leu Leu Gln  Asn Leu Lys
    1190                1195                1200

Leu Gly  Asp Asp Gln Tyr Val  Arg Ser Gly Lys Asp  His Val Ser
    1205                1210                1215

Thr Leu  Leu Thr Trp His Met  His Lys Leu Val Glu  Val Pro Phe
    1220                1225                1230

Pro Val  Val Asn Ala Met Met  Lys Ser Tyr Val Lys  Ser Lys Leu
    1235                1240                1245

Lys Leu  Leu Lys Gly Ser Gly  Thr Thr Val Thr Glu  Arg Ile Phe
    1250                1255                1260

Arg Glu  Tyr Phe Glu Met Gly  Val Val Pro Ser His  Ile Ser Ser
    1265                1270                1275

Leu Ile  Asp Met Gly Gln Gly  Ile Leu His Asn Ala  Ser Asp Phe
    1280                1285                1290
```

-continued

```
Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
    1415                 1420                 1425

Cys Ile  Gln Arg Arg Thr Leu  Asp Leu Leu Lys Tyr  Ala Asn Phe
    1430                 1435                 1440

Pro Leu  Asp Pro Phe Leu Leu  Asn Thr His Thr Asp  Val Lys Asp
    1445                 1450                 1455

Trp Leu  Asp Gly Ser Arg Gly  Tyr Arg Ile Gln Arg  Leu Ile Glu
    1460                 1465                 1470

Glu Leu  Cys Pro Ser Glu Thr  Lys Ile Met Arg Lys  Leu Val Arg
    1475                 1480                 1485

Arg Leu  His His Lys Leu Lys  Asn Gly Glu Cys Asn  Glu Glu Phe
    1490                 1495                 1500

Phe Leu  Asp Leu Phe Asn Arg  Glu Lys Lys Glu Ala  Ile Leu Gln
    1505                 1510                 1515

Leu Gly  Glu Ile Leu Gly Leu  Glu Asp Asp Leu Asn  Glu Leu Ala
    1520                 1525                 1530

Ser Ile  Asn Trp Leu Asn Leu  Asn Glu Met Phe Pro  Leu Arg Met
    1535                 1540                 1545

Val Leu  Arg Gln Lys Val Val  Tyr Pro Ser Val Met  Thr Phe Gln
    1550                 1555                 1560

Glu Glu  Lys Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Val Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Met Tyr Ile Arg  Lys Val Leu Glu Asp  Leu Thr Met
    1625                 1630                 1635

Asp Glu  His Val Thr Arg Val  His Lys Gln Asp Gly  Val Met Leu
    1640                 1645                 1650

Tyr Ile  Cys Asp Lys Gln Arg  His Pro Glu Ala His  Arg Asp His
    1655                 1660                 1665

Ile Asn  Leu Leu Arg Pro Leu  Leu Trp Asp Tyr Ile  Cys Ile Ser
    1670                 1675                 1680
```

```
Leu Ser  Asn Ser Phe Glu Leu  Gly Val Trp Val Leu  Ala Glu Pro
    1685                 1690                 1695

Val Lys  Gly Lys Asn Glu Ser  Asn Ser Ala Val Arg  His Leu Asn
    1700                 1705                 1710

Pro Cys  Asp Tyr Val Ala Arg  Lys Pro Glu Ser Ser  Arg Leu Leu
    1715                 1720                 1725

Glu Asp  Lys Val Ser Leu Asn  His Val Ile Gln Ser  Val Arg Arg
    1730                 1735                 1740

Leu Tyr  Pro Lys Ile Phe Glu  Asp Gln Leu Leu Pro  Phe Met Phe
    1745                 1750                 1755

Asp Val  Ser Ser Lys Asn Met  Arg Trp Ser Pro Arg  Ile Lys Phe
    1760                 1765                 1770

Leu Asp  Leu Cys Val Leu Ile  Asp Ile Asn Ser Glu  Ser Leu Ser
    1775                 1780                 1785

Leu Ile  Ser His Val Val Lys  Trp Lys Arg Asp Glu  His Tyr Thr
    1790                 1795                 1800

Val Leu  Phe Ser Asp Leu Val  Asn Ser His Gln Arg  Ser Asp Ser
    1805                 1810                 1815

Ser Leu  Val Asp Glu Phe Val  Val Ser Thr Arg Asp  Val Cys Lys
    1820                 1825                 1830

Asn Phe  Leu Lys Gln Val Tyr  Phe Glu Ser Phe Val  Arg Glu Phe
    1835                 1840                 1845

Val Ala  Thr Ala Arg Thr Leu  Gly Asn Phe Ser Trp  Phe Pro His
    1850                 1855                 1860

Lys Asp  Met Met Pro Ser Glu  Asp Gly Ala Glu Ala  Leu Gly Pro
    1865                 1870                 1875

Phe Gln  Ser Phe Ile Leu Lys  Val Val Asn Lys Lys  Ile Glu Arg
    1880                 1885                 1890

Pro Met  Phe Arg Asn Asp Leu  Gln Phe Gly Phe Gly  Trp Phe Ser
    1895                 1900                 1905

Tyr Arg  Val Gly Asp Val Val  Cys Asn Ala Ala Met  Leu Ile Lys
    1910                 1915                 1920

Gln Gly  Leu Thr Asp Pro Lys  Ala Phe Lys Ser Leu  Arg Asp Leu
    1925                 1930                 1935

Trp Asp  Tyr Met Leu Ser Ser  Thr Glu Gly Ile Leu  Glu Phe Ser
    1940                 1945                 1950

Ile Thr  Val Asp Phe Thr His  Asn Gln Asn Asn Thr  Asp Cys Leu
    1955                 1960                 1965

Arg Lys  Phe Ser Leu Ile Phe  Val Val Lys Cys Gln  Leu Gln Ser
    1970                 1975                 1980

Pro Gly  Val Ala Asp Tyr Leu  Ser Cys Ser His Phe  Phe Lys Gly
    1985                 1990                 1995

Glu Val  Asp Arg Arg Leu Leu  Asp Glu Cys Leu Asn  Leu Leu Arg
    2000                 2005                 2010

Thr Asp  Pro Ile Phe Lys Ala  Asn Asp Gly Val Phe  Asp Ile Arg
    2015                 2020                 2025

Ser Glu  Glu Phe Glu Asp Tyr  Met Glu Asp Pro Leu  Thr Leu Gly
    2030                 2035                 2040

Asp Ser  Leu Glu Leu Glu Leu  Ile Gly Ser Arg Arg  Ile Leu Asn
    2045                 2050                 2055

Glu Ile  Lys Ser Thr Asp Phe  Glu Arg Ile Gly Pro  Glu Trp Glu
    2060                 2065                 2070

Pro Val  Pro Leu Thr Ile Arg  Lys Gly Ala Leu Phe  Glu Gly Arg
```

-continued

```
    2075                 2080                 2085

Asn Phe  Val Gln Asn Ile Ser  Val Lys Leu Glu Thr  Lys Asp Met
    2090                 2095                 2100

Arg Val  Phe Leu Ala Glu Leu  Glu Gly Cys Gly Lys  Ile Gly Asp
    2105                 2110                 2115

Val Leu  Gly Ser Leu Leu Leu  His Arg Phe Arg Thr  Gly Glu His
    2120                 2125                 2130

Leu Met  Glu Ser Glu Ile Ser  Thr Val Leu Gln Glu  Leu Cys Met
    2135                 2140                 2145

Asp Arg  Ser Val Met Leu Thr  Pro Leu Ser Phe Val  Pro Asp Trp
    2150                 2155                 2160

Phe Thr  Phe Arg Asp Cys Arg  Leu Cys Phe Ser Arg  Ser Lys Asn
    2165                 2170                 2175

Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp


<210> SEQ ID NO 25
<211> LENGTH: 1497
<212> TYPE: DNA
<213> ORGANISM: Lymphocytic choriomeningitis virus (mutant P52)

<400> SEQUENCE: 25

atgggtcaga ttgtgacaat gtttgaggct ttgcctcaca tcattgatga ggtcatcaac     60

attgtcatta ttgtgctcat tataatcacg agcatcaaag ctgtgtacaa tttcgccacc    120

tgtgggatat tagcactggt cagcttcctt tttttggctg gtaggtcctg tggcatgtac    180

ggccttaatg gtcccgacat ctataaaggg gtttaccagt tcaaatcagt ggagtttgat    240

atgtctcact taaatctgac gatgcccaat gcgtgctcag ccaacaactc tcatcactac    300

atcagtatgg gaagctctgg actggagcta actttcacta acgactccat ccttaatcac    360

aatttttgca acttaacctc cgctttcaac aaaaagactt ttgaccatac actcatgagt    420

atagtctcga gtctgcacct cagtattaga gggaattcca accacaaagc agtgtcttgt    480

gattttaaca atggcatcac cattcaatac aacttgtcat tttcggaccc acagagcgct    540

atgagccagt gttggacttt cagaggtaga gtcttggaca tgtttagaac tgcctttgga    600

ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aatacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140

gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320
```

-continued atgttttcaa catcagcata tctaatcagc atctttctgc atcttgtgaa gataccaaca 1380
catagacaca taaagggcgg ttcatgtcca aagccacacc gcttgaccaa caaggggatc 1440
tgtagttgtg gtgcattcaa ggtgcctggt gtaaaaacta tctggaaaag acgctga 1497

<210> SEQ ID NO 26
<211> LENGTH: 498
<212> TYPE: PRT
<213> ORGANISM: Lymphocytic choriomeningitis virus (mutant P52)

<400> SEQUENCE: 26

Met Gly Gln Ile Val Thr Met Phe Glu Ala Leu Pro His Ile Ile Asp
1 5 10 15

Glu Val Ile Asn Ile Val Ile Ile Val Leu Ile Ile Ile Thr Ser Ile
20 25 30

Lys Ala Val Tyr Asn Phe Ala Thr Cys Gly Ile Leu Ala Leu Val Ser
35 40 45

Phe Leu Phe Leu Ala Gly Arg Ser Cys Gly Met Tyr Gly Leu Asn Gly
50 55 60

Pro Asp Ile Tyr Lys Gly Val Tyr Gln Phe Lys Ser Val Glu Phe Asp
65 70 75 80

Met Ser His Leu Asn Leu Thr Met Pro Asn Ala Cys Ser Ala Asn Asn
85 90 95

Ser His His Tyr Ile Ser Met Gly Ser Ser Gly Leu Glu Leu Thr Phe
100 105 110

Thr Asn Asp Ser Ile Leu Asn His Asn Phe Cys Asn Leu Thr Ser Ala
115 120 125

Phe Asn Lys Lys Thr Phe Asp His Thr Leu Met Ser Ile Val Ser Ser
130 135 140

Leu His Leu Ser Ile Arg Gly Asn Ser Asn His Lys Ala Val Ser Cys
145 150 155 160

Asp Phe Asn Asn Gly Ile Thr Ile Gln Tyr Asn Leu Ser Phe Ser Asp
165 170 175

Pro Gln Ser Ala Met Ser Gln Cys Trp Thr Phe Arg Gly Arg Val Leu
180 185 190

Asp Met Phe Arg Thr Ala Phe Gly Gly Lys Tyr Met Arg Ser Gly Trp
195 200 205

Gly Trp Ala Gly Ser Asp Gly Lys Thr Thr Trp Cys Ser Gln Thr Ser
210 215 220

Tyr Gln Tyr Leu Ile Ile Gln Asn Arg Thr Trp Glu Asn His Cys Arg
225 230 235 240

Tyr Ala Gly Pro Phe Gly Met Ser Arg Ile Leu Phe Ala Gln Glu Lys
245 250 255

Thr Lys Phe Leu Thr Arg Arg Leu Ala Gly Thr Phe Thr Trp Thr Leu
260 265 270

Ser Asp Ser Ser Gly Val Glu Asn Pro Gly Gly Tyr Cys Leu Thr Lys
275 280 285

Trp Met Ile Leu Ala Ala Glu Leu Lys Cys Phe Gly Asn Thr Ala Val
290 295 300

Ala Lys Cys Asn Val Asn His Asp Glu Glu Phe Cys Asp Met Leu Arg
305 310 315 320

Leu Ile Asp Tyr Asn Lys Ala Ala Leu Ser Lys Phe Lys Gln Asp Val
325 330 335

Glu Ser Ala Leu His Val Phe Lys Thr Thr Val Asn Ser Leu Ile Ser

-continued

```
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg
```

<210> SEQ ID NO 27
<211> LENGTH: 1677
<212> TYPE: DNA
<213> ORGANISM: Lymphocytic choriomeningitis virus (mutant P52)

<400> SEQUENCE: 27

```
atgtctttgt ccaaagaagt caaaagcttt cagtggacac aggcgttgag gagggagttg     60

cagagtttta catcagatgt aaaggctgcc gtcatcaagg acgcaaccag tcttctaaat    120

gggttggact tttctgaagt cagcaacgtt cagaggatca tgagaaagga aaggagggat    180

gataaagact tgcagagact caggagtctt aaccagactg tgcattctct tgttgatctg    240

aagtctacat caaagaaaaa tgttctgaaa gtgggaagac ttagtgcaga ggaattgatg    300

acccttgcag ctgatcttga gaagctgaag gccaaaatta tgagaactga gaggcctcaa    360

gcttctggag tctacatggg aaatttgaca gcacaacaac ttgatcaaag atcccaaata    420

ctgcaaatgg ttgggatgag aagacctcag cagggtgcaa gtggtgtagt aagggtttgg    480

gatgtgaagg actcatcact tctgaacaat cagttcggca caatgccaag cctgacaatg    540

gcttgcatgg caaaacagtc acagacccca ctcaatgatg ttgtgcaggc actcacagac    600

cttggcttac tttacacagt caaatacccg aatctcagtg atcttgaaag gctaaaggat    660

aaacacccag ttctgggggt cattactgaa cagcaatcta gtatcaatat ctctggttat    720

aatttcagtc ttggtgcagc tgtgaaagcg ggggcagctc tgctagatgg agggaacatg    780

ctggaatcta tcttgatcaa accgagcaac agtgaggatc tcctaaaagc agtcctcggg    840

gccaagaaga aactcaacat gtttgtctca gatcaagttg gagatagaaa tccctatgaa    900

aacatccttt ataaagtctg tctttcaggt gaaggatggc catacatagc ctgtagaacg    960

tcagttgtgg ggagagcatg ggagaacaca acaattgatc tcacaaatga aaaacttgtt   1020

gccaactcat ctaggccagt gcctggagca gcaggcccac ctcaggtggg cttgagttac   1080

agtcagacaa tgctgttgaa agacttgatg ggagggattg atcccaatgc tcccacatgg   1140

attgacattg agggcaggtt caatgatcca gtggagatag caatattcca accacaaaat   1200
```

-continued

```
gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaayagaagg gacataaaac tcattgatgt tgagatgacc   1440

aaggaggcct caagagaata tgaagataaa gtgtgggaca aatatggctg gctatgcaaa   1500

atgcacactg gggtagtgag agacaaaaag aagaaagaga tcaccccaca ctgtgcactc   1560

atggactgca tcatttttga gagtgcttcc aaggcaagac tccctgatct aaaaaccgtt   1620

cacaacatcc tgccacatga tttaatcttc agaggaccca atgttgtgac actctaa      1677


<210> SEQ ID NO 28
<211> LENGTH: 558
<212> TYPE: PRT
<213> ORGANISM: Lymphocytic choriomeningitis virus (mutant P52)

<400> SEQUENCE: 28

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
```

```
            290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

<210> SEQ ID NO 29
<211> LENGTH: 273
<212> TYPE: DNA
<213> ORGANISM: Lymphocytic choriomeningitis virus (mutant P52)

<400> SEQUENCE: 29

```
atgggccaag gcaagtccaa agaagaaagg gacaccagca atacaggcag agcagagctt      60

ttgccagaca ccacctatct tggtcctcta aattgtaaat catgttggca gaaatttgac     120

agcttggtta gatgccatga ccactatctt tgcagacact gtctgaatct cctgctgtca     180

gtttccgaca gatgtcctct ctgtaagtat ccactgccaa ccaaactgaa ggtgtcaaca     240

gtcccaagct ccccacctcc ctatgaggag tga                                  273
```

<210> SEQ ID NO 30
<211> LENGTH: 90
<212> TYPE: PRT
<213> ORGANISM: Lymphocytic choriomeningitis virus (mutant P52)

<400> SEQUENCE: 30

```
Met Gly Gln Gly Lys Ser Lys Glu Glu Arg Asp Thr Ser Asn Thr Gly
1               5                   10                  15
```

```
Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Pro Pro Pro Tyr Glu Glu
                85                  90


<210> SEQ ID NO 31
<211> LENGTH: 6630
<212> TYPE: DNA
<213> ORGANISM: Lymphocytic choriomeningitis virus (mutant P52)

<400> SEQUENCE: 31

atggatgaaa ctattgcaga tttgagagag ttgtgtctaa attacataga acaggacgag      60

aggctgtcaa ggcaaaaact caacttcctg ggacaaagag aacccagaat ggtgctaatt     120

gagggactca aattgttatc acgctgtata gagatagaca gtgcagacaa aagtggttgc     180

atacacaacc acgatgacaa atctgttgaa acaatcctaa tagactctgg gattgtgtgt     240

ccaggactgc cactcatcat ccctgatggt tataagttga ttgacaattc ccttattctt     300

cttgaatgtt ttgttagaag cacaccagct agttttgaaa agaagttcat tgaggacacc     360

aacaaactag catgcatcaa agaagatctt gctgttgcag gcatcacact ggttccaata     420

gtggatggtc gttgtgatta tgataacagt ttcatgccag aatgggtgaa ttttaagttc     480

agagacctcc tatttaaact cctggagtat tctagtcaag atgagaaagt ttttgaggag     540

tctgaatact tcaggctctg tgagtctctt aagaccactg ttgacaaacg ttccggcatg     600

gactcaatga aaattttgaa agacgcaaga tcatttcata acgatgagat tatgaaaatg     660

tgccacgatg gtgtcaaccc caacatgagt tgcgatgatg tggtctttgg cataaattcc     720

ttttttggca ggtttaggag ggacctgtta aatgggaaac tcaaaaggaa tttccaaaag     780

gtcagccctg gggcttaat caaggaattc tctgaacttt atgaaaccct tactgataat      840

gatgacatat taatgttgag caaagaggca gttgaatcct gcccccttaat gaggttcatt    900

acagcagaga cccatgggca tgagagagga agcgatgcta acactgagta tgaaaggcta     960

ctctctatgt tgaacaaggt gaaaagttta aaattattaa acactagaag gagacagctg    1020

ctgaacttag atgtcttatg tctttcttca cttattaagc agtcaatttc caaagggttg    1080

gaaaatgata aacattgggt tggttgttgc tacagtagtg tgaatgatag gcttgtgagc    1140

cttcaaagta ccaaagaaga attcatgaga cttttgaaga acagaagaaa atcaagagtg    1200

cacaaaaagg catctcttga tgagcttttt agggtatcca taaatgagtt catagcaaaa    1260

atccagaaat gcctatcaac agtgggactt agttttgagc attacggact atcagaatgc    1320

ctcgtgcaag aatgccatat accatttgct gaatttgaga actttatgag agccgggact    1380

catcctgtaa tgcattacac aaaatttgaa gattacactt tccagcctaa catagagcaa    1440

ttgaggggtt tacagagttt gagaaaactg tcatctgttt gtttggctct aacaaacagc    1500

atgaaaacaa gctcagttgc aaggttgaga cagaaccaac tggggtctgt gagatatcaa    1560

gtggtggagt gcaaagaggt gttttgccag ataataaaac tggattccga agagtatcat    1620

ctactatatc agaaaactgg agaatcatcg aggtgttatt ccatacaagg tccggatggt    1680
```

-continued

```
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg trtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaacccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aaacagaagt agacaaattg   2640
gaagatgatc cggtagatgt gtgtttcgag gggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
```

-continued

```
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag tttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
ttcccccata aggacatgat gccatctgaa gatggcgctg aagcactggg acccttccaa   5640
tcatttattt tgaaagtggt gaacaagaaa atagagaggc ccatgtttag gaatgacttg   5700
cagtttggtt ttggttggtt ctcttatcgt gtgggggatg ttgtgtgtaa tgccgctatg   5760
ttaattaagc agggtttgac agatccaaaa gcatttaaat ctttaagaga tttgtgggat   5820
tacatgctca gcagcacaga ggggatattg gagttctcaa tcacagtgga tttcacacac   5880
aaccagaaca acactgactg cttgaggaaa ttttcattga tctttgtggt taaatgccaa   5940
ttacagagtc caggtgtagc tgattactta tcgtgctctc attccttcaa aggtgaggtt   6000
gacaggagat tattagatga gtgtctcaat ctgttgagga cagaccccat ctttaaagcg   6060
aatgatggag tctttgacat taggtctgaa gagtttgaag attacatgga agaccctttg   6120
acacttggtg attcactaga acttgaacta ataggttcta gaaggattct gaatgagatc   6180
aaatctactg actttgagag gatagggcct gagtgggaac ctgtgcctct gaccataagg   6240
aagggtgccc tctttgaggg gaggaacttt gttcagaatr tctctgtgaa attggagaca   6300
aaggacatga gggtctttct ggcagagctc gagggctgtg gaaaaattgg tgatgtcctc   6360
ggcagcctcc tcctgcaccg attcagaact ggtgagcact tgatggagtc agaaataagt   6420
```

rcagttcttc aggagctctg catggacaga tccgtcatgc tgacaccatt atcttttgtg 6480
ccagattggt tcaccttcag agattgtagg ctctgcttca gcaggtcaaa gaacactgta 6540
atgtatgaga caactggggg caggttcaga ctcaagggga aatcctgtga cgattggctg 6600
gcggagcggg tggccgagga gatcgactag 6630

<210> SEQ ID NO 32
<211> LENGTH: 2209
<212> TYPE: PRT
<213> ORGANISM: Lymphocytic choriomeningitis virus (mutant P52)
<220> FEATURE:
<221> NAME/KEY: MISC_FEATURE
<222> LOCATION: (2094)..(2094)
<223> OTHER INFORMATION: Xaa can be Ile or Val
<220> FEATURE:
<221> NAME/KEY: MISC_FEATURE
<222> LOCATION: (2141)..(2141)
<223> OTHER INFORMATION: Xaa can be Thr or Ala

<400> SEQUENCE: 32

Met Asp Glu Thr Ile Ala Asp Leu Arg Glu Leu Cys Leu Asn Tyr Ile
1 5 10 15

Glu Gln Asp Glu Arg Leu Ser Arg Gln Lys Leu Asn Phe Leu Gly Gln
20 25 30

Arg Glu Pro Arg Met Val Leu Ile Glu Gly Leu Lys Leu Leu Ser Arg
35 40 45

Cys Ile Glu Ile Asp Ser Ala Asp Lys Ser Gly Cys Ile His Asn His
50 55 60

Asp Asp Lys Ser Val Glu Thr Ile Leu Ile Asp Ser Gly Ile Val Cys
65 70 75 80

Pro Gly Leu Pro Leu Ile Ile Pro Asp Gly Tyr Lys Leu Ile Asp Asn
85 90 95

Ser Leu Ile Leu Leu Glu Cys Phe Val Arg Ser Thr Pro Ala Ser Phe
100 105 110

Glu Lys Lys Phe Ile Glu Asp Thr Asn Lys Leu Ala Cys Ile Lys Glu
115 120 125

Asp Leu Ala Val Ala Gly Ile Thr Leu Val Pro Ile Val Asp Gly Arg
130 135 140

Cys Asp Tyr Asp Asn Ser Phe Met Pro Glu Trp Val Asn Phe Lys Phe
145 150 155 160

Arg Asp Leu Leu Phe Lys Leu Leu Glu Tyr Ser Ser Gln Asp Glu Lys
165 170 175

Val Phe Glu Glu Ser Glu Tyr Phe Arg Leu Cys Glu Ser Leu Lys Thr
180 185 190

Thr Val Asp Lys Arg Ser Gly Met Asp Ser Met Lys Ile Leu Lys Asp
195 200 205

Ala Arg Ser Phe His Asn Asp Glu Ile Met Lys Met Cys His Asp Gly
210 215 220

Val Asn Pro Asn Met Ser Cys Asp Asp Val Val Phe Gly Ile Asn Ser
225 230 235 240

Phe Phe Gly Arg Phe Arg Arg Asp Leu Leu Asn Gly Lys Leu Lys Arg
245 250 255

Asn Phe Gln Lys Val Ser Pro Gly Gly Leu Ile Lys Glu Phe Ser Glu
260 265 270

Leu Tyr Glu Thr Leu Thr Asp Asn Asp Asp Ile Leu Met Leu Ser Lys
275 280 285

Glu Ala Val Glu Ser Cys Pro Leu Met Arg Phe Ile Thr Ala Glu Thr

```
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720
```

-continued

```
Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                 1005

Cys Arg  Lys Phe Phe Ser Glu  Gly Asp Trp Phe Ser  Cys Met Lys
    1010                 1015                 1020

Met Ile  Leu Leu Gln Met Asn  Ala Asn Ala Tyr Ser  Gly Lys Tyr
    1025                 1030                 1035

Arg His  Met Gln Arg Gln Ser  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125
```

-continued

```
Asp Leu  Arg Thr Lys Met Phe  Thr Arg Leu Val Glu  Asp Tyr Phe
    1130                 1135                 1140

Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260

Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
    1415                 1420                 1425

Cys Ile  Gln Arg Arg Thr Leu  Asp Leu Leu Lys Tyr  Ala Asn Phe
    1430                 1435                 1440

Pro Leu  Asp Pro Phe Leu Leu  Asn Thr His Thr Asp  Val Lys Asp
    1445                 1450                 1455

Trp Leu  Asp Gly Ser Arg Gly  Tyr Arg Ile Gln Arg  Leu Ile Glu
    1460                 1465                 1470

Glu Leu  Cys Pro Ser Glu Thr  Lys Ile Met Arg Lys  Leu Val Arg
    1475                 1480                 1485

Arg Leu  His His Lys Leu Lys  Asn Gly Glu Cys Asn  Glu Glu Phe
    1490                 1495                 1500

Phe Leu  Asp Leu Phe Asn Arg  Glu Lys Lys Glu Ala  Ile Leu Gln
    1505                 1510                 1515

Leu Gly  Glu Ile Leu Gly Leu  Glu Asp Asp Leu Asn  Glu Leu Ala
```

```
    1520                1525                1530

Ser Ile  Asn Trp Leu Asn Leu  Asn Glu Met Phe Pro  Leu Arg Met
    1535                1540                1545

Val Leu  Arg Gln Lys Val Val  Tyr Pro Ser Val Met  Thr Phe Gln
    1550                1555                1560

Glu Glu  Lys Ile Pro Ser Leu  Ile Lys Thr Leu Gln  Asn Lys Leu
    1565                1570                1575

Cys Ser  Lys Phe Thr Arg Gly  Ala Gln Lys Leu Leu  Ser Glu Ala
    1580                1585                1590

Ile Asn  Lys Ser Ala Phe Gln  Ser Cys Val Ser Ser  Gly Phe Ile
    1595                1600                1605

Gly Leu  Cys Lys Thr Leu Gly  Ser Arg Cys Val Arg  Asn Lys Asn
    1610                1615                1620

Arg Glu  Asn Met Tyr Ile Arg  Lys Val Leu Glu Asp  Leu Thr Met
    1625                1630                1635

Asp Glu  His Val Thr Arg Val  His Lys Gln Asp Gly  Val Met Leu
    1640                1645                1650

Tyr Ile  Cys Asp Lys Gln Arg  His Pro Glu Ala His  Arg Asp His
    1655                1660                1665

Ile Asn  Leu Leu Arg Pro Leu  Leu Trp Asp Tyr Ile  Cys Ile Ser
    1670                1675                1680

Leu Ser  Asn Ser Phe Glu Leu  Gly Val Trp Val Leu  Ala Glu Pro
    1685                1690                1695

Val Lys  Gly Lys Asn Glu Ser  Asn Ser Ala Val Arg  His Leu Asn
    1700                1705                1710

Pro Cys  Asp Tyr Val Ala Arg  Lys Pro Glu Ser Ser  Arg Leu Leu
    1715                1720                1725

Glu Asp  Lys Val Ser Leu Asn  His Val Ile Gln Ser  Val Arg Arg
    1730                1735                1740

Leu Tyr  Pro Lys Ile Phe Glu  Asp Gln Leu Leu Pro  Phe Met Ser
    1745                1750                1755

Asp Val  Ser Ser Lys Asn Met  Arg Trp Ser Pro Arg  Ile Lys Phe
    1760                1765                1770

Leu Asp  Leu Cys Val Leu Ile  Asp Ile Asn Ser Glu  Ser Leu Ser
    1775                1780                1785

Leu Ile  Ser His Val Val Lys  Trp Lys Arg Asp Glu  His Tyr Thr
    1790                1795                1800

Val Leu  Phe Ser Asp Leu Val  Asn Ser His Gln Arg  Ser Asp Ser
    1805                1810                1815

Ser Leu  Val Asp Glu Phe Val  Val Ser Thr Arg Asp  Val Cys Lys
    1820                1825                1830

Asn Phe  Leu Lys Gln Val Tyr  Phe Glu Ser Phe Val  Arg Glu Phe
    1835                1840                1845

Val Ala  Thr Ala Arg Thr Leu  Gly Asn Phe Ser Trp  Phe Pro His
    1850                1855                1860

Lys Asp  Met Met Pro Ser Glu  Asp Gly Ala Glu Ala  Leu Gly Pro
    1865                1870                1875

Phe Gln  Ser Phe Ile Leu Lys  Val Val Asn Lys Lys  Ile Glu Arg
    1880                1885                1890

Pro Met  Phe Arg Asn Asp Leu  Gln Phe Gly Phe Gly  Trp Phe Ser
    1895                1900                1905

Tyr Arg  Val Gly Asp Val Val  Cys Asn Ala Ala Met  Leu Ile Lys
    1910                1915                1920
```

-continued

```
Gln Gly  Leu Thr Asp Pro Lys  Ala Phe Lys Ser Leu  Arg Asp Leu
    1925                 1930                 1935

Trp Asp  Tyr Met Leu Ser Ser  Thr Glu Gly Ile Leu  Glu Phe Ser
    1940                 1945                 1950

Ile Thr  Val Asp Phe Thr His  Asn Gln Asn Asn Thr  Asp Cys Leu
    1955                 1960                 1965

Arg Lys  Phe Ser Leu Ile Phe  Val Val Lys Cys Gln  Leu Gln Ser
    1970                 1975                 1980

Pro Gly  Val Ala Asp Tyr Leu  Ser Cys Ser His Ser  Phe Lys Gly
    1985                 1990                 1995

Glu Val  Asp Arg Arg Leu Leu  Asp Glu Cys Leu Asn  Leu Leu Arg
    2000                 2005                 2010

Thr Asp  Pro Ile Phe Lys Ala  Asn Asp Gly Val Phe  Asp Ile Arg
    2015                 2020                 2025

Ser Glu  Glu Phe Glu Asp Tyr  Met Glu Asp Pro Leu  Thr Leu Gly
    2030                 2035                 2040

Asp Ser  Leu Glu Leu Glu Leu  Ile Gly Ser Arg Arg  Ile Leu Asn
    2045                 2050                 2055

Glu Ile  Lys Ser Thr Asp Phe  Glu Arg Ile Gly Pro  Glu Trp Glu
    2060                 2065                 2070

Pro Val  Pro Leu Thr Ile Arg  Lys Gly Ala Leu Phe  Glu Gly Arg
    2075                 2080                 2085

Asn Phe  Val Gln Asn Xaa Ser  Val Lys Leu Glu Thr  Lys Asp Met
    2090                 2095                 2100

Arg Val  Phe Leu Ala Glu Leu  Glu Gly Cys Gly Lys  Ile Gly Asp
    2105                 2110                 2115

Val Leu  Gly Ser Leu Leu Leu  His Arg Phe Arg Thr  Gly Glu His
    2120                 2125                 2130

Leu Met  Glu Ser Glu Ile Ser  Xaa Val Leu Gln Glu  Leu Cys Met
    2135                 2140                 2145

Asp Arg  Ser Val Met Leu Thr  Pro Leu Ser Phe Val  Pro Asp Trp
    2150                 2155                 2160

Phe Thr  Phe Arg Asp Cys Arg  Leu Cys Phe Ser Arg  Ser Lys Asn
    2165                 2170                 2175

Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp
```

```
<210> SEQ ID NO 33
<211> LENGTH: 1497
<212> TYPE: DNA
<213> ORGANISM: Lymphocytic choriomeningitis virus (mutant P91)

<400> SEQUENCE: 33

atgggtcaga ttgtgacaat gtttgaggct ttgcctcaca tcattgatga ggtcatcaac      60

attgtcatta ttgtgctcat tataatcacg agcatcaaag ctgtgtacaa tttcgccacc     120

tgtgggatat tagcactggt cagcttcctt tttttggctg gtaggtcctg tggcatgtac     180

ggccttaatg gtcccgacat ctataaaggg gtttaccagt tcaaatcagt ggagtttgat     240

atgtctcact taaatctgac gatgcccaat gcgtgctcag ccaacaactc tcatcactac     300

atcagtatgg gaagctctgg actggagcta actttcacta acgactccat ccttaatcac     360
```

-continued aatttttgca acttaacctc cgctttcaac aaaaagactt ttgaccatac actcatgagt 420
atagtctcga gtctgcacct cagtattaga gggaattcca accacaaagc agtgtcttgt 480
gattttaaca atggcatcac cattcaatac aacttgtcat tttcggaccc acagagcgct 540
atgagccagt gttggacttt cagaggtaga gtcttggaca tgtttagaac tgcctttgga 600
ggaaaataca tgagaagtgg ctggggctgg gcaggttcag atggcaagac cacttggtgc 660
agccaaacaa gctatcagta cctaatcata caaaacagga cttgggaaaa ccactgtaga 720
tatgcaggcc cttttgggat gtctagaatc ctctttgctc aggaaaagac aaagtttctc 780
actaggagac ttgcaggcac attcacctgg accctgtcag actcctcagg agtagaaaat 840
ccaggtggtt attgcctgac caaatggatg atccttgctg cagagctcaa atgttttggg 900
aatacagctg ttgcaaaatg taatgtcaat catgatgaag agttctgtga catgctacga 960
ctaattgatt acaacaaggc cgccctgagt aagttcaagc aagatgtaga gtctgccttg 1020
catgtattca aaacaacagt aaattctctg atttccgatc agctgttgat gaggaatcat 1080
ctaagagatc taatgggggt accatactgt aattactcaa agttctggta tctggaacat 1140
gctaagactg gtgagactag tgtacccaag tgctggcttg tcactaatgg ctcctacttg 1200
aatgagaccc actttagtga tcaaatcgaa caagaagcag ataacatgat cacagagatg 1260
ttgaggaagg actacataaa aagacaaggg agtactcctt tagccttaat ggatcttttg 1320
atgttttcaa catcagcata tctaatcagc atctttctgc atcttgtgaa gataccaaca 1380
catagacaca taaagggcgg ttcatgtcca aagccacacc gcttgaccaa caaggggatc 1440
tgtagttgtg gtgcattcaa ggtgcctggt gtaaaaacta tctggaaaag acgctga 1497

<210> SEQ ID NO 34
<211> LENGTH: 498
<212> TYPE: PRT
<213> ORGANISM: Lymphocytic choriomeningitis virus (mutant P91)

<400> SEQUENCE: 34

Met Gly Gln Ile Val Thr Met Phe Glu Ala Leu Pro His Ile Ile Asp
1 5 10 15

Glu Val Ile Asn Ile Val Ile Ile Val Leu Ile Ile Ile Thr Ser Ile
20 25 30

Lys Ala Val Tyr Asn Phe Ala Thr Cys Gly Ile Leu Ala Leu Val Ser
35 40 45

Phe Leu Phe Leu Ala Gly Arg Ser Cys Gly Met Tyr Gly Leu Asn Gly
50 55 60

Pro Asp Ile Tyr Lys Gly Val Tyr Gln Phe Lys Ser Val Glu Phe Asp
65 70 75 80

Met Ser His Leu Asn Leu Thr Met Pro Asn Ala Cys Ser Ala Asn Asn
85 90 95

Ser His His Tyr Ile Ser Met Gly Ser Ser Gly Leu Glu Leu Thr Phe
100 105 110

Thr Asn Asp Ser Ile Leu Asn His Asn Phe Cys Asn Leu Thr Ser Ala
115 120 125

Phe Asn Lys Lys Thr Phe Asp His Thr Leu Met Ser Ile Val Ser Ser
130 135 140

Leu His Leu Ser Ile Arg Gly Asn Ser Asn His Lys Ala Val Ser Cys
145 150 155 160

Asp Phe Asn Asn Gly Ile Thr Ile Gln Tyr Asn Leu Ser Phe Ser Asp
165 170 175

```
Pro Gln Ser Ala Met Ser Gln Cys Trp Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg
```

<210> SEQ ID NO 35
<211> LENGTH: 1677
<212> TYPE: DNA
<213> ORGANISM: Lymphocytic choriomeningitis virus (mutant P91)

<400> SEQUENCE: 35

```
atgtctttgt ccaaagaagt caaaagcttt cagtggacac aggcgttgag gagggagttg      60

cagagtttta catcagatgt aaaggctgcc gtcatcaagg acgcaaccag tcttctaaat     120

gggttggact tttctgaagt cagcaacgtt cagaggatca tgagaaagga aaggagggat     180

gataaagact tgcagagact caggagtctt aaccagactg tgcattctct tgttgatctg     240
```

-continued

```
aagtctacat caaagaaaaa tgttctgaaa gtgggaagac ttagtgcaga ggaattgatg    300

acccttgcag ctgatcttga gaagctgaag gccaaaatta tgagaactga gaggcctcaa    360

gcttctggag tctacatggg aaatttgaca gcacaacaac ttgatcaaag atcccaaata    420

ctgcaaatgg ttgggatgag aagacctcag cagggtgcaa gtggtgtagt aagggtttgg    480

gatgtgaagg actcatcact tctgaacaat cagttcggca caatgccaag cctgacaatg    540

gcttgcatgg caaaacagtc acagacccca ctcaatgatg ttgtgcaggc actcacagac    600

cttggcttac tttacacagt caaatacccg aatctcagtg atcttgaaag gctaaaggat    660

aaacacccag ttctgggggt cattactgaa cagcaatcta gtatcaatat ctctggttat    720

aatttcagtc ttggtgcagc tgtgaaagcg ggggcagctc tgctagatgg agggaacatg    780

ctggaatcta tcttgatcaa accgagcaac agtgaggatc tcctaaaagc agtcctcggg    840

gccaagaaga aactcaacat gtttgtctca gatcaagttg gagatagaaa tccctatgaa    900

aacatccttt ataaagtctg tctttcaggt gaaggatggc catacatagc ctgtagaacg    960

tcagttgtgg ggagagcatg ggagaacaca acaattgatc tcacaaatga aaaacttgtt   1020

gccaactcat ctaggccagt gcctggagca gcaggcccac ctcaggtggg cttgagttac   1080

agtcagacaa tgctgttgaa agacttgatg ggagggattg atcccaatgc tcccacatgg   1140

attgacattg agggcaggtt caatgatcca gtggagatag caatattcca accacaaaat   1200

gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaatagaagg gacataaaac tcattgatgt tgagatgacc   1440

aaggaggcct caagagaata tgaagataaa gtgtgggaca aatatggctg gctatgcaaa   1500

atgcacactg ggtagtgag agacaaaaag aagaaagaga tcaccccaca ctgtgcactc   1560

atggactgca tcatttttga gagtgcttcc aaggcaagac tccctgatct aaaaaccgtt   1620

cacaacatcc tgccacatga tttaatcttc agaggaccca atgttgtgac actctaa      1677
```

<210> SEQ ID NO 36
<211> LENGTH: 558
<212> TYPE: PRT
<213> ORGANISM: Lymphocytic choriomeningitis virus (mutant P91)

<400> SEQUENCE: 36

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125
```

-continued

```
Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540
```

Pro His Asp Leu Ile Phe Arg Gly Pro Asn Val Val Thr Leu
545 550 555

<210> SEQ ID NO 37
<211> LENGTH: 273
<212> TYPE: DNA
<213> ORGANISM: Lymphocytic choriomeningitis virus (mutant P91)

<400> SEQUENCE: 37
atgggccaag gcaagtccaa agaagaaagg gacaccagca atacaggcag agcagagctt 60
ttgccagaca ccacctatct tggtcctcta aattgtaaat catgttggca gaaatttgac 120
agcttggtta gatgccatga ccactatctt tgcagacact gtctgaatct cctgctgtca 180
gtttccgaca gatgtcctct ctgtaagtat ccactgccaa ccaaactgaa ggtgtcaaca 240
gtcccaagct ccccacctcc ctatgaggag tga 273

<210> SEQ ID NO 38
<211> LENGTH: 90
<212> TYPE: PRT
<213> ORGANISM: Lymphocytic choriomeningitis virus (mutant P91)

<400> SEQUENCE: 38

Met Gly Gln Gly Lys Ser Lys Glu Glu Arg Asp Thr Ser Asn Thr Gly
1 5 10 15

Arg Ala Glu Leu Leu Pro Asp Thr Thr Tyr Leu Gly Pro Leu Asn Cys
20 25 30

Lys Ser Cys Trp Gln Lys Phe Asp Ser Leu Val Arg Cys His Asp His
35 40 45

Tyr Leu Cys Arg His Cys Leu Asn Leu Leu Leu Ser Val Ser Asp Arg
50 55 60

Cys Pro Leu Cys Lys Tyr Pro Leu Pro Thr Lys Leu Lys Val Ser Thr
65 70 75 80

Val Pro Ser Ser Pro Pro Pro Tyr Glu Glu
85 90

<210> SEQ ID NO 39
<211> LENGTH: 6630
<212> TYPE: DNA
<213> ORGANISM: Lymphocytic choriomeningitis virus (mutant P91)

<400> SEQUENCE: 39
atggatgaaa ctattgcaga tttgagagag ttgtgtctaa attacataga acaggacgag 60
aggctgtcaa ggcaaaaact caacttcctg ggacaaagag aacccagaat ggtgctaatt 120
gagggactca aattgttatc acgctgtata gagatagaca gtgcagacaa aagtggttgc 180
atacacaacc acgatgacaa atctgttgaa acaatcctaa tagactctgg gattgtgtgt 240
ccaggactgc cactcatcat ccctgatggt tataagttga ttgacaattc ccttattctt 300
cttgaatgtt ttgttagaag cacaccagct agttttgaaa agaagttcat tgaggacacc 360
aacaaactag catgcatcaa agaagatctt gctgttgcag gcatcacact ggttccaata 420
gtggatggtc gttgtgatta tgataacagt ttcatgccag aatgggtgaa ttttaagttc 480
agagacctcc tatttaaact cctggagtat tctagtcaag atgagaaagt ttttgaggag 540
tctgaatact tcaggctctg tgagtctctt aagaccactg ttgacaaacg ttccggcatg 600
gactcaatga aaattttgaa agacgcaaga tcatttcata acgatgagat tatgaaaatg 660
tgccacgatg gtgtcaaccc caacatgagt tgcgatgatg tggtctttgg cataaattcc 720

-continued

```
tttttggca ggtttaggag ggacctgtta aatgggaaac tcaaaaggaa tttccaaaag    780
gtcagccctg gggcttaat caaggaattc tctgaacttt atgaaaccct tactgataat    840
gatgacatat taatgttgag caaagaggca gttgaatcct gccccttaat gaggttcatt    900
acagcagaga cccatgggca tgagagagga agcgatgcta acactgagta tgaaaggcta    960
ctctctatgt tgaacaaggt gaaaagttta aaattattaa acactagaag gagacagctg   1020
ctgaacttag atgtcttatg tctttcttca cttattaagc agtcaatttc caaagggttg   1080
gaaaatgata aacattgggt tggttgctgc tacagtagtg tgaatgatag gcttgtgagc   1140
cttcaaagta ccaaagaaga attcatgaga cttttgaaga acagaagaaa atcaagagtg   1200
cacaaaaagg catctcttga tgagcttttt agggtatcca taaatgagtt catagcaaaa   1260
atccagaaat gcctatcaac agtgggactt agttttgagc attacggact atcagaatgc   1320
ctcgtgcaag aatgccatat accatttgct gaatttgaga actttatgag agccgggact   1380
catcctgtaa tgcattacac aaaatttgaa gattacactt tccagcctaa catagagcaa   1440
ttgaggggtt tacagagttt gagaaaactg tcatctgttt gtttggctct aacaaacagc   1500
atgaaaacaa gctcagttgc aaggttgaga cagaaccaac tggggtctgt gagatatcaa   1560
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaaccccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aaacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
```

atgcagaggc agagcttaaa ttttaaattt gactgggaca aattggaaga agatgtaaga 3180
attagtgaaa gggaaagcaa ttctgaatct ctaagtaagg ccctttcatt gacaaaatgc 3240
atgagtgctg ctctaaagaa tctgtgtttt tactcagaag aatcaccaac atcatacact 3300
tcagttggcc ctgactctgg gagactaaaa tttgcattgt catacaaaga gcaggttggg 3360
ggaaatagag agctttacat tggggatttg aggacaaaaa tgttcacaag attggtagaa 3420
gattattttg aatccttttc tagtttcttt tcaggatctt gtttaaacaa tgataaagag 3480
tttgaaaatg caatcttgtc aatgactatc aatgtgagag aagggttgtt aaactacagc 3540
atggatcaca gcaaatgggg accaatgatg tgcccattcc tattcttaat gcttctccaa 3600
aatctcaaac tgggtgatga tcagtacgtg cgttctggaa aagatcatgt tagcaccttg 3660
ttgacttggc atatgcataa acttgttgaa gtccctttcc ctgttgtgaa tgcaatgatg 3720
aaatcatatg ttaaatcaaa actcaagctt ctcaaagggt caggaacgac tgttacggag 3780
agaatcttta gagagtattt tgaaatgggg gtggtgccat ctcacatatc tagtctcatt 3840
gacatgggac aggggatcct acacaatgct tctgattttt acggtttaat tagtgaaagg 3900
tttatcaatt attgtattgg tgtcattttt ggagagaggc cagaagccta tacatcaagt 3960
gatgatcaga tcactttatt tgacaagaga ttgagtgact tagttgatag tgacccagaa 4020
gaagtccttg tcttgctgga attccactct cacttaagtg gtttgttgaa caagttcatc 4080
agtccaaaaa gtgtggttgg gcggtttgca gcggaattca aatccagatt ttatgtgtgg 4140
ggggaggagg tccctctcct cacgaaattt gtgtctgcgg cactacacaa tgttaagtgt 4200
aaagaaccgc atcaactttg tgagacaata gatacgattg ctgatcaagc tatagcaaat 4260
ggagttccag ttttttagt aaactgtatc cagaggagga cactggatct cttgaaatat 4320
gctaatttcc ctttagatcc attcttgtta aacactcaca ctgatgtaaa ggattggtta 4380
gatggttcta gaggttatag aatccaaaga ctcattgaag aattgtgtcc cagtgaaaca 4440
aagatcatga gaaaacttgt aagaagacta catcacaaac tcaagaacgg tgaatgtaac 4500
gaggaatttt ttctagacct cttcaacagg gaaaaggaag aggccatcct tcaattggga 4560
gagattcttg gtcttgagga tgatcttaat gagttggcaa gcatcaattg gttgaatctg 4620
aatgaaatgt tcccattgag gatggttctg agacaaaaag tggtttaccc atcagtaatg 4680
acctttcaag aggaaaagat cccctcattg attaaaacac tccaaaataa gctttgtagt 4740
aagttcacaa gaggtgcaca gaagctgttg tcagaggcaa tcaacaaatc agcttttcag 4800
agttgtgtct catccggctt tataggtctc tgtaagactt taggaagtag gtgtgtgaga 4860
aataaaaaca gggaaaatat gtatatcaga aaggtgcttg aagatctgac catggatgaa 4920
catgtcacaa gggttcacaa acaagatggt gtgatgttgt acatttgcga caagcagaga 4980
cacccagagg ctcaccgtga ccacatcaac cttttgaggc cccttctctg ggactacatt 5040
tgcatctcat tgagcaactc ttttgagctg ggtgtttggg ttttagcaga acctgtgaaa 5100
ggaaagaacg agagtaattc ggctgttagg cacttaaatc catgtgatta tgtagcaaga 5160
aaacctgaga gttcgagact actagaggat aaagtgagtt tgaatcatgt aattcaatct 5220
gtgaggcgac tgtaccccaa aatctttgag gatcagttgc tcccattcat gtctgatgtg 5280
agctcaaaaa atatgagatg gagtcccagg attaaattcc ttgacctttg tgtgctgatt 5340
gacatcaact cagagtcttt gtcactcatt tctcatgttg tcaaatggaa gagggacgaa 5400
cattacactg tgctgttttc tgatctcgtc aactctcacc aacggtcaga ctcaagttta 5460

-continued gttgatgaat ttgttgtcag cacaagggat gtctgcaaga actttttgaa gcaagtgtat 5520
ttcgaatcat ttgtacgaga gtttgttgca acagctagga ccttaggtaa cttttcatgg 5580
ttcccccata aggacatgat gccatctgaa gatggcgctg aagcactggg acccttccaa 5640
tcatttattt tgaaagtggt gaacaagaaa atagagaggc ccatgtttag gaatgacttg 5700
cagtttggtt ttggttggtt ctcttatcgt gtggggggatg ttgtgtgtaa tgccgctatg 5760
ttaattaagc agggtttgac agatccaaaa gcatttaaat ctttaagaga tttgtgggat 5820
tacatgctca gcagcacaga ggggatattg gagttctcaa tcacagtgga tttcacacac 5880
aaccagaaca acactgactg cttgaggaaa ttttcattga tctttgtggt taaatgccaa 5940
ttacagagtc caggtgtagc tgattactta tcgtgctctc attccttcaa aggtgaggtt 6000
gacaggagat tattagatga gtgtctcaat ctgttgagga cagaccccat ctttaaagcg 6060
aatgatggag tctttgacat taggtctgaa gagtttgaag attacatgga agaccctttg 6120
acacttggtg attcactaga acttgaacta ataggttcta gaaggattct gaatgagatc 6180
aaatctactg actttgagag gatagggcct gagtgggaac ctgtgcctct gaccataagg 6240
aagggtgccc tctttgaggg gaggaacttt gttcagaata tctctgtgaa attggagaca 6300
aaggacatga gggtctttct ggcagagctc gagggctgtg gaaaaattgg tgatgtcctc 6360
ggcagcctcc tcctgcaccg attcagaact ggtgagcact tgatggagtc agaaataagt 6420
acagttcttc aggagctctg catggacaga tccgtcatgc tgacaccatt atcttttgtg 6480
ccagattggt tcaccttcag agattgtagg ctctgcttca gcargtcaaa gaacactgta 6540
atgtatgaga caactggggg caggttcaga ctcaagggga aatcctgtga cgattggctg 6600
gcggagcggg tggccgagga gatcgactag 6630

<210> SEQ ID NO 40
<211> LENGTH: 2209
<212> TYPE: PRT
<213> ORGANISM: Lymphocytic choriomeningitis virus (mutant P91)
<220> FEATURE:
<221> NAME/KEY: MISC_FEATURE
<222> LOCATION: (2175)..(2175)
<223> OTHER INFORMATION: Xaa can be Arg or Lys

<400> SEQUENCE: 40

Met Asp Glu Thr Ile Ala Asp Leu Arg Glu Leu Cys Leu Asn Tyr Ile
1 5 10 15

Glu Gln Asp Glu Arg Leu Ser Arg Gln Lys Leu Asn Phe Leu Gly Gln
20 25 30

Arg Glu Pro Arg Met Val Leu Ile Glu Gly Leu Lys Leu Leu Ser Arg
35 40 45

Cys Ile Glu Ile Asp Ser Ala Asp Lys Ser Gly Cys Ile His Asn His
50 55 60

Asp Asp Lys Ser Val Glu Thr Ile Leu Ile Asp Ser Gly Ile Val Cys
65 70 75 80

Pro Gly Leu Pro Leu Ile Ile Pro Asp Gly Tyr Lys Leu Ile Asp Asn
85 90 95

Ser Leu Ile Leu Leu Glu Cys Phe Val Arg Ser Thr Pro Ala Ser Phe
100 105 110

Glu Lys Lys Phe Ile Glu Asp Thr Asn Lys Leu Ala Cys Ile Lys Glu
115 120 125

Asp Leu Ala Val Ala Gly Ile Thr Leu Val Pro Ile Val Asp Gly Arg
130 135 140

-continued

```
Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
```

-continued

```
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990
```

-continued

```
Ser Ala Val Lys Glu Gln Cys Gly  Leu Asp Glu Met Ala  Arg Asn Leu
        995                 1000                 1005

Cys Arg  Lys Phe Phe Ser Glu  Gly Asp Trp Phe Ser  Cys Met Lys
    1010                 1015                 1020

Met Ile  Leu Leu Gln Met Asn  Ala Asn Ala Tyr Ser  Gly Lys Tyr
    1025                 1030                 1035

Arg His  Met Gln Arg Gln Ser  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125

Asp Leu  Arg Thr Lys Met Phe  Thr Arg Leu Val Glu  Asp Tyr Phe
    1130                 1135                 1140

Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260

Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380
```

-continued

```
Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
    1415                 1420                 1425

Cys Ile  Gln Arg Arg Thr Leu  Asp Leu Leu Lys Tyr  Ala Asn Phe
    1430                 1435                 1440

Pro Leu  Asp Pro Phe Leu Leu  Asn Thr His Thr Asp  Val Lys Asp
    1445                 1450                 1455

Trp Leu  Asp Gly Ser Arg Gly  Tyr Arg Ile Gln Arg  Leu Ile Glu
    1460                 1465                 1470

Glu Leu  Cys Pro Ser Glu Thr  Lys Ile Met Arg Lys  Leu Val Arg
    1475                 1480                 1485

Arg Leu  His His Lys Leu Lys  Asn Gly Glu Cys Asn  Glu Glu Phe
    1490                 1495                 1500

Phe Leu  Asp Leu Phe Asn Arg  Glu Lys Glu Glu Ala  Ile Leu Gln
    1505                 1510                 1515

Leu Gly  Glu Ile Leu Gly Leu  Glu Asp Asp Leu Asn  Glu Leu Ala
    1520                 1525                 1530

Ser Ile  Asn Trp Leu Asn Leu  Asn Glu Met Phe Pro  Leu Arg Met
    1535                 1540                 1545

Val Leu  Arg Gln Lys Val Val  Tyr Pro Ser Val Met  Thr Phe Gln
    1550                 1555                 1560

Glu Glu  Lys Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Val Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Met Tyr Ile Arg  Lys Val Leu Glu Asp  Leu Thr Met
    1625                 1630                 1635

Asp Glu  His Val Thr Arg Val  His Lys Gln Asp Gly  Val Met Leu
    1640                 1645                 1650

Tyr Ile  Cys Asp Lys Gln Arg  His Pro Glu Ala His  Arg Asp His
    1655                 1660                 1665

Ile Asn  Leu Leu Arg Pro Leu  Leu Trp Asp Tyr Ile  Cys Ile Ser
    1670                 1675                 1680

Leu Ser  Asn Ser Phe Glu Leu  Gly Val Trp Val Leu  Ala Glu Pro
    1685                 1690                 1695

Val Lys  Gly Lys Asn Glu Ser  Asn Ser Ala Val Arg  His Leu Asn
    1700                 1705                 1710

Pro Cys  Asp Tyr Val Ala Arg  Lys Pro Glu Ser Ser  Arg Leu Leu
    1715                 1720                 1725

Glu Asp  Lys Val Ser Leu Asn  His Val Ile Gln Ser  Val Arg Arg
    1730                 1735                 1740

Leu Tyr  Pro Lys Ile Phe Glu  Asp Gln Leu Leu Pro  Phe Met Ser
    1745                 1750                 1755

Asp Val  Ser Ser Lys Asn Met  Arg Trp Ser Pro Arg  Ile Lys Phe
    1760                 1765                 1770

Leu Asp  Leu Cys Val Leu Ile  Asp Ile Asn Ser Glu  Ser Leu Ser
```

```
    1775                1780                1785

Leu Ile  Ser His Val Val Lys  Trp Lys Arg Asp Glu  His Tyr Thr
    1790                1795                1800

Val Leu  Phe Ser Asp Leu Val  Asn Ser His Gln Arg  Ser Asp Ser
    1805                1810                1815

Ser Leu  Val Asp Glu Phe Val  Val Ser Thr Arg Asp  Val Cys Lys
    1820                1825                1830

Asn Phe  Leu Lys Gln Val Tyr  Phe Glu Ser Phe Val  Arg Glu Phe
    1835                1840                1845

Val Ala  Thr Ala Arg Thr Leu  Gly Asn Phe Ser Trp  Phe Pro His
    1850                1855                1860

Lys Asp  Met Met Pro Ser Glu  Asp Gly Ala Glu Ala  Leu Gly Pro
    1865                1870                1875

Phe Gln  Ser Phe Ile Leu Lys  Val Val Asn Lys Lys  Ile Glu Arg
    1880                1885                1890

Pro Met  Phe Arg Asn Asp Leu  Gln Phe Gly Phe Gly  Trp Phe Ser
    1895                1900                1905

Tyr Arg  Val Gly Asp Val Val  Cys Asn Ala Ala Met  Leu Ile Lys
    1910                1915                1920

Gln Gly  Leu Thr Asp Pro Lys  Ala Phe Lys Ser Leu  Arg Asp Leu
    1925                1930                1935

Trp Asp  Tyr Met Leu Ser Ser  Thr Glu Gly Ile Leu  Glu Phe Ser
    1940                1945                1950

Ile Thr  Val Asp Phe Thr His  Asn Gln Asn Asn Thr  Asp Cys Leu
    1955                1960                1965

Arg Lys  Phe Ser Leu Ile Phe  Val Val Lys Cys Gln  Leu Gln Ser
    1970                1975                1980

Pro Gly  Val Ala Asp Tyr Leu  Ser Cys Ser His Ser  Phe Lys Gly
    1985                1990                1995

Glu Val  Asp Arg Arg Leu Leu  Asp Glu Cys Leu Asn  Leu Leu Arg
    2000                2005                2010

Thr Asp  Pro Ile Phe Lys Ala  Asn Asp Gly Val Phe  Asp Ile Arg
    2015                2020                2025

Ser Glu  Glu Phe Glu Asp Tyr  Met Glu Asp Pro Leu  Thr Leu Gly
    2030                2035                2040

Asp Ser  Leu Glu Leu Glu Leu  Ile Gly Ser Arg Arg  Ile Leu Asn
    2045                2050                2055

Glu Ile  Lys Ser Thr Asp Phe  Glu Arg Ile Gly Pro  Glu Trp Glu
    2060                2065                2070

Pro Val  Pro Leu Thr Ile Arg  Lys Gly Ala Leu Phe  Glu Gly Arg
    2075                2080                2085

Asn Phe  Val Gln Asn Ile Ser  Val Lys Leu Glu Thr  Lys Asp Met
    2090                2095                2100

Arg Val  Phe Leu Ala Glu Leu  Glu Gly Cys Gly Lys  Ile Gly Asp
    2105                2110                2115

Val Leu  Gly Ser Leu Leu Leu  His Arg Phe Arg Thr  Gly Glu His
    2120                2125                2130

Leu Met  Glu Ser Glu Ile Ser  Thr Val Leu Gln Glu  Leu Cys Met
    2135                2140                2145

Asp Arg  Ser Val Met Leu Thr  Pro Leu Ser Phe Val  Pro Asp Trp
    2150                2155                2160

Phe Thr  Phe Arg Asp Cys Arg  Leu Cys Phe Ser Xaa  Ser Lys Asn
    2165                2170                2175
```

```
Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp
```

<210> SEQ ID NO 41
<211> LENGTH: 1497
<212> TYPE: DNA
<213> ORGANISM: Lymphocytic choriomeningitis virus (mutant P52-1)

<400> SEQUENCE: 41

```
atgggtcaga ttgtgacaat gtttgaggct ttgcctcaca tcattgatga ggtcatcaac     60

attgtcatta ttgtgctcat tataatcacg agcatcaaag ctgtgtacaa tttcgccacc    120

tgtgggatat tagcactggt cagcttcctt tttttggctg gtaggtcctg tggcatgtac    180

ggcctcaatg gtcccgacat ctataaaggg gtttaccagt tcaaatcagt ggagtttgat    240

atgtctcact taaatctgac gatgcccaat gcgtgctcag ccaacaactc tcatcactac    300

atcagtatgg gaagctctgg actggagcta actttcacta acgactccat ccttaatcac    360

aatttttgca acttaacctc cgctttcaac aaaaagactt ttgaccatac actcatgagt    420

atagtctcga gtctgcacct cagtattaga gggaattcca accacaaagc agtgtcttgt    480

gattttaaca atggcatcac cattcaatac aacttgtcat tttcggaccc acagagcgct    540

atgagccagt gttggacttt cagaggtaga gtcttggaca tgtttagaac tgcctttgga    600

ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aatacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140

gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497
```

<210> SEQ ID NO 42
<211> LENGTH: 498
<212> TYPE: PRT
<213> ORGANISM: Lymphocytic choriomeningitis virus (mutant P52-1)

<400> SEQUENCE: 42

```
Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
```

-continued

```
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Met Ser Gln Cys Trp Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445
```

```
Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg


<210> SEQ ID NO 43
<211> LENGTH: 1677
<212> TYPE: DNA
<213> ORGANISM: Lymphocytic choriomeningitis virus (mutant P52-1)

<400> SEQUENCE: 43

atgtctttgt ccaaagaagt caaaagcttt cagtggacac aggcgttgag gagggagttg     60

cagagtttta catcagatgt aaaggctgcc gtcatcaagg acgcaaccag tcttctaaat    120

gggttggact tttctgaagt cagcaacgtt cagaggatca tgagaaagga aaggagggat    180

gataaagact tgcagagact caggagtctt aaccagactg tgcattctct tgttgatctg    240

aagtctacat caaagaaaaa tgttctgaaa gtgggaagac ttagtgcaga ggaattgatg    300

acccttgcag ctgatcttga gaagctgaag gccaaaatta tgagaactga gaggcctcaa    360

gcttctggag tctacatggg aaatttgaca gcacaacaac ttgatcaaag atcccaaata    420

ctgcaaatgg ttgggatgag aagacctcag cagggtgcaa gtggtgtagt aagggtttgg    480

gatgtgaagg actcatcact tctgaacaat cagttcggca caatgccaag cctgacaatg    540

gcttgcatgg caaaacagtc acagacccca ctcaatgatg ttgtgcaggc actcacagac    600

cttggcttac tttacacagt caaataccg aatctcagtg atcttgaaag gctaaaggat     660

aaacacccag ttctgggggt cattactgaa cagcaatcta gtatcaatat ctctggttat    720

aatttcagtc ttggtgcagc tgtgaaagcg ggggcagctc tgctagatgg agggaacatg    780

ctggaatcta tcttgatcaa accgagcaac agtgaggatc tcctaaaagc agtcctcggg    840

gccaagaaga aactcaacat gtttgtctca gatcaagttg gagatagaaa tccctatgaa    900

aacatccttt ataaagtctg tctttcaggt gaaggatggc catacatagc ctgtagaacg    960

tcagttgtgg ggagagcatg ggagaacaca acaattgatc tcacaaatga aaaacttgtt   1020

gccaactcat ctaggccagt gcctggagca gcaggcccac ctcaggtggg cttgagttac   1080

agtcagacaa tgctgttgaa agacttgatg ggagggattg atcccaatgc tcccacatgg   1140

attgacattg agggcaggtt caatgatcca gtggagatag caatattcca accacaaaat   1200

gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaatagaagg gacataaaac tcattgatgt tgagatgacc   1440

aaggaggcct caagagaata tgaagataaa gtgtgggaca aatatggctg gctatgcaaa   1500

atgcacactg ggtagtgag agacaaaaag aagaaagaga tcaccccaca ctgtgcactc    1560

atggactgca tcatttttga gagtgcttcc aaggcaagac tccctgatct aaaaaccgtt   1620

cacaacatcc tgccacatga tttaatcttc agaggaccca atgttgtgac actctaa      1677


<210> SEQ ID NO 44
<211> LENGTH: 558
```

-continued

<212> TYPE: PRT
<213> ORGANISM: Lymphocytic choriomeningitis virus (mutant P52-1)

<400> SEQUENCE: 44

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400
```

```
Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555


<210> SEQ ID NO 45
<211> LENGTH: 273
<212> TYPE: DNA
<213> ORGANISM: Lymphocytic choriomeningitis virus (mutant P52-1)

<400> SEQUENCE: 45

atgggccaag gcaagtccaa agaagaaagg gacaccagca atacaggcag agcagagctt      60

ttgccagaca ccacctatct tggtcctcta aattgtaaat catgttggca gaaatttgac     120

agcttggtta gatgccatga ccactatctt tgcagacact gtctgaatct cctgctgtca     180

gtttccgaca gatgtcctct ctgtaagtat ccactgccaa ccaaactgaa ggtgtcaaca     240

gtcccaagct ccccacctcc ctatgaggag tga                                  273


<210> SEQ ID NO 46
<211> LENGTH: 90
<212> TYPE: PRT
<213> ORGANISM: Lymphocytic choriomeningitis virus (mutant P52-1)

<400> SEQUENCE: 46

Met Gly Gln Gly Lys Ser Lys Glu Glu Arg Asp Thr Ser Asn Thr Gly
1               5                   10                  15

Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Pro Pro Pro Tyr Glu Glu
                85                  90


<210> SEQ ID NO 47
<211> LENGTH: 6630
<212> TYPE: DNA
```

<213> ORGANISM: Lymphocytic choriomeningitis virus (mutant P52-1)

<400> SEQUENCE: 47

```
atggatgaaa ctattgcaga tttgagagag ttgtgtctaa attacataga acaggacgag     60
aggctgtcaa ggcaaaaact caacttcctg ggacaaagag aacccagaat ggtgctaatt    120
gagggactca aattgttatc acgctgtata gagatagaca gtgcagacaa aagtggttgc    180
atacacaacc acgatgacaa atctgttgaa acaatcctaa tagactctgg gattgtgtgt    240
ccaggactgc cactcatcat ccctgatggt tataagttga ttgacaattc ccttattctt    300
cttgaatgtt ttgttagaag cacaccagct agttttgaaa agaagttcat tgaggacacc    360
aacaaactag catgcatcaa agaagatctt gctgttgcag gcatcacact ggttccaata    420
gtggatggtc gttgtgatta tgataacagt ttcatgccag aatgggtgaa ttttaagttc    480
agagacctcc tatttaaact cctggagtat tctagtcaag atgagaaagt ttttgaggag    540
tctgaatact tcaggctctg tgagtctctt aagaccactg ttgacaaacg ttccggcatg    600
gactcaatga aaattttgaa agacgcaaga tcatttcata acgatgagat tatgaaaatg    660
tgccacgatg gtgtcaaccc caacatgagt tgcgatgatg tggtctttgg cataaattcc    720
ttttttggca ggtttaggag ggacctgtta aatgggagac tcaaaaggaa tttccaaaag    780
gtcagccctg gggcttaat caaggaattc tctgaacttt atgaaaccct tactgataat    840
gatgacatat taatgttgag caaagaggca gttgaatcct gccccttaat gaggttcatt    900
acagcagaga cccatgggca tgagagagga agcgatgcta acactgagta tgaaaggcta    960
ctctctatgt tgaacaaggt gaaaagttta aaattattaa acactagaag gagacagctg   1020
ctgaacttag atgtcttatg tctttcttca cttattaagc agtcaatttc caaagggttg   1080
gaaaatgata aacattgggt tggttgttgc tacagtagtg tgaatgatag gcttgtgagc   1140
cttcaaagta ccaaagaaga attcatgaga cttttgaaga acagaagaaa atcaagagtg   1200
cacaaaaagg catctcttga tgagcttttt agggtatcca taaatgagtt catagcaaaa   1260
atccagaaat gcctatcaac agtgggactt agttttgagc attacggact atcagaatgc   1320
ctcgtgcaag aatgccatat accatttgct gaatttgaga actttatgag agccgggact   1380
catcctgtaa tgcattacac aaaatttgaa gattacactt tccagcctaa catagagcaa   1440
ttgaggggtt tacagagttt gagaaaactg tcatctgttt gtttggctct aacaaacagc   1500
atgaaaacaa gctcagttgc aaggttgaga cagaaccaac tggggtctgt gagatatcaa   1560
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
```

-continued

```
tcaacccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttctagga aaacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagtttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggga aagatcatgt tagcaccttg   3660
ttgacttggc atatgcataa acttgttgaa gtcccttttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag ttttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaatgaaag aggccatcct tcaattggga   4560
gagattcttg gtcttgagga tgatctcaat gagttggcaa gcatcaattg gttgaatctg   4620
```

-continued

```
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
ttcccccata aggacatgat gccatctgaa gatggcgctg aagcactggg acccttccaa   5640
tcatttattt tgaaagtggt gaacaagaaa atagagaggc ccatgtttag gaatgacttg   5700
cagtttggtt ttggttggtt ctcttatcgt gtggggggatg ttgtgtgtaa tgccgctatg   5760
ttaattaagc agggtttgac agatccaaaa gcatttaaat ctttaagaga tttgtgggat   5820
tacatgctca gcagcacaga ggggatattg gagttctcaa tcacagtgga tttcacacac   5880
aaccagaaca acactgactg cttgaggaaa ttttcattga tctttgtggt taaatgccaa   5940
ttacagagtc caggtgtagc tgattactta tcgtgctctc atttcttcaa aggtgaggtt   6000
gacaggagat tattagatga gtgtctcaat ctgttgagga cagaccccat ctttaaagcg   6060
aatgatggag tctttgacat taggtctgaa gagtttgaag attacatgga agaccctttg   6120
acacttggtg attcactaga acttgaacta ataggttcta gaaggattct gaatgagatc   6180
aaatctactg actttgagag gatagggcct gagtgggaac ctgtgcctct gaccataagg   6240
aagggtgccc tctttgaggg gaggaacttt gttcagaata tctctgtgaa attggagaca   6300
aaggacatga gggtctttct ggcagagctc gagggctgtg gagaaattgg tgatgtcctc   6360
ggcagcctcc tcctgcaccg attcagaact ggtgagcact tgatggagtc agaaataagt   6420
rcagttcttc aggagctctg catggacaga tccgtcatgc tgacaccatt atcttttgtg   6480
ccagattggt tcaccttcag agattgtagg ctctgcttca gcaggtcaaa gaacactgta   6540
atgtatgaga cagctggggg caggttcaga ctcaagggga aatcctgtga cgattggctg   6600
gcggagcggg tggccgagga gatcgactag                                   6630
```

<210> SEQ ID NO 48
<211> LENGTH: 2209
<212> TYPE: PRT
<213> ORGANISM: Lymphocytic choriomeningitis virus (mutant P52-1)

<400> SEQUENCE: 48

```
Met Asp Glu Thr Ile Ala Asp Leu Arg Glu Leu Cys Leu Asn Tyr Ile
1               5                   10                  15
```

-continued

```
Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Arg Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
```

```
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860
```

```
Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                 1005

Cys Arg  Lys Phe Phe Ser Glu  Gly Asp Trp Phe Ser  Cys Met Lys
    1010                 1015                 1020

Met Ile  Leu Leu Gln Met Asn  Ala Asn Ala Tyr Ser  Gly Lys Tyr
    1025                 1030                 1035

Arg His  Met Gln Arg Gln Ser  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125

Asp Leu  Arg Thr Lys Met Phe  Thr Arg Leu Val Glu  Asp Tyr Phe
    1130                 1135                 1140

Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260
```

-continued

```
Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
    1415                 1420                 1425

Cys Ile  Gln Arg Arg Thr Leu  Asp Leu Leu Lys Tyr  Ala Asn Phe
    1430                 1435                 1440

Pro Leu  Asp Pro Phe Leu Leu  Asn Thr His Thr Asp  Val Lys Asp
    1445                 1450                 1455

Trp Leu  Asp Gly Ser Arg Gly  Tyr Arg Ile Gln Arg  Leu Ile Glu
    1460                 1465                 1470

Glu Leu  Cys Pro Ser Glu Thr  Lys Ile Met Arg Lys  Leu Val Arg
    1475                 1480                 1485

Arg Leu  His His Lys Leu Lys  Asn Gly Glu Cys Asn  Glu Glu Phe
    1490                 1495                 1500

Phe Leu  Asp Leu Phe Asn Arg  Glu Met Lys Glu Ala  Ile Leu Gln
    1505                 1510                 1515

Leu Gly  Glu Ile Leu Gly Leu  Glu Asp Asp Leu Asn  Glu Leu Ala
    1520                 1525                 1530

Ser Ile  Asn Trp Leu Asn Leu  Asn Glu Met Phe Pro  Leu Arg Met
    1535                 1540                 1545

Val Leu  Arg Gln Lys Val Val  Tyr Pro Ser Val Met  Thr Phe Gln
    1550                 1555                 1560

Glu Glu  Lys Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Val Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Met Tyr Ile Arg  Lys Val Leu Glu Asp  Leu Thr Met
    1625                 1630                 1635

Asp Glu  His Val Thr Arg Val  His Lys Gln Asp Gly  Val Met Leu
    1640                 1645                 1650

Tyr Ile  Cys Asp Lys Gln Arg  His Pro Glu Ala His  Arg Asp His
```

```
    1655                1660                1665

Ile Asn  Leu Leu Arg Pro Leu  Leu Trp Asp Tyr Ile  Cys Ile Ser
    1670                1675                1680

Leu Ser  Asn Ser Phe Glu Leu  Gly Val Trp Val Leu  Ala Glu Pro
    1685                1690                1695

Val Lys  Gly Lys Asn Glu Ser  Asn Ser Ala Val Arg  His Leu Asn
    1700                1705                1710

Pro Cys  Asp Tyr Val Ala Arg  Lys Pro Glu Ser Ser  Arg Leu Leu
    1715                1720                1725

Glu Asp  Lys Val Ser Leu Asn  His Val Ile Gln Ser  Val Arg Arg
    1730                1735                1740

Leu Tyr  Pro Lys Ile Phe Glu  Asp Gln Leu Leu Pro  Phe Met Ser
    1745                1750                1755

Asp Val  Ser Ser Lys Asn Met  Arg Trp Ser Pro Arg  Ile Lys Phe
    1760                1765                1770

Leu Asp  Leu Cys Val Leu Ile  Asp Ile Asn Ser Glu  Ser Leu Ser
    1775                1780                1785

Leu Ile  Ser His Val Val Lys  Trp Lys Arg Asp Glu  His Tyr Thr
    1790                1795                1800

Val Leu  Phe Ser Asp Leu Val  Asn Ser His Gln Arg  Ser Asp Ser
    1805                1810                1815

Ser Leu  Val Asp Glu Phe Val  Val Ser Thr Arg Asp  Val Cys Lys
    1820                1825                1830

Asn Phe  Leu Lys Gln Val Tyr  Phe Glu Ser Phe Val  Arg Glu Phe
    1835                1840                1845

Val Ala  Thr Ala Arg Thr Leu  Gly Asn Phe Ser Trp  Phe Pro His
    1850                1855                1860

Lys Asp  Met Met Pro Ser Glu  Asp Gly Ala Glu Ala  Leu Gly Pro
    1865                1870                1875

Phe Gln  Ser Phe Ile Leu Lys  Val Val Asn Lys Lys  Ile Glu Arg
    1880                1885                1890

Pro Met  Phe Arg Asn Asp Leu  Gln Phe Gly Phe Gly  Trp Phe Ser
    1895                1900                1905

Tyr Arg  Val Gly Asp Val Val  Cys Asn Ala Ala Met  Leu Ile Lys
    1910                1915                1920

Gln Gly  Leu Thr Asp Pro Lys  Ala Phe Lys Ser Leu  Arg Asp Leu
    1925                1930                1935

Trp Asp  Tyr Met Leu Ser Ser  Thr Glu Gly Ile Leu  Glu Phe Ser
    1940                1945                1950

Ile Thr  Val Asp Phe Thr His  Asn Gln Asn Asn Thr  Asp Cys Leu
    1955                1960                1965

Arg Lys  Phe Ser Leu Ile Phe  Val Val Lys Cys Gln  Leu Gln Ser
    1970                1975                1980

Pro Gly  Val Ala Asp Tyr Leu  Ser Cys Ser His Phe  Phe Lys Gly
    1985                1990                1995

Glu Val  Asp Arg Arg Leu Leu  Asp Glu Cys Leu Asn  Leu Leu Arg
    2000                2005                2010

Thr Asp  Pro Ile Phe Lys Ala  Asn Asp Gly Val Phe  Asp Ile Arg
    2015                2020                2025

Ser Glu  Glu Phe Glu Asp Tyr  Met Glu Asp Pro Leu  Thr Leu Gly
    2030                2035                2040

Asp Ser  Leu Glu Leu Glu Leu  Ile Gly Ser Arg Arg  Ile Leu Asn
    2045                2050                2055
```

```
Glu Ile  Lys Ser Thr Asp Phe  Glu Arg Ile Gly Pro  Glu Trp Glu
    2060                 2065                 2070

Pro Val  Pro Leu Thr Ile Arg  Lys Gly Ala Leu Phe  Glu Gly Arg
    2075                 2080                 2085

Asn Phe  Val Gln Asn Ile Ser  Val Lys Leu Glu Thr  Lys Asp Met
    2090                 2095                 2100

Arg Val  Phe Leu Ala Glu Leu  Glu Gly Cys Gly Glu  Ile Gly Asp
    2105                 2110                 2115

Val Leu  Gly Ser Leu Leu Leu  His Arg Phe Arg Thr  Gly Glu His
    2120                 2125                 2130

Leu Met  Glu Ser Glu Ile Ser  Thr Val Leu Gln Glu  Leu Cys Met
    2135                 2140                 2145

Asp Arg  Ser Val Met Leu Thr  Pro Leu Ser Phe Val  Pro Asp Trp
    2150                 2155                 2160

Phe Thr  Phe Arg Asp Cys Arg  Leu Cys Phe Ser Arg  Ser Lys Asn
    2165                 2170                 2175

Thr Val  Met Tyr Glu Thr Ala  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp


<210> SEQ ID NO 49
<211> LENGTH: 1497
<212> TYPE: DNA
<213> ORGANISM: Lymphocytic choriomeningitis virus (mutant P52-1.3)

<400> SEQUENCE: 49

atgggtcaga ttgtgacaat gtttgaggct ttgcctcaca tcattgatga ggtcatcaac     60

attgtcatta ttgtgctcat tataatcacg agcatcaaag ctgtgtacaa tttcgccacc    120

tgtgggatat tagcactggt cagcttcctt tttttggctg gtaggtcctg tggcatgtac    180

ggccttaatg gtcccgacat ctataaaggg gtttaccagt tcaaatcagt ggagtttgat    240

atgtctcact taaatctgac gatgcccaat gcgtgctcag ccaacaactc tcatcactac    300

atcagtatgg gaagctctgg actggagcta actttcacta acgactccat ccttaatcac    360

aatttttgca acttaacctc cgctttcaac aaaaagactt ttgaccatac actcatgagt    420

atagtctcga gtctgcacct cagtattaga gggaattcca accacaaagc agtgtcttgt    480

gattttaaca atggcatcac cattcaatac aacttgtcat tttcggaccc acagagcgct    540

ataagccagt gttggacttt cagaggtaga gtcttggaca tgtttagaac tgcctttgga    600

ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aacacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140
```

-continued

```
gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497
```

<210> SEQ ID NO 50
<211> LENGTH: 498
<212> TYPE: PRT
<213> ORGANISM: Lymphocytic choriomeningitis virus (mutant P52-1.3)

<400> SEQUENCE: 50

```
Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Ile Ser Gln Cys Trp Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320
```

-continued

```
Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg


<210> SEQ ID NO 51
<211> LENGTH: 1677
<212> TYPE: DNA
<213> ORGANISM: Lymphocytic choriomeningitis virus (mutant P52-1.3)

<400> SEQUENCE: 51

atgtctttgt ccaaagaagt caaaagcttt cagtggacac aggcgttgag gagggagttg      60

cagagtttta catcagatgt aaaggctgcc gtcatcaagg acgcaaccag tcttctaaat     120

gggttggact tttctgaagt cagcaacgtt cagaggatca tgagaaagga aaggagggat     180

gataaagact tgcagagact caggagtctt aaccagactg tgcattctct tgttgatctg     240

aagtctacat caaagaaaaa tgttctgaaa gtgggaagac ttagtgcaga ggaattgatg     300

acccttgcag ctgatctcga gaagctgaag gccaaaatta tgagaactga gaggcctcaa     360

gcttctggag tctacatggg aaatttgaca gcacaacaac ttgatcaaag atcccaaata     420

ctgcaaatgg ttgggatgag aagacctcag cagggtgcaa gtggtgtagt aagggtttgg     480

gatgtgaagg actcatcact tctgaacaat cagttcggca caatgccaag cctgacaatg     540

gcttgcatgg caaaacagtc acagacccca ctcaatgatg ttgtgcaggc actcacagac     600

cttggcttac tttacacagt caaatacccg aatctcagtg atcttgaaag gctaaaggat     660

aaacacccag ttctgggggt cattactgaa cagcaatcta gtatcaatat ctctggttat     720

aatttcagtc ttggtgcagc tgtgaaagcg ggggcagctc tgctagatgg agggaacatg     780

ctggaatcta tcttgatcaa accgagcaac agtgaggatc tcctaaaagc agtcctcggg     840

gccaagaaga aactcaacat gtttgtctca gatcaagttg gagatagaaa tccctatgaa     900

aacatccttt ataaagtctg tctttcaggt gaaggatggc catacatagc ctgtagaacg     960

tcagttgtgg ggagagcatg ggagaacaca acaattgatc tcacaaatga aaaacttgtt    1020

gccaactcat ctaggccagt gcctggagca gcaggcccac ctcaggtggg cttgagttac    1080
```

agtcagacaa tgctgttgaa agacttgatg ggagggattg atcccaatgc tcccacatgg 1140
attgacattg agggcaggtt caatgatcca gtggagatag caatattcca accacaaaat 1200
gggcaattca tacattttta cagggaacct acggaccaga agcaattcaa gcaggactca 1260
aagtattcac acggcatgga tcttgctgat ctcttcaatg cacagcctgg gctgacctca 1320
tcagttatag gtgctctccc acaagggatg gttttgagct gtcaaggttc tgatgacatc 1380
agaaagcttc tggactcaca aaatagaagg gacataaaac tcattgatgt tgagatgacc 1440
aaggaggcct caagagaata tgaagataaa gtgtgggaca aatatggctg gctatgcaaa 1500
atgcacactg ggtagtgag agacaaaaag aagaaagaga tcaccccaca ctgtgcactc 1560
atggactgca tcatttttga gagtgcttcc aaggcaagac tccctgatct aaaaaccgtt 1620
cacaacatcc tgccacatga tttaatcttc agaggaccca atgttgtgac actctaa 1677

<210> SEQ ID NO 52
<211> LENGTH: 558
<212> TYPE: PRT
<213> ORGANISM: Lymphocytic choriomeningitis virus (mutant P52-1.3)

<400> SEQUENCE: 52

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

```
Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

<210> SEQ ID NO 53
<211> LENGTH: 273
<212> TYPE: DNA
<213> ORGANISM: Lymphocytic choriomeningitis virus (mutant P52-1.3)

<400> SEQUENCE: 53

```
atgggccaag gcaagtccaa agaagaaagg gacaccagca atacaggcag agcagagctt      60

ttgccagaca ccacctatct tggtcctcta aattgtaaat catgttggca gaaatttgac     120

agcttggtta gatgccatga ccactatctt tgcagacact gtctgaatct cctgctgtca     180

gtttccgaca gatgtcctct ctgtaagtat ccactgccaa ccaaactgaa ggtgtcaaca     240

gtcccaagct ccccacctcc ctatgaggag tga                                  273
```

<210> SEQ ID NO 54
<211> LENGTH: 90
<212> TYPE: PRT
<213> ORGANISM: Lymphocytic choriomeningitis virus (mutant P52-1.3)

<400> SEQUENCE: 54

Met Gly Gln Gly Lys Ser Lys Glu Glu Arg Asp Thr Ser Asn Thr Gly
1 5 10 15

Arg Ala Glu Leu Leu Pro Asp Thr Thr Tyr Leu Gly Pro Leu Asn Cys
20 25 30

Lys Ser Cys Trp Gln Lys Phe Asp Ser Leu Val Arg Cys His Asp His
35 40 45

Tyr Leu Cys Arg His Cys Leu Asn Leu Leu Leu Ser Val Ser Asp Arg
50 55 60

Cys Pro Leu Cys Lys Tyr Pro Leu Pro Thr Lys Leu Lys Val Ser Thr
65 70 75 80

Val Pro Ser Ser Pro Pro Pro Tyr Glu Glu
85 90

<210> SEQ ID NO 55
<211> LENGTH: 6630
<212> TYPE: DNA
<213> ORGANISM: Lymphocytic choriomeningitis virus (mutant P52-1.3)

<400> SEQUENCE: 55
atggatgaaa ctattgcaga tttgagagag ttgtgtctaa attacataga acaggacgag 60
aggctgtcaa ggcaaaaact caacttcctg ggacaaagag aacccagaat ggtgctaatt 120
gagggactca aattgttatc acgctgtata gagatagaca gtgcagacaa aagtggttgc 180
atacacaacc acgatgacaa atctgttgaa acaatcctaa tagactctgg gattgtgtgt 240
ccaggactgc cactcatcat ccctgatggt tataagttga ttgacaattc ccttattctt 300
cttgaatgtt ttgttagaag cacaccagct agttttgaaa agaagttcat tgaggacacc 360
aacaaactag catgcatcaa agaagatctt gctgttgcag gcatcacact ggttccaata 420
gtggatggtc gttgtgatta tgataacagt ttcatgccag aatgggtgaa ttttaagttc 480
agagacctcc tatttaaact cctggagtat tctagtcaag atgagaaagt ttttgaggag 540
tctgaatact tcaggctctg tgagtctctt aagaccactg ttgacaaacg ttccggcatg 600
gactcaatga aaattttgaa agacgcaaga tcatttcata acgatgagat tatgaaaatg 660
tgccacgatg gtgtcaaccc caacatgagt tgcgatgatg tggtctttgg cataaattcc 720
ttttttggca ggtttaggag ggacctgtta aatgggaaac tcaaaaggaa tttccaaaag 780
gtcagccctg gggcttaat caaggaattc tctgaacttt atgaaaccct tactgataat 840
gatgacatat taatgttgag caaagaggca gttgaatcct gcccccttaat gaggttcatt 900 acagcagaga cccatgggca tgagagagga agcgatgcta acactgagta tgaaaggcta 960
ctctctatgt taaacaaggt gaaaagttta aaattattaa acactagaag gagacagctg 1020
ctgaacttag atgtcttatg tctttcttca cttattaagc agtcaatttc caaagggttg 1080
gaaaatgata aacattgggt tggttgttgc tacagtagtg tgaatgatag gcttgtgagc 1140
cttcaaagta ccaaagaaga attcatgaga cttttgaaga acagaagaaa atcaagagtg 1200
cacaaaaagg catctcttga tgagcttttt agggtatcca taaatgagtt catagcaaaa 1260
atccagaaat gcctatcaac agtgggactt agttttgagc attacggact atcagaatgc 1320
ctcgtgcaag aatgccatat accatttgct gaatttgaga actttatgag agccgggact 1380
catcctgtaa tgcattacac aaaatttgaa gattacactt tccagcctaa catagagcaa 1440
ttgaggggtt tacagagttt gagaaaactg tcatctgttt gtttggctct aacaaacagc 1500
atgaaaacaa gctcagttgc aaggttgaga cagaaccaac tggggtctgt gagatatcaa 1560

-continued

```
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaacccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aaacagaagt agacaaatta   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattactttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
```

-continued

```
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag ttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgaccttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
ttcccccata aggacatgat gccatctgaa gatggcgctg aagcactggg acccttccaa   5640
tcatttattt tgaaagtggt gaacaagaaa atagagaggc ccatgtttag gaatgacttg   5700
cagtttggtt ttggttggtt ctcttatcgt gtgggggatg ttgtgtgtaa tgccgctatg   5760
ttaattaagc agggtttgac agatccaaaa gcatttaaat ctttaagaga tttgtgggat   5820
tacatgctca gcagcacaga ggggatattg gagttctcaa tcacagtgga tttcacacac   5880
aaccagaaca acactgactg cttgaggaaa ttttcattga tctttgtggt taaatgccaa   5940
ttacagagtc caggtgtagc tgattactta tcgtgctctc attccttcaa aggtgaggtt   6000
gacaggagat tattagatga gtgtctcaat ctgttgagga cagaccccat ctttaaagcg   6060
aatgatggag tctttgacat taggtctgaa gagtttgaag attacatgga agaccctttg   6120
acacttggtg attcactaga acttgaacta ataggttcta gaaggattct gaatgagatc   6180
aaatctactg actttgagag gatagggcct gagtgggaac ctgtgcctct gaccataagg   6240
aagggtgccc tctttgaggg gaggaacttt gttcagaata tctctgtgaa attggagaca   6300
```

aaggacatga gggtctttct ggcagagctc gagggctgtg gaaaaattgg tgatgtcctc 6360
ggcagcctcc tcctgcaccg attcagaact ggtgagcact tgatggagtc agaaataagt 6420
acagttcttc aggagctctg catggacaga tccgtcatgc tgacaccatt atcttttgtg 6480
ccagattggt tcaccttcag agattgtagg ctctgcttca gcaggtcaaa gaacactgta 6540
atgtatgaga caactggggg caggttcaga ctcaagggga aatcctgtga cgattggctg 6600
gcggagcggg tggccgagga gatcgactag 6630

<210> SEQ ID NO 56
<211> LENGTH: 2209
<212> TYPE: PRT
<213> ORGANISM: Lymphocytic choriomeningitis virus (mutant P52-1.3)

<400> SEQUENCE: 56

Met Asp Glu Thr Ile Ala Asp Leu Arg Glu Leu Cys Leu Asn Tyr Ile
1 5 10 15

Glu Gln Asp Glu Arg Leu Ser Arg Gln Lys Leu Asn Phe Leu Gly Gln
20 25 30

Arg Glu Pro Arg Met Val Leu Ile Glu Gly Leu Lys Leu Leu Ser Arg
35 40 45

Cys Ile Glu Ile Asp Ser Ala Asp Lys Ser Gly Cys Ile His Asn His
50 55 60

Asp Asp Lys Ser Val Glu Thr Ile Leu Ile Asp Ser Gly Ile Val Cys
65 70 75 80

Pro Gly Leu Pro Leu Ile Ile Pro Asp Gly Tyr Lys Leu Ile Asp Asn
85 90 95

Ser Leu Ile Leu Leu Glu Cys Phe Val Arg Ser Thr Pro Ala Ser Phe
100 105 110

Glu Lys Lys Phe Ile Glu Asp Thr Asn Lys Leu Ala Cys Ile Lys Glu
115 120 125

Asp Leu Ala Val Ala Gly Ile Thr Leu Val Pro Ile Val Asp Gly Arg
130 135 140

Cys Asp Tyr Asp Asn Ser Phe Met Pro Glu Trp Val Asn Phe Lys Phe
145 150 155 160

Arg Asp Leu Leu Phe Lys Leu Leu Glu Tyr Ser Ser Gln Asp Glu Lys
165 170 175

Val Phe Glu Glu Ser Glu Tyr Phe Arg Leu Cys Glu Ser Leu Lys Thr
180 185 190

Thr Val Asp Lys Arg Ser Gly Met Asp Ser Met Lys Ile Leu Lys Asp
195 200 205

Ala Arg Ser Phe His Asn Asp Glu Ile Met Lys Met Cys His Asp Gly
210 215 220

Val Asn Pro Asn Met Ser Cys Asp Asp Val Val Phe Gly Ile Asn Ser
225 230 235 240

Phe Phe Gly Arg Phe Arg Arg Asp Leu Leu Asn Gly Lys Leu Lys Arg
245 250 255

Asn Phe Gln Lys Val Ser Pro Gly Gly Leu Ile Lys Glu Phe Ser Glu
260 265 270

Leu Tyr Glu Thr Leu Thr Asp Asn Asp Asp Ile Leu Met Leu Ser Lys
275 280 285

Glu Ala Val Glu Ser Cys Pro Leu Met Arg Phe Ile Thr Ala Glu Thr
290 295 300

His Gly His Glu Arg Gly Ser Asp Ala Asn Thr Glu Tyr Glu Arg Leu

-continued

```
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735
```

-continued

```
Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
    1010                1015                1020

Met Ile  Leu Leu Gln Met Asn  Ala Asn Ala Tyr Ser  Gly Lys Tyr
    1025                1030                1035

Arg His  Met Gln Arg Gln Ser  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Lys Cys  Met Ser Ala
    1070                1075                1080

Ala Leu  Lys Asn Leu Cys Phe  Tyr Ser Glu Glu Ser  Pro Thr Ser
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125

Asp Leu  Arg Thr Lys Met Phe  Thr Arg Leu Val Glu  Asp Tyr Phe
    1130                1135                1140
```

-continued

```
Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260

Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
    1415                 1420                 1425

Cys Ile  Gln Arg Arg Thr Leu  Asp Leu Leu Lys Tyr  Ala Asn Phe
    1430                 1435                 1440

Pro Leu  Asp Pro Phe Leu Leu  Asn Thr His Thr Asp  Val Lys Asp
    1445                 1450                 1455

Trp Leu  Asp Gly Ser Arg Gly  Tyr Arg Ile Gln Arg  Leu Ile Glu
    1460                 1465                 1470

Glu Leu  Cys Pro Ser Glu Thr  Lys Ile Met Arg Lys  Leu Val Arg
    1475                 1480                 1485

Arg Leu  His His Lys Leu Lys  Asn Gly Glu Cys Asn  Glu Glu Phe
    1490                 1495                 1500

Phe Leu  Asp Leu Phe Asn Arg  Glu Lys Lys Glu Ala  Ile Leu Gln
    1505                 1510                 1515

Leu Gly  Glu Ile Leu Gly Leu  Glu Asp Asp Leu Asn  Glu Leu Ala
    1520                 1525                 1530

Ser Ile  Asn Trp Leu Asn Leu  Asn Glu Met Phe Pro  Leu Arg Met
```

```
    1535                1540                1545

Val Leu  Arg Gln Lys Val Val  Tyr Pro Ser Val Met  Thr Phe Gln
    1550                1555                1560

Glu Glu  Lys Ile Pro Ser Leu  Ile Lys Thr Leu Gln  Asn Lys Leu
    1565                1570                1575

Cys Ser  Lys Phe Thr Arg Gly  Ala Gln Lys Leu Leu  Ser Glu Ala
    1580                1585                1590

Ile Asn  Lys Ser Ala Phe Gln  Ser Cys Val Ser Ser  Gly Phe Ile
    1595                1600                1605

Gly Leu  Cys Lys Thr Leu Gly  Ser Arg Cys Val Arg  Asn Lys Asn
    1610                1615                1620

Arg Glu  Asn Met Tyr Ile Arg  Lys Val Leu Glu Asp  Leu Thr Met
    1625                1630                1635

Asp Glu  His Val Thr Arg Val  His Lys Gln Asp Gly  Val Met Leu
    1640                1645                1650

Tyr Ile  Cys Asp Lys Gln Arg  His Pro Glu Ala His  Arg Asp His
    1655                1660                1665

Ile Asn  Leu Leu Arg Pro Leu  Leu Trp Asp Tyr Ile  Cys Ile Ser
    1670                1675                1680

Leu Ser  Asn Ser Phe Glu Leu  Gly Val Trp Val Leu  Ala Glu Pro
    1685                1690                1695

Val Lys  Gly Lys Asn Glu Ser  Asn Ser Ala Val Arg  His Leu Asn
    1700                1705                1710

Pro Cys  Asp Tyr Val Ala Arg  Lys Pro Glu Ser Ser  Arg Leu Leu
    1715                1720                1725

Glu Asp  Lys Val Ser Leu Asn  His Val Ile Gln Ser  Val Arg Arg
    1730                1735                1740

Leu Tyr  Pro Lys Ile Phe Glu  Asp Gln Leu Leu Pro  Phe Met Ser
    1745                1750                1755

Asp Val  Ser Ser Lys Asn Met  Arg Trp Ser Pro Arg  Ile Lys Phe
    1760                1765                1770

Leu Asp  Leu Cys Val Leu Ile  Asp Ile Asn Ser Glu  Ser Leu Ser
    1775                1780                1785

Leu Ile  Ser His Val Val Lys  Trp Lys Arg Asp Glu  His Tyr Thr
    1790                1795                1800

Val Leu  Phe Ser Asp Leu Val  Asn Ser His Gln Arg  Ser Asp Ser
    1805                1810                1815

Ser Leu  Val Asp Glu Phe Val  Val Ser Thr Arg Asp  Val Cys Lys
    1820                1825                1830

Asn Phe  Leu Lys Gln Val Tyr  Phe Glu Ser Phe Val  Arg Glu Phe
    1835                1840                1845

Val Ala  Thr Ala Arg Thr Leu  Gly Asn Phe Ser Trp  Phe Pro His
    1850                1855                1860

Lys Asp  Met Met Pro Ser Glu  Asp Gly Ala Glu Ala  Leu Gly Pro
    1865                1870                1875

Phe Gln  Ser Phe Ile Leu Lys  Val Val Asn Lys Lys  Ile Glu Arg
    1880                1885                1890

Pro Met  Phe Arg Asn Asp Leu  Gln Phe Gly Phe Gly  Trp Phe Ser
    1895                1900                1905

Tyr Arg  Val Gly Asp Val Val  Cys Asn Ala Ala Met  Leu Ile Lys
    1910                1915                1920

Gln Gly  Leu Thr Asp Pro Lys  Ala Phe Lys Ser Leu  Arg Asp Leu
    1925                1930                1935
```

Trp Asp Tyr Met Leu Ser Ser Thr Glu Gly Ile Leu Glu Phe Ser
1940 1945 1950

Ile Thr Val Asp Phe Thr His Asn Gln Asn Asn Thr Asp Cys Leu
1955 1960 1965

Arg Lys Phe Ser Leu Ile Phe Val Val Lys Cys Gln Leu Gln Ser
1970 1975 1980

Pro Gly Val Ala Asp Tyr Leu Ser Cys Ser His Ser Phe Lys Gly
1985 1990 1995

Glu Val Asp Arg Arg Leu Leu Asp Glu Cys Leu Asn Leu Leu Arg
2000 2005 2010

Thr Asp Pro Ile Phe Lys Ala Asn Asp Gly Val Phe Asp Ile Arg
2015 2020 2025

Ser Glu Glu Phe Glu Asp Tyr Met Glu Asp Pro Leu Thr Leu Gly
2030 2035 2040

Asp Ser Leu Glu Leu Glu Leu Ile Gly Ser Arg Arg Ile Leu Asn
2045 2050 2055

Glu Ile Lys Ser Thr Asp Phe Glu Arg Ile Gly Pro Glu Trp Glu
2060 2065 2070

Pro Val Pro Leu Thr Ile Arg Lys Gly Ala Leu Phe Glu Gly Arg
2075 2080 2085

Asn Phe Val Gln Asn Ile Ser Val Lys Leu Glu Thr Lys Asp Met
2090 2095 2100

Arg Val Phe Leu Ala Glu Leu Glu Gly Cys Gly Lys Ile Gly Asp
2105 2110 2115

Val Leu Gly Ser Leu Leu Leu His Arg Phe Arg Thr Gly Glu His
2120 2125 2130

Leu Met Glu Ser Glu Ile Ser Thr Val Leu Gln Glu Leu Cys Met
2135 2140 2145

Asp Arg Ser Val Met Leu Thr Pro Leu Ser Phe Val Pro Asp Trp
2150 2155 2160

Phe Thr Phe Arg Asp Cys Arg Leu Cys Phe Ser Arg Ser Lys Asn
2165 2170 2175

Thr Val Met Tyr Glu Thr Thr Gly Gly Arg Phe Arg Leu Lys Gly
2180 2185 2190

Lys Ser Cys Asp Asp Trp Leu Ala Glu Arg Val Ala Glu Glu Ile
2195 2200 2205

Asp

<210> SEQ ID NO 57
<211> LENGTH: 1497
<212> TYPE: DNA
<213> ORGANISM: Lymphocytic choriomeningitis virus (mutant P52-2.1)

<400> SEQUENCE: 57
atgggtcaga ttgtgacaat gtttgaggct ttgcctcaca tcattgatga ggtcatcaac 60
attgttatta ttgtgctcat tataatcacg agcatcaaag ctgtgtacaa tttcgccacc 120
tgtgggatat tagcactggt cagcttcctt tttttggctg gtaggtcctg tggcatgtac 180
ggccttaatg gtcccgacat ctataaaggg gtttaccagt tcaaatcagt ggagtttgat 240
atgtctcact taaatctgac gatgcccaat gcgtgctcag ccaacaactc tcatcactac 300
atcagtatgg gaagctctgg actggagcta actttcacta acgactccat ccttaatcac 360
aatttttgca acttaacctc cgctttcaac aaaaagactt ttgaccatac actcatgagt 420

```
atagtctcga gtctgcacct cagtattaga gggaattcca accacaaagc agtgtcttgt    480

gattttaaca atggcatcac cattcaatac aacttgtcat tttcggaccc acagagcgct    540

atgagccagt gtaggacttt cagaggtaga gtcttggaca tgtttagaac tgcctttgga    600

ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aatacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140

gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497
```

<210> SEQ ID NO 58
<211> LENGTH: 498
<212> TYPE: PRT
<213> ORGANISM: Lymphocytic choriomeningitis virus (mutant P52-2.1)

<400> SEQUENCE: 58

```
Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Met Ser Gln Cys Arg Thr Phe Arg Gly Arg Val Leu
            180                 185                 190
```

Asp Met Phe Arg Thr Ala Phe Gly Gly Lys Tyr Met Arg Ser Gly Trp
195 200 205

Gly Trp Ala Gly Ser Asp Gly Lys Thr Thr Trp Cys Ser Gln Thr Ser
210 215 220

Tyr Gln Tyr Leu Ile Ile Gln Asn Arg Thr Trp Glu Asn His Cys Arg
225 230 235 240

Tyr Ala Gly Pro Phe Gly Met Ser Arg Ile Leu Phe Ala Gln Glu Lys
245 250 255

Thr Lys Phe Leu Thr Arg Arg Leu Ala Gly Thr Phe Thr Trp Thr Leu
260 265 270

Ser Asp Ser Ser Gly Val Glu Asn Pro Gly Gly Tyr Cys Leu Thr Lys
275 280 285

Trp Met Ile Leu Ala Ala Glu Leu Lys Cys Phe Gly Asn Thr Ala Val
290 295 300

Ala Lys Cys Asn Val Asn His Asp Glu Glu Phe Cys Asp Met Leu Arg
305 310 315 320

Leu Ile Asp Tyr Asn Lys Ala Ala Leu Ser Lys Phe Lys Gln Asp Val
325 330 335

Glu Ser Ala Leu His Val Phe Lys Thr Thr Val Asn Ser Leu Ile Ser
340 345 350

Asp Gln Leu Leu Met Arg Asn His Leu Arg Asp Leu Met Gly Val Pro
355 360 365

Tyr Cys Asn Tyr Ser Lys Phe Trp Tyr Leu Glu His Ala Lys Thr Gly
370 375 380

Glu Thr Ser Val Pro Lys Cys Trp Leu Val Thr Asn Gly Ser Tyr Leu
385 390 395 400

Asn Glu Thr His Phe Ser Asp Gln Ile Glu Gln Glu Ala Asp Asn Met
405 410 415

Ile Thr Glu Met Leu Arg Lys Asp Tyr Ile Lys Arg Gln Gly Ser Thr
420 425 430

Pro Leu Ala Leu Met Asp Leu Leu Met Phe Ser Thr Ser Ala Tyr Leu
435 440 445

Ile Ser Ile Phe Leu His Leu Val Lys Ile Pro Thr His Arg His Ile
450 455 460

Lys Gly Gly Ser Cys Pro Lys Pro His Arg Leu Thr Asn Lys Gly Ile
465 470 475 480

Cys Ser Cys Gly Ala Phe Lys Val Pro Gly Val Lys Thr Ile Trp Lys
485 490 495

Arg Arg

<210> SEQ ID NO 59
<211> LENGTH: 1677
<212> TYPE: DNA
<213> ORGANISM: Lymphocytic choriomeningitis virus (mutant P52-2.1)

<400> SEQUENCE: 59
atgtctttgt ccaaagaagt caaaagcttt cagtggacac aggcgttgag gagggagttg 60
cagagtttta catcagatgt aaaggctgcc gtcatcaagg acgcaaccag tcttctaaat 120
gggttggact tttctgaagt cagcaacgtt cagaggatca tgagaaagga aaggagggat 180
gataaagact tgcagagact caggagtctt aaccagactg tgcattctct tgttgatctg 240
aagtctacat caaagaaaaa tgttctgaaa gtgggaagac ttagtgcaga ggaattgatg 300
acccttgcag ctgatcttga gaagctgaag gccaaaatta tgagaactga gaggcctcaa 360

```
gcttctggag tctacatggg aaatttgaca gcacaacaac ttgatcaaag atcccaaata    420

ctgcaaatgg ttgggatgag aagacctcag cagggtgcaa gtggtgtagt aagggtttgg    480

gatgtgaagg actcatcact tctgaacaat cagttcggca caatgccaag cctgacaatg    540

gcttgcatgg caaaacagtc acagacccca ctcaatgatg ttgtgcaggc actcacagac    600

cttggcttac tttacacagt caaataccg aatctcagtg atcttgaaag gctaaaggat    660

aaacacccag ttctgggggt cattactgaa cagcaatcta gtatcaatat ctctggttat    720

aatttcagtc ttggtgcagc tgtgaaagcg ggggcagctc tgctagatgg agggaacatg    780

ctggaatcta tcttgatcaa accgagcaac agtgaggatc tcctaaaagc agtcctcggg    840

gccaaaaaga aactcaacat gtttgtctca gatcaagttg gagatagaaa tccctatgaa    900

aacatccttt ataaagtctg tctttcaggt gaaggatggc catacatagc ctgtagaacg    960

tcagttgtgg ggagagcatg ggagaacaca acaattgatc tcacaaatga aaaacttgtt   1020

gccaactcat ctaggccagt gcctggagca gcaggcccac ctcaggtggg cttgagttac   1080

agtcagacaa tgctgttgaa agacttgatg ggagggattg atcccaatgc tcccacatgg   1140

attgacattg agggcaggtt caatgatcca gtggagatag caatattcca accacaaaat   1200

gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaatagaagg gacataaaac tcattgatgt tgagatgacc   1440

aaggaggcct caagagaata tgaagataaa gtgtgggaca aatatggctg gctatgcaaa   1500

atgcacactg ggtagtgag agacaaaaag aagaaagaga tcaccccaca ctgtgcactc   1560

atggactgca tcatttttga gagtgcttcc aaggcaagac tccctgatct aaaaaccgtt   1620

cacaacatcc tgccacatga tttaatcttc agaggaccca atgttgtgac actctaa      1677
```

<210> SEQ ID NO 60
<211> LENGTH: 558
<212> TYPE: PRT
<213> ORGANISM: Lymphocytic choriomeningitis virus (mutant P52-2.1)

<400> SEQUENCE: 60

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140
```

-continued

```
Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

<210> SEQ ID NO 61
<211> LENGTH: 273
<212> TYPE: DNA
<213> ORGANISM: Lymphocytic choriomeningitis virus (mutant P52-2.1)

<400> SEQUENCE: 61
atgggccaag gcaagtccaa agaagaaagg gacaccagca atacaggcag agcagagctt 60
ttgccagaca ccacctatct tggtcctcta aattgtaaat catgttggca gaaatttgac 120
agcttggtta gatgccatga ccactatctt tgcagacact gtctgaatct cctgctgtca 180
gtttccgaca gatgtcctct ctgtaagtat ccactgccaa ccaaactgaa ggtgtcaaca 240
gtcccaagct ccccacctcc ctatgaggag tga 273

<210> SEQ ID NO 62
<211> LENGTH: 90
<212> TYPE: PRT
<213> ORGANISM: Lymphocytic choriomeningitis virus (mutant P52-2.1)

<400> SEQUENCE: 62

Met Gly Gln Gly Lys Ser Lys Glu Glu Arg Asp Thr Ser Asn Thr Gly
1               5                   10                  15

Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Pro Pro Pro Tyr Glu Glu
                85                  90

<210> SEQ ID NO 63
<211> LENGTH: 6630
<212> TYPE: DNA
<213> ORGANISM: Lymphocytic choriomeningitis virus (mutant P52-2.1)

<400> SEQUENCE: 63
atggatgaaa ctattgcaga tttgagagag ttgtgtctaa attacataga acaggacgaa 60
aggctgtcaa ggcaaaaact caacttcctg ggacaaagag aacccagaat ggtgctaatt 120
gagggactca aattgttatc acgctgtata gagatagaca gtgcagacaa aagtggttgc 180
atacacaacc acgatgacaa atctgttgaa acaatcctaa tagactctgg gattgtgtgt 240
ccaggactgc cactcatcat ccctgatggt tataagttga ttgacaattc ccttattctt 300
cttgaatgtt ttgttagaag cacaccagct agttttgaaa agaagttcat tgaggacacc 360
aacaaactag catgcatcaa agaagatctt gctgttgcag gcatcacact ggttccaata 420
gtggatggtc gttgtgatta tgataacagt ttcatgccag aatgggtgaa ttttaagttc 480
agagacctcc tatttaaact cctggagtat tctagtcaag atgagaaagt ttttgaggag 540
tctgaatact tcaggctctg tgagtctctt aagaccactg ttgacaaacg ttccggcatg 600
gactcaatga aaattttgaa agacgcaaga tcatttcata acgatgagat tatgaaaatg 660
tgccacgatg gtgtcaaccc caacatgagt tgcgatgatg tggtctttgg cataaattcc 720
ttttttggca ggtttaggag ggacctgtta aatgggaaac tcaaaaggaa tttccaaaag 780
gtcagccctg gggcttaat caaggaattc tctgaacttt atgaaaccct tactgataat 840

```
gatgacatat taatgttgag caaagaggca gttgaatcct gccccttaat gaggttcatt    900
acagcagaga cccatgggca tgagagagga agcgatgcta acactgagta tgaaaggcta    960
ctctctatgt tgaacaaggt gaaaagttta aaattattaa acactagaag gagacagctg   1020
ctgaacttag atgtcttatg tctttcttca cttattaagc agtcaatttc caaagggttg   1080
gaaaatgata aacattgggt tggttgttgc tacagtagtg tgaatgatag gcttgtgagc   1140
cttcaaagta ccaaagaaga attcatgaga cttttgaaga acagaagaaa atcaagagtg   1200
cacaaaaagg catctcttga tgagcttttt agggtatcca taaatgagtt catagcaaaa   1260
atccagaaat gcctatcaac agtgggactt agttttgagc attacggact atcagaatgc   1320
ctcgtgcaag aatgccatat accatttgct gaatttgaga actttatgag agccgggact   1380
catcctgtaa tgcattacac aaaatttgaa gattacactt tccagcctaa catagagcaa   1440
ttgaggggtt tacagagttt gagaaaactg tcatctgttt gtttggctct aacaaacagc   1500
atgaaaacaa gctcagttgc aaggttgaga cagaaccaac tggggtctgt gagatatcaa   1560
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa atttaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaacccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aaacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
```

-continued

```
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag ttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
```

ttcccccata aggacatgat gccatctgaa gatggcgctg aagcactggg acccttccaa 5640
tcatttattt tgaaagtggt gaacaagaaa atagagaggc ccatgtttag gaatgacttg 5700
cagtttggtt ttggttggtt ctcttatcgt gtgggggatg ttgtgtgtaa tgccgctatg 5760
ttaattaagc agggtttgac agatccaaaa gcatttaaat ctttaagaga tttgtgggat 5820
tacatgctca gcagcacaga ggggatattg gagttctcaa tcacagtgga tttcacacac 5880
aaccagaaca acactgactg cttgaggaaa ttttcattga tctttgtggt taaatgccaa 5940
ttacagagtc caggtgtagc tgattactta tcgtgctctc atttcttcaa aggtgaggtt 6000
gacaggagat tattagatga gtgtctcaat ctgttgagga cagaccccat ctttaaagcg 6060
aatgatggag tctttgacat taggtctgaa gagtttgaag attacatgga agaccctttg 6120
acacttggtg attcactaga acttgaacta ataggttcta gaaggattct gaatgagatc 6180
aaatctactg actttgagag gatagggcct gagtgggaac ctgtgcctct gaccataagg 6240
aagggtgccc tctttgaggg gaggaacttt gttcagaata tctctgtgaa attggagaca 6300
aaggacatga gggtctttct ggcagagctc gagggctgtg gagaaattgg tgatgtcctc 6360
ggcagcctcc tcctgcaccg attcagaact ggtgagcact tgatggagtc agaaataagt 6420
acagttcttc aggagctctg catggacaga tccgtcatgc tgacaccatt atcttttgtg 6480
ccagattggt tcaccttcag agattgtagg ctctgcttca gcaggtcaaa gaacactgta 6540
atgtatgaga caactggggg caggttcaga ctcaagggga aatcctgtga cgattggctg 6600
gcggagcggg tggccgagga gatcgactag 6630

<210> SEQ ID NO 64
<211> LENGTH: 2209
<212> TYPE: PRT
<213> ORGANISM: Lymphocytic choriomeningitis virus (mutant P52-2.1)

<400> SEQUENCE: 64

Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr

-continued

```
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605
```

-continued

```
Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735

Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
    1010                 1015                 1020
```

-continued

```
Met Ile  Leu Leu Gln Met Asn  Ala Asn Ala Tyr Ser  Gly Lys Tyr
    1025                 1030                 1035

Arg His  Met Gln Arg Gln Ser  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125

Asp Leu  Arg Thr Lys Met Phe  Thr Arg Leu Val Glu  Asp Tyr Phe
    1130                 1135                 1140

Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260

Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
```

```
    1415                1420                1425

Cys Ile  Gln Arg Arg Thr Leu  Asp Leu Leu Lys Tyr  Ala Asn Phe
    1430                1435                1440

Pro Leu  Asp Pro Phe Leu Leu  Asn Thr His Thr Asp  Val Lys Asp
    1445                1450                1455

Trp Leu  Asp Gly Ser Arg Gly  Tyr Arg Ile Gln Arg  Leu Ile Glu
    1460                1465                1470

Glu Leu  Cys Pro Ser Glu Thr  Lys Ile Met Arg Lys  Leu Val Arg
    1475                1480                1485

Arg Leu  His His Lys Leu Lys  Asn Gly Glu Cys Asn  Glu Glu Phe
    1490                1495                1500

Phe Leu  Asp Leu Phe Asn Arg  Glu Lys Lys Glu Ala  Ile Leu Gln
    1505                1510                1515

Leu Gly  Glu Ile Leu Gly Leu  Glu Asp Asp Leu Asn  Glu Leu Ala
    1520                1525                1530

Ser Ile  Asn Trp Leu Asn Leu  Asn Glu Met Phe Pro  Leu Arg Met
    1535                1540                1545

Val Leu  Arg Gln Lys Val Val  Tyr Pro Ser Val Met  Thr Phe Gln
    1550                1555                1560

Glu Glu  Lys Ile Pro Ser Leu  Ile Lys Thr Leu Gln  Asn Lys Leu
    1565                1570                1575

Cys Ser  Lys Phe Thr Arg Gly  Ala Gln Lys Leu Leu  Ser Glu Ala
    1580                1585                1590

Ile Asn  Lys Ser Ala Phe Gln  Ser Cys Val Ser Ser  Gly Phe Ile
    1595                1600                1605

Gly Leu  Cys Lys Thr Leu Gly  Ser Arg Cys Val Arg  Asn Lys Asn
    1610                1615                1620

Arg Glu  Asn Met Tyr Ile Arg  Lys Val Leu Glu Asp  Leu Thr Met
    1625                1630                1635

Asp Glu  His Val Thr Arg Val  His Lys Gln Asp Gly  Val Met Leu
    1640                1645                1650

Tyr Ile  Cys Asp Lys Gln Arg  His Pro Glu Ala His  Arg Asp His
    1655                1660                1665

Ile Asn  Leu Leu Arg Pro Leu  Leu Trp Asp Tyr Ile  Cys Ile Ser
    1670                1675                1680

Leu Ser  Asn Ser Phe Glu Leu  Gly Val Trp Val Leu  Ala Glu Pro
    1685                1690                1695

Val Lys  Gly Lys Asn Glu Ser  Asn Ser Ala Val Arg  His Leu Asn
    1700                1705                1710

Pro Cys  Asp Tyr Val Ala Arg  Lys Pro Glu Ser Ser  Arg Leu Leu
    1715                1720                1725

Glu Asp  Lys Val Ser Leu Asn  His Val Ile Gln Ser  Val Arg Arg
    1730                1735                1740

Leu Tyr  Pro Lys Ile Phe Glu  Asp Gln Leu Leu Pro  Phe Met Ser
    1745                1750                1755

Asp Val  Ser Ser Lys Asn Met  Arg Trp Ser Pro Arg  Ile Lys Phe
    1760                1765                1770

Leu Asp  Leu Cys Val Leu Ile  Asp Ile Asn Ser Glu  Ser Leu Ser
    1775                1780                1785

Leu Ile  Ser His Val Val Lys  Trp Lys Arg Asp Glu  His Tyr Thr
    1790                1795                1800

Val Leu  Phe Ser Asp Leu Val  Asn Ser His Gln Arg  Ser Asp Ser
    1805                1810                1815
```

Ser Leu Val Asp Glu Phe Val Val Ser Thr Arg Asp Val Cys Lys
1820 1825 1830

Asn Phe Leu Lys Gln Val Tyr Phe Glu Ser Phe Val Arg Glu Phe
1835 1840 1845

Val Ala Thr Ala Arg Thr Leu Gly Asn Phe Ser Trp Phe Pro His
1850 1855 1860

Lys Asp Met Met Pro Ser Glu Asp Gly Ala Glu Ala Leu Gly Pro
1865 1870 1875

Phe Gln Ser Phe Ile Leu Lys Val Val Asn Lys Lys Ile Glu Arg
1880 1885 1890

Pro Met Phe Arg Asn Asp Leu Gln Phe Gly Phe Gly Trp Phe Ser
1895 1900 1905

Tyr Arg Val Gly Asp Val Val Cys Asn Ala Ala Met Leu Ile Lys
1910 1915 1920

Gln Gly Leu Thr Asp Pro Lys Ala Phe Lys Ser Leu Arg Asp Leu
1925 1930 1935

Trp Asp Tyr Met Leu Ser Ser Thr Glu Gly Ile Leu Glu Phe Ser
1940 1945 1950

Ile Thr Val Asp Phe Thr His Asn Gln Asn Asn Thr Asp Cys Leu
1955 1960 1965

Arg Lys Phe Ser Leu Ile Phe Val Val Lys Cys Gln Leu Gln Ser
1970 1975 1980

Pro Gly Val Ala Asp Tyr Leu Ser Cys Ser His Phe Phe Lys Gly
1985 1990 1995

Glu Val Asp Arg Arg Leu Leu Asp Glu Cys Leu Asn Leu Leu Arg
2000 2005 2010

Thr Asp Pro Ile Phe Lys Ala Asn Asp Gly Val Phe Asp Ile Arg
2015 2020 2025

Ser Glu Glu Phe Glu Asp Tyr Met Glu Asp Pro Leu Thr Leu Gly
2030 2035 2040

Asp Ser Leu Glu Leu Glu Leu Ile Gly Ser Arg Arg Ile Leu Asn
2045 2050 2055

Glu Ile Lys Ser Thr Asp Phe Glu Arg Ile Gly Pro Glu Trp Glu
2060 2065 2070

Pro Val Pro Leu Thr Ile Arg Lys Gly Ala Leu Phe Glu Gly Arg
2075 2080 2085

Asn Phe Val Gln Asn Ile Ser Val Lys Leu Glu Thr Lys Asp Met
2090 2095 2100

Arg Val Phe Leu Ala Glu Leu Glu Gly Cys Gly Glu Ile Gly Asp
2105 2110 2115

Val Leu Gly Ser Leu Leu Leu His Arg Phe Arg Thr Gly Glu His
2120 2125 2130

Leu Met Glu Ser Glu Ile Ser Thr Val Leu Gln Glu Leu Cys Met
2135 2140 2145

Asp Arg Ser Val Met Leu Thr Pro Leu Ser Phe Val Pro Asp Trp
2150 2155 2160

Phe Thr Phe Arg Asp Cys Arg Leu Cys Phe Ser Arg Ser Lys Asn
2165 2170 2175

-continued

```
Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp
```